(12) United States Patent
Balog et al.

(10) Patent No.: US 12,059,420 B2
(45) Date of Patent: *Aug. 13, 2024

(54) INHIBITORS OF INDOLEAMINE 2,3-DIOXYGENASE AND METHODS OF THEIR USE

(71) Applicant: BRISTOL-MYERS SQUIBB COMPANY, Princeton, NJ (US)

(72) Inventors: James Aaron Balog, Princeton, NJ (US); Jay A. Markwalder, Princeton, NJ (US); Weifang Shan, Princeton, NJ (US); David K. Williams, Princeton, NJ (US); Susheel Jethanand Nara, Bangalore (IN); Saumya Roy, Bangalore (IN); Soodamani Thangavel, Bangalore (IN); Srinivas Cheruku, Bangalore (IN); Ramesh Kumar Sistla, Bangalore (IN)

(73) Assignee: Bristol-Myers Squibb Company, Princeton, NJ (US)

( * ) Notice: Subject to any disclaimer, the term of this patent is extended or adjusted under 35 U.S.C. 154(b) by 551 days.

This patent is subject to a terminal disclaimer.

(21) Appl. No.: 17/261,954

(22) PCT Filed: Jul. 22, 2019

(86) PCT No.: PCT/US2019/042771
§ 371 (c)(1),
(2) Date: Jan. 21, 2021

(87) PCT Pub. No.: WO2020/023355
PCT Pub. Date: Jan. 30, 2020

(65) Prior Publication Data
US 2021/0299126 A1    Sep. 30, 2021

Related U.S. Application Data

(60) Provisional application No. 62/701,880, filed on Jul. 23, 2018.

(51) Int. Cl.
| | | |
|---|---|---|
| *A61K 31/506* | (2006.01) | |
| *A61K 31/4418* | (2006.01) | |
| *A61K 31/4439* | (2006.01) | |
| *A61K 31/4725* | (2006.01) | |
| *A61K 31/496* | (2006.01) | |

(Continued)

(52) U.S. Cl.
CPC ........ *A61K 31/506* (2013.01); *A61K 31/4418* (2013.01); *A61K 31/4439* (2013.01); *A61K 31/4725* (2013.01); *A61K 31/496* (2013.01); *A61K 31/501* (2013.01); *A61K 31/519* (2013.01); *A61K 31/5377* (2013.01); *A61K 39/3955* (2013.01); *C07D 213/74* (2013.01); *C07D 213/75* (2013.01); *C07D 401/14* (2013.01); *C07D 403/10* (2013.01); *C07D 403/14* (2013.01); *C07D 405/14* (2013.01); *C07D 413/10* (2013.01); *C07D 413/14* (2013.01); *C07D 417/10* (2013.01); *C07D 417/14* (2013.01); *C07D 487/04* (2013.01)

(58) Field of Classification Search
CPC .............. A61K 31/506; A61K 31/4418; A61K 31/4439; A61K 31/4725; A61K 31/496; A61K 31/501; A61K 31/519; A61K 31/5377; A61K 39/3955; C07D 213/74; C07D 213/75; C07D 401/14; C07D 403/10; C07D 403/14; C07D 405/14; C07D 413/10; C07D 413/14; C07D 417/10; C07D 417/14; C07D 487/04; C07D 417/12; C07D 401/10; A61P 35/00
USPC ....................................................... 514/236
See application file for complete search history.

(56) References Cited

U.S. PATENT DOCUMENTS 9,675,571 B2 *   6/2017   Balog .................... A61P 15/00
9,758,492 B2 *   9/2017   Markwalder ........ C07D 413/12
(Continued)

FOREIGN PATENT DOCUMENTS

WO        99/29310 A2     6/1999
WO     2004/094409 A1    11/2004
(Continued)

OTHER PUBLICATIONS

Hammer et al.,Bioorg. Med. Chem. Lett. 26 (2016) 292-300 293, "2,4-Diaminopyrimidines as dual ligands at the histamine H1 and H4 receptor—H1/H4-receptor selectivity" (Year: 2016).*
Williams et al. Bioorganic & Medicinal Chemistry Letters, vol. 28, Issue 4, Feb. 15, 2018, pp. 732-736, Development of a series of novel o-phenylenediamine-based indoleamine 2,3-dioxygenase 1 (IDO1) inhibitors (Year: 2018).*
(Continued)

*Primary Examiner* — Jared Barsky
*Assistant Examiner* — Liyuan Mou
(74) *Attorney, Agent, or Firm* — BakerHostetler

(57) ABSTRACT

The present invention provides compounds of formula (I): wherein all of the variables are as defined herein. These compounds are inhibitors of indoleamine 2,3-dioxygenase (IDO), which may be used as medicaments for the treatment of proliferative disorders, such as cancer, viral infections and/or autoimmune diseases.

6 Claims, No Drawings

(51) Int. Cl.

| | |
|---|---|
| *A61K 31/501* | (2006.01) |
| *A61K 31/519* | (2006.01) |
| *A61K 31/5377* | (2006.01) |
| *A61K 39/395* | (2006.01) |
| *C07D 213/74* | (2006.01) |
| *C07D 213/75* | (2006.01) |
| *C07D 401/14* | (2006.01) |
| *C07D 403/10* | (2006.01) |
| *C07D 403/14* | (2006.01) |
| *C07D 405/14* | (2006.01) |
| *C07D 413/10* | (2006.01) |
| *C07D 413/14* | (2006.01) |
| *C07D 417/10* | (2006.01) |
| *C07D 417/14* | (2006.01) |
| *C07D 487/04* | (2006.01) |

(56) References Cited

U.S. PATENT DOCUMENTS

| | | | | |
|---|---|---|---|---|
| 9,765,018 | B2 * | 9/2017 | Markwalder | C07C 311/09 |
| 9,790,169 | B2 * | 10/2017 | Balog | A61K 31/505 |
| 9,895,330 | B2 * | 2/2018 | Markwalder | C07D 261/08 |
| 10,399,932 | B2 * | 9/2019 | Balog | A61P 35/02 |
| 10,399,933 | B2 * | 9/2019 | Balog | C07D 409/12 |
| 10,959,986 | B2 * | 3/2021 | Balog | A61K 31/341 |

FOREIGN PATENT DOCUMENTS

| | | |
|---|---|---|
| WO | 2006/029879 | 3/2006 |
| WO | 2006/105021 A2 | 10/2006 |
| WO | 2006/122150 A1 | 11/2006 |
| WO | 2007/005874 A2 | 1/2007 |
| WO | 2007/075598 A2 | 7/2007 |
| WO | 2008/036642 A2 | 3/2008 |
| WO | 2008/036653 A2 | 3/2008 |
| WO | 2008/132601 A1 | 11/2008 |
| WO | 2009/009116 | 1/2009 |
| WO | 2009/044273 A2 | 4/2009 |
| WO | 2009/073620 A2 | 6/2009 |
| WO | 2010/019570 A2 | 2/2010 |
| WO | 2010/077634 A1 | 7/2010 |
| WO | 2011/028683 | 3/2011 |
| WO | 2011/056652 A1 | 5/2011 |
| WO | 2011/070024 A1 | 6/2011 |
| WO | 2011/107553 A1 | 9/2011 |
| WO | 2011/109400 A2 | 9/2011 |
| WO | 2011/131407 A1 | 10/2011 |
| WO | 2011/140249 A2 | 11/2011 |
| WO | 2012/032423 A1 | 3/2012 |
| WO | 2012/142237 A1 | 10/2012 |
| WO | 2013/079174 A1 | 6/2013 |
| WO | 2013/087699 A1 | 6/2013 |
| WO | 2013/119716 A1 | 8/2013 |
| WO | 2013/132044 A1 | 9/2013 |
| WO | 2013/169264 A1 | 11/2013 |
| WO | 2014/008218 A1 | 1/2014 |
| WO | 2014/036357 A1 | 3/2014 |
| WO | 2014/150646 A1 | 9/2014 |
| WO | 2016/073738 A2 | 5/2016 |
| WO | 2016/073770 A1 | 5/2016 |
| WO | 2016/073774 A2 | 5/2016 |
| WO | 2016/161279 A1 | 10/2016 |
| WO | WO-2017051353 A1 * | 3/2017 ......... A61K 31/4184 |

OTHER PUBLICATIONS

Brandacher, G. et al., Prognostic value of indoleamine 2,3-dioxygenase expression in colorectal cancer: effect on tumor-infiltrating T cells, Feb. 15, 2006, 1144-1151, Dec. 4.

Bundgaard, H., Prodrugs as a mean to improve the delivery of peptide drugs. Adv. Drug Del. Rev. 8:1-38 (1992).

Goldstein et al., J. Biological efficacy of a chimeric antibody to the epidermal growth factor receptor in a human tumor xenograft model. Clin Cancer Res. 1995;1(11):1311-1318.

Ishiyama, et al., Palladium(0)-Catalyzed Cross-Coupling Reaction of Alkoxydiboron with Haloarenes: A Direct Procedure for Arylboronic Esters J.Org. Chem, 1995, 60, 7508-7510.

Kakeya, N. et al., Studies on Prodrugs of Cephalosporins. I. Synthesis and Biological Properties of Glycyloxybenzoyloxymethyl and Glycylaminobenzoyloxymethyl Esters of 7ß-[2-(2-Aminothiazol-4-yl)-(Z)-2-methoxyiminoacetamido]-3-methyl-3-cephem-4-carboxylic Acid, Chem. Pharm. Bull., 32:692 (1984).

Kohl et al., Inhibition of farnesyltransferase induces regression of mammary and salivary carcinomas in ras transgenic mice, Nat. Med., 1, 792-797 (1995).

Littlejohn, T.K. et al., Expression and Purification of Recombinant Human Indoleamine 2,3-Dioxygenase, Protein Expression Purification, 19:22-29 (Jun. 2000).

Nielsen, N.M. et al., Glycolamide esters as biolabile prodrugs of carboxylic acid agents: synthesis, stability, bioconversion, and physicochemical properties. J Pharm Sci. 1988;77(4):285-298.

Sarkar SA, Wong R, Hackl SI, et al., Induction of indoleamine 2,3-dioxygenase by interferon-gamma in human islets, Diabetes 2007;56:72-79.

Sausville, Cyclin-Dependent Kinase Modulators Studied at the NCI: Pre-Clinical and Clinical Studies, Curr. Med. Chem. Anti-Canc. Agents, 3:47-56 (2003).

Scheller et al., Paclitaxel Balloon Coating, a Novel Method for Prevention and Therapy of Restenosis, Circulation, 110:810-814 (2004).

Sekulic et al., A Direct Linkage Between the Phosphoinositide 3-Kinase-AKT Signaling Pathway and the Mammalian Target of Rapamycin in Mitogen-stimulated and Transformed Cells, Cancer Res., 60:3504-3513 (Jul. 2000).

Serafini P, et al., Myeloid suppressor cells in cancer: Recruitment, phenotype, properties, and mechanisms of immune suppression, Seminars in Cancer Biology, 16(I):53-65 (Feb. 2006).

Surry, D.S. et al., Dialkylbiaryl Phosphines in Pd-Catalyzed Amination: A User's Guide, Chem. Sci., 2:27-50 (2011).

Testa, B. et al., Hydrolysis in Drug andProdrugMetabolism. Chemistry, Biochemistry andEnzymology VCHA and Wiley-VCH, Zurich, Switzerland (2003).

Mahos et ah, A Specif Inhibitor of Phosphatidylinositol 3-Kinase, 2-(4-Morpholinyl)-8-phenyl-4H-1-benzopyran-4-one (LY294002), J. Biol. Chem., 269:5241-5248 (1994).

Zou et al., Heck-type coupling vs. conjugate addition in phosphine-rhodium catalyzed reactions of aryl boronic acids with a, ß-unsaturated carbonyl compounds: a systematic investigation, Dalton Trans., 28:3055 (2007).

* cited by examiner

INHIBITORS OF INDOLEAMINE 2,3-DIOXYGENASE AND METHODS OF THEIR USE

CROSS-REFERENCE TO RELATED APPLICATIONS

This application is the National Stage Application of International Patent Application No. PCT/US2019/01042771 filed Jul. 22, 2019, which claims the priority benefit of U.S. Provisional Application No. 62/701,880, filed Jul. 23, 2018; the contents of which are herein incorporated by reference in their entirety.

FIELD OF THE INVENTION

The invention relates generally to compounds that modulate or inhibit the enzymatic activity of indoleamine 2,3-dioxygenase (IDO), pharmaceutical compositions containing said compounds and methods of treating proliferative disorders, such as cancer, viral infections and/or autoimmune diseases utilizing the compounds of the invention.

BACKGROUND OF THE INVENTION

Indoleamine 2,3-dioxygenase (IDO; also known as IDOL) is an IFN-γ target gene that plays a role in immunomodulation. IDO is an oxidoreductase and one of two enzymes that catalyze the first and rate-limiting step in the conversion of tryptophan to N-formyl-kynurenine. It exists as a 41 kD monomer that is found in several cell populations, including immune cells, endothelial cells, and fibroblasts. IDO is relatively well-conserved between species, with mouse and human sharing 63% sequence identity at the amino acid level. Data derived from its crystal structure and site-directed mutagenesis show that both substrate binding and the relationship between the substrate and iron bound dioxygenase are necessary for activity. A homolog to IDO (IDO2) has been identified that shares 44% amino acid sequence homology with IDO, but its function is largely distinct from that of IDO. (See, e.g., Serafini P, et al., *Semin. Cancer Biol.*, 16(1):53-65 (February 2006) and Ball, H. J. et al., *Gene,* 396(1):203-213 (July 2007)).

IDO plays a major role in immune regulation, and its immunosuppressive function manifests in several manners. Importantly, IDO regulates immunity at the T cell level, and a nexus exists between IDO and cytokine production. In addition, tumors frequently manipulate immune function by upregulation of IDO. Thus, modulation of IDO can have a therapeutic impact on a number of diseases, disorders and conditions.

A pathophysiological link exists between IDO and cancer. Disruption of immune homeostasis is intimately involved with tumor growth and progression, and the production of IDO in the tumor microenvironment appears to aid in tumor growth and metastasis. Moreover, increased levels of IDO activity are associated with a variety of different tumors (Brandacher, G. et al., *Clin. Cancer Res.,* 12(4):1144-1151 (Feb. 15, 2006)).

Treatment of cancer commonly entails surgical resection followed by chemotherapy and radiotherapy. The standard treatment regimens show highly variable degrees of long-term success because of the ability of tumor cells to essentially escape by regenerating primary tumor growth and, often more importantly, seeding distant metastasis. Recent advances in the treatment of cancer and cancer-related diseases, disorders and conditions comprise the use of combination therapy incorporating immunotherapy with more traditional chemotherapy and radiotherapy. Under most scenarios, immunotherapy is associated with less toxicity than traditional chemotherapy because it utilizes the patient's own immune system to identify and eliminate tumor cells.

In addition to cancer, IDO has been implicated in, among other conditions, immunosuppression, chronic infections, and autoimmune diseases or disorders (e.g., rheumatoid arthritis). Thus, suppression of tryptophan degradation by inhibition of IDO activity has tremendous therapeutic value. Moreover, inhibitors of IDO can be used to enhance T cell activation when the T cells are suppressed by pregnancy, malignancy, or a virus (e.g., HIV). Although their roles are not as well defined, IDO inhibitors may also find use in the treatment of patients with neurological or neuropsychiatric diseases or disorders (e.g., depression).

Small molecule inhibitors of IDO have been developed to treat or prevent IDO-related diseases. For example, the IDO inhibitors 1-methyl-DL-tryptophan; p-(3-benzofuranyl)-DL-alanine; p-[3-benzo(b)thienyl]-DL-alanine; and 6-nitro-L-tryptophan have been used to modulate T cell-mediated immunity by altering local extracellular concentrations of tryptophan and tryptophan metabolites (WO 99/29310). Compounds having IDO inhibitory activity are further reported in, for example, WO 2004/094409, WO2014/150646, WO2016/073770, WO2016/073738, and WO2016/073774.

In view of the role played by indoleamine 2,3-dioxygenase in a diverse array of diseases, disorders and conditions, and the limitations (e.g., efficacy) of current IDO inhibitors, new IDO modulators, and compositions and methods associated therewith, are needed.

SUMMARY OF THE INVENTION

The invention is directed to compounds of formula (I):

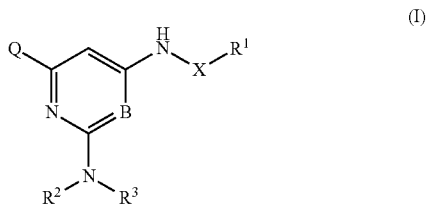

wherein all of the variables are as defined herein below.

Also within the scope of the invention are pharmaceutically acceptable salts, stereoisomers, tautomers, and solvates of the compounds of formula (I).

The invention is also directed to pharmaceutical compositions comprising one or more compounds of the invention. The invention is also directed to methods of treating cancer using one or more compounds of the invention.

The invention also provides processes and intermediates for making the compounds of formula (I) or pharmaceutically acceptable salts, stereoisomers, tautomers, and solvates thereof.

The compounds of the invention may be used in therapy. The compounds of the invention may be used for the manufacture of a medicament for the treatment of cancer.

The compounds of the invention can be used alone, in combination with other compounds of the present invention, or in combination with one or more other agent(s).

Other features and advantages of the invention will be apparent from the following detailed description and claims.

DETAILED DESCRIPTION OF THE INVENTION

Compounds of the Invention

In a first aspect, the present invention provides, inter alia, a compound of formula (I):

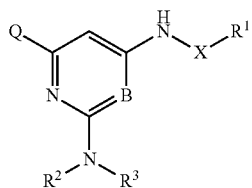

wherein:
B is CH or N;
Q is $C_3$-$C_6$ alkyl substituted with C(O)OH or phenyl substituted with W and $R^4$;
X is selected from: a bond, C(O), —C(O)$CR^5R^6$— and —C(O)$NR^7$—;
W is selected from: C(O)OH, C(O)$NH_2$, —S(O)$_2$$NHR^a$,

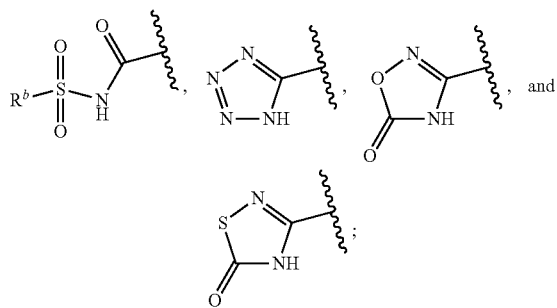

$R^1$ is selected from: $C_1$-$C_6$ alkyl, $C_3$-$C_6$ cycloalkyl, tetrahydro-2H-pyranyl, morpholinyl, phenyl, naphthalenyl, thiophenyl, thiazolyl, isoxazolyl, 1H-imidazolyl, pyrazolyl, 1,3,4-thiadiazolyl, 1H-tetrazolyl, pridinyl, pyrimidinyl, pyridazinyl, pyrazinyl, benzo[d][1,3]dioxolyl, benzo[b]thiophenyl, benzo[d]thiazolyl, benzo[d]oxazolyl, 1-($C_1$-$C_4$ alkyl)-1H-indolyl, pyrazolo[1,5-a]pyrimidinyl, [1,2,4]triazolo[4,3-b]pyridazinyl, 7H-pyrrolo[2,3-d]pyrimidinyl, and quinolin-2-yl; wherein each moiety is substituted with 0 to 2 $R^e$;
$R^2$ is selected from: $C_1$-$C_4$ alkyl, tetrahydro-2H-pyran-4-yl, pyrimidinylmethyl, 1-$R^d$-piperidin-4-yl, —(CH$_2$)$_{0-1}$-($C_3$-$C_6$ cycloalkyl substituted with 0 to 2 $R^e$), and —(CH$_2$)$_{0-1}$-(phenyl substituted with 0 to 2 $R^e$);
$R^3$ is $C_1$-$C_4$ alkyl substituted with 0 to 1 $R^f$, —CH$_2$—($C_3$-$C_6$ cycloalkyl), or benzyl;
alternatively, —NR$^2$R$^3$ is selected from:

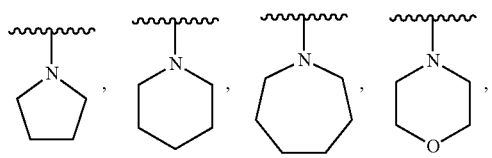

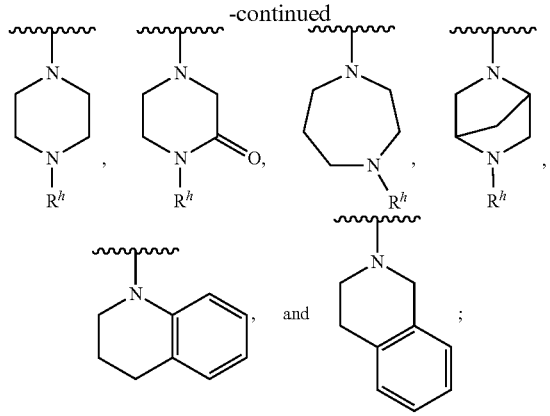

wherein each moiety is substituted with 0 to 2 $R^g$;
$R^4$ is H, halo, $C_1$-$C_4$ alkyl, $C_1$-$C_4$ halolkyl, $C_1$-$C_4$ alkoxy or $C_1$-$C_4$ halolkoxy;
$R^5$ and $R^6$ are independently H, F, Cl, or $C_1$-$C_4$ alkyl;
alternatively, $R^5$ and $R^6$, together with the carbon atom to which they are attached, combine to form a $C_3$-$C_6$ cycloalkylene;
$R^7$ is H or $C_1$-$C_4$ alkyl;
$R^a$ is independently H, C(O)($C_1$-$C_4$ alkyl), or C(O)Ph;
$R^b$ is independently $C_1$-$C_4$ alkyl, $C_5$-$C_6$ cycloalkyl, or 4-($C_1$-$C_4$ alkyl)-piperazin-1-yl;
$R^c$ is independently selected from: halo, CN, $C_1$-$C_6$ alkyl, $C_1$-$C_6$ halolkyl, $C_1$-$C_6$ alkoxy, $C_1$-$C_6$ halolkoxy, CH$_2$OH, C(O)OH, C(O)NH$_2$, —S(O)$_2$($C_1$-$C_4$ alkyl), phenyl, and morpholinyl;
$R^d$ is independently H or C(O)O($C_1$-$C_4$ alkyl);
$R^e$ is independently selected from: halo, $C_1$-$C_4$ alkyl, $C_1$-$C_4$ halolkyl, $C_1$-$C_4$ alkoxy, and $C_1$-$C_4$halolkoxy;
$R^f$ is independently selected from: halo, OH, $C_1$-$C_4$ halolkyl, $C_1$-$C_4$ alkoxy, $C_1$-$C_4$ halolkoxy, C(O)N($C_1$-$C_4$ alkyl)$_2$, phenyl, 4-($C_1$-$C_4$ alkyl)-piperazin-1-yl, and $C_1$-$C_4$ alkyl substituted with 0 to 1 OH;
$R^g$ is independently selected from: halo, $C_1$-$C_4$halolkyl, $C_1$-$C_4$ alkoxy, and $C_1$-$C_4$ halolkoxy; and
$R^h$ is independently selected from: H, $C_1$-$C_4$ alkyl, C(O)($C_1$-$C_4$ alkyl), C(O)Ph, —CH$_2$C(O)NH($C_1$-$C_4$ alkyl,), —(CH$_2$)$_{0-1}$-(phenyl substituted with 0 to 2 $R^e$), and

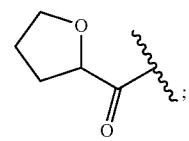 [SMILES: *C(=O)C1CCCO1]

or a pharmaceutically acceptable salt thereof.

In a second aspect, the present invention provides a compound of formula (I), within the scope of the first aspect, wherein:
Q is $C_3$-$C_6$ alkyl substituted with C(O)OH.

In a third aspect, the present invention provides a compound of formula (I), within the scope of the first aspect, wherein:

Q is

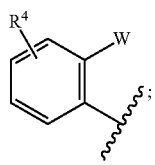;

wherein:
W is selected from: C(O)NH$_2$, —S(O)$_2$NHR$^a$,

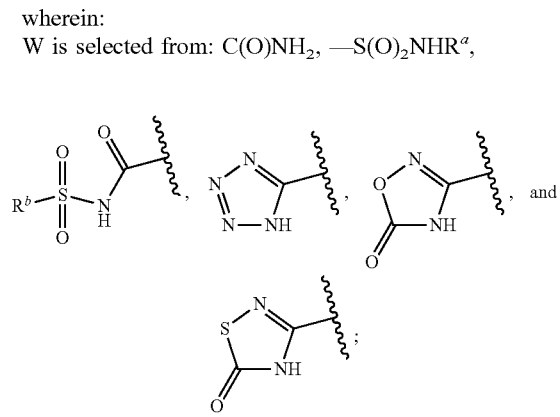, and

R$^a$ is independently H or C(O)(C$_1$-C$_4$ alkyl);
R$^b$ is independently C$_1$-C$_4$ alkyl or C$_5$-C$_6$ cycloalkyl.

In a fourth aspect, the present invention provides a compound of formula (I), within the scope of the first or third aspect, wherein:

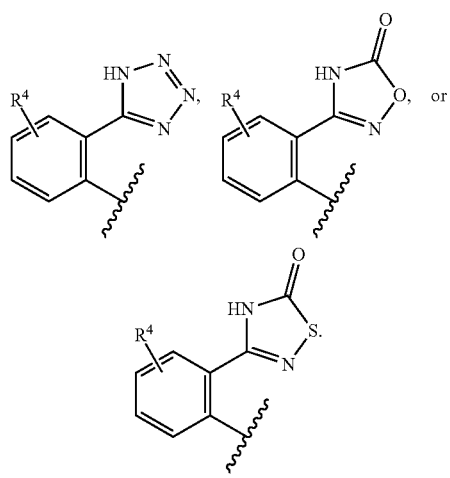

In a fifth aspect, the present invention provides a compound of formula (I), within the scope of the first to fourth aspects, wherein:
X is selected from: a bond, C(O), —C(O)CHR$^5$—, —CONR$^7$— and

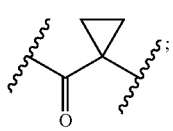 [SMILES: *C(=O)C1(*)CC1];

R$^2$ is selected from: C$_1$-C$_4$ alkyl, tetrahydro-2H-pyran-4-yl, pyrimidinylmethyl, 1-R$^d$-piperidin-4-yl, —(CH$_2$)$_{0-1}$—(C$_3$-C$_6$ cycloalkyl substituted with 0 to 2 R$^e$), and (CH$_2$)$_{0-1}$-(phenyl substituted with 0 to 2 R$^e$);
R$^3$ is C$_1$-C$_4$ alkyl substituted with 0 to 1 R$^f$, —CH$_2$—(C$_3$-C$_6$ cycloalkyl), or benzyl;
alternatively, —NR$^2$R$^3$ is selected from:

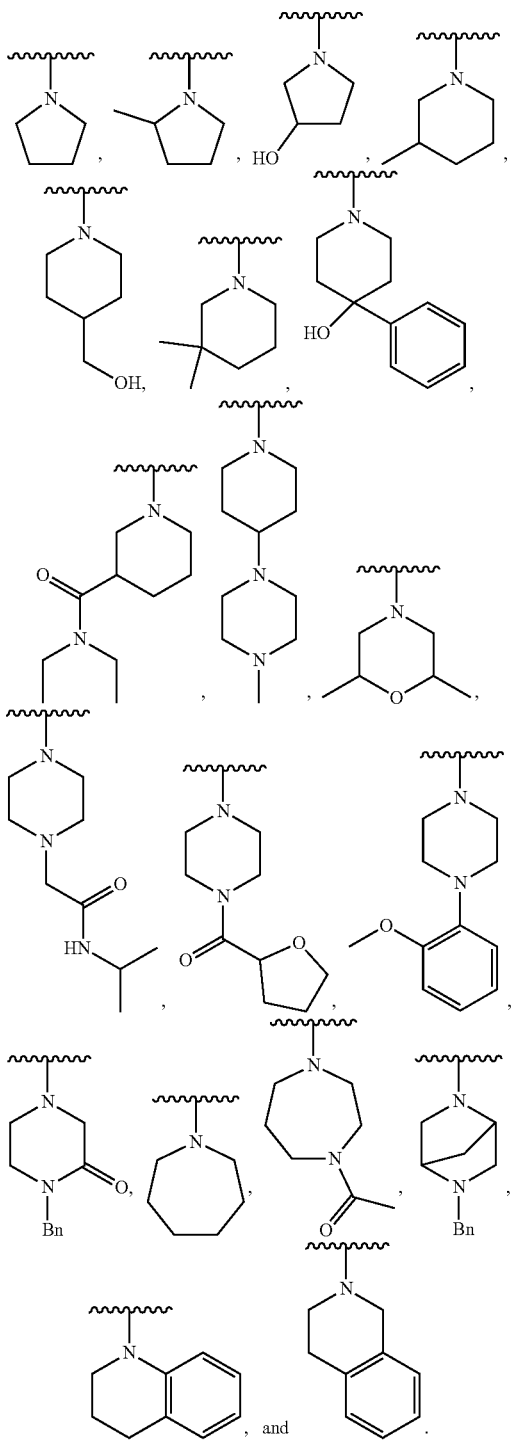

In a sixth aspect, within the scope of the first, third to fifth aspects, the present invention provides a compound of formula (II),

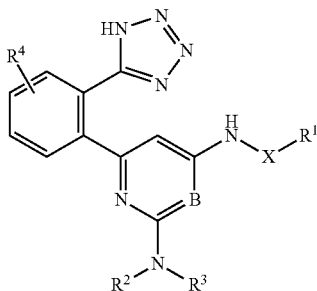

(II)

B is CH or N;
X is a bond, C(O), —C(O)CH₂—, —C(O)CHF—, —C(O)NH—, —C(O)N(CH₃)—, or

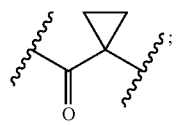 [SMILES: *C(=O)C1(*)CC1]

R¹ is selected from: C₁-C₆ alkyl, C₅-C₆ cycloalkyl, phenyl, naphthalenyl, thiophenyl, thiazolyl, isoxazolyl, pyrazolyl, 1,3,4-thiadiazolyl, pridinyl, pyrimidinyl, pyridazinyl, pyrazinyl, benzo[d][1,3]dioxolyl, benzo[b]thiophenyl, benzo[d]thiazolyl, benzo[d]oxazolyl, 1-methyl-1H-indolyl, pyrazolo[1,5-a]pyrimidinyl, [1,2,4]triazolo[4,3-b]pyridazinyl, 7H-pyrrolo[2,3-d]pyrimidinyl, and quinolinyl; wherein each moiety is substituted with 0 to 2 R$^c$;
R$^c$ is independently selected from: halo, CN, C₁-C₄ alkyl, C₁-C₄ alkoxy, CHF₂, CF₃, OCF₃, —OCF₂CHF₂, CH₂OH, C(O)NH₂, phenyl, and morpholinyl;
R² is selected from: C₁-C₄ alkyl, cyclopropylmethyl, cyclohexyl, benzyl, 4-F-benzyl, and pyrimidin-2-ylmethyl;
R³ is C₁-C₄ alkyl substituted with 0 to 1 R$^f$, cyclopropylmethyl, or benzyl;
alternatively, —NR²R³ is

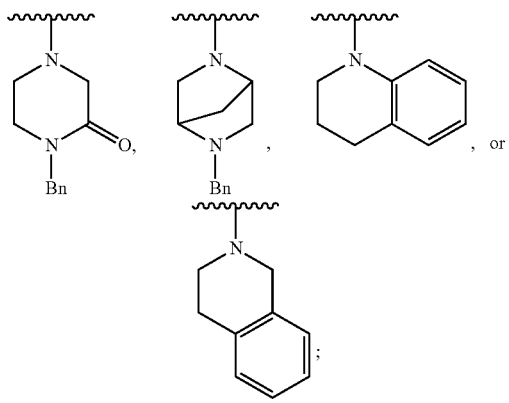

R⁴ is H, F, or CH₃; and
R$^f$ is CF₃ or OCH₃;
or a pharmaceutically acceptable salt, a stereoisomer, a tautomer, or a solvate thereof.

In a seventh aspect, the invention provides a compound selected from the exemplified examples or a pharmaceutically acceptable salt thereof.

In another aspect, the present invention provides a compound selected from any subset list of compounds or a single compound from the exemplified examples within the scope of any of the above aspects.

In some aspects, B is CH. In other aspects, B is N.

In some aspects, Q is C₃-C₆ alkyl substituted with C(O)OH. In other aspects, Q is phenyl substituted with W and R⁴. In other aspects, Q is

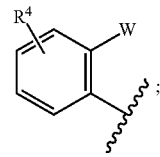

wherein:
W is selected from: C(O)NH₂, —S(O)₂NHR$^a$,

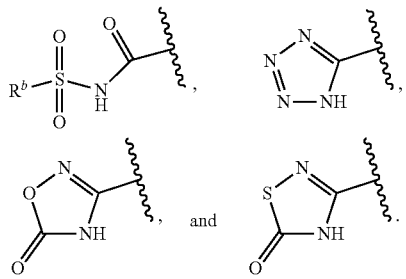

In other aspects, Q is

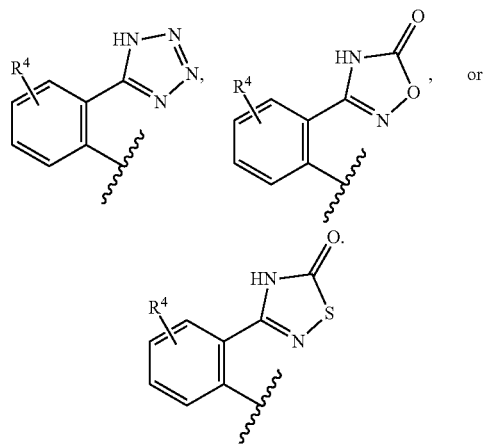

In some aspects, X is a bond, C(O), —C(O)CHR⁵—, —C(O)NR⁷—, or

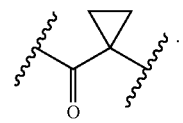 [SMILES: *C(=O)C1(*)CC1]

In other aspects, X is a bond, C(O), —C(O)CH₂—, —C(O)CHF—, —C(O)NH—, —C(O)N(CH₃)—, or

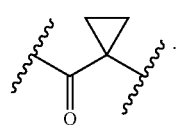 [SMILES: *C(=O)C1(*)CC1].

In other aspects, X is a bond. In other aspects, X is C(O), —C(O)CHR⁵—, —C(O)NR⁷—, or

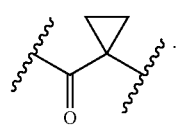 [SMILES: *C(=O)C1(*)CC1].

In other aspects, X is C(O). In other aspects, X is —C(O)CHR⁵—. In other aspects, X is —C(O)NR⁷—. In other aspects, X is

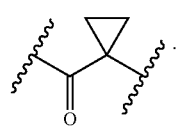 [SMILES: *C(=O)C1(*)CC1].

In some aspects, W is C(O)NH₂, —S(O)₂NHRᵃ,

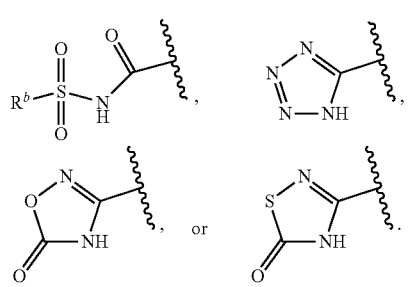.

In other aspects, W is C(O)OH. In other aspects, W is C(O)NH₂, S(O)₂NHRᵃ,

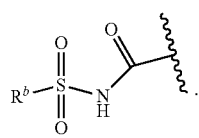.

In other aspects, W is C(O)NH₂. In other aspects, W is —SO₂NHRᵃ or

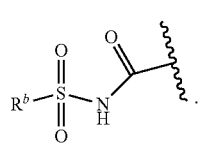.

In other aspects, W is —S(O)₂NHRᵃ. In other aspects, W is

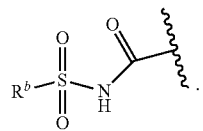.

In other aspects, W is

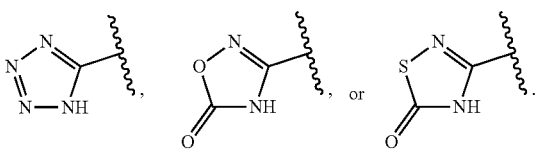 [SMILES: *c1nnn[nH]1 ; *c1noc(=O)[nH]1 ; *c1nsc(=O)[nH]1].

In other aspects, W is

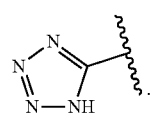.

In other aspects, W is

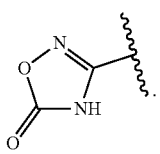.

In other aspects, W is

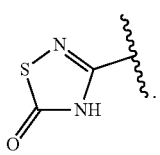.

In some aspects, R¹ is selected from: C₁-C₆ alkyl, C₅-C₆ cycloalkyl, phenyl, naphthalenyl, thiophenyl, thiazolyl, isoxazolyl, pyrazolyl, 1,3,4-thiadiazolyl, pridinyl, pyrimidinyl, pyridazinyl, pyrazinyl, benzo[d][1,3]dioxolyl, benzo[b]thiophenyl, benzo[d]thiazolyl, benzo[d]oxazolyl, 1-methyl-1H-indolyl, pyrazolo[1,5-a]pyrimidinyl, [1,2,4]triazolo[4,3-b]pyridazinyl, 7H-pyrrolo[2,3-d]pyrimidinyl, and quinolinyl; wherein each moiety is substituted with 0 to 2 Rᶜ.

In some aspects, R² is C₁-C₄ alkyl, tetrahydro-2H-pyran-4-yl, pyrimidinylmethyl, 1-Rᵈ-piperidin-4-yl, —(CH₂)₀₋₁—(C₃-C₆ cycloalkyl substituted with 0 to 2 Rᵉ), or —(CH₂)₀₋₁-(phenyl substituted with 0 to 2 Rᵉ); and R³ is C₁-C₄ alkyl substituted with 0 to 1 Rᶠ, —CH₂—(C₃-C₆ cycloalkyl), or benzyl. In other aspects, NR²R³ is

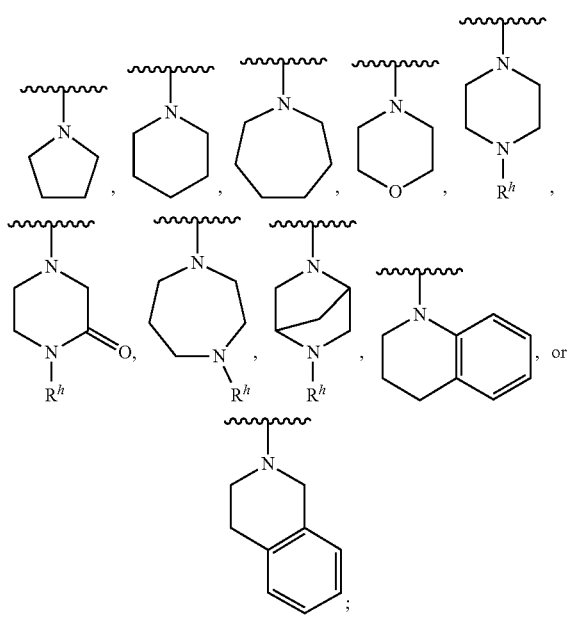

wherein each moiety is substituted with 0 to 2 $R^g$.

In some aspects, $R^2$ is $C_1$-$C_4$ alkyl, cyclopropylmethyl, cyclohexyl, benzyl, 4-F-benzyl, or pyrimidin-2-ylmethyl; $R^3$ is $C_1$-$C_4$ alkyl substituted with 0 to 1 $R^5$, cyclopropylmethyl, or benzyl; alternatively, —$NR^2R^3$ is

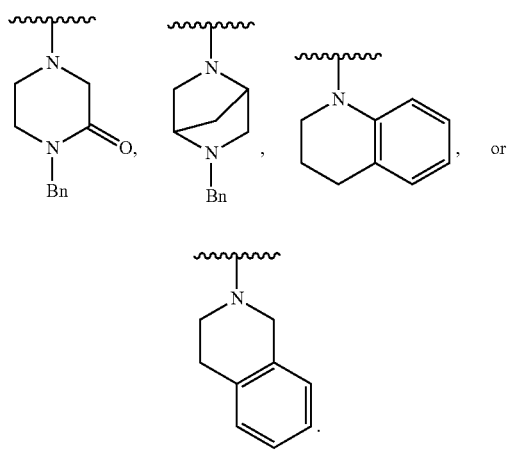

In other aspects, $R^2$ is $C_1$-$C_4$ alkyl, cyclopropylmethyl, cyclohexyl, benzyl, 4-F-benzyl, or pyrimidin-2-ylmethyl; $R^3$ is $C_1$-$C_4$ alkyl substituted with 0 to 1 $R^5$, cyclopropylmethyl, or benzyl. In other aspects, —$NR^2R^3$ is

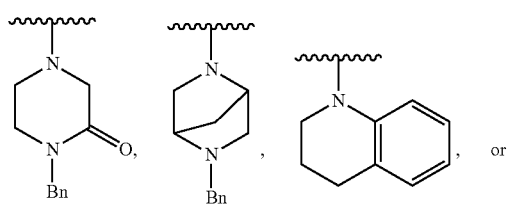

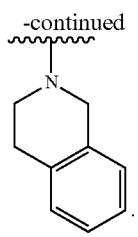

In some aspects, $R^4$ is H, halo, or $C_1$-$C_4$ alkyl. In other aspects, $R^4$ is H, F, or $CH_3$.

In some aspects, $R^5$ and $R^6$ are independently H, F, Cl, or $C_1$-$C_4$ alkyl. In other aspects, $R^5$ and $R^6$, together with the carbon atom to which they are attached, combine to form a $C_3$-$C_6$ cycloalkylene.

In some aspects, $R^7$ is H. In other aspects, $R^7$ is $C_1$-$C_4$ alkyl.

In another embodiment, the compounds of the invention have human IDO $IC_{50}$ values >50 nM but ≤1 μM. In another embodiment, the compounds of the invention have human IDO $IC_{50}$ values ≤50 nM. In another embodiment, the compounds of the invention have human IDO $IC_{50}$ values <5 nM.

OTHER EMBODIMENTS OF THE INVENTION

In another embodiment, the present invention provides a composition comprising one or more compounds of the present invention and/or a pharmaceutically acceptable salt thereof, a stereoisomer thereof, a tautomer thereof, or a solvate thereof.

In another embodiment, the present invention provides a pharmaceutical composition comprising a pharmaceutically acceptable carrier and at least one of the compounds of the present invention and/or a pharmaceutically acceptable salt thereof, a stereoisomer thereof, a tautomer thereof, or a solvate thereof.

In another embodiment, the present invention provides a pharmaceutical composition, comprising a pharmaceutically acceptable carrier and a therapeutically effective amount of at least one of the compounds of the present invention and/or a pharmaceutically acceptable salt thereof, a stereoisomer thereof, a tautomer thereof, or a solvate thereof.

In another embodiment, the present invention provides a process for making a compound of the present invention and/or a pharmaceutically acceptable salt thereof, a stereoisomer thereof, a tautomer thereof, or a solvate thereof.

In another embodiment, the present invention provides an intermediate for making a compound of the present invention and/or a pharmaceutically acceptable salt thereof, a stereoisomer thereof, a tautomer thereof, or a solvate thereof.

In another embodiment, the present invention provides a method for the treatment and/or prophylaxis of various types of cancer, viral infections and/or autoimmune diseases, comprising administering to a patient in need of such treatment and/or prophylaxis a therapeutically effective amount of one or more compounds of the present invention and/or a pharmaceutically acceptable salt thereof, a stereoisomer thereof or a tautomer thereof, alone, or, optionally, in combination with another compound of the present invention and/or at least one other type of therapeutic agent, such as a chemotherapeutic agent or a signal transductor inhibitor.

In another embodiment, the present invention provides a compound of the present invention, and/or a pharmaceutically acceptable salt thereof, a stereoisomer thereof or a tautomer thereof, for use in therapy.

In another embodiment, the present invention provides a combined preparation of a compound of the present invention, and/or a pharmaceutically acceptable salt thereof, a stereoisomer thereof or a tautomer thereof, and additional therapeutic agent(s) for simultaneous, separate or sequential use in therapy.

In another embodiment, the present invention provides a combined preparation of a compound of the present invention, and/or a pharmaceutically acceptable salt thereof, a stereoisomer thereof or a tautomer thereof, and additional therapeutic agent(s) for simultaneous, separate or sequential use in the treatment and/or prophylaxis of multiple diseases or disorders associated with the enzymatic activity of IDO.

In another embodiment, the additional therapeutic agent(s) are YERVOY, OPDIVO, or KEYTRUDA, or a combination thereof.

In another aspect, the invention provides a method of treating a patient suffering from or susceptible to a medical condition that is sensitive to enzymatic activity of IDO. A number of medical conditions can be treated. The method comprises administering to the patient a therapeutically effective amount of a composition comprising a compound described herein and/or a pharmaceutically acceptable salt thereof, a stereoisomer thereof or a tautomer thereof. For example, the compounds described herein may be used to treat or prevent viral infections, proliferative diseases (e.g., cancer), and autoimmune diseases.

It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

Therapeutic Applications

The compounds and pharmaceutical compositions of the present invention are useful in treating or preventing any disease or conditions that are sensitive to enzymatic activity of IDO. These include viral and other infections (e.g., skin infections, GI infection, urinary tract infections, genitourinary infections, systemic infections), proliferative diseases (e.g., cancer), and autoimmune diseases (e.g., rheumatoid arthritis, lupus). The compounds and pharmaceutical compositions may be administered to animals, preferably mammals (e.g., domesticated animals, cats, dogs, mice, rats), and more preferably humans. Any method of administration may be used to deliver the compound or pharmaceutical composition to the patient. In certain embodiments, the compound or pharmaceutical composition is administered orally. In other embodiments, the compound or pharmaceutical composition is administered parenterally.

Compounds of the invention can modulate activity of the enzyme indoleamine-2,3-dioxygenase (IDO). The term "modulate" is meant to refer to an ability to increase or decrease activity of an enzyme or receptor. Accordingly, compounds of the invention can be used in methods of modulating IDO by contacting the enzyme with any one or more of the compounds or compositions described herein. In some embodiments, compounds of the present invention can act as inhibitors of IDO. In further embodiments, the compounds of the invention can be used to modulate activity of IDO in cell or in an individual in need of modulation of the enzyme by administering a modulating (e.g., inhibiting) amount of a compound of the invention.

Compounds of the invention can inhibit activity of the enzyme indoleamine-2,3-dioxygenase (IDO). For example, the compounds of the invention can be used to inhibit activity of IDO in cell or in an individual in need of modulation of the enzyme by administering an inhibiting amount of a compound of the invention.

The present invention further provides methods of inhibiting the degradation of tryptophan in a system containing cells expressing IDO such as a tissue, living organism, or cell culture. In some embodiments, the present invention provides methods of altering (e.g., increasing) extracellular tryptophan levels in a mammal by administering an effective amount of a compound of composition provided herein. Methods of measuring tryptophan levels and tryptophan degradation are routine in the art.

The present invention further provides methods of inhibiting immunosuppression such as IDO-mediated immunosuppression in a patient by administering to the patient an effective amount of a compound or composition recited herein. IDO-mediated immunosuppression has been associated with, for example, cancers, tumor growth, metastasis, viral infection, and viral replication.

The present invention further provides methods of treating diseases associated with activity or expression, including abnormal activity and/or overexpression, of IDO in an individual (e.g., patient) by administering to the individual in need of such treatment a therapeutically effective amount or dose of a compound of the present invention or a pharmaceutical composition thereof. Example diseases can include any disease, disorder or condition that is directly or indirectly linked to expression or activity of the IDO enzyme, such as over expression or abnormal activity. An IDO-associated disease can also include any disease, disorder or condition that can be prevented, ameliorated, or cured by modulating enzyme activity. Examples of IDO-associated diseases include cancer, viral infection such as HIV infection, HCV infection, depression, neurodegenerative disorders such as Alzheimer's disease and Huntington's disease, trauma, age-related cataracts, organ transplantation (e.g., organ transplant rejection), and autoimmune diseases including asthma, rheumatoid arthritis, multiple sclerosis, allergic inflammation, inflammatory bowel disease, psoriasis and systemic lupus erythematosus.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the IDO enzyme with a compound of the invention includes the administration of a compound of the present invention to an individual or patient, such as a human, having IDO, as well as, for example, introducing a compound of the invention into a sample containing a cellular or purified preparation containing the IDO enzyme.

The term "IDO inhibitor" refers to an agent capable of inhibiting the activity of indoleamine 2,3-dioxygenase (IDO) and thereby reversing IDO-mediated immunosuppression. The IDO inhibitor may inhibit IDO1 and/or IDO2 (INDOL1). An IDO inhibitor may be a reversible or irreversible IDO inhibitor. "A reversible IDO inhibitor" is a compound that reversibly inhibits IDO enzyme activity either at the catalytic site or at a non-catalytic site and "an irreversible IDO inhibitor" is a compound that irreversibly destroys IDO enzyme activity.

Types of cancers that may be treated with the compounds of this invention include, but are not limited to, brain cancers, skin cancers, bladder cancers, ovarian cancers, breast cancers, gastric cancers, pancreatic cancers, prostate cancers, colon cancers, blood cancers, lung cancers and bone cancers. Examples of such cancer types include neuroblastoma, intestine carcinoma such as rectum carcinoma, colon carcinoma, familiar adenomatous polyposis carcinoma and hereditary non-polyposis colorectal cancer, esophageal carcinoma, labial carcinoma, larynx carcinoma, hypopharynx carcinoma, tongue carcinoma, salivary gland carcinoma, gastric carcinoma, adenocarcinoma, medullary thyroid carcinoma, papillary thyroid carcinoma, renal carcinoma, kidney parenchymal carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, diffuse large B-cell lymphoma (DLBCL), hepatocellular carcinoma, gall bladder carcinoma, bronchial carcinoma, small cell lung carcinoma, non-small cell lung carcinoma, multiple myeloma, basalioma, teratoma, retinoblastoma, choroid melanoma, seminoma, rhabdomyosarcoma, craniopharyngioma, osteosarcoma, chondrosarcoma, myosarcoma, liposarcoma, fibrosarcoma, Ewing sarcoma and plasmacytoma.

Thus, according to another embodiment, the invention provides a method of treating an autoimmune disease by providing to a patient in need thereof a compound or composition of the present invention. Examples of such autoimmune diseases include, but are not limited to, collagen diseases such as rheumatoid arthritis, systemic lupus erythematosus, Sharp's syndrome, CREST syndrome (calcinosis, Raynaud's syndrome, esophageal dysmotility, telangiectasia), dermatomyositis, vasculitis (Morbus Wegener's) and Sjögren's syndrome, renal diseases such as Goodpasture's syndrome, rapidly-progressing glomerulonephritis and membranoproliferative glomerulonephritis type II, endocrine diseases such as type-I diabetes, autoimmune polyendocrinopathy-candidiasis-ectodermal dystrophy (APECED), autoimmune parathyroidism, pernicious anemia, gonad insufficiency, idiopathic Morbus Addison's, hyperthyreosis, Hashimoto's thyroiditis and primary myxedema, skin diseases such as pemphigus vulgaris, bullous pemphigoid, herpes gestationis, epidermolysis bullosa and erythema multiforme major, liver diseases such as primary biliary cirrhosis, autoimmune cholangitis, autoimmune hepatitis type-1, autoimmune hepatitis type-2, primary sclerosing cholangitis, neuronal diseases such as multiple sclerosis, myasthenia gravis, myasthenic Lambert-Eaton syndrome, acquired neuromyotomy, Guillain-Barre syndrome (Muller-Fischer syndrome), stiff-man syndrome, cerebellar degeneration, ataxia, opsoclonus, sensoric neuropathy and achalasia, blood diseases such as autoimmune hemolytic anemia, idiopathic thrombocytopenic purpura (Morbus Werlhof), infectious diseases with associated autoimmune reactions such as AIDS, malaria and Chagas disease.

One or more additional pharmaceutical agents or treatment methods such as, for example, anti-viral agents, chemotherapeutics or other anticancer agents, immune enhancers, immunosuppressants, radiation, anti-tumor and anti-viral vaccines, cytokine therapy (e.g., IL2 and GM-CSF), and/or tyrosine kinase inhibitors can be optionally used in combination with the compounds of the present invention for treatment of IDO-associated diseases, disorders or conditions. The agents can be combined with the present compounds in a single dosage form, or the agents can be administered simultaneously or sequentially as separate dosage forms.

Suitable chemotherapeutic or other anticancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (CYTOXAN®), ifosfamide, melphalan, chlorambucil, pipobroman, triethylene-melamine, triethylenethiophosphoramine, busulfan, carmustine, lomustine, streptozocin, dacarbazine, and temozolomide.

In the treatment of melanoma, suitable agents for use in combination with the compounds of the present invention include: dacarbazine (DTIC), optionally, along with other chemotherapy drugs such as carmustine (BCNU) and cisplatin; the "Dartmouth regimen", which consists of DTIC, BCNU, cisplatin and tamoxifen; a combination of cisplatin, vinblastine, and DTIC, temozolomide or YERVOY®. Compounds according to the invention may also be combined with immunotherapy drugs, including cytokines such as interferon alpha, interleukin 2, and tumor necrosis factor (TNF) in the treatment of melanoma.

Compounds of the invention may also be used in combination with vaccine therapy in the treatment of melanoma. Anti-melanoma vaccines are, in some ways, similar to the anti-virus vaccines which are used to prevent diseases caused by viruses such as polio, measles, and mumps. Weakened melanoma cells or parts of melanoma cells called antigens may be injected into a patient to stimulate the body's immune system to destroy melanoma cells.

Melanomas that are confined to the arms or legs may also be treated with a combination of agents including one or more compounds of the invention, using a hyperthermic isolated limb perfusion technique. This treatment protocol temporarily separates the circulation of the involved limb from the rest of the body and injects high doses of chemotherapy into the artery feeding the limb, thus providing high doses to the area of the tumor without exposing internal organs to these doses that might otherwise cause severe side effects. Usually the fluid is warmed to 102° to 104° F. Melphalan is the drug most often used in this chemotherapy procedure. This can be given with another agent called tumor necrosis factor (TNF).

Suitable chemotherapeutic or other anticancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anticancer agents further include, for example, certain natural products and their derivatives (for example, vinca alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (Taxol), mithramycin, deoxycoformycin, mitomycin-C, L-asparaginase, interferons (especially IFN-a), etoposide, and teniposide.

Other cytotoxic agents include navelbene, CPT-11, anastrazole, letrazole, capecitabine, reloxafine, and droloxafine.

Also suitable are cytotoxic agents such as epidophyllotoxin; an antineoplastic enzyme; a topoisomerase inhibitor; procarbazine; mitoxantrone; platinum coordination complexes such as cisplatin and carboplatin; biological response modifiers; growth inhibitors; antihormonal therapeutic agents; leucovorin; tegafur; and haematopoietic growth factors.

Other anticancer agent(s) include antibody therapeutics such as trastuzumab (HERCEPTIN®), antibodies to costimulatory molecules such as CTLA-4, 4-1BB and PD-1, or antibodies to cytokines (IL-1O or TGF-β).

Other anticancer agents also include those that block immune cell migration such as antagonists to chemokine receptors, including CCR2 and CCR4.

Other anticancer agents also include those that augment the immune system such as adjuvants or adoptive T cell transfer.

Anticancer vaccines include dendritic cells, synthetic peptides, DNA vaccines and recombinant viruses.

The pharmaceutical composition of the invention may optionally include at least one signal transduction inhibitor (STI). A "signal transduction inhibitor" is an agent that selectively inhibits one or more vital steps in signaling pathways, in the normal function of cancer cells, thereby leading to apoptosis. Suitable STIs include, but are not limited to: (i) bcr/abl kinase inhibitors such as, for example, STI 571 (GLEEVEC®); (ii) epidermal growth factor (EGF) receptor inhibitors such as, for example, kinase inhibitors (IRESSA®, SSI-774) and antibodies (Imclone: C225 [Goldstein et al., *Clin. Cancer Res.*, 1:1311-1318 (1995)], and Abgenix: ABX-EGF); (iii) her-2/neu receptor inhibitors such as farnesyl transferase inhibitors (FTI) such as, for example, L-744,832 (Kohl et al., *Nat. Med.*, 1(8):792-797 (1995)); (iv) inhibitors of Akt family kinases or the Akt pathway, such as, for example, rapamycin (see, for example, Sekulic et al., *Cancer Res.*, 60:3504-3513 (2000)); (v) cell cycle kinase inhibitors such as, for example, flavopiridol and UCN-01 (see, for example, Sausville, *Curr. Med. Chem. Anti-Canc. Agents*, 3:47-56 (2003)); and (vi) phosphatidyl inositol kinase inhibitors such as, for example, LY294002 (see, for example, Vlahos et al., *J. Biol. Chem.*, 269:5241-5248 (1994)). Alternatively, at least one STI and at least one IDO inhibitor may be in separate pharmaceutical compositions. In a specific embodiment of the present invention, at least one IDO inhibitor and at least one STI may be administered to the patient concurrently or sequentially. In other words, at least one IDO inhibitor may be administered first, at least one STI may be administered first, or at least one IDO inhibitor and at least one STI may be administered at the same time. Additionally, when more than one IDO inhibitor and/or STI is used, the compounds may be administered in any order.

The present invention further provides a pharmaceutical composition for the treatment of a chronic viral infection in a patient comprising at least one IDO inhibitor, optionally, at least one chemotherapeutic drug, and, optionally, at least one antiviral agent, in a pharmaceutically acceptable carrier. The pharmaceutical compositions may include at least one IDO inhibitor of the instant invention in addition to at least one established (known) IDO inhibitor. In a specific embodiment, at least one of the IDO inhibitors of the pharmaceutical composition is selected from the group consisting of compounds of formulas (I) and (II).

Also provided is a method for treating a chronic viral infection in a patient by administering an effective amount of the above pharmaceutical composition.

In a specific embodiment of the present invention, at least one IDO inhibitor and at least one chemotherapeutic agent may be administered to the patient concurrently or sequentially. In other words, at least one IDO inhibitor may be administered first, at least one chemotherapeutic agent may be administered first, or at least one IDO inhibitor and the at least one STI may be administered at the same time. Additionally, when more than one IDO inhibitor and/or chemotherapeutic agent is used, the compounds may be administered in any order. Similarly, any antiviral agent or STI may also be administered at any point in comparison to the administration of an IDO inhibitor.

Chronic viral infections that may be treated using the present combinatorial treatment include, but are not limited to, diseases caused by: hepatitis C virus (HCV), human papilloma virus (HPV), cytomegalovirus (CMV), herpes simplex virus (HSV), Epstein-Barr virus (EBV), varicella zoster virus, Coxsackie virus, human immunodeficiency virus (HIV). Notably, parasitic infections (e.g., malaria) may also be treated by the above methods wherein compounds known to treat the parasitic conditions are optionally added in place of the antiviral agents.

In yet another embodiment, the pharmaceutical compositions comprising at least one IDO inhibitor of the instant invention may be administered to a patient to prevent arterial restenosis, such as after balloon endoscopy or stent placement. In a particular embodiment, the pharmaceutical composition further comprises at least one taxane (e.g., paclitaxel (Taxol); see, e.g., Scheller et al., *Circulation*, 110:810-814 (2004)).

Suitable antiviral agents contemplated for use in combination with the compounds of the present invention can comprise nucleoside and nucleotide reverse transcriptase inhibitors (NRTIs), non-nucleoside reverse transcriptase inhibitors (NNRTIs), protease inhibitors and other antiviral drugs.

Examples of suitable NRTIs include zidovudine (AZT); didanosine (ddl); zalcitabine (ddC); stavudine (d4T); lamivudine (3TC); abacavir (1592U89); adefovir dipivoxil [bis(POM)-PMEA]; lobucavir (BMS-180194); BCH-I0652; emtricitabine [(−) FTC]; beta-L-FD4 (also called beta-L-D4C and named beta-L-2′,3′-dicleoxy-5-fluoro-cytidene); DAPD, ((−)-beta-D-2,6-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4 (1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfinavir (AG-1343); amprenavir (141W94); lasinavir (BMS-234475); DMP-450; BMS-2322623; ABT-378; and AG-1549. Other antiviral agents include hydroxyurea, ribavirin, IL-2, IL-12, pentafuside and Yissum Project No. 11607.

Combination with an Immuno-Oncology Agent

Further provided herein are methods of treatment wherein a compound of the present invention is administered with one or more immuno-oncology agents. The immuno-oncology agents used herein, also known as cancer immunotherapies, are effective to enhance, stimulate, and/or upregulate immune responses in a subject.

In one aspect, the Compound of the present invention is sequentially administered prior to administration of the immuno-oncology agent. In another aspect, the Compound of the present invention is administered concurrently with the immunology-oncology agent. In yet another aspect, the Compound of the present invention is sequentially administered after administration of the immuno-oncology agent.

In another aspect, the Compound of the present invention may be co-formulated with an immuno-oncology agent.

Immuno-oncology agents include, for example, a small molecule drug, antibody, or other biologic or small molecule. Examples of biologic immuno-oncology agents include, but are not limited to, cancer vaccines, antibodies, and cytokines. In one aspect, the antibody is a monoclonal antibody. In another aspect, the monoclonal antibody is humanized or human.

In one aspect, the immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses (often referred to as immune checkpoint regulators).

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α 1β2, FAS, FASL, RELT, DR6, TROY, NGFR.

In another aspect, the immuno-oncology agent is a cytokine that inhibits T cell activation (e.g., IL-6, IL-10, TGF-ß, VEGF, and other immunosuppressive cytokines) or a cytokine that stimulates T cell activation, for stimulating an immune response.

In one aspect, T cell responses can be stimulated by a combination of the Compound of the present invention and one or more of (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4, and (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

Other agents that can be combined with the Compound of the present invention for the treatment of cancer include antagonists of inhibitory receptors on NK cells or agonists of activating receptors on NK cells. For example, the Compound of the present invention can be combined with antagonists of KIR, such as lirilumab.

Yet other agents for combination therapies include agents that inhibit or deplete macrophages or monocytes, including but not limited to CSF-1R antagonists such as CSF-1R antagonist antibodies including RG7155 (WO 11/70024, WO 11/107553, WO 11/131407, WO 13/87699, WO 13/119716, WO 13/132044) or FPA-008 (WO 11/140249, WO 13/169264, WO 14/036357).

In another aspect, the Compound of the present invention can be used with one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell anergy or exhaustion) and agents that trigger innate immune activation and/or inflammation at tumor sites.

In one aspect, the immuno-oncology agent is a CTLA-4 antagonist, such as an antagonistic CTLA-4 antibody. Suitable CTLA-4 antibodies include, for example, YERVOY® (ipilimumab) or tremelimumab.

In another aspect, the immuno-oncology agent is a PD-1 antagonist, such as an antagonistic PD-1 antibody. Suitable PD-1 antibodies include, for example, OPDIVO® (nivolumab), KEYTRUDA® (pembrolizumab), or MEDI-0680 (AMP-514; WO 2012/145493). The immuno-oncology agent may also include pidilizumab (CT-011), though its specificity for PD-1 binding has been questioned. Another approach to target the PD-1 receptor is the recombinant protein composed of the extracellular domain of PD-L2 (B7-DC) fused to the Fc portion of IgG1, called AMP-224.

In another aspect, the immuno-oncology agent is a PD-L1 antagonist, such as an antagonistic PD-L1 antibody. Suitable PD-L1 antibodies include, for example, MPDL3280A (RG7446; WO 2010/077634), durvalumab (MEDI4736), BMS-936559 (WO 2007/005874), and MSB0010718C (WO 2013/79174).

In another aspect, the immuno-oncology agent is a LAG-3 antagonist, such as an antagonistic LAG-3 antibody. Suitable LAG3 antibodies include, for example, BMS-986016 (WO 10/19570, WO 14/08218), or IMP-731 or IMP-321 (WO 08/132601, WO 09/44273).

In another aspect, the immuno-oncology agent is a CD137 (4-1BB) agonist, such as an agonistic CD 137 antibody. Suitable CD137 antibodies include, for example, urelumab and PF-05082566 (WO 12/32433).

In another aspect, the immuno-oncology agent is a GITR agonist, such as an agonistic GITR antibody. Suitable GITR antibodies include, for example, BMS-986153, BMS-986156, TRX-518 (WO 06/105021, WO 09/009116) and MK-4166 (WO 11/028683).

In another aspect, the immuno-oncology agent is an IDO antagonist. Suitable IDO antagonists include, for example, INCB-024360 (WO 2006/122150, WO 07/75598, WO 08/36653, WO 08/36642), indoximod, or NLG-919 (WO 09/73620, WO 09/1156652, WO 11/56652, WO 12/142237).

In another aspect, the immuno-oncology agent is an OX40 agonist, such as an agonistic OX40 antibody. Suitable OX40 antibodies include, for example, MEDI-6383 or MEDI-6469.

In another aspect, the immuno-oncology agent is an OX40L antagonist, such as an antagonistic OX40 antibody. Suitable OX40L antagonists include, for example, RG-7888 (WO 06/029879).

In another aspect, the immuno-oncology agent is a CD40 agonist, such as an agonistic CD40 antibody. In yet another embodiment, the immuno-oncology agent is a CD40 antagonist, such as an antagonistic CD40 antibody. Suitable CD40 antibodies include, for example, lucatumumab or dacetuzumab.

In another aspect, the immuno-oncology agent is a CD27 agonist, such as an agonistic CD27 antibody. Suitable CD27 antibodies include, for example, varlilumab.

In another aspect, the immuno-oncology agent is MGA271 (to B7H3) (WO 11/109400).

The present invention also includes pharmaceutical kits useful, for example, in the treatment or prevention of IDO-associated diseases or disorders, obesity, diabetes and other diseases referred to herein which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, as will be readily apparent to those skilled in the art. Instructions, either as inserts or as labels, indicating quantities of the components to be administered, guidelines for administration, and/or guidelines for mixing the components, can also be included in the kit.

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

Pharmaceutical Compositions and Dosing

The invention also provides pharmaceutically acceptable compositions which comprise a therapeutically effective amount of one or more of the compounds of the present invention, formulated together with one or more pharmaceutically acceptable carriers (additives) and/or diluents, and optionally, one or more additional therapeutic agents described above.

The compounds of this invention can be administered for any of the uses described herein by any suitable means, for example, orally, such as tablets, capsules (each of which includes sustained release or timed release formulations), pills, powders, granules, elixirs, tinctures, suspensions (including nanosuspensions, micro suspensions, spray-dried dispersions), syrups, and emulsions; sublingually; buccally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted.

Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, Jr., L. V. et al., *Remington: The Science and Practice of Pharmacy* (2 Volumes), 22nd Edition, Pharmaceutical Press (2012).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.001 to about 5000 mg per day, preferably between about 0.01 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more other therapeutic agent(s), e.g., an anticancer agent or other pharmaceutically active material.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient will range from about 0.01 to about 50 mg per kilogram of body weight per day.

If desired, the effective daily dose of the active compound may be administered as two, three, four, five, six or more sub-doses administered separately at appropriate intervals throughout the day, optionally, in unit dosage forms. In certain aspects of the invention, dosing is one administration per day.

While it is possible for a compound of the present invention to be administered alone, it is preferable to administer the compound as a pharmaceutical formulation (composition).

Definitions

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

For purposes of clarity and in accordance with standard convention in the art, the symbol

is used in formulas and tables to show the bond that is the point of attachment of the moiety or substituent to the core/nucleus of the structure.

Additionally, for purposes of clarity, where a substituent has a dash (–) that is not between two letters or symbols; this is used to indicate a point of attachment for a substituent. For example, —OCH$_3$ is attached through the oxygen atom.

Additionally, for purposes of clarity, when there is no substituent shown at the end of a solid line, this indicates that there is a methyl (CH$_3$) group connected to the bond.

As used herein, the terms "alkyl" and "alkylene" (also referred to as "alk") are intended to include both branched and straight-chain saturated aliphatic hydrocarbon groups having the specified number of carbon atoms. For example, "C$_1$-C$_6$ alkyl" or "C$_{1-6}$ alkyl" denotes alkyl having 1 to 6 carbon atoms. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). "C$_1$-C$_6$" alkylene" denotes alkylene having 1 to 6 carbon atoms. Example alkylene groups include, but are not limited to, methylene (—CH$_2$—), ethylene (—CH$_2$CH$_2$—), and the like.

The term "alkoxy" or "alkyloxy" refers to an —O-alkyl group. For example, "C$_1$ to C$_6$ alkoxy" or "C$_{1-6}$ alkoxy" (or alkyloxy), is intended to include C$_1$, C$_2$, C$_3$, C$_4$, C$_5$, and C$_6$ alkoxy groups. Example alkoxy groups include, but are not limited to, methoxy, ethoxy, propoxy (e.g., n-propoxy and isopropoxy), and t-butoxy.

As used herein, "aryl" refers to an aromatic ring system which includes, but not limited to phenyl, biphenyl, indanyl, 1-naphthyl, 2-naphthyl and terahydronaphthyl.

"Halo" or "halogen" includes fluoro, chloro, bromo, and iodo.

"Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "C$_{1-6}$ haloalkoxy", is intended to include C$_1$, C$_2$, C$_3$, C$_4$, C$_5$, and C$_6$ haloalkoxy groups. Examples of haloalkoxy include, but are not limited to, trifluoromethoxy, 2,2,2-trifluoroethoxy, and pentafluorothoxy.

The term "cycloalkyl" refers to hydrocarbon rings having the indicated number of ring atoms (e.g., C$_{3-10}$ cycloalkyl) and being fully saturated or having no more than one double bond between ring vertices. "Cycloalkyl" is also meant to refer to bicyclic and polycyclic hydrocarbon rings such as, for example, bicyclo[2.2.1]heptane, bicyclo[2.2.2]octane, adamantane, etc.

The term "cycloheteroalkyl" refers to a cycloalkyl ring having the indicated number of ring vertices (or members) and having from one to five heteroatoms selected from N, O, and S, which replace one to five of the carbon vertices, and wherein the nitrogen and sulfur atoms are optionally oxidized, and the nitrogen atom(s) are optionally quaternized. The cycloheteroalkyl may be a monocyclic, a bicyclic or a polycyclic ring system. Non limiting examples of cycloheteroalkyl groups include pyrrolidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrhydrothiophene, quinuclidine, and the like. A cycloheteroalkyl group can be attached to the remainder of the molecule through a ring carbon or a heteroatom.

As used herein, "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, 1,2,4-thiadiazolyl, isothiazolyl, purinyl, carbazolyl, indazolyl, quinolyl, isoquinolyl, benzimidazolyl, imidazopyridinyl, indolinyl, benzodioxolanyl and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and S(O)$_p$, wherein p is 0, 1 or 2).

As referred to herein, the term "substituted" means that at least one hydrogen atom is replaced with a non-hydrogen group, provided that normal valencies are maintained and that the substitution results in a stable compound.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Allen, Jr., L. V., ed., *Remington: The Science and Practice of Pharmacy*, 22nd Edition, Pharmaceutical Press, London, UK (2012).

In addition, compounds of the present invention may have prodrug forms. Any compound that will be converted in vivo to provide the bioactive agent (i.e., a compound of formula (I)) is a prodrug within the scope and spirit of the invention. Various forms of prodrugs are well known in the art. For examples of such prodrug derivatives, see:
a) Bundgaard, H., ed., *Design of Prodrugs*, Elsevier (1985), and Widder, K. et al., eds., *Methods in Enzymology*, 112:309-396, Academic Press (1985);
b) Bundgaard, H., Chapter 5: "Design and Application of Prodrugs", *A Textbook of Drug Design and Development*, pp. 113-191, Krogsgaard-Larsen, P. et al., eds., Harwood Academic Publishers (1991);
c) Bundgaard, H., *Adv. Drug Deliv. Rev.*, 8:1-38 (1992);
d) Nielsen, N. M. et al., *J. Pharm. Sci.*, 77:285 (1988);
e) Kakeya, N. et al., *Chem. Pharm. Bull.*, 32:692 (1984); and
f) Rautio, J., ed., *Prodrugs and Targeted Delivery (Methods and Principles in Medicinal Chemistry)*, Vol. 47, Wiley-VCH (2011).

Compounds containing a carboxy group can form physiologically hydrolyzable esters that serve as prodrugs by being hydrolyzed in the body to yield formula (I) compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of the present invention include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well-known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (Second Edition, reproduced, 2006); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, Third Edition, Academic Press, San Diego, CA (2008).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The term "solvate" means a physical association of a compound of this invention with one or more solvent molecules, whether organic or inorganic. This physical association includes hydrogen bonding. In certain instances the solvate will be capable of isolation, for example, when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

As used herein, the term "patient" refers to organisms to be treated by the methods of the present invention. Such organisms preferably include, but are not limited to, mammals (e.g., murines, simians, equines, bovines, porcines, canines, felines, and the like), and most preferably refers to humans.

As used herein, the term "effective amount" means that amount of a drug or pharmaceutical agent, i.e., a compound of the invention, that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. An effective amount can be administered in one or more administrations, applications or dosages and is not intended to be limited to a particular formulation or administration route. The term also includes within its scope amounts effective to enhance normal physiological function As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

Methods of Preparation

The compounds of the present invention may be prepared by methods such as those illustrated in the following Schemes utilizing chemical transformations known to those skilled in the art. Solvents, temperatures, pressures, and other reaction conditions may readily be selected by one of ordinary skill in the art. Starting materials are commercially available or readily prepared by one of ordinary skill in the art. These Schemes are illustrative and are not meant to limit the possible techniques one skilled in the art may use to manufacture compounds disclosed herein. Different methods may be evident to those skilled in the art. Additionally, the various steps in the synthesis may be performed in an alternate sequence or order to give the desired compound(s). Further, the representation of The reactions in these Schemes as discrete steps does not preclude their being performed in tandem, either by telescoping multiple steps in the same reaction vessel or by performing multiple steps without purifying or characterizing the intermediate(s). In addition, many of the compounds prepared by the methods below can be further modified using conventional chemistry well known to those skilled in the art.

Reference can also be made to International Publication Nos. WO2016/073738, WO2016/073770, and WO2016/073774.

References to many of these chemical transformations employed herein can be found in Smith, M. B. et al., *March's Advanced Organic Chemistry Reactions, Mechanisms, and Structure*, Fifth Edition, Wiley-Interscience, New York (2001), or other standard texts on the topic of synthetic organic chemistry. Certain transformations may require that reactive functional groups be masked by protecting group(s). A convenient reference which provides conditions for introduction, removal, and relative susceptibility to reaction conditions of these groups is Greene, T. W. et al., *Protective Groups in Organic Synthesis*, Third Edition, Wiley-Interscience, New York (1999).

Scheme 1 depicts one potential preparation of compounds of the invention. A dihalo heteroaromatic compound of general structure i can be treated with a dialkyl amine ii in the presence of a base, such as Hunig's base, with or without the addition of heat to provide a compound of general structure iii. The halide of general structure iii can be coupled to a boronic ester of general structure iv by utilizing standard Suzuki coupling conditions, well-known to one skilled in the art, to give a compound of general structure v. An amine of general structure vi can be prepared by treating a compound of general structure v under reducing conditions, such as Pd on carbon under an atmosphere of hydrogen gas. The amine vi can then be acylated under a variety of conditions well-known to one skilled in the art including but not limited to an isocyanate of general structure vii or a carboxylic acid of general structure viii to afford the corresponding urea and amide, respectively, which are compounds of Formula (I).

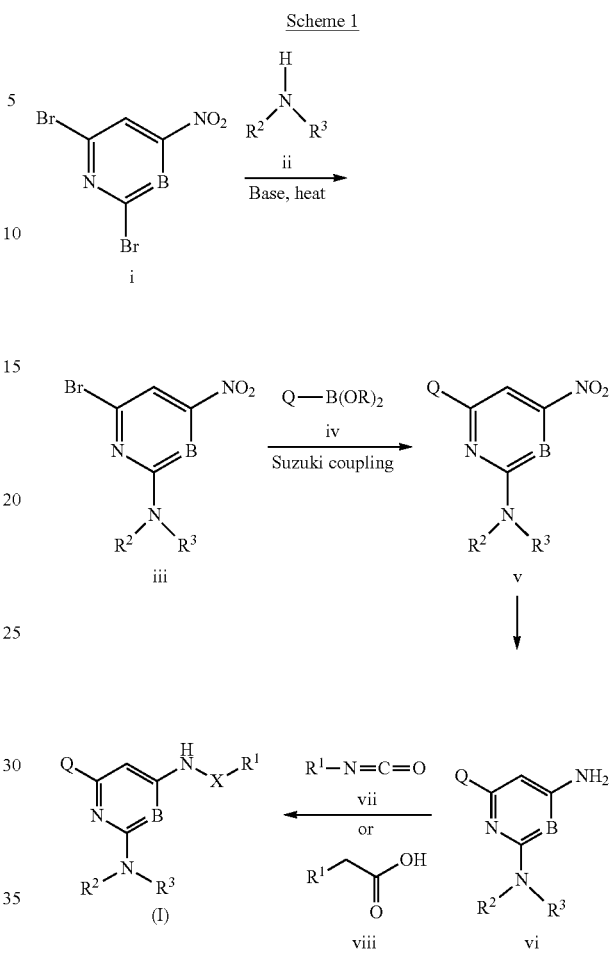

In another embodiment, compounds of general structure ix can be treated with an amine ii to afford the diamine of general structure x (Scheme 2). Treatment of the diamine x with an isocyanate vii will afford the urea of general structure xi. Coupling of the aryl chloride xi with a boronic ester iv under standard Suzuki coupling conditions will give a compound of Formula (I).

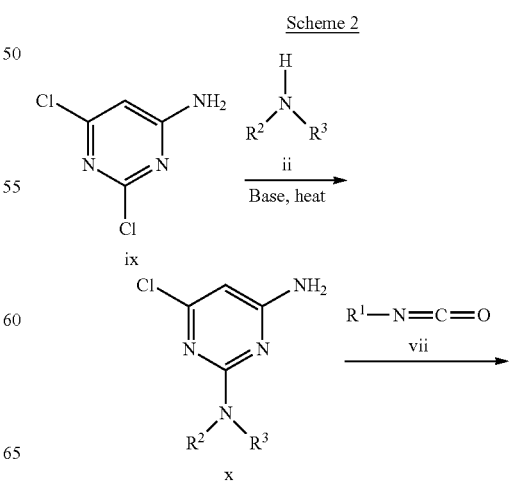

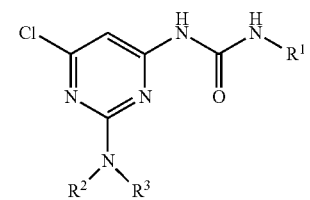

xi

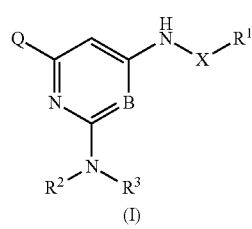

Q—B(OR)₂ iv

Suzuki coupling

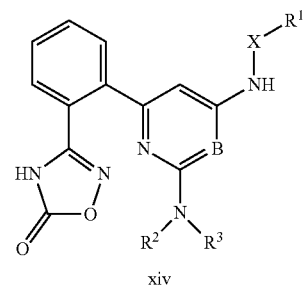

(I)

Scheme 3 depicts another embodiment where a compound of general structure xi can be treated with a boronic ester of general structure xii under standard Suzuki coupling conditions to afford a compound of general structure xiii. The nitrile in compound xiii can be treated sequentially with hydroxyamine hydrochloride and carbonyldiimidazole (CDI) to afford an oxadiazolone of general structure xiv, which is a compound of the invention.

Scheme 3

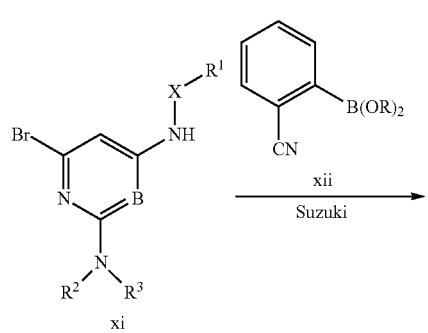

xi xii

Suzuki

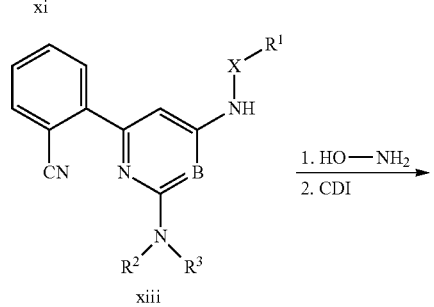

1. HO—NH₂
2. CDI xiii

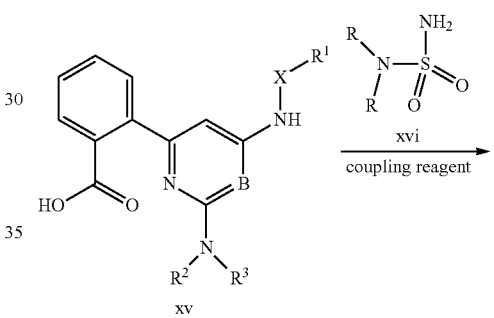

xiv

As shown in Scheme 4, a carboxylic acid of general structure xv can be treated with a substituted sulfamide of general structure xvi in the presence of a coupling reagent such as TBTU and an organic base such as TEA to afford a compound of general structure xvii, which is also a compound of the invention.

Scheme 4

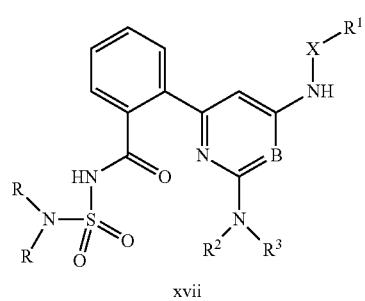

xvii

In another embodiment shown in Scheme 5, amines of general structure vi can undergo a palladium catalyzed coupling to both aryl and heteroaryl halides xviii to afford N-arylated compounds of general structure xix, which is a compound of the invention. Coupling can be accomplished by utilizing conditions established by Buchwald and Hartwig (i.e., Pd₂(dba)₃, Xantphos and base) that are well-known to one skilled in the art (Surry, D. S. et al., *Chem. Sci.*, 2:27-50 (2011)).

Scheme 5

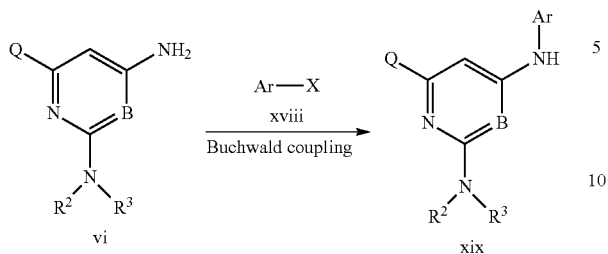

In another embodiment, aryl halides of general structure xx can be converted to a boronic ester of general structure xxi by utilizing the standard conditions developed by Miyaura (T. Ishiyama, M. Murata, N. Miyaura, *J. Org. Chem.*, 1995, 60, 7508-7510.) such as a Pd catalyst such as Pd(PPh$_3$)$_4$ or 1,1'-bis(diphenylphosphino)ferrocenedichloro palladium(II) and diborane. Rhodium catalyzed 1,4-conjugate addition of the boronic ester xxi to an unsaturated ester xxii is a well-known transformation (Zou, G. et al., *Dalton Trans.*, 28:3055 (2007)) and can be accomplished using a rhodium[1] catalyst, for example, [Rh(COD)Cl]$_2$ in the presence of a strong base such as NaOH to afford saturated esters of the general structure xxiii. Hydrolysis of the ester in xxiii by treatment with a strong base, such as LiOH, will afford the corresponding carboxylic acid xxiv, which is a compound of the invention.

Scheme 6

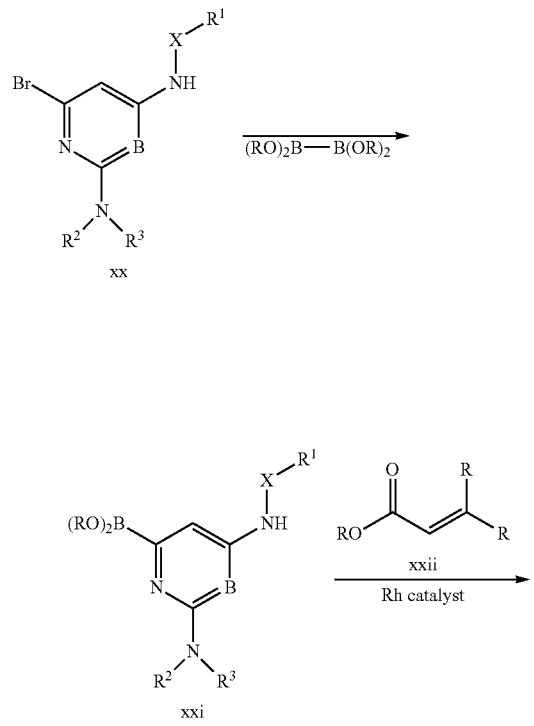

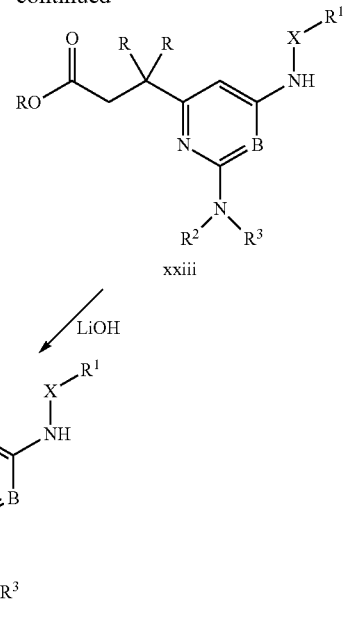

EXAMPLES

The following Examples are put forth so as to provide those of ordinary skill in the art with a complete disclosure and description of how to make and use the present invention, and are not intended to limit the scope of what the inventors regard as their invention, nor are they intended to represent that the experiments below were performed or that they are all of the experiments that may be performed. It is to be understood that exemplary descriptions written in the present tense were not necessarily performed, but rather that the descriptions can be performed to generate data and the like of a nature described therein. Efforts have been made to ensure accuracy with respect to numbers used (e.g., amounts, temperature, etc.), but some experimental errors and deviations should be accounted for.

Unless indicated otherwise, parts are parts by weight, molecular weight is weight average molecular weight, temperature is in degrees Celsius (° C.), and pressure is at or near atmospheric. Standard abbreviations are used, including the following: 1×=once; 2×=twice; 3×=thrice; rt or RT=room temperature; T$_r$=retention time; wt=wildtype; bp=base pair(s); kb=kilobase(s); nt=nucleotides(s); as =amino acid(s); s or sec=second(s); min=minute(s); h or hr=hour(s); ng=nanogram; μg=microgram; mg=milligram; g=gram; kg=kilogram; dl or dL=deciliter; μl or μL=microliter; ml or mL=milliliter; l or L=liter; μM=micromolar; mM=millimolar; M=molar; kDa=kilodalton; i.m.=intramuscular(ly); i.p.=intraperitoneal (ly); SC or SQ=subcutaneous(ly); QD=daily; BID=twice daily; QW=weekly; QM=monthly; BW=body weight; U=unit; ns=not statistically significant; PBS=phosphate-buffered saline; IHC=immunohistochemistry; DMEM=Dulbecco's Modification of Eagle's Medium; LG=leaving group; conc.=concentrate or concentrated; aq=aqueous; sat or sat'd=saturated; MW=molecular weight; mp=melting point; MS or Mass Spec=mass spectrometry; ESI=electrospray ionization mass spectroscopy; HR=high resolution; HRMS=high resolution mass spectrometry;

LCMS liquid chromatography mass spectrometry; HPLC=high performance liquid chromatography; RP HPLC=reverse phase HPLC; SFC=Supercritical Fluid Chromatography; TLC or tlc=thin layer chromatography; NMR=nuclear magnetic resonance spectroscopy; "$^1$H" for proton, "δ" for delta, "s" for singlet, "d" for doublet, "t" for triplet, "q" for quartet, "m" for multiplet, "br" for broad, "Hz" for hertz; and "α", "β", "R", "S", "E", and "Z" are stereochemical designations familiar to one skilled in the art.

Me methyl
Et ethyl
Pr propyl
i-Pr isopropyl
Bu butyl
i-Bu isobutyl
t-Bu tert-butyl
Ph phenyl
Bn benzyl
Hex hexanes
MeOH methanol
EtOH ethanol
i-PrOH or IPA isopropanol
AcOH or HOAc acetic acid
BINAP 1,1'-binaphthyl-2,2'-diamine
BOP (benzotriazol-1-yloxy)tris(dimethylamino)phosphonium hexafluorophosphate
CDCl$_3$ deutero-chloroform
CHCl$_3$ chloroform
cDNA complimentary DNA
DBU 2,3,4,6,7,8,9,10-Octahydropyrimidol[1,2-a]azepine
DCE 1,2-cichloroethane
DCM dichloromethane
DIPEA N,N-diisopropylethyl amine
DMAP dimethylaminopyridine
DMF dimethyl formamide
DMSO dimethyl sulfoxide
DIAD Diisopropyl azodicarboxylate
EDTA ethylenediaminetetraacetic acid
EtOAc ethyl acetate
Et$_2$O diethyl ether
AlCl$_3$ aluminum chloride
Boc tert-butyloxycarbonyl
CH$_2$Cl$_2$ dichloromethane
CH$_3$CN or ACN acetonitrile
Cs$_2$CO$_3$ cesium carbonate
CDI carbonyldiimidazole
HCl hydrochloric acid
H$_2$SO$_4$ sulfuric acid
Hunig's base diisopropylethylamine
K$_2$CO$_3$ potassium carbonate
KOAc potassium acetate
mCPBA or m-CPBA meta-chloroperbenzoic acid
Pd/C palladium on carbon
PS polystyrene
SiO$_2$ silica oxide
SnCl$_2$ tin(II) chloride
TBTU 2-(1H-benzotriazole-1-yl)-1,1,3,3-tetramethylaminium tetrafluoroborate
TEA triethylamine
TFA trifluoroacetic acid
TFAA trifluoroacetic anhydride
THF tetrahydrofuran
TMSCHN$_2$ trimethyl silyldiazomethane
LHMDS Lithium hexamethyldisilazide
MTBE MethyltertButyl ether
MgSO$_4$ magnesium sulfate
NMP N-Methylpyrrolidone
MsOH or MSA methylsulfonic acid
NaCl sodium chloride
NaH sodium hydride
NaHCO$_3$ sodium bicarbonate
NaOH sodium hydroxide
Na$_2$SO$_3$ sodium sulfite
Na$_2$SO$_4$ sodium sulfate
NH$_3$ ammonia
NH$_4$Cl ammonium chloride
NH$_4$OH ammonium hydroxide
XantPhos 4,5-bis(diphenylphosphino)-9,9-dimethylxanthene HPLC/MS and Preparatory/Analytical HPLC Methods Employed in Characterization or Purification of Examples Analytical HPLC/MS was performed using the following methods:

Method N: Kinetex XB-C18 (75×3) mm, 2.6 μm; Mobile Phase A: 10 mM NH$_4$OAc in Water: Acetonitrile (98:02); Mobile Phase B: 10 mM NH$_4$OAc in Water: Acetonitrile (02:98); Gradient: 20-100% B over 4 minutes, flow rate 1 mL/min, then a 0.6 minute hold at 100% B flow rate 1.5 mL/min; then Gradient: 100-20% B over 0.1 minutes, flow rate 1.5 mL/min.

Method O: Column: Ascentis Express C18 (50×2.1) mm, 2.7 μm; flow rate 1.1 mL/min; gradient time 3 min; Temperature: 50° C., 0% Solvent B to 100% Solvent B; monitoring at 220 nm (Solvent A: 95% Water: 5% Acetonitrile; 10 mM NH$_4$OAc; Solvent B: 5% Water: 95% Acetonitrile; 10 mM NH$_4$OAc).

Method P: Column: Ascentis Express C18 (50×4.6) mm, 2.7 μm, flow rate 4 mL/min; gradient: 0 to 100% solvent B over 4 min; Temperature: 50° C. Monitoring at 220 nm (Solvent A: 95:05 water: CH$_3$CN with 10 mM NH$_4$OAc and Solvent B: 05:95 water: CH$_3$CN with 10 mM NH$_4$OAc)

Method Q: Column: Ascentis Express C18 (50×4.6) mm, 2.7 μm, flow rate 4 mL/min; gradient: 0 to 100% solvent B over 4 min; Temperature: 50° C.; monitoring at 220 nm (Solvent A: 95:05 water: CH$_3$CN with 0.1% TFA and Solvent B: 05:95 water: CH$_3$CN with 0.1% TFA)

Method R: Column: Ascentis Express C18 (50×2.1) mm, 2.7 μm, flow rate 1.1 mL/min; gradient: 0 to 100% solvent B over 3 min; Temperature: 50° C.; monitoring at 220 nm (Solvent A: 95:05 water: CH$_3$CN with 0.1% TFA and Solvent B: 05:95 water: CH$_3$CN with 0.1% TFA)

Method S: Column: Chiralpak ASH (250×4.6) mm, 5.0 μm; Isocratic Mode, CO$_2$: Co-Solvent (85:15), Co-Solvent: 0.2% DEA in Methanol; Co-Solvent percentage: 15%, Column Temperature: 22.1° C.; Back Pressure: 100 bars; Total Flow: 3 g/min; CO$_2$ flow: 2.55 g/min; Co-Solvent flow: 0.45 g/min.

Method T: Column: Acquity BEH C18 (2.1×50 mm) 1.7 um; Mobile phase A: Buffer:ACN (95:5); Mobile phase B: Buffer:ACN (5:95), Buffer: 5 mM Ammonium Acetate; Gradient: 20-90% B over 1.1 minutes, then a 0.6 minute hold at 90% B, flow rate 0.5 mL/min.

Method U: Column: Kinetex XB-C18 (75×3) mm, 2.6 μm; Mobile Phase A: 10 mM NH$_4$COOH in Water: Acetonitrile (98:02; Mobile Phase B: 10 mM NH$_4$COOH in Water: Acetonitrile (02:98); Gradient: 20-100% B over 4 minutes, flow rate 1 mL/min, then a 0.6 minute hold at 100% B flow rate 1.5 mL/min; then Gradient: 100-20% B over 0.1 minutes, flow rate 1.5 mL/min.

Method V: Column: Chiralpak ASH (250×4.6) mm, 5.0 μm; Isocratic Mode, Co-Solvent: 0.2% DEA in Methanol; Co-Solvent percentage: 20%, Column Temperature: 20.2° C.; Back Pressure: 100 bars; Total Flow: 3 g/min; CO$_2$ flow: 2.4 g/min; Co-Solvent flow: 0.6 g/min.

Method W: Column: Chiralpak ASH (250×4.6) mm, 5.0 µm; Isocratic Mode, Co-Solvent: 0.2% DEA in Methanol; Co-Solvent percentage: 30%, Column Temperature: 20.2° C.; Back Pressure: 100 bars; Total Flow: 3 g/min; $CO_2$ flow: 2.1 g/min; Co-Solvent flow: 0.9 g/min.

Method X: Column: Chiralpak ASH (250×4.6) mm, 5.0 µm; Isocratic Mode, Co-Solvent: 0.2% DEA in Methanol; Co-Solvent percentage: 25%, Column Temperature: 24.3° C.; Back Pressure: 100 bars; Total Flow: 3 g/min; $CO_2$ flow: 2.5 g/min; Co-Solvent flow: 0.75 g/min.

Method Y: Column: Chiralpak ASH (250×4.6) mm, 5.0 µm; Isocratic Mode, Co-Solvent: 0.2% DEA in Methanol; Co-Solvent percentage: 25%, Column Temperature: 27.1° C.; Back Pressure: 100 bars; Total Flow: 3 g/min; $CO_2$ flow: 2.25 g/min; Co-Solvent flow: 0.75 g/min.

Method Z: Column: Chiralcel-OJH (250×4.6) mm, 5.0 µm; Isocratic Mode, Co-Solvent: 0.2% DEA in Methanol; Co-Solvent percentage: 30%, Column Temperature: 26° C.; Back Pressure: 100 bars; Total Flow: 3 g/min; $CO_2$ flow: 2.1 g/min; Co-Solvent flow: 0.9 g/min.

Method AA: Column: Acquity BEH C18 (2.1×50 mm) 1.7 um; Mobile phase A: 0.1% TFA in water; Mobile phase B: Acetonitrile; Gradient: 2-98% B over 1 minutes, then a 0.6 minute hold at 98% B.

Method AB: Column: Lux Cellulose-4 (250×4.6) mm, 5.0 µm; Isocratic Mode, Co-Solvent: 0.2% DEA in Methanol; Co-Solvent percentage: 30%, Column Temperature: 24.2° C.; Back Pressure: 100 bars; Total Flow: 3 g/min; $CO_2$ flow: 2.1 g/min; Co-Solvent flow: 0.9 g/min.

Method AC: Column: Chiralcel-ASH (250×4.6) mm, 5.0 µm; Isocratic Mode, Co-Solvent: 0.2% DEA in Methanol; Co-Solvent percentage: 30%, Column Temperature: 26° C.; Back Pressure: 100 bars; Total Flow: 3 g/min; $CO_2$ flow: 2.1 g/min; Co-Solvent flow: 0.9 g/min Method AD: Kinetex XB-C18 (75×3) mm, 2.6 µm; Mobile Phase A: 0.1% HCOOH in Water: Mobile Phase B: 100% Acetonitrile Gradient: 20-100% B over 4 minutes, flow rate 1 mL/min, then a 0.6 minute hold at 100% B flow rate 1.5 mL/min; flow rate 1.5 mL/min.

Method AE: Column: HP-5MS (Part Number: Agilent 19091S-433); (250×30) mm; 0.25 µm; Injection volume 3 µl, runtime 17 min (GCMS).

Method AF: Column: Chiralpak AD-H (250×4.6) mm, 5.0 µm; Isocratic Mode, Co-Solvent: 0.25% DEA in Methanol; Co-Solvent percentage: 30%, Column Temperature: 25° C.; Back Pressure: 100 bars; Total Flow: 3 g/min; $CO_2$ flow: 2.1 g/min; Co-Solvent flow: 0.9 g/min.

Method AG: Column: Chiralcel-ASH (250×21) mm, 5.0 µm; Isocratic Mode, Co-Solvent: 0.25% DEA in Methanol; Co-Solvent percentage: 45%, Column Temperature: 25° C.; Back Pressure: 100 bars; Total Flow: 75 g/min.

Method AH: Column: Chiralcel-ASH (250×4.6) mm, 5.0 µm; Isocratic Mode, Co-Solvent: 0.2% DEA in Methanol; Co-Solvent percentage: 40%, Column Temperature: 25° C.; Back Pressure: 100 bars; Total Flow: 4 g/min.

Method AI: Column: Chiralcel-ASH (250×4.6) mm, 5.0 µm; Isocratic Mode, Co-Solvent: 0.2% DEA in Methanol; Co-Solvent percentage: 30%, Column Temperature: 24.7° C.; Back Pressure: 95 bars; Total Flow: 4 g/min; $CO_2$ flow: 2.4 g/min; Co-Solvent flow: 1.6 g/min.

Method AJ: Column: Chiralpak AD-H (250×30) mm, 5.0 µm; Isocratic Mode, Co-Solvent: 0.25% DEA in Methanol; Co-Solvent percentage: 30%, Column Temperature: 25° C.; Back Pressure: 100 bars; Total Flow: 120 g/min Method AK: Column: Chiralpak AD-H (250×4.6) mm, 5.0 µm; Isocratic Mode, Co-Solvent: 0.25% DEA in Methanol; Co-Solvent percentage: 40%, Column Temperature: 25° C.; Back Pressure: 100 bars; Total Flow: 4 g/min; $CO_2$ flow: 2.4 g/min; Co-Solvent flow: 1.6 g/min.

Method AM: Column: Chiralpak IA (250×4.6) mm, 5.0 µm; Isocratic Mode, Co-Solvent: 0.2% DEA in Methanol; Co-Solvent percentage: 30%, Column Temperature: 21° C.; Back Pressure: 100 bars; Total Flow: 3 g/min; $CO_2$ flow: 2.1 g/min; Co-Solvent flow: 0.9 g/min.

Method AN: Column: Chiralpak IA (250×4.6) mm, 5.0 µm; Isocratic Mode, Co-Solvent: 0.2% DEA in Methanol; Co-Solvent percentage: 20%, Column Temperature: 21° C.; Back Pressure: 100 bars; Total Flow: 3 g/min; $CO_2$ flow: 2.4 g/min; Co-Solvent flow: 0.6 g/min.

Method AU: Column: Xbridge C18 (50×3.0) mm, 1.7 µm; flow rate 1.0 mL/min; gradient time 0 min 0% Solvent B to 2 min 100% Solvent B, then a 1.0 minute hold at 100% B, monitoring at 220 nm (Solvent A: 10 mM 98% Ammonium formate, 2% Acetonitrile Solvent B: 10 mM 2% Ammonium formate, 98% Acetonitrile).

Method AV: Column: Acquity BEH C8 (2.1×50 mm) 1.7 um; Mobile phase A: Buffer:ACN (95:5); Mobile phase B: Buffer:ACN (5:95), Buffer: 5 mM Ammonium Acetate; Gradient: 20-90% B over 1.1 minutes, then a 0.6 minute hold at 90% B, flow rate 0.5 mL/min.

Method AQ: Column: Chiralpak OD-H (250×4.6) mm, 5.0 µm, Co-Solvent: 0.2% DEA in Methanol; Co-Solvent percentage: 40%, Column Temperature: 30° C.; Back Pressure: 100 bars; Total Flow: 3 g/min; Method AR: Column: Lux Cellulose-2 (250×4.6) mm, 5.0 µm; Isocratic Mode, Co-Solvent: 0.2% DEA in Methanol; Co-Solvent percentage: 10%, Column Temperature: 30° C.; Back Pressure: 100 bars; Total Flow: 3 g/min.

Method AS: Column: Whelk-01(R,R) (4.6×250)mm, 5 u; Co-Solvent: 0.2% DEA in IPA; Co-Solvent percentage: 15%, Column Temperature: 20.6° C.; Back Pressure: 100 bars; Total Flow: 3 g/min.

Method AT: Column: Acentis Express C18 (50×2.1) mm, 1.7 µm; flow rate 1.0 mL/min; gradient time 0 min 20% Solvent B to 4 min 100% Solvent B, then a 0.6 minute hold at 100% B, monitoring at 220 nm (Solvent A: 10 mM 98% Ammonium formate, 2% Acetonitrile; Solvent B: 10 mM 2% Ammonium formate, 98% Acetonitrile).

Method AU: Column: Waters XBridge C18, 19×150 mm, 5-µm particles; Mobile Phase A: 10-mM ammonium acetate; Mobile Phase B: acetonitrile; gradient: 5-45% B over 25 minutes, then a 5-minute hold at 100% B; Flow: 15 mL/min.

Method AV: Column: Lux Cellulose-2 (250×4.6) mm, 5.0 µm; Isocratic Mode, Co-Solvent: 25% (0.2% DEA in Methanol; Co-Solvent percentage: 75%, Column Temperature: 30° C.; Back Pressure: 100 bars; Total Flow: 3 g/min; $CO_2$ flow: 2.1 g/min; Co-Solvent flow: 0.9 g/min.

Method AV: Column: Chiralpak IC (250×4.6) mm, 5.0 µm; Isocratic Mode, Co-Solvent: 0.25% DEA in Ethanol; Co-Solvent percentage: 30%, Column Temperature: 30° C.; Back Pressure: 100 bars; Total Flow: 3 g/min; $CO_2$ flow: 2.1 g/min; Co-Solvent flow: 0.9 g/min.

Method AW: Column: YMC Amylose SA (250×4.6) mm, 5.0 µm; Isocratic Mode, Co-Solvent: (0.2% DEA in Ethanol; Co-Solvent percentage: 20%, Column Temperature: 30° C.; Back Pressure: 100 bars; Total Flow: 3 g/min; $CO_2$ flow: 2.1 g/min; Co-Solvent flow: 0.9 g/min.

Method AX: Column: Luna C18 4.6×30 mm 3u, 5 µm, Flow rate: 4.0 mL/min, Mobile Phase: A: 90/10 water-MeOH, 0.05% TFA; B: 10/90 water-MeOH, 0.05% TFA. Gradient: 0 to 100% B over 5 min.

Method AY: Column: Luna C18 4.6×30 mm 3u, 5 µm, Flow rate: 4.0 mL/min, Mobile Phase: A: 90/10 water-MeOH, 0.05% TFA; B: 10/90 water-MeOH, 0.05% TFA. Gradient: 0 to 100% B over 5 min.

Method AZ: Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min; Detection: UV at 220 nm.

Method AAA: Column: Waters Acquity UPLC BEH C18, 2.1×50 mm, 1.7-µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.11 mL/min; Detection: UV at 220 nm.

Method AAB: Waters Acquity SDS using the following method: Linear Gradient of 2% to 98% solvent B over 1.7 min; UV visualization at 220 nm; Column: BEH C18 2.1 mm×50 mm; 1.7 um particle (Heated to Temp. 50° C.); Flow rate: 0.8 ml/min; Mobile phase A: 100% Water, 0.05% TFA; Mobile phase B: 100% Acetonitrile, 0.05% TFA.

Example 1

N-(2-(2-(1H-tetrazol-5-yl)phenyl)-6-(benzyl(ethyl) amino) pyridin-4-yl)-2-(p-tolyl)acetamide

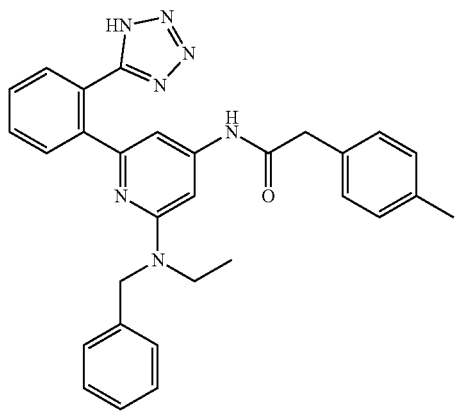 [SMILES: CCN(Cc1ccccc1)c1cc(NC(=O)Cc2ccc(C)cc2)cc(-c2ccccc2-c2nnn[nH]2)n1]

1A.
N-benzyl-6-bromo-N-ethyl-4-nitropyridin-2-amine

A solution of 2,6-dibromo-4-nitropyridine (5.0 g, 17.74 mmol) in dioxane (100 mL) was treated with DIPEA (6.20 mL, 35.5 mmol), N-benzylethanamine, HCl (3.65 g, 21.28 mmol) and heated to 100° C. in a sealed tube for 18 h. LC-MS indicated completion. The dioxane was concentrated in vacuum, and the residue partitioned between 1N HCl (150 mL) and ethyl acetate (300 mL). The organic layer was separated, dried over $Na_2SO_4$ and concentrated in vacuo. Purification via flash chromatography gave 1A (yellow liquid, 5.0 g, 14.87 mmol, 84% yield). $^1$H NMR (300 MHz, CHLOROFORM-d) δ 8.19 (s, 1H), 7.23-7.37 (m, 5H), 7.06 (d, J=1.5 Hz, 1H), 4.77 (s, 2H), 3.60 (q, J=7.2 Hz, 2H), 1.20 (t, J=7.2 Hz, 3H).

1B. 6-(2-(1H-tetrazol-5-yl)phenyl)-N-benzyl-N-ethyl-4-nitropyridin-2-amine

To a suspension of 1A (200 mg, 0.595 mmol), 5-(2-(4,4,5,5-tetramethyl-1,3,2-dioxaborolan-2-yl)phenyl)-1H-tetrazole (243 mg, 0.892 mmol) and tripotassium phosphate (379 mg, 1.785 mmol) in degassed dioxane (4.0 mL) was added $PdCl_2(dppf)$-$CH_2Cl_2$ Adduct (48.6 mg, 0.059 mmol). The mixture was placed in preheated oil bath at 85° C., stirred it for 18 h. The reaction was cooled to RT, diluted with ethyl acetate (100 mL) and the mixture was filtered through celite. The filtrate was washed with water (50 mL), dried and concentrated. Purification via flash chromatography gave 1B (pale yellow solid, 200 mg, 0.315 mmol, 53% yield). LC-MS Anal. Calc'd for $C_{21}H_{19}N_7O_2$ 401.1, found [M+H] 402.2. $T_r$=0.92 min (Method T).

1C. 6-(2-(1H-tetrazol-5-yl)phenyl)-N2-benzyl-N2-ethylpyridine-2,4-diamine

To a solution of 1B (200 mg, 0.498 mmol) in Ethanol (3.0 mL) was added water (0.5 mL) followed by ammonium chloride (133 mg, 2.491 mmol). The mixture was stirred for 5 min, and then treated with zinc (163 mg, 2.491 mmol) at 0° C. The mixture was stirred at RT for 18 h. LC-MS indicated completion. The reaction mixture was diluted with DCM (200 mL), washed with water (50 mL), brine (50 mL), dried over $Na_2SO_4$ and concentrated. Purification by preparative HPLC gave 1C (off white solid, 100 mg, 0.268 mmol, 54% yield). LC-MS Anal. Calc'd for $C_{21}H_{21}N_7$ 371.18, found [M+H] 372.2. $T_r$=1.379 min (Method N).

Example 1

To a solution of 1C (100 mg, 0.269 mmol), 2-(p-tolyl) acetic acid (81 mg, 0.538 mmol) in DMF (1.0 mL) was added 2,4,6-tripropyl-1,3,5,2,4,6-trioxatriphosphorinane-2,4,6-trioxide (343 mg, 0.538 mmol), followed by DIPEA (0.141 mL, 0.808 mmol) at ambient temperature. The reaction mixture was stirred at RT for 18 h. LC-MS indicated completion. The reaction mixture was diluted with DCM (200 ML), washed with 10% $NaHCO_3$ solution, brine, dried over $Na_2SO_4$, concentrated. Purification by preparative HPLC gave Example 1 (off white solid, 55 mg, 0.108 mmol, 40% yield). LC-MS Anal. Calc'd for $C_{30}H_{29}N_7O$ 503.24, found [M+H] 504.2. $T_r$=2.178 min (Method N). $^1$H NMR (300 MHz, DMSO-d6) δ 10.31 (bs, 1H), 7.67 (d, J=3.90 Hz, 2H), 7.62 (bs, 2H), 7.10-7.28 (m, 9H), 7.00 (s, 1H), 6.85 (bs, 2H), 4.38 (bs, 2H), 3.57 (s, 2H), 3.18 (d, J=5.40 Hz, 2H), 2.27 (s, 3H), 0.88 (t, J=6.90 Hz, 3H).

Example 2

1-(6-(2-(1H-tetrazol-5-yl)phenyl)-2-(cyclohexyl(isobutyl)amino) pyrimidin-4-yl)-3-(p-tolyl)urea

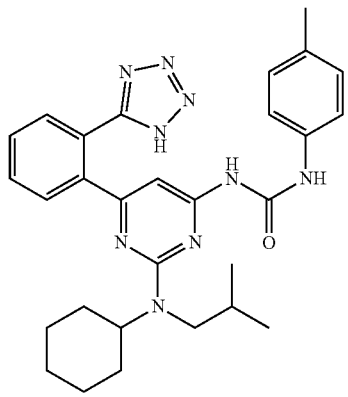 [SMILES: Cc1ccc(NC(=O)Nc2cc(-c3ccccc3-c3nnn[nH]3)nc(N(CC(C)C)C3CCCCC3)n2)cc1]

2A. 6-chloro-N2-cyclohexyl-N2-isobutylpyrimidine-2,4-diamine

A solution of 2,6-dichloropyrimidin-4-amine (1.0 g, 6.10 mmol) in dioxane (20 mL) was treated with DIPEA (1.598 mL, 9.15 mmol), N-isobutylcyclohexanamine (1.704 g, 10.98 mmol) and heated to 80° C. for 24 h. The dioxane was concentrated in vacuo, and the residue partitioned between water (50 mL) and $CHCl_3$ (100 mL). The organic layer was separated and the aqueous layer was further extracted with $CHCl_3$ (100 mL). The combined extracts were dried ($Na_2SO_4$) and concentrated. Purification via flash chromatography gave 2A (white solid, 550 mg, 1.92 mmol, 32% yield). LC-MS Anal. Calc'd for $C_{14}H_{23}ClN_4$ 282.1, found [M+H] 283.2. $T_r$=1.29 min (Method V).

2B. 1-(6-chloro-2-(cyclohexyl(isobutyl)amino)pyrimidin-4-yl)-3-(p-tolyl)urea To a solution of 2A (200 mg, 0.707 mmol) in DCM (2.0 mL) was added 1-isocyanato-4-methylbenzene (104 mg, 0.778 mmol) at ambient temperature. The reaction mixture was stirred at 45° C. for 18 h. 1-Isocyanato-4-methylbenzene (104 mg, 0.778 mmol) was added to the reaction mixture. The reaction continued for 24 h. The solvent was removed under vacuum. The above material was recrystallized from methanol to afford 2B (white solid, 150 mg, 0.25 mmol, 36% yield). LC-MS Anal. Calc'd for $C_{22}H_{30}ClN_5O$ 415.2, found [M+H] 416.2. $T_r$=1.40 min (Method V).

Example 2

To a suspension of (2-(1H-tetrazol-5-yl)phenyl)boronic acid (137 mg, 0.721 mmol), 2B (100 mg, 0.240 mmol) and tetrakis(triphenylphosphine)palladium (13.89 mg, 0.012 mmol) in degassed DMF (1 mL) was added aq. $K_2CO_3$ (133 mg, 0.962 mmol). The mixture was placed under nitrogen and heated at 95° C. for 18 h. The reaction mixture was cooled to RT, diluted with water, extracted with DCM (2×50 mL). The organic layer was washed with 10% $NaHCO_3$ solution, brine, dried over $Na_2SO_4$ and concentrated. Purification via flash chromatography gave Example 2 (yellow solid, 28 mg, 0.053 mmol, 22% yield). LC-MS Anal. Calc'd for $C_{29}H_{35}N_9O$ 525.29, found [M+H] 526.4. $T_r$=2.29 min (Method R). $^1$H NMR (300 MHz, DMSO-d6) δ 9.96 (bs, 1H), 9.37 (s, 1H), 7.68-7.73 (m, 4H), 7.37 (d, J=6.30 Hz, 2H), 7.13 (d, J=6.30 Hz, 2H), 6.94 (s, 1H), 3.69 (s, 1H), 2.26 (s, 3H), 2.05 (s, 2H), 1.86 (s, 1H), 1.60-1.70 (m, 2H), 1.50-1.60 (m, 2H), 1.30-1.50 (m, 3H), 1.10-1.20 (m, 3H), 1.05-1.10 (m, 1H), 0.73 (d, J=3.60 Hz, 6H).

Example 3

N-(6-(2-(1H-tetrazol-5-yl)phenyl)-2-(cyclohexyl(isobutyl)amino) pyrimidin-4-yl)-2-(p-tolyl)acetamide

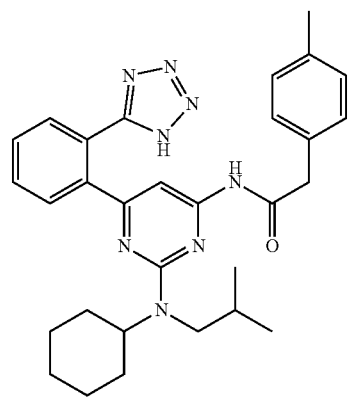 [SMILES: Cc1ccc(CC(=O)Nc2cc(-c3ccccc3-c3nnn[nH]3)nc(N(CC(C)C)C3CCCCC3)n2)cc1]

Example 3 was obtained following the procedure in Example 2 utilizing p-tolyl acetic acid. LC-MS Anal. Calc'd for $C_{30}H_{36}N_8O$ 524.30, found [M+H] 525.4. $T_r$=2.37 min (Method R). $^1$H NMR (400 MHz, DMSO-d6) δ 10.04 (bs, 1H), 7.67 (d, J=16.00 Hz, 1H), 7.35-7.41 (m, 1H), 7.25-7.35 (m, 1H), 7.19-7.25 (m, 2H), 7.15 (d, J=8.0 Hz, 211), 7.09 (d, J=8.0 Hz, 2H), 6.89 (s, 1H), 4.07-4.23 (m, 3H), 2.26 (s, 3H), 1.99-2.00 (m, 1H), 1.89-1.90 (m, 2H), 1.58-1.70 (m, 3H), 1.44-1.56 (m, 511), 1.24-1.27 (m, 2H), 0.82 (d, J=6.80 Hz, 6H).

Example-4

1-(6-(2-(1H-tetrazol-5-yl)phenyl)-2-(benzyl(ethyl)amino)pyrimidin-4-yl)-3-(p-tolyl)urea

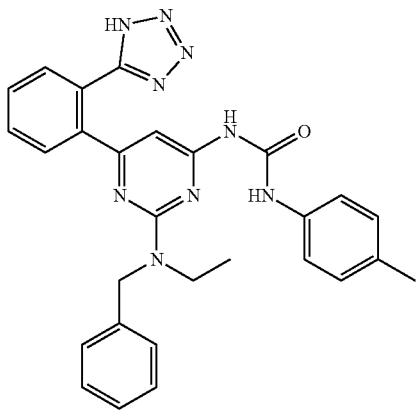 [SMILES: CCN(Cc1ccccc1)c1nc(NC(=O)Nc2ccc(C)cc2)cc(-c2ccccc2-c2nnn[nH]2)n1]

Example 4 was prepared following the procedure for Example 2 by utilizing benzylethylamine. LC-MS Anal. Calc'd for $C_{28}H_{27}N_9O$ 505.23, found [M−H] 504.2. $T_r$=2.16 min (Method U). $^1$H NMR (400 MHz, DMSO-d6) δ 10.04 (s, 1H), 9.60 (s, 1H), 7.69-7.75 (m, 4H), 7.24-7.31 (m, 4H), 7.05-7.14 (m, 6H), 6.82 (s, 1H), 4.74 (s, 2H), 3.20-3.25 (m, 2H), 2.08 (s, 3H), 0.83-0.85 (m, 3H).

Example 5

1-(6-(2-(1H-tetrazol-5-yl)phenyl)-2-(cyclohexyl(isobutyl)amino) pyrimidin-4-yl)-3-(pyrimidin-5-yl)urea

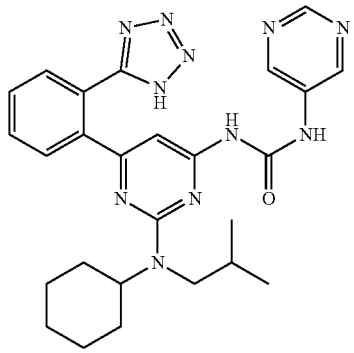 [SMILES: CC(C)CN(c1nc(NC(=O)Nc2cncnc2)cc(-c2ccccc2-c2nnn[nH]2)n1)C1CCCCC1]

Example 5 was prepared following the procedure for Example 2 by utilizing pyrimidin-5-amine. LC-MS Anal. Calc'd for $C_{26}H_{31}N_{11}O$ 513.27, found [M−H] 512.2. $T_r$=2.05 min (Method U). $^1$H NMR (300 MHz, DMSO-d6) δ 10.11 (bs, 1H), 9.60 (s, 1H), 8.96 (s, 2H), 8.89 (s, 1H), 7.67-7.74 (m, 4H), 7.03 (s, 1H), 3.17 (bs, 2H), 2.02 (s, 1H), 1.60-1.80 (m, 2H), 1.50-1.60 (m, 2H), 1.00-1.50 (m, 7H), 0.74 (d, J=4.5 Hz, 6H).

Example 6

1-(6-(2-(1H-tetrazol-5-yl)phenyl)-2-(benzyl(ethyl)amino) pyrimidin-4-yl)-3-(pyrimidin-5-yl)urea

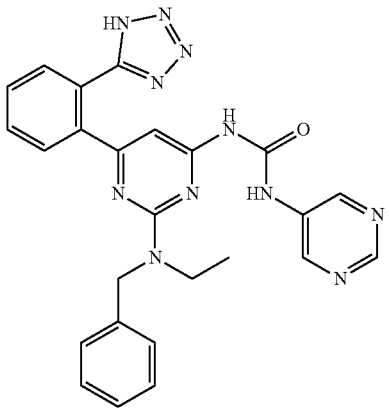 [SMILES: CCN(Cc1ccccc1)c1nc(NC(=O)Nc2cncnc2)cc(-c2ccccc2-c2nnn[nH]2)n1]

Example 6 was prepared following the procedure for Example 2 utilizing N-benzylethanamine. LC-MS Anal. Calc'd for $C_{25}H_{23}N_{11}O$ 493.2, found [M+H] 494.2. $T_r$=1.46 min (Method U). $^1$H NMR (300 MHz, DMSO-d6) δ 10.42 (bs, 1H), 9.86 (s, 1H), 8.84 (s, 1H), 8.62 (s, 2H), 7.69-7.75 (m, 4H), 7.14-7.30 (m, 5H), 6.87 (s, 1H), 4.75 (s, 1H), 4.34 (s, 1H), 3.13 (s, 2H), 0.80-1.04 (m, 3H).

Example 7

N-(6-(2-(1H-tetrazol-5-yl)phenyl)-2-(benzyl(ethyl)amino) pyrimidin-4-yl)-2-(p-tolyl)acetamide

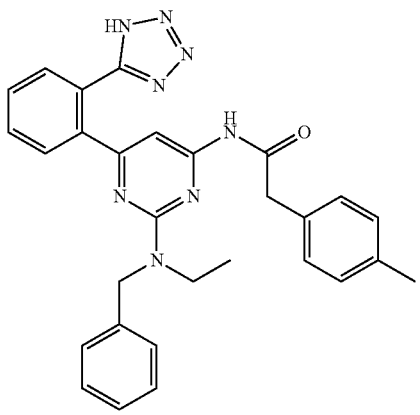

Example 7 was prepared following the procedure for Example 2 utilizing 2-(p-tolyl)acetic acid. LC-MS Anal. Calc'd for $C_{29}H_{28}N_8O$ 504.23, found [M+H] 505.2. $T_r$=1.32 min (Method U). $^1$H NMR (300 MHz, DMSO-d6) δ 10.58 (s, 1H), 7.66-7.72 (m, 4H), 7.30-7.47 (m, 1H), 7.08-7.29 (m, 9H), 4.55 (bs, 2H), 3.69 (s, 2H), 3.03 (bs, 2H), 2.27 (s, 3H), 0.83 (bs, 3H).

Example 8

N-(6-(2-(1H-tetrazol-5-yl)phenyl)-2-(benzyl(isobutyl)amino) pyrimidin-4-yl)-2-(p-tolyl)acetamide

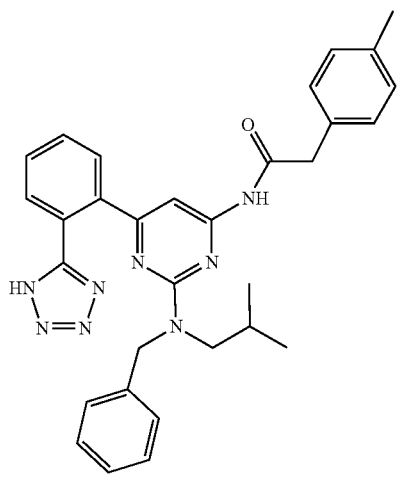 [SMILES: Cc1ccc(CC(=O)Nc2cc(-c3ccccc3-c3nnn[nH]3)nc(N(Cc3ccccc3)CC(C)C)n2)cc1]

8A. N2-benzyl-6-chloro-N2-isobutylpyrimidine-2,4-diamine

A solution of 2,6-dichloropyrimidin-4-amine (5.0 g, 30.5 mmol) in dioxane (70 mL) was treated with DIPEA (10.65 mL, 61.0 mmol), N-benzyl-2-methylpropan-1-amine (5.97 g, 36.6 mmol) and heated to 100° C. for 24 h. The dioxane was concentrated in vacuo, and the residue partitioned between water (50 mL) and $CHCl_3$ (100 mL). The organic layer was separated and the aqueous layer was further extracted with $CHCl_3$ (100 mL). The combined extracts were dried ($Na_2SO_4$) and concentrated. Purification via flash chromatography gave 8A (yellow liquid, 5.2 g, 17.88 mmol, 59% yield). LC-MS Anal. Calc'd for $C_{15}H_{19}ClN_4$ 282.1, found [M+H] 283.2. $T_r$=1.21 min (Method T).

8B. N-(2-(benzyl(isobutyl)amino)-6-chloropyrimidin-4-yl)-2-(p-tolyl)acetamide To a solution of 8A, 2-(p-tolyl)acetic acid (1.291 g, 8.60 mmol) in DCM (6.0 mL) was added $POCl_3$ (0.801 mL, 8.60 mmol) followed by pyridine (0.834 mL, 10.32 mmol) at 0° C. The reaction mixture was stirred at RT for 12 h. LC-MS indicated completion. The reaction mixture was diluted with DCM (200 mL), washed with water (2×20 mL), 10% $NaHCO_3$ solution (20 mL), brine (20 mL), dried over $Na_2SO_4$ and concentrated under reduced pressure. Purification via flash chromatography gave 8B (yellow solid, 520 mg, 1.229 mmol, 36% yield). LC-MS Anal. Calc'd for $C_{24}H_{27}ClN_4O$ 422.2, found [M+H] 423.2. $T_r$=1.48 min (Method U).

8C. N-(2-(benzyl(isobutyl)amino)-6-(2-(1-trityl-1H-tetrazol-5-yl)phenyl)pyrimidin-4-yl)-2-(p-tolyl)acetamide In a 25 mL sealed tube under argon were combined 8B (100 mg, 0.236 mmol), (2-(1-trityl-1H-tetrazol-5-yl)phenyl) boronic acid (204 mg, 0.473 mmol), potassium phosphate tribasic (151 mg, 0.709 mmol) in 1,4-dioxane (3.0 mL). Then 0.2 mL water was added. The mixture was purged with Argon for 20 min. $PdCl_2(dppf)$-$CH_2Cl_2$ Adduct (19.31 mg, 0.024 mmol) was then added. The reaction was purged for another 10 min with Argon. The reaction mixture was heated at 85° C. in an oil bath for overnight. The solvent was concentrated under reduced pressure, dissolved in DCM (10 mL) and filtered through a pad of celite. Celite pad was rinsed with DCM (2×10 mL). The solvent was concentrated under reduced pressure. Purification via flash chromatography gave 8C (yellow solid, 150 mg, 0.194 mmol, 82% yield). LC-MS Anal. Calc'd for $C_{50}H_{46}N_8O$ 774.4, found [M+H] 775.6. $T_r$=1.54 min (Method T).

Example 8

To a solution of 8C (150 mg, 0.194 mmol) in DCM (1.5 mL) was added TFA (0.746 mL, 9.68 mmol) at RT. The reaction was stirred for 18 h. The solvent was removed to get the crude product. Preparative HPLC gave Example 8 (white solid, 20 mg, 0.037 mmol, 19% yield). LC-MS Anal. Calc'd for $C_{31}H_{32}N_8O$ 532.27, found [M+H] 533.2. $T_r$=2.7 min (Method U). $^1$H NMR (400 MHz, DMSO-d6) δ 10.5 (s, 1H), 7.71-7.65 (m, 4H), 7.28 (bs, 1H), 7.22-7.08 (m, 9H), 4.80-4.2 (m, 2H), 3.69 (s, 2H), 2.27 (s, 3H), 0.71 (bs, 6H) (Note: one singlet $CH_2$ and one multiplet CH buried under solvent peak).

Example 9

N-(6-(2-(1H-tetrazol-5-yl)phenyl)-2-(benzyl(isobutyl)amino) pyrimidin-4-yl)-2-fluoro-4-methylbenzamide

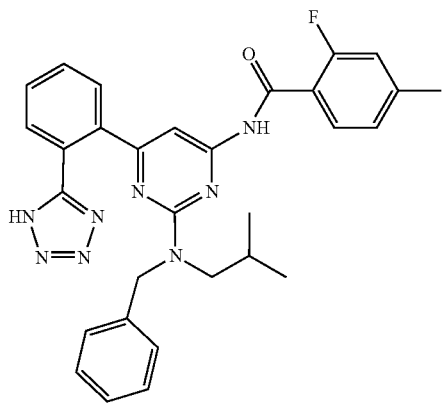 [SMILES: Cc1ccc(C(=O)Nc2cc(-c3ccccc3-c3nnn[nH]3)nc(N(Cc3ccccc3)CC(C)C)n2)c(F)c1]

Example 9 was prepared following the procedure for Example 8 by utilizing 2-fluoro-4-methylbenzoic acid. LC-MS Anal. Calc'd for $C_{30}H_{29}FN_8O$ 536.2, found [M+H] 537.2. $T_r$=2.5 min (Method U). $^1$H NMR (400 MHz, DMSO-d6) δ 10.5 (s, 1H), 7.71-7.65 (m, 4H), 7.48 (bs, 1H), 7.35-7.08 (m, 9H), 4.96-4.36 (m, 2H), 3.74 (s, 2H), 0.71 (bs, 6H) (Note: one singlet $CH_3$ and one multiplet CH buried under solvent peak).

Example 10

1-(6-(2-(1H-tetrazol-5-yl)phenyl)-2-(benzyl(isobutyl)amino) pyrimidin-4-yl)-3-(p-tolyl)urea

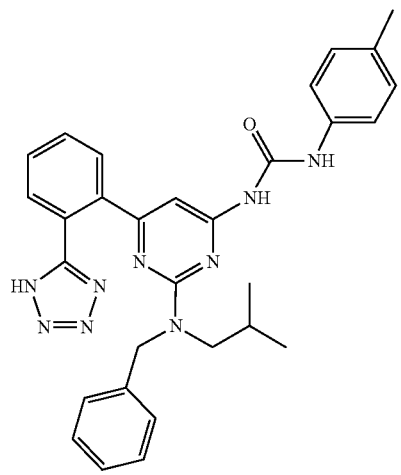 [SMILES: Cc1ccc(NC(=O)Nc2cc(-c3ccccc3-c3nnn[nH]3)nc(N(Cc3ccccc3)CC(C)C)n2)cc1]

10A. 1-(2-(benzyl(isobutyl)amino)-6-chloropyrimidin-4-yl)-3-(p-tolyl)urea

To a solution of 8A (300 mg, 1.032 mmol) in DCE (3.0 mL) under nitrogen atmosphere was added 1-isocyanato-4-methylbenzene (206 mg, 1.548 mmol) at ambient temperature. The reaction mixture was stirred at 65° C. for 18 h. The solvent was removed under reduced pressure. The above material was recrystallized from methanol to afford 10A (Off white solid, 250 mg, 0.590 mmol, 57% yield). LC-MS Anal. Calc'd for $C_{23}H_{26}ClN_5O$ 423.2, found [M+H] 424.2. $T_r=1.31$ min (Method T).

10B. 1-(2-(benzyl(isobutyl)amino)-6-(2-(1-trityl-1H-tetrazol-5-yl)phenyl)pyrimidin-4-yl)-3-(p-tolyl)urea Compound 10B was prepared following the procedure for 8C by utilizing 10A. LC-MS Anal. Calc'd for $C_{49}H_{45}N_9O$ 775.3, found [M+H] 776.2. $T_r=1.54$ min (Method T).

Example 10

Example 10 was prepared following the procedure for Example 8 by utilizing 10B. LC-MS Anal. Calc'd for $C_{30}H_{31}N_9O$ 533.2, found [M+H] 534.2. $T_r=2.8$ min (Method U). $^1$H NMR (400 MHz, DMSO-d6) δ 10.0 (bs, 1H), 9.53 (s, 1H), 7.74-7.68 (m, 4H), 7.29-7.06 (m, 9H), 6.88 (s, 1H), 4.96-4.36 (m, 2H), 2.33 (s, 3H), 0.72 (bs, 6H) (Note: one multiplet $CH_2$ and one multiplet CH buried under solvent peak).

Example 11

N-(6-(2-(1H-tetrazol-5-yl)phenyl)-2-(benzyl (isobutyl)amino) pyrimidin-4-yl)-2-(2-fluoro-4-methylphenyl)acetamide

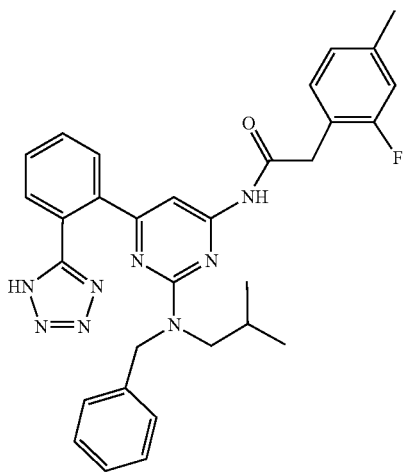 [SMILES: Cc1ccc(CC(=O)Nc2cc(-c3ccccc3-c3nnn[nH]3)nc(N(Cc3ccccc3)CC(C)C)n2)c(F)c1]

Example 11 was prepared following the procedure for Example 8 utilizing N-(2-(benzyl(isobutyl)amino)-6-(2-(1-trityl-1H-tetrazol-5-yl)phenyl)pyrimidin-4-yl)-2-(2-fluoro-4-methylphenyl)acetamide (200 mg, 0.252 mmol). LC-MS Anal. Calc'd for $C_{31}H_{31}FN_8O$ 550.2, found [M+H] 551.2. $T_r=2.7$ min (Method U). $^1$H NMR (300 MHz, DMSO-d$_6$) δ 10.6 (s, 1H), 7.71-7.65 (m, 4H), 7.47 (bs, 1H), 7.28-7.19 (m, 4H), 7.09-6.96 (m, 4H), 4.80-4.24 (m, 2H), 3.79 (s, 2H), 2.27 (s, 3H), 0.72 (bs, 6H) (Note: one singlet $CH_2$ and one multiplet CH buried under solvent peak).

Example 12

1-(2-(benzyl(propyl)amino)-6-(2-(5-oxo-4,5-dihydro-1,2,4-oxadiazol-3-yl)phenyl)pyridin-4-yl)-3-(4-chloro-2-fluorophenyl)urea

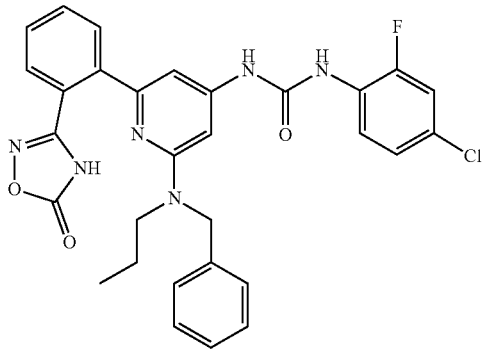 [SMILES: CCCN(Cc1ccccc1)c1cc(NC(=O)Nc2ccc(Cl)cc2F)cc(-c2ccccc2-c2noc(=O)[nH]2)n1]

12A. N-benzyl-6-bromo-4-nitro-N-propylpyridin-2-amine

In a sealed tube, 2,6-dibromo-4-nitropyridine (1.6 g, 5.68 mmol) in 1,4-dioxane (20 mL) was taken. Then N-benzyl-propan-1-amine (2.54 g, 17.03 mmol) was added to the reaction mixture. The reaction mixture was stirred at 110° C. for 3 h. LC-MS indicated completion. The reaction mass was concentrated under reduced pressure to get crude compound. Purification via flash chromatography gave 12A (Pale yellow liquid, 1.5 g, 4.28 mmol, 75% yield). LC-MS Anal. Calc'd for $C_{15}H_{16}BrN_3O_2$ 349.04, found [M+H] 350.2, $T_r=1.89$ min. (Method T).

12B. 2-(6-(benzyl(propyl)amino)-4-nitropyridin-2-yl)benzonitrile

The solution of 12A (0.900 g, 2.57 mmol) in 1,4-dioxane (15 mL) in a sealed tube, (2-cyanophenyl)boronic acid (0.755 g, 5.14 mmol) and potassium phosphate tribasic (1.636 g, 7.71 mmol) were added. Then 0.2 mL water was added to the reaction mixture. The reaction mixture was purged with Argon for 10 min, followed by addition of $PdCl_2$(dppf)-$CH_2Cl_2$ Adduct (0.210 g, 0.257 mmol). The reaction mixture was purged with Argon for another 5 min. The reaction mixture was stirred at 95° C. for 12 h. LC-MS indicated completion. The mixture then was diluted with water (40 mL) and extracted with ethyl acetate (3×30 mL). The combined organic layer was washed with brine (30 mL), dried over anhydrous sodium sulfate, concentrated under reduced pressure to get crude compound. Purification via flash chromatography gave 12B (Gummy liquid, 0.4 g, 1.07 mmol, 41% yield). LC-MS Anal. Calc'd for $C_{22}H_{20}N_4O_2$ 372.15, found [M+H] 373.4, $T_r=1.83$ min. (Method T).

12C. 2-(4-amino-6-(benzyl(propyl)amino)pyridin-2-yl)benzonitrile

To a stirred solution of 12B (0.400 g, 1.074 mmol) in acetic acid (4 mL) under nitrogen atmosphere was added iron (0.300 g, 5.37 mmol) at 0° C. and the reaction mixture was brought to RT and was stirred for 3 h. LC-MS indicated completion. The suspension was filtered through a pad of Celite and the filter cake was rinsed with DCM (4×30 mL). Combined filtrate and rinses were concentrated under reduced pressure. Purification via flash chromatography gave 12C (Gummy liquid, 0.31 g, 0.905 mmol, 84% yield). LC-MS Anal. Calc'd for $C_{22}H_{22}N_4$ 342.18, found [M+H] 343.4, $T_r$=1.61 min. (Method T).

12D. 1-(2-(benzyl(propyl)amino)-6-(2-cyanophenyl)pyridin-4-yl)-3-(4-chloro-2-fluorophenyl)urea To a stirred solution of 12C (0.310 g, 0.905 mmol) in THF (4 mL) under nitrogen atmosphere was added TEA (0.252 mL, 1.811 mmol), followed by 4-chloro-2-fluoro-1-isocyanatobenzene (0.311 g, 1.811 mmol). The reaction mixture was heated to 55° C. and stirred for 2 h. LC-MS indicated completion. The reaction mixture was concentrated under reduced pressure to get crude compound. Purification via flash chromatography gave 12D (Off white solid, 0.44 g, 0.856 mmol, 95% yield). LC-MS Anal. Calc'd for $C_{29}H_{25}ClFN_5O$ 513.17, found [M+H] 514.3, $T_r$=1.86 min. (Method T).

12E. (E)-2-(6-(benzyl(propyl)amino)-4-(3-(4-chloro-2-fluorophenyl)ureido)pyridin-2-yl)-N'-hydroxybenzimidamide To a stirred solution of 12D (0.440 g, 0.856 mmol) in ethanol (6 mL) under nitrogen atmosphere was added hydroxylamine hydrochloride (0.119 g, 1.712 mmol) followed by DIPEA (0.449 mL, 2.57 mmol). The reaction mixture was refluxed to 80° C. and was stirred for 12 h. LC-MS indicated completion. The reaction mass was concentrated under reduced pressure to get residue, which was diluted with water (20 mL) and ethyl acetate (30 mL). Aqueous layer was extracted with ethyl acetate (30 mL). The combined organic layer was washed with brine (15 mL), dried over anhydrous sodium sulfate, and concentrated under reduced pressure to get crude compound. Purification via flash chromatography gave 12E (Off white solid, 0.12 g, 0.219 mmol, 25% yield). LC-MS Anal. Calc'd for $C_{29}H_{28}ClFN_6O_2$ 546.19, found [M+H] 547.3. $T_r$=1.56 min. (Method T).

Example 12

To a stirred solution of 12E (0.120 g, 0.219 mmol) in 1,4-dioxane (3 mL) under nitrogen atmosphere was added CDI (0.053 g, 0.329 mmol) followed by DBU (0.036 mL, 0.241 mmol). The reaction mixture was refluxed at 110° C. and was stirred for 2 h, then was concentrated under reduced pressure to get residue which was dissolved in DCM (30 mL), washed with water (20 mL) and brine (20 mL), dried over anhydrous sodium sulfate. Organic layer was filtered and concentrated under reduced pressure to get crude compound. Preparative HPLC gave Example 12 (off white solid, 35 mg, 0.059 mmol, 26.7% yield). LC-MS Anal. Calc'd for $C_{30}H_{26}ClFN_6O_3$ 572.17, found [M+H] 573.0. $T_r$=4.08 min (Method U). $^1$H NMR (400 MHz, DMSO-$d_6$) δ 12.25 (bs, 1H), 9.26 (s, 1H), 8.72 (d, J=2.26 Hz, 1H), 8.12 (t, J=8.91 Hz, 1H), 7.43-7.77 (m, 5H), 7.10-7.40 (m, 6H), 6.96 (brs, 1H), 6.62 (brs, 1H), 4.66 (s, 2H), 3.20-3.30 (s, 2H), 1.40-1.60 (m, 2H), 0.83 (d, J=14.81 Hz, 3H).

Example 13

1-(4-chloro-2-fluorophenyl)-3-(2-((4-fluorobenzyl)(propyl)amino)-6-(2-(5-oxo-4,5-dihydro-1,2,4-oxadiazol-3-yl)phenyl)pyridin-4-yl)urea

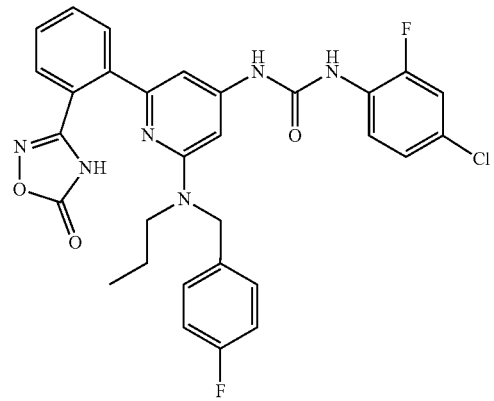 [SMILES: CCCN(Cc1ccc(F)cc1)c1cc(NC(=O)Nc2ccc(Cl)cc2F)cc(-c2ccccc2-c2noc(=O)[nH]2)n1]

Example 13 was prepared following the procedure for Example 12 by utilizing N-(4-fluorobenzyl)propan-1-amine. LC-MS Anal. Calc'd for $C_{30}H_{25}ClF_2N_6O_3$ 590.16, found [M-H] 589.0. $T_r$=3.49 min (Method U). $^1$H NMR (400 MHz, DMSO-$d_6$) δ 12.12 (bs, 1H), 9.25 (s, 1H), 8.66-8.82 (m, 1H), 8.13 (t, J=8.88 Hz, 1H), 7.40-7.62 (m, 3H), 7.04-7.30 (m, 9H), 4.55 (s, 2H), 3.44-3.60 (m, 2H), 1.40-1.61 (m, 2H), 0.84 (d, J=14.68 Hz, 3H).

Example 14

1-(2-(benzyl(propyl)amino)-6-(2-(5-oxo-4,5-dihydro-1,2,4-thiadiazol-3-yl)phenyl)pyridin-4-yl)-3-(p-tolyl)urea

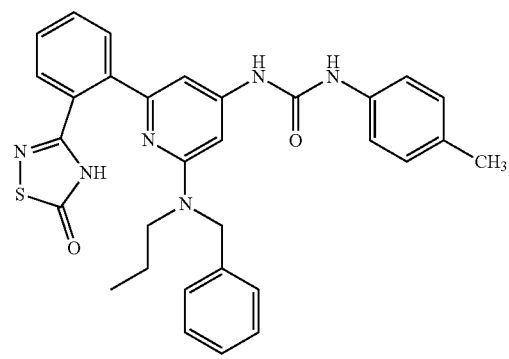 [SMILES: CCCN(Cc1ccccc1)c1cc(NC(=O)Nc2ccc(C)cc2)cc(-c2ccccc2-c2nsc(=O)[nH]2)n1]

14A. (E)-2-(6-(benzyl(propyl)amino)-4-(3-(p-tolyl)ureido)pyridin-2-yl)-N'-hydroxybenzimidamide Compound 14A was prepared following the procedure as described for 12E by utilizing 1-isocyanato-4-methylbenzene. LC-MS Anal. Calc'd for $C_{30}H_{32}N_6O_2$ 508.25, found [M+H] 509.4. $T_r$=1.11 min (Method T).

Example 14

To a solution of 14A (0.190 g, 0.374 mmol) in THF (2 mL) under nitrogen atmosphere was added 1,1'-thiocarbonyldiimidazole (0.072 g, 0.403 mmol). The reaction mixture was stirred at RT for 12 h. After a suspension of silica gel (230-400) (2 g) in CHCl$_3$-MeOH (5:1) was added to the resulting mixture which was stirred at RT for 24 h. LC-MS indicated completion. The reaction mixture was filtered through a pad of celite. The filtrate was concentrated under reduced pressure to get crude compound. Preparative HPLC gave Example 14 (off white solid, 1.5 mg, 2.53 μmol, 1% yield). LC-MS Anal. Calc'd for C$_{31}$H$_{30}$N$_6$O$_2$S 550.21, found [M+H] 551.0. T$_r$=3.40 min (Method U). $^1$H NMR (400 MHz, DMSO-d$_6$) δ 12.81 (s, 1H), 8.62 (s, 2H), 7.29 (d, J=16.94 Hz, 8H), 7.19 (d, J=9.66 Hz, 3H), 7.08 (d, J=8.16 Hz, 4H), 4.65 (s, 2H), 2.32 (s, 3H), 1.13-1.30 (m, 4H), 0.82 (t, J=7.28 Hz, 3H).

Example 15

N-(2-(2-(1H-tetrazol-5-yl)phenyl)-6-(benzyl(3,3,3-trifluoropropyl)amino) pyridin-4-yl)-2-(p-tolyl)acetamide

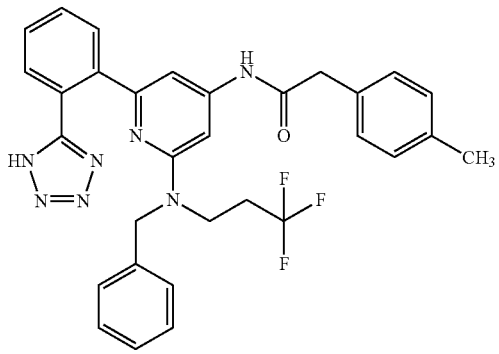 [SMILES: Cc1ccc(CC(=O)Nc2cc(-c3ccccc3-c3nnn[nH]3)nc(N(CCC(F)(F)F)Cc3ccccc3)c2)cc1]

15A. N2-benzyl-6-chloro-N2-(3,3,3-trifluoropropyl) pyrimidine-2,4-diamine

In a sealed tube 2,6-dichloropyrimidin-4-amine (0.600 g, 3.66 mmol) in 1,4-Dioxane (10 mL) was taken. Then N-benzyl-3,3,3-trifluoropropan-1-amine, HCl (1.315 g, 5.49 mmol), followed by DIPEA (1.917 mL, 10.98 mmol) were added to the reaction mixture, which was stirred at 100° C. for 12 h. LC-MS indicated completion. The reaction mixture was concentrated under reduced pressure to get crude compound. Purification via flash chromatography gave 15A (Gummy liquid, 200 mg, 0.605 mmol, 16% yield). LC-MS Anal. Calc'd for C$_{14}$H$_{14}$ClF$_3$N$_4$ 330.08, found [M+H] 331.1. T$_r$=1.02 min. (Method AA).

15B. N-(2-(benzyl(3,3,3-trifluoropropyl)amino)-6-chloropyrimidin-4-yl)-2-(p-tolyl)acetamide To a solution of 15A (0.200 g, 0.605 mmol) and 2-(p-tolyl)acetic acid (0.227 g, 1.512 mmol) in Dichloromethane (10 mL) under nitrogen atmosphere at 0° C. was added POCl$_3$ (0.141 mL, 1.512 mmol), followed by pyridine (0.147 mL, 1.814 mmol). The reaction mixture was stirred at RT for 12 h. LC-MS indicated completion. The reaction mixture was diluted with dichloromethane (40 mL) and water (30 mL). DCM layer was washed with 10% sodium bicarbonate solution (30 mL) and brine (30 mL), dried over anhydrous sodium sulfate, concentrated under reduced pressure to get crude compound. Purification via flash chromatography gave 15B (Gummy liquid, 70 mg, 0.151 mmol, 25% yield). LC-MS Anal. Calc'd for C$_{23}$H$_{22}$ClF$_3$N$_4$O 462.14, found [M+H] 463.3. T$_r$=1.474 mm. (Method U)

15C. N-(2-(benzyl(3,3,3-trifluoropropyl)amino)-6-(2-(1-trityl-1H-tetrazol-5-yl)phenyl)pyrimidin-4-yl)-2-(p-tolyl) acetamide Compound 15C was prepared following the procedures from 12A to 12B by utilizing N-(2-(benzyl(3,3,3-trifluoropropyl)amino)-6-chloropyrimidin-4-yl)-2-(p-tolyl)acetamide. LC-MS Anal. Calc'd for C$_{49}$H$_{41}$F$_3$N$_8$O 814.33, found [M+H] 815.4. T$_r$=1.56 min. (Method T).

Example 15

To a stirred solution of 15C (0.060 g, 0.074 mmol) in Dichloromethane (2 mL) under nitrogen atmosphere was added TFA (1 mL, 12.98 mmol). The reaction mixture was stirred at RT for 2 h. LC-MS indicated completion. Preparative HPLC gave Example 15 (off white solid, 6 mg, 10.16 μmol, 14% yield). LC-MS Anal. Calc'd for C$_{30}$H$_{27}$F$_3$N$_8$O 572.22, found [M+H] 573.2. T$_r$=2.72 min (Method U). $^1$H NMR (400 MHz, DMSO-d$_6$) δ 10.50 (s, 1H), 7.23-7.36 (m, 4H), 7.05-7.21 (m, 10H), 4.81 (s, 2H), 3.67 (s, 2H), 3.45-3.55 (m, 2H), 2.62-2.74 (m, 1H), 2.20-2.37 (m, 4H).

Example 16

2-(6-(benzyl(propyl)amino)-4-(3-(p-tolyl)ureido) pyridin-2-yl)benzoic acid

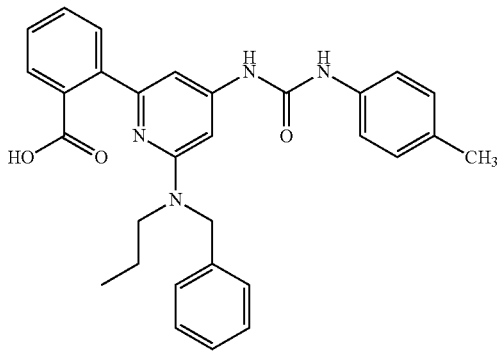 [SMILES: CCCN(Cc1ccccc1)c1cc(NC(=O)Nc2ccc(C)cc2)cc(-c2ccccc2C(=O)O)n1]

16A. N-benzyl-6-bromo-4-nitro-N-propylpyridin-2-amine

Compound 16A was prepared following the procedure for 12A utilizing 2,6-dibromo-4-nitropyridine. LC-MS Anal. Calc'd for C$_{15}$H$_{16}$BrN$_3$O$_2$ 349.04, found [M+H] 352.2. T$_r$=1.89 min. (Method T).

16B. methyl 2-(6-(benzyl(propyl)amino)-4-nitropyridin-2-yl)benzoate

Compound 16B was prepared following the procedure for 12B utilizing 5A and (2-(methoxycarbonyl)phenyl)boronic acid. LC-MS Anal. Calc'd for $C_{23}H_{23}N_3O_4$ 405.16, found [M+H] 406.2. $T_r$=3.88 min. (Method U).

16C. methyl 2-(4-amino-6-(benzyl(propyl)amino)pyridin-2-yl)benzoate

To a solution of 16B (0.100 g, 0.247 mmol) in ethanol (3 mL), water (0.600 mL) was added ammonium chloride (0.066 g, 1.233 mmol). The reaction mixture was stirred at RT for 10 min, then zinc (0.113 g, 1.726 mmol) was added. The reaction mixture was stirred at 55° C. for 2 h. LC-MS indicated completion. The reaction mixture was cooled to RT, filtered through a pad of celite, and washed with ethyl acetate (4×30 mL). Ethyl acetate layer was diluted with water (40 mL) and back extracted with ethyl acetate (30 mL). The combined organic layer was washed with brine (40 mL), dried over anhydrous sodium sulfate, and concentrated under reduced pressure to get 16C (Gummy solid, 70 mg, 0.186 mmol, 76% yield). LC-MS Anal. Calc'd for $C_{23}H_{25}N_3O_2$ 375.19, found [M+H] 376.4. $T_r$=1.18 min. (Method T).

16D. methyl 2-(6-(benzyl(propyl)amino)-4-(3-(p-tolyl)ureido)pyridin-2-yl)benzoate To a stirred solution of 16C (0.500 g, 1.332 mmol) in THF (15 mL) under nitrogen atmosphere were added TEA (0.371 mL, 2.66 mmol), 1-isocyanato-4-methylbenzene (0.532 g, 4.00 mmol). The reaction mixture was stirred at 55° C. for 12 h. LC-MS indicated completion. The reaction mass was concentrated under reduced pressure to get crude compound. Purification via flash chromatography gave 16D (Off white solid, 650 mg, 1.278 mmol, 96% yield). LC-MS Anal. Calc'd for $C_{31}H_{32}N_4O_3$ 508.24, found [M+H] 509.2. $T_r$=1.32 min. (Method T).

Example 16

To a stirred solution of 16D (0.450 g, 0.885 mmol) in THF (9 mL), water (3 mL) and Methanol (6 mL) was added lithium hydroxide monohydrate (0.297 g, 7.08 mmol). The reaction mixture was stirred at 60° C. for 12 h. LC-MS indicated completion. The reaction mixture was concentrated under reduced pressure to get residue which was acidified to pH~2 by using 1.5 N HCl and extracted with 5% Methanol in DCM (2×25 mL). The combined organic layer was washed with brine (20 mL), dried over anhydrous sodium sulfate, and concentrated under reduced pressure to get crude compound. Flash chromatography, followed by Preparative HPLC gave Example 16 (off white solid, 260 mg, 0.423 mmol, 48% yield). LC-MS Anal. Calc'd for $C_{30}H_{30}N_4O_3$ 494.23, found [M+H] 495.2. $T_r$=2.76 min. (Method U). $^1$H NMR (400 MHz, DMSO-$d_6$) δ 12.543 (s, 1H), 8.876 (s, 1H), 7.23-7.67 (m, 11H), 7.10 (s, 2H), 6.92 (s, 1H), 4.77 (s, 2H), 3.49 (brs, 2H), 2.24 (s, 3H), 1.47-1.65 (m, 2H), 0.86 (t, J=7.31 Hz, 3H).

Example 17

2-(6-(benzyl(propyl)amino)-4-(2-(p-tolyl)acetamido)pyridin-2-yl)benzoic acid

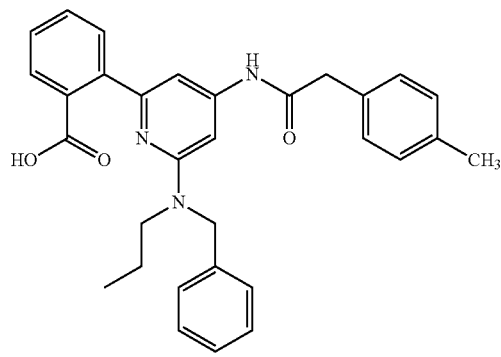 [SMILES: CCCN(Cc1ccccc1)c1cc(NC(=O)Cc2ccc(C)cc2)cc(-c2ccccc2C(=O)O)n1]

17A. N-benzyl-6-bromo-4-nitro-N-propylpyridin-2-amine

Compound 17A was prepared following the procedure for 12A utilizing 2,6-dibromo-4-nitropyridine. LC-MS Anal. Calc'd for $C_{15}H_{16}BrN_3O_2$ 349.04, found [M+H] 350.2 $T_r$=1.89 min. (Method T).

17B. methyl 2-(6-(benzyl(propyl)amino)-4-nitropyridin-2-yl)benzoate

Compound 17B was prepared following the procedure for 12B by utilizing 17A. LC-MS Anal. Calc'd for $C_{23}H_{23}N_3O_4$ 405.16, found [M+H] 406.2. $T_r$=1.36 min. (Method T).

17C. methyl 2-(4-amino-6-(benzyl(propyl)amino)pyridin-2-yl)benzoate

Compound 17C was prepared following the procedure from 16A to 16C by utilizing 17B. LC-MS Anal. Calc'd for $C_{23}H_{25}N_3O_2$ 375.19, found [M+H] 376.2. $T_r$=1.18 min. (Method T).

17D. methyl 2-(6-(benzyl(propyl)amino)-4-(2-(p-tolyl)acetamido)pyridin-2-yl)benzoate To a stirred solution of 17C (0.700 g, 1.864 mmol) and 2-(p-tolyl)acetic acid (0.700 g, 4.66 mmol) in dichloromethane (20 mL) under nitrogen atmosphere at 0° C. was added POCl$_3$ (0.434 mL, 4.66 mmol) followed by pyridine (0.452 mL, 5.59 mmol). The reaction mixture was stirred at RT for 12 h. LC-MS indicated completion. The reaction mixture was diluted with DCM (70 mL). DCM layer was washed with water (2×40 mL) and 10% NaHCO$_3$ solution (2×40 mL), dried over anhydrous sodium sulfate, and concentrated under reduced pressure to get crude compound. Purification via flash chromatography gave 17D (Brown solid, 580 mg, 1.143 mmol, 61% yield). LC-MS Anal. Calc'd for $C_{32}H_{33}N_3O_3$ 507.25, found [M+H] 508.5. $T_r$=1.28 min. (Method T).

Example 17

To a stirred solution of 17D (0.580 g, 1.143 mmol) in THF (10 mL), methanol (10 mL) and water (4 mL) was added lithium hydroxide monohydrate (0.240 g, 5.71 mmol). The reaction mixture was stirred at 60° C. for 12 h. LC-MS indicated completion. The reaction mixture was concentrated under reduced pressure to get residue. The residue was acidified to pH~2 by using 1.5 N HCl and it was extracted with 5% Methanol in DCM (2×25 mL). The combined organic layer was washed with brine (20 mL), dried over anhydrous sodium sulfate, concentrated under reduced pressure to get crude compound. Flash chromatography, followed by Preparative HPLC gave Example 17 (off white solid, 430 mg, 0.701 mmol, 61% yield). LC-MS Anal. Calc'd for $C_{31}H_{31}N_3O_3$ 493.23, found [M+H] 494.2. $T_r$=2.51 min (Method U). $^1$H NMR (300 MHz, DMSO-d$_6$) δ 10.35 (s, 1H), 7.45-7.54 (m, 2H), 7.29 (d, J=6.75 Hz, 2H), 7.16-7.25 (m, 9H), 7.07-7.15 (m, 2H), 4.73 (s, 2H), 3.6-3.4 (m, 4H), 2.27 (s, 3H), 1.51-1.60 (m, 2H), 0.84 (t, J=7.32 Hz, 3H).

Example 18

2-(6-(benzyl(propyl)amino)-4-(3-(p-tolyl)ureido)pyridin-2-yl)-N-((4-methylpiperazin-1-yl)sulfonyl)benzamide

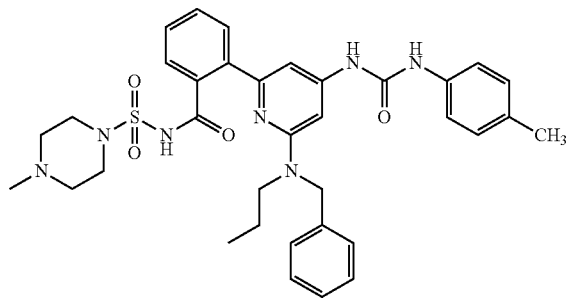

To a stirred solution of Example 16 (0.150 g, 0.206 mmol), TBTU (0.099 g, 0.309 mmol) in THF (4 mL) under nitrogen atmosphere was added TEA (0.086 mL, 0.619 mmol). The reaction mixture was stirred for at RT for 30 min, then 4-methylpiperazine-1-sulfonamide (0.111 g, 0.619 mmol) was added. The reaction mixture was stirred at RT for 12 h, then quenched with water (15 mL) and extracted with dichloromethane (2×15 mL). The combined organic layer was washed with brine (20 mL), dried over anhydrous sodium sulfate, and concentrated under reduced pressure to get crude compound. Preparative HPLC gave Example 18 (off white solid, 30 mg, 0.045 mmol, 22% yield). LC-MS Anal. Calc'd for $C_{35}H_{41}N_7O_4S$ 655.29, found [M+H] 656.2. $T_r$=2.74 min. (Method U). $^1$H NMR (300 MHz, DMSO-d$_6$) δ 11.47 (s, 1H), 8.74 (s, 1H), 8.66 (s, 1H), 7.40-7.57 (m, 4H), 7.16-7.35 (m, 7H), 7.08 (d, J=8.31 Hz, 3H), 6.90 (s, 1H), 4.79 (s, 2H), 3.40 (d, J=15.39 Hz, 2H), 3.17 (s, 4H), 2.15-2.31 (m, 10H), 1.57 (d, J=7.84 Hz, 2H), 0.86 (t, J=7.41 Hz, 3H).

Example 19

2-(6-(benzyl(propyl)amino)-4-(2-(p-tolyl)acetamido)pyridin-2-yl)-N-(cyclopropylsulfonyl)benzamide

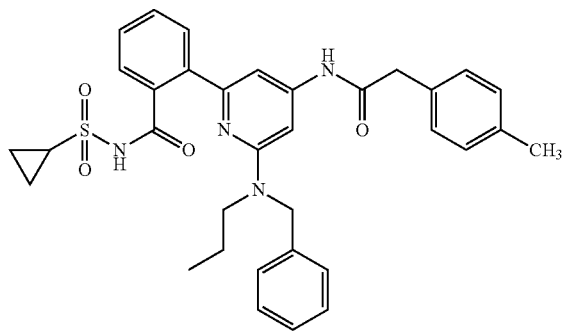 [SMILES: CCCN(Cc1ccccc1)c1cc(NC(=O)Cc2ccc(C)cc2)cc(-c2ccccc2C(=O)NS(=O)(=O)C2CC2)n1]

To a stirred solution of Example 17 (0.150 g, 0.206 mmol), TBTU (0.146 g, 0.456 mmol) in THF (4 mL) under nitrogen atmosphere was added TEA (0.127 mL, 0.912 mmol). The reaction mixture was stirred at RT for 30 min, then cyclopropanesulfonamide (0.110 g, 0.912 mmol) was added. The reaction mixture was stirred at RT for 12 h, then quenched with water (15 mL) and extracted with dichloromethane (2×15 mL). The combined organic layer was washed with brine (20 mL), dried over anhydrous sodium sulfate, and concentrated under reduced pressure to get crude compound. Preparative HPLC gave Example 19 (off white solid, 15 mg, 0.025 mmol, 9% yield). LC-MS Anal. Calc'd for $C_{34}H_{36}N_4O_4S$ 596.24, found [M+H] 597.2. $T_r$=3.22 min. (Method U). $^1$H NMR (400 MHz, DMSO-d$_6$) δ 11.86 (s, 1H), 10.21-10.33 (m, 1H), 7.43-7.59 (m, 4H), 7.10-7.32 (m, 10H), 6.83 (s, 1H), 4.76 (s, 2H), 3.59 (s, 2H), 2.91 (s, 1H), 2.63-2.76 (m, 2H), 2.34 (t, J=1.88 Hz, 3H), 1.54 (d, J=7.53 Hz, 2H), 0.91-1.10 (m, 4H), 0.85 (s, 3H).

Example 20

2-(6-(benzyl(propyl)amino)-4-(3-(p-tolyl)ureido)pyridin-2-yl)-N-(cyclopropylsulfonyl)benzamide

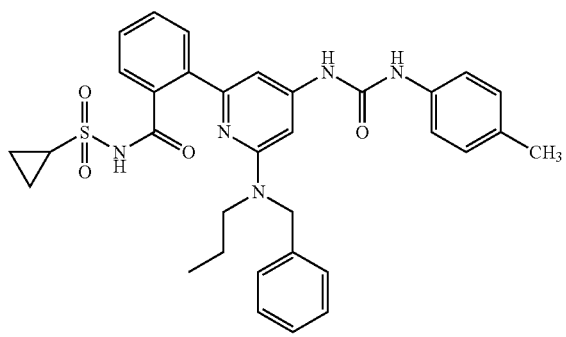 [SMILES: CCCN(Cc1ccccc1)c1cc(NC(=O)Nc2ccc(C)cc2)cc(-c2ccccc2C(=O)NS(=O)(=O)C2CC2)n1]

Example 20 was prepared following the procedure for Example 18 utilizing cyclopropanesulfonamide. LC-MS Anal. Calc'd for $C_{33}H_{35}N_5O_4S$ 597.24, found [M+H] 598.2. $T_r$=3.18 min. (Method U). $^1$H NMR (400 MHz, DMSO-d$_6$) δ 11.98 (s, 1H), 8.82 (s, 1H), 8.65 (s, 1H), 7.58 (s, 2H), 7.47 (d, J=2.95 Hz, 2H), 7.16-7.36 (m, 7H), 7.10 (d, J=8.22 Hz, 2H), 7.01 (s, 1H), 6.62 (s, 1H), 4.78 (s, 2H), 3.37-3.46 (m, 2H), 2.91-3.02 (m, 1H), 2.25 (s, 3H), 1.47-1.61 (m, 2H), 0.98-1.12 (m, 4H), 0.87 (t, J=7.37 Hz, 3H).

Example 21

2-(6-(benzyl(propyl)amino)-4-(2-(p-tolyl)acetamido) pyridin-2-yl)-N-(methylsulfonyl)benzamide

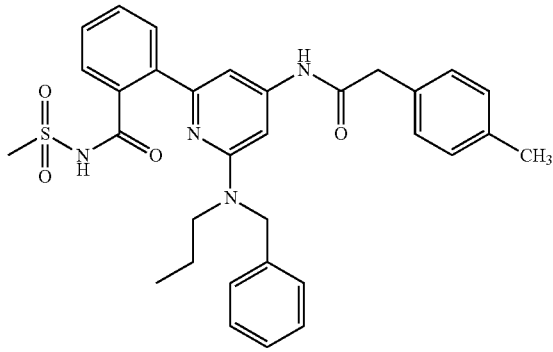

Example 21 was prepared following the procedure for Example 19 utilizing methanesulfonamide. LC-MS Anal. Calc'd for $C_{32}H_{34}N_4O_4S$ 570.23, found [M+H] 571.2. $T_r$=2.62 min (Method U). $^1$H NMR (300 MHz, DMSO-$d_6$) δ 12.03 (s, 1H), 10.30 (s, 1H), 7.41-7.60 (m, 4H), 7.05-7.33 (m, 10H), 6.85 (s, 1H), 4.76 (s, 2H), 3.58 (s, 2H), 3.51 (s, 3H), 3.16 (brs, 2H), 2.27 (s, 3H), 1.53 (d, J=7.36 Hz, 2H), 0.85 (t, J=7.32 Hz, 3H).

Example 22

N-(6-(2-(1H-tetrazol-5-yl)phenyl)-2-(benzyl(cyclopropylmethyl)amino) pyrimidin-4-yl)-2-(p-tolyl)acetamide

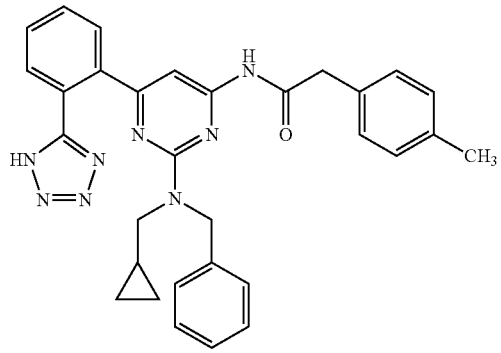 [SMILES: Cc1ccc(CC(=O)Nc2cc(-c3ccccc3-c3nnn[nH]3)nc(N(Cc3ccccc3)CC3CC3)n2)cc1]

22A. N2-benzyl-6-chloro-N2-(cyclopropylmethyl)pyrimidine-2,4-diamine

In a sealed tube 2,6-dichloropyrimidin-4-amine (0.600 g, 3.66 mmol) in 1,4-dioxane (4 mL) was taken. Then N-benzyl-1-cyclopropylmethanamine (0.885 g, 5.49 mmol), followed by DIPEA (1.917 mL, 10.98 mmol) were added to the reaction mixture. The reaction was stirred at 100° C. for 12 h. LC-MS indicated completion. The reaction mixture was concentrated under reduced pressure to get crude compound. Purification via flash chromatography gave 22A (Gummy liquid, 190 mg, 0.658 mmol, 17% yield). LC-MS Anal. Calc'd for $C_{15}H_{17}ClN_4$ 288.11, found [M+H] 289.4. $T_r$=1.13 min. (Method T).

22B. N-(2-(benzyl(cyclopropylmethyl)amino)-6-chloropyrimidin-4-yl)-2-(p-tolyl)acetamide To a stirred solution of 22A (0.190 g, 0.658 mmol) and 2-(p-tolyl)acetic acid (0.247 g, 1.645 mmol) in dichloromethane (10 mL) under nitrogen atmosphere at 0° C. was added POCl$_3$ (0.153 mL, 1.645 mmol) followed by pyridine (0.160 mL, 1.974 mmol). The reaction mixture was stirred at RT for 12 h. LC-MS indicated completion. The reaction mixture was diluted with dichloromethane (40 mL) and water (30 mL). DCM layer was washed with 10% sodium bicarbonate solution (30 mL) and brine (30 mL), dried over anhydrous sodium sulfate and concentrated under reduced pressure to get crude compound. Purification via flash chromatography gave 22B (Off white solid, 170 mg, 0.404 mmol, 61% yield). LC-MS Anal. Calc'd for $C_{24}H_{25}ClN_4O$ 420.17, found [M+H] 421.2. $T_r$=4.10 min. (Method U).

22C. N-(2-(benzyl(cyclopropylmethyl)amino)-6-(2-(1-trityl-1H-tetrazol-5-yl)phenyl)pyrimidin-4-yl)-2-(p-tolyl)acetamide Compound 22C was prepared following the procedure from 12A to 12B by utilizing 22B. LC-MS Anal. Calc'd for $C_{50}H_{44}N_8O$ 772.36, found [M+H] 773.5. $T_r$=1.49 min. (Method T).

Example 22

To a stirred solution of 22C (0.045 g, 0.058 mmol) in dichloromethane (2 mL) under nitrogen atmosphere was added TFA (1 mL, 12.98 mmol). The reaction mixture was stirred at RT for 3 h. LC-MS indicated completion. Preparative HPLC gave Example 22 (off white solid, 7 mg, 0.013 mmol, 22% yield). LC-MS Anal. Calc'd for $C_{31}H_{30}N_8O$ 530.25, found [M+H] 531.2. $T_r$=2.46 min. (Method U). $^1$H NMR (400 MHz, DMSO-d6): δ 10.53 (s, 1H), 7.68 (s, 4H), 7.03-7.23 (m, 10H), 4.85 (s, 2H), 3.67 (s, 2H), 2.64-2.77 (m, 2H), 2.19-2.36 (m, 3H), 1.23 (s, 1H), 0.30 (m, 2H), 0.07 (m, 2H).

Example 23

N-(6-(2-(1H-tetrazol-5-yl)phenyl)-2-(benzyl(propyl)amino) pyrimidin-4-yl)-2-(p-tolyl)acetamide

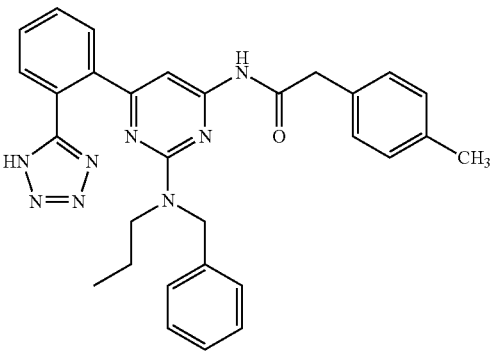 [SMILES: CCCN(Cc1ccccc1)c1nc(NC(=O)Cc2ccc(C)cc2)cc(-c2ccccc2-c2nnn[nH]2)n1]

Example 23 was prepared following the procedure for Example 22 utilizing N benzylpropan-1-amine. LC-MS Anal. Calc'd for $C_{30}H_{30}N_8O$ 518.25, found [M+H] 519.2. $T_r$=2.36 min (Method U). $^1$H NMR (300 MHz, DMSO-$d_6$): δ 10.55 (s, 1H), 7.00-7.82 (m, 14H), 4.49-5.01 (m, 2H), 3.69 (s, 2H), 2.75-3.07 (m, 2H), 2.27 (s, 3H), 1.08-1.41 (m, 2H), 0.69 (brs, 3H).

Example 24

2-(6-(benzyl(propyl)amino)-4-(3-(p-tolyl)ureido) pyridin-2-yl)-N-(methylsulfonyl)benzamide

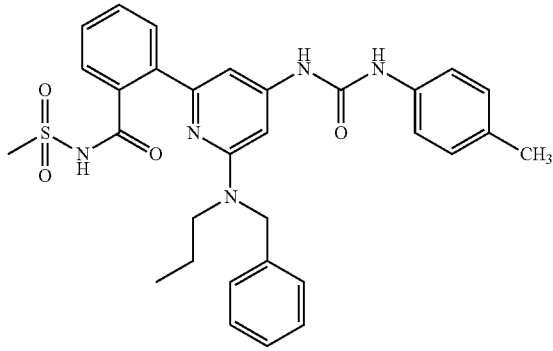

Example 24 was prepared following the procedure for Example 18 utilizing methanesulfonamide. LC-MS Anal. Calc'd for $C_{31}H_{33}N_5O_4S$ 571.22, found [M+H] 572.2. $T_r$=2.72 min (Method U). $^1$H NMR (400 MHz, DMSO-$d_6$) δ 12.06 (s, 1H), 8.64 (s, 1H), 8.85 (s, 1H), 7.52-7.65 (m, 3H), 7.48 (s, 2H), 7.15-7.37 (m, 8H), 6.93-7.12 (m, 1H), 6.62 (s, 1H), 4.77 (s, 2H), 3.49 (s, 2H), 3.23 (s, 3H), 2.28-2.42 (m, 3H), 1.55 (q, J=7.65 Hz, 2H), 0.86 (t, J=7.37 Hz, 3H).

Example 25

2-(6-(benzyl(propyl)amino)-4-(2-(p-tolyl)acetamido) pyridin-2-yl)-N-((4-methylpiperazin-1-yl)sulfonyl) benzamide

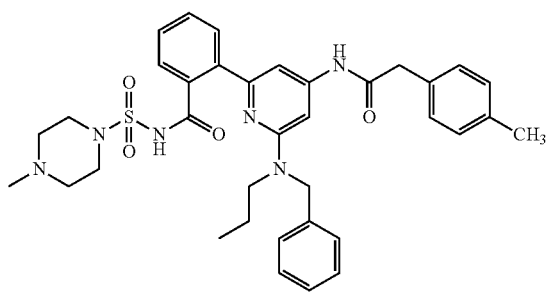

Example 25 was prepared following the procedure for Example 19 utilizing 4-methylpiperazine-1-sulfonamide. LC-MS Anal. Calc'd for $C_{36}H_{42}N_6O_4S$ 654.29, found [M+H] 655.2. $T_r$=2.72 min (Method U). $^1$H NMR (300 MHz, DMSO-$d_6$) δ 11.44 (s, 1H), 10.24 (s, 1H), 7.40-7.53 (m, 4H), 7.05-7.29 (m, 10H), 6.84 (s, 1H), 4.77 (s, 2H), 3.59 (s, 2H), 3.16 (s, 4H), 2.11-2.33 (m, 11H), 1.51 (d, J=7.84 Hz, 2H), 0.84 (t, J=7.34 Hz, 3H).

Example 26

1-(2-(benzyl(propyl)amino)-6-(5-methyl-2-(5-oxo-4, 5-dihydro-1,2,4-oxadiazol-3-yl)phenyl)pyridin-4-yl)-3-(p-tolyl)urea

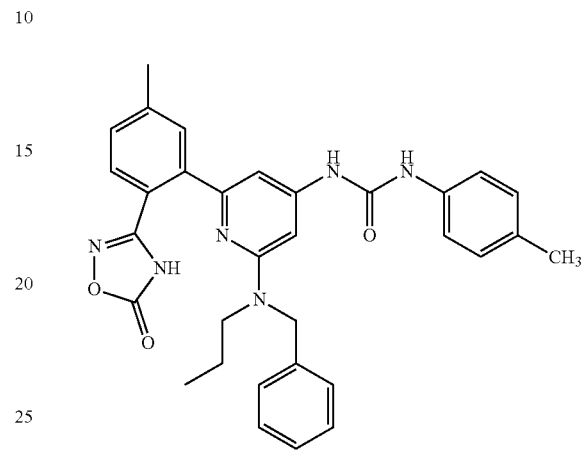

Example 26 was prepared following the procedure for Example 12 by utilizing (E)-2-(6-(benzyl(propyl)amino)-4-(3-(p-tolyl)ureido)pyridin-2-yl)-N'-hydroxy-4-methylbenzimidamide. LC-MS Anal. Calc'd for $C_{32}H_{32}N_6O_3$ 548.25, found [M+H] 549.2. $T_r$=3.45 min (Method U). $^1$H NMR (400 MHz, DMSO-$d_6$) δ 12.18 (s, 1H), 8.83 (s, 1H), 8.63 (s, 1H), 7.43-7.57 (m, 2H), 7.13-7.40 (m, 10H), 6.99-7.10 (m, 1H), 6.59 (s, 1H), 4.55 (s, 2H), 3.44 (s, 2H), 2.62-2.72 (m, 3H), 2.14-2.45 (m, 3H), 1.50 (s, 2H), 0.83 (d, J=14.68 Hz, 3H).

Example 27

2-(6-(benzyl (propyl) amino)-4-(3-(p-tolyl) ureido) pyridin-2-yl) benzene sulfonamide

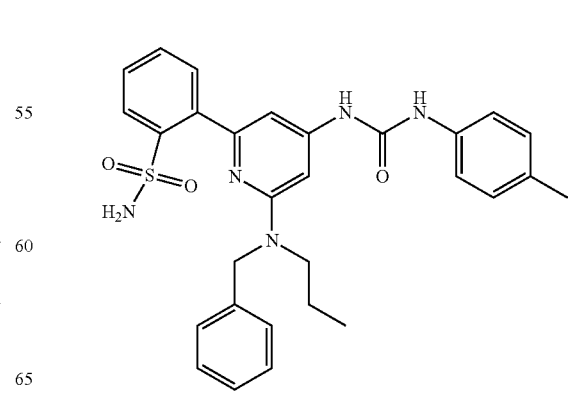

27A. N-benzyl-6-bromo-4-nitro-N-propylpyridin-2-amine

To a stirred solution of 2,6-dibromo-4-nitropyridine (3.0 g, 10.64 mmol), N-benzylpropan-1-amine (4.76 g, 31.9 mmol) in dioxane (4.0 mL) was heated to 100° C. and maintained for 3 h. The reaction mixture concentrated under reduced pressure. The residue was partitioned between 1N HCl (150 ml) and Ethyl acetate (300 ml). The organic layer was separated, dried over $Na_2SO_4$ and concentrated under reduced pressure to get 27A (orange liquid, 2.4 g, 6.85 mmol, 64% yield). LC-MS Anal. Calc'd for $C_{15}H_{16}BrN_3O_2$ 350.2, found [M+H] 351.0. $T_r$=3.92 min (Method U).

27B. 2-(6-(benzyl (propyl) amino)-4-nitropyridin-2-yl)-N-(tert-butyl) benzene sulfonamide Compound 27B was prepared following the procedure for 8C by utilizing 27A. LC-MS Anal. Calc'd for $C_{25}H_{30}N_4O_4S$ 482.5, found [M+H] 483.5. $T_r$=3.9 min (Method U).

27C. 2-(4-amino-6-(benzyl (propyl) amino) pyridin-2-yl)-N-(tert-butyl) benzene sulfonamide To a stirred solution of 27B (0.100 g, 0.207 mmol) in ethanol (2.5 mL) and water (0.5 mL), ammonium chloride (0.055 g, 1.036 mmol) was added and stirred for 10 min at RT. Zinc (0.095 g, 1.450 mmol) powder was added to the solution at 0° C. and slowly brought to RT. The reaction mixture was maintained at same temperature for 3 h, then was diluted with DCM (20 mL), washed with water (5 mL), brine (5 mL), dried over $Na_2SO_4$ and concentrated under reduced pressure. Purification via flash chromatography gave 27C (orange semi solid, 80 mg, 0.177 mmol, 85% yield). LC-MS Anal. Calc'd for $C_{25}H_{32}N_4O_2S$ 452.6, found [M+H] 453.7. $T_r$=3.59 min (Method U).

27D. 2-(6-(benzyl (propyl) amino)-4-(3-(p-tolyl) ureido) pyridin-2-yl)-N-(tert-butyl) benzene sulfonamide Compound 27D was prepared following the procedure for 2B by utilizing 27C. LC-MS Anal. Calc'd for $C_{33}H_{39}N_5O_3S$ 585.8, found [M+H] 587.2. $T_r$=4.08 min (Method U).

Example 27

To a stirred solution of 27D (0.090 g, 0.154 mmol) in dry DCM (2.0 mL), under nitrogen atmosphere TFA (0.059 mL, 0.768 mmol) was added at RT. The reaction mixture was heated to 65° C. and maintained for 48 h, then was cooled to RT. The solvent was removed under reduced pressure. Preparative HPLC gave Example-27 (off-white solid, 41 mg, 0.063 mmol, 41% yield). LC-MS Analysis 1. Calc'd for $C_{29}H_{31}N_5O_3S$, 529.6 found [M+H] 531.2. $T_r$=3.3 min (Method U). $^1$H NMR (300 MHz, DMSO-$d_6$) δ 9.32-8.57 (m, 2H), 8.08-7.93 (m, 1H), 7.69 (m, 3H), 7.41-7.19 (m, 9H), 7.08 (d, J=8.1 Hz, 3H), 6.84 (s, 1H), 4.77 (m, 2H), 3.44 (m, 2H), 2.24 (s, 3H), 1.61 (m, 2H), 0.85 (t, J=6.99 Hz, 3H).

Example 28

N-(2-(benzyl (propyl) amino)-6-(2-(5-oxo-2,5-dihydro-1,2,4-oxadiazol-3-yl)phenyl)pyridin-4-yl)-2-(p-tolyl)acetamide

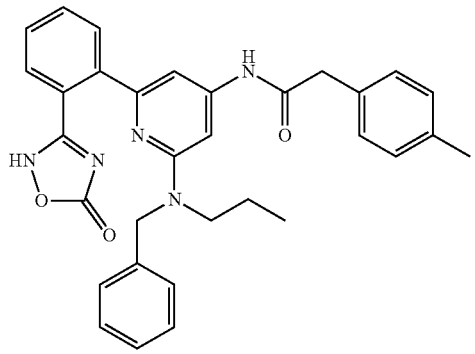 [SMILES: CCCN(Cc1ccccc1)c1cc(NC(=O)Cc2ccc(C)cc2)cc(-c2ccccc2-c2nc(=O)o[nH]2)n1]

28A. 2-(6-(benzyl (propyl) amino)-4-nitropyridin-2-yl) benzonitrile

Example 28A was prepared following the procedure for 12B by utilizing 27A and (2-cyanophenyl) boronic acid. LC-MS Anal. Calc'd for $C_{22}H_{20}N_4O_2$ 372.4, found [M+H] 373.2. $T_r$=1.18 min (Method R).

28B. 2-(4-amino-6-(benzyl (propyl) amino) pyridin-2-yl) benzonitrile

To a stirred solution of 28A (0.850 g, 2.282 mmol) in Acetic Acid (8.5 mL), iron powder (0.637 g, 11.41 mmol) was added at 0° C. The reaction mixture stirred at RT for 3 h, then was filtered through celite bed and washed with DCM (20 mL). The organic layer was washed with water, brine, dried over sodium sulfate, and concentrated under reduced pressure. Purification via flash chromatography gave 28B (light yellow liquid, 650 mg, 1.898 mmol, 83% yield). LC-MS Anal. Calc'd for $C_{22}H_{22}N_4$ 342.4, found [M+H] 343.2. $T_r$=0.79 min (Method R).

28C. N-(2-(benzyl (propyl) amino)-6-(2-cyanophenyl) pyridin-4-yl)-2-(p-tolyl) acetamide Compound 28C was prepared following the procedure for Example 1 by utilizing 28B and 2-(p-tolyl) acetic acid. LC-MS Anal. Calc'd for $C_{31}H_{30}N_4O$ 474.5, found [M+H] 475.3. T-=1.37 min (Method T).

28D. (Z)—N-(2-(benzyl (propyl) amino)-6-(2-(N'-hydroxycarbamimidoyl) phenyl) pyridin-4-yl)-2-(p-tolyl) acetamide Compound 28D was prepared following the procedure for 12E by utilizing 28C. LC-MS Anal. Calc'd for $C_{31}H_{33}N_5O_2$ 507.6, found [M+H] 508.3. $T_r$=1.20 min (Method T).

Example 28

Example 28 was prepared following the procedure for Example 12 by utilizing 28D. LC-MS Anal. Calc'd for $C_{32}H_{31}N_5O_3$, 533.6 found [M−H] 532.2. $T_r$=3.30 min (Method U). ¹H NMR (400 MHz, DMSO-d$_6$) δ 10.31 (s, 1H), 7.72-7.50 (m, 4H), 7.25 (d, J=7.53 Hz, 2H), 7.22-7.07 (m, 8H), 6.85 (s, 1H), 4.61 (s, 2H), 3.58 (s, 2H), 3.28 (m, 2H), 2.25 (s, 3H), 1.43 (m, 2H), 0.78 (t, J=7.53 Hz, 3H).

Example 29

2-(6-(benzyl (propyl) amino)-4-(3-(p-tolyl) ureido) pyridin-2-yl) benzamide

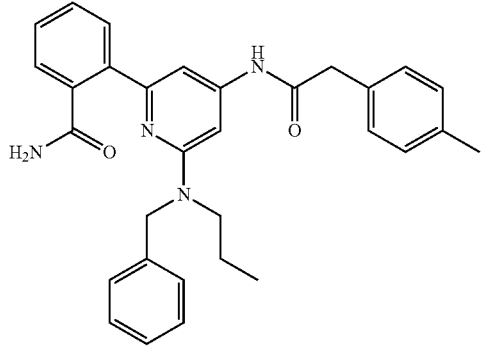 [SMILES: CCCN(Cc1ccccc1)c1cc(NC(=O)Cc2ccc(C)cc2)cc(-c2ccccc2C(N)=O)n1]

Example 29 was obtained as by product during synthesis of 28D. Preparative HPLC gave Example 29. LC-MS Anal. Calc'd for C$_{31}$H$_{32}$N$_4$O$_2$, 492.61 found [M+H] 494.2. T$_r$=3.21 min (Method N). ¹H NMR (400 MHz, DMSO-d$_6$) δ 10.24 (s, 1H), 7.58 (s, 1H), 7.45-7.39 (m, 4H), 7.35-7.10 (m, 10H), 7.04 (d, J=1.2 Hz, 1H),), 6.89 (d, J=8.00 Hz, 1H), 4.76 (s, 2H), 3.58 (s, 2H), 3.39-3.30 (m, 2H), 2.27 (s, 3H), 1.58-1.52 (m, 2H), 0.85 (t, J=7.20 Hz, 3H).

Example 30

N-(2-(benzyl (isobutyl) amino)-6-(2-(5-oxo-2,5-dihydro-1,2,4-oxadiazol-3-yl)phenyl)pyridin-4-yl)-2-(p-tolyl)acetamide

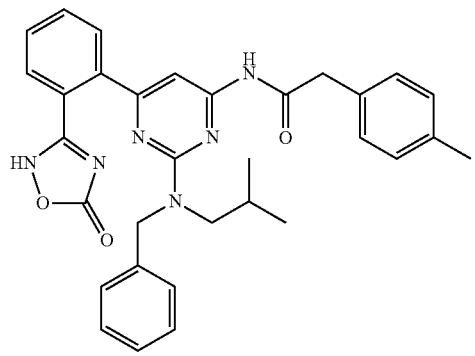 [SMILES: Cc1ccc(CC(=O)Nc2cc(-c3ccccc3-c3nc(=O)o[nH]3)nc(N(Cc3ccccc3)CC(C)C)n2)cc1]

Example 30 was prepared following the procedure for Example 28 by using N-benzyl-2-methylpropan-1-amine. Preparative HPLC gave Example 30. LC-MS Anal. Calc'd for C$_{32}$H$_{32}$N$_6$O$_3$, 548.6 found [M+H] 550.2. T$_r$=3.43 min (Method U). ¹H NMR (400 MHz, DMSO-d$_6$) δ 12.36 (s, 1H), 10.57 (s, 1H), 7.76-7.69 (m, 2H), 7.65-7.60 (m, 2H), 7.60-7.56 (m, 1H), 7.38-7.28 (m, 2H), 7.19 (s, 5H), 7.13 (s, 2H), 4.98-4.81 (brs, 2H), 3.30-3.15 (m, 2H), 3.68 (s, 2H), 3.21-3.1 (m, 2H), 2.27 (s, 3H), 2.054-1.87 (m, 1H), 0.80 (brs, 6H).

Example 31

1-(2-(benzyl (propyl) amino)-6-(2-(5-oxo-4,5-dihydro-1,2,4-oxadiazol-3-yl) phenyl)pyridin-4-yl)-3-(p-tolyl) urea

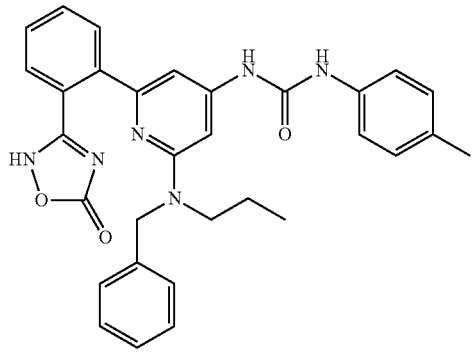 [SMILES: CCCN(Cc1ccccc1)c1cc(NC(=O)Nc2ccc(C)cc2)cc(-c2ccccc2-c2nc(=O)o[nH]2)n1]

31A. 1-(2-(benzyl (propyl) amino)-6-(2-cyanophenyl) pyridin-4-yl)-3-(p-tolyl) urea To a stirred solution of 28B (0.350 g, 1.022 mmol) in THF (3.0 mL), 1-isocyanato-4-methylbenzene (0.163 g, 1.227 mmol) was added at RT. The reaction mixture was heated to 55° C. and maintained for 2 h, then was concentrated completely under reduced pressure. Purification via flash chromatography gave example 31. LC-MS Anal. Calc'd for C$_{30}$H$_{29}$N$_5$O 475.2 found [M+H] 476.2. T$_r$=3.8 min (Method U).

31B. (Z)-2-(6-(benzyl (propyl) amino)-4-(3-(p-tolyl) ureido) pyridin-2-yl)-N'-hydroxy benzimidamide Compound 31B was prepared following the procedure for 12E by using 31A. LC-MS Anal. Calc'd for C$_{30}$H$_{32}$N$_6$O$_2$ 508.2, found [M+H] 509.2 T$_r$=1.19 min (Method T).

Example 31

Example 31 was prepared following the procedure for Example 28 by using 31B. LC-MS Analysis 1. Calc'd for C$_{31}$H$_{30}$N$_6$O$_3$, 534.2 found [M+H] 535.2. T$_r$=3.29 min (Method U). ¹H NMR (400 MHz, DMSO-d$_6$) δ 12.25 (brs, 1H), 8.84 (s, 1H), 8.64 (s, 1H), 7.74-7.66 (m, 4H), 7.70-7.60 (m, 4H), 7.35-7.26 (m, 3H), 7.25-7.15 (m, 2H), 7.11-6.90 (m, 1H), 6.62 (s, 1H), 4.64 (s, 2H), 3.30-3.15 (m, 2H) 2.23 (s, 3H), 1.52-1.546 (m, 2H), 0.82 (t, J=7.20 Hz, 3H).

Example 32

N-((2-(6-(benzyl (propyl) amino)-4-(3-(p-tolyl) ureido) pyridin-2-yl)phenyl)sulfonyl) benzamide

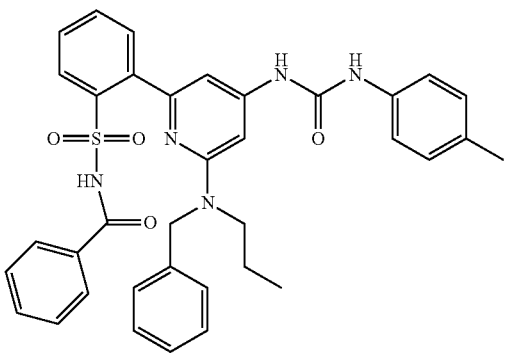 [SMILES: CCCN(Cc1ccccc1)c1cc(NC(=O)Nc2ccc(C)cc2)cc(-c2ccccc2S(=O)(=O)NC(=O)c2ccccc2)n1]

To a stirred solution of Example 27 (0.080 g, 0.124 mmol) in DCM (2.0 mL) at 0° C., TEA (0.035 mL, 0.249 mmol) followed by benzoyl chloride (0.017 g, 0.124 mmol) was added. The reaction mixture was stirred at RT overnight, then was diluted with DCM (200 mL), washed with 10% NaHCO$_3$ solution, brine, dried over Na$_2$SO$_4$, and concentrated under reduced pressure. Preparative HPLC gave Example 32 (off-white solid, 31 mg, 0.055 mmol, 31% yield). LC-MS Anal. Calc'd for C$_{36}$H$_{35}$N$_5$O$_4$S, 633.8 found [M+H] 635.2. T$_r$=3.21 min (Method U). $^1$H NMR (400 MHz, DMSO-d$_6$) δ 7.99-7.94 (m, 1H), 7.75 (m, 2H), 7.64 (m, 1H), 7.44 (m, 2H), 7.32-7.22 (m, 11H), 7.31 (d, J=6.0 Hz, 3H), 4.72-4.43 (m, 2H), 3.38 (m, 2H), 2.24 (s, 3H), 1.52 (m, 2H), 0.85 (m, 3H).

Example 33

N-(2-(benzyl (propyl) amino)-6-(2-sulfamoylphenyl) pyridin-4-yl)-2-(p-tolyl) acetamide

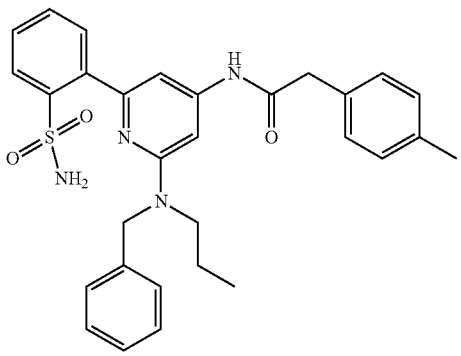 [SMILES: CCCN(Cc1ccccc1)c1cc(NC(=O)Cc2ccc(C)cc2)cc(-c2ccccc2S(N)(=O)=O)n1]

33A. N-(2-(benzyl (propyl) amino)-6-(2-(N-(tert-butyl) sulfamoyl) phenyl) pyridin-4-yl)-2-(p-tolyl) acetamide Compound 33A was prepared following the procedure for Example 1 by using 27C. LC-MS Anal. Calc'd for C$_{34}$H$_{40}$N$_4$O$_3$S, 584.7 found [M+H] 585.6. T$_r$=1.36 min (Method R).

Example 33 was prepared following the procedure for Example 27 by using 33A. LC-MS Anal. Calc'd for C$_{30}$H$_{32}$N$_4$O$_3$S, 528.6 found [M+H] 529.2. T$_r$=3.34 min (Method N). $^1$H NMR (400 MHz, DMSO-d$_6$) δ 8.02-7.96 (m, 1H), 7.80-7.30 (m, 4H), 7.28-7.05 (m, 11H), 6.90 (s, 1H), 4.79 (brs, 2H), 3.68-3.45 (m, 2H), 3.43-3.33 (m, 2H), 2.27 (s, 3H), 1.62-1.56 (m, 2H), 0.84 (t, J=7.2 Hz, 3H).

Example 34

N-(2-(2-(N-acetylsulfamoyl) phenyl)-6-(benzyl(propyl)amino) pyridin-4-yl)-2-(p-tolyl) acetamide

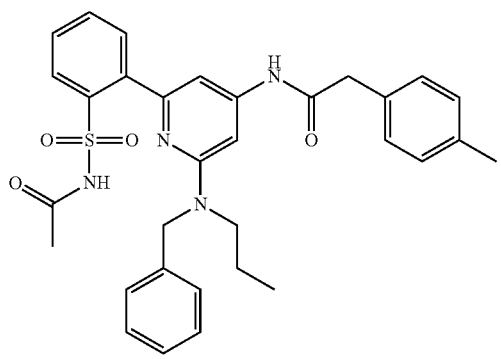 [SMILES: CCCN(Cc1ccccc1)c1cc(NC(=O)Cc2ccc(C)cc2)cc(-c2ccccc2S(=O)(=O)NC(C)=O)n1]

To a stirred solution of Example 33 in pyridine (0.5 mL), DMAP (1.426 mg, 0.012 mmol, acetic anhydride (6.61 μl, 0.070 mmol) was added at RT. The reaction was stirred for overnight, then was diluted with DCM, and washed with 10% bicarbonate solution. The organic layer was dried over sodium sulfate concentrated to yield off-white solid. Preparative HPLC gave Example 34 (off-white solid, 12.5 mg, 0.021 mmol, 55% yield) LC-MS Analysis 1. Calc'd for C$_{32}$H$_{34}$N$_4$O$_4$S, 570.7 found [M+H] 572.2. T$_r$=3.60 min (Method N). $^1$H NMR (300 MHz, DMSO-d$_6$) δ 11.70 (brs, 1H), 10.37 (brs, 1H), 8.05 (m, 1H), 7.72 (m, 2H), 7.39-7.05 (m, 11H), 6.88 (s, 1H), 4.74 (m, 2H), 3.37 (brs, 2H), 2.27 (s, 3H), 1.80 (s, 3H), 1.57 (m, 2H), 0.84 (t, J=7.55 Hz, 3H). (Note: one multiplet CH$_2$ buried under solvent peak).

Example 35

N-((2-(6-(benzyl (propyl)amino)-4-(3-(p-tolyl) ureido)pyridin-2-yl) phenyl)sulfonyl) acetamide

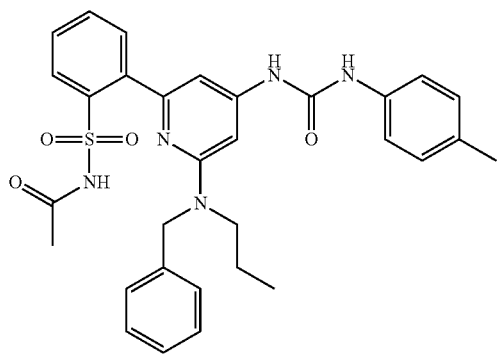 [SMILES: CCCN(Cc1ccccc1)c1cc(NC(=O)Nc2ccc(C)cc2)cc(-c2ccccc2S(=O)(=O)NC(C)=O)n1]

To a stirred solution of Example 27 (0.080 g, 0.124 mmol) in DCM (2.0 mL) at 0° C., TEA (0.035 mL, 0.249 mmol) followed by acetyl chloride (0.01060 mL, 0.149 mmol) was added. The reaction mixture was stirred overnight, then was diluted with DCM, and washed with 10% sodium bicarbonate solution. The organic layer was dried over sodium sulfate and concentrated under reduced pressure to get crude compound. Preparative HPLC gave Example 35 (Off-white solid, 33 mg, 0.057 mmol, 46% yield). LC-MS Analysis. Calc'd for $C_{31}H_{33}N_5O_4S$, 571.7 found [M+H] 573.2. $T_r$=2.95 min (Method U). $^1$H NMR (400 MHz, DMSO-$d_6$) δ 11.6 (s, 1H), 8.78 (s, 1H), 8.65 (s, 1H), 8.01-7.99 (d, J=7.18 Hz, 1H), 7.69-7.50 (m, 2H), 7.37 (d, J=7.18 Hz, 1H), 7.28-7.20 (m, 7H), 7.08 (d, J=8.00 Hz, 2H), 6.83 (s, 1H), 6.71 (s, 1H), 4.74 (s, 2H), 3.40-3.29 (m, 2H), 2.23 (s, 3H), 1.76 (s, 3H), 1.46-1.61 (m, 2H), 0.81 (t, J=7.37 Hz, 3H).

Example 36

1-(2-(2-(1H-tetrazol-5-yl)phenyl)-6-(benzyl(propyl) amino) pyridin-4-yl)-3-(2-(trifluoromethyl)phenyl) urea

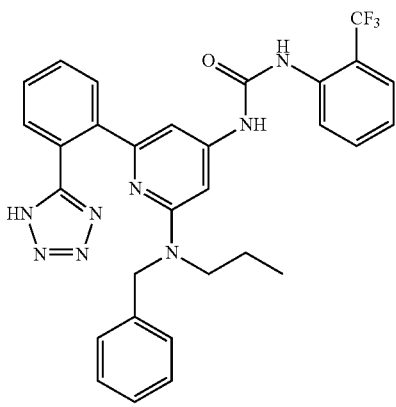 [SMILES: CCCN(Cc1ccccc1)c1cc(NC(=O)Nc2ccccc2C(F)(F)F)cc(-c2ccccc2-c2nnn[nH]2)n1]

36A. 6-(2-(1H-tetrazol-5-yl) phenyl)-N-benzyl-4-nitro-N-propylpyridin-2-amine

Compound 36A was prepared following the procedure for 8C by utilizing 27A and 5-(2-(4,4,5,5-tetramethyl-1,3,2-dioxaborolan-2-yl)phenyl)-1H-tetrazole. LC-MS Anal. Calc'd for $C_{22}H_{21}N_7O_2$ 415.4, found [M+H] 416.2. $T_r$=0.96 min (Method T). 36B. 6-(2-(1H-tetrazol-5-yl) phenyl)-N2-benzyl-N2-propylpyridine-2,4-diamine Compound 36B was prepared following the procedure for 1C by utilizing 36A. LC-MS Anal. Calc'd for $C_{22}H_{23}N_7$ 385.4, found [M+H] 386.2. $T_r$=0.76 min (Method R).

Example 36

Example 36 was prepared following the procedure for 2B by utilizing 1-isocyanato-2-(trifluoromethyl) benzene. LC-MS Anal. Calc'd for $C_{30}H_{27}F_3N_8O$, 572.5 found [M+H] 573.2. $T_r$=2.5 min (Method N). $^1$H NMR (400 MHz, DMSO-$d_6$) δ 9.33 (s, 1H), 8.18 (s, 1H), 7.82-7.76 (m, 7H), 7.29 (m, 3H), 7.25-7.13 (m, 3H), 6.80-6.71 (m, 1H), 6.42-6.55 (m, 1H), 4.56 (s, 2H), 3.25-3.15 (m, 2H), 1.49-1.38 (m, 2H), 0.80 (m, 3H).

Example 37

1-(2-(2-(1H-tetrazol-5-yl)phenyl)-6-(benzyl(propyl) amino) pyridin-4-yl)-3-(6-methyl-pyridazin-3-yl) urea

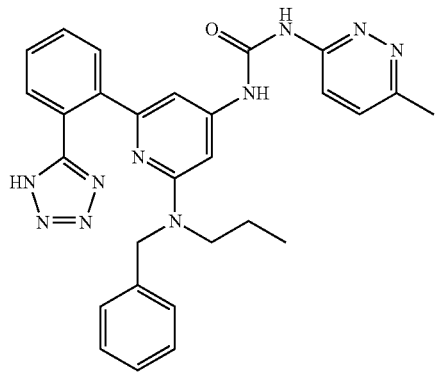 [SMILES: CCCN(Cc1ccccc1)c1cc(NC(=O)Nc2ccc(C)nn2)cc(-c2ccccc2-c2nnn[nH]2)n1]

To a stirred solution of 36B (0.050 g, 0.130 mmol), 6-methylpyridazin-3-amine (0.021 g, 0.195 mmol), in dry DCE (2.0 mL), CDI (0.063 g, 0.389 mmol) was added at RT. The reaction mixture heated to 70° C. and maintained overnight, then was diluted with DCM, and washed with 10% sodium bicarbonate solution. The organic layer was dried over sodium sulfate and concentrated under reduced pressure to get crude compound. Preparative HPLC gave Example 37 (Off-white solid, 7.5 mg, 0.014 mmol, 12% yield) LC-MS Analysis. Calc'd for $C_{28}H_{28}N_{10}O$, 520.58 found [M+H] 521.5 $T_r$=1.9 min (Method U). $^1$H NMR (400 MHz, DMSO-$d_6$) δ 9.74-9.69 (m, 2H), 7.94 (d, J=9.2 Hz, 1H), 7.75-7.52 (m, 5H), 7.35-7.25 (m, 2H), 7.22 (t, J=7.2 Hz, 1H), 7.10 (d, J=7.28 Hz, 2H), 6.85 (s, 1H), 6.64 (m, 1H), 4.42 (brs, 2H), 3.08 (brs, 2H), 2.59-2.50 (m, 3H), 1.34 (m, 2H), 0.76 (t, J=7.28 Hz, 3H).

Example 38

2-(6-(benzyl (propyl) amino)-4-(3-(p-tolyl) ureido) pyridin-2-yl) benzamide

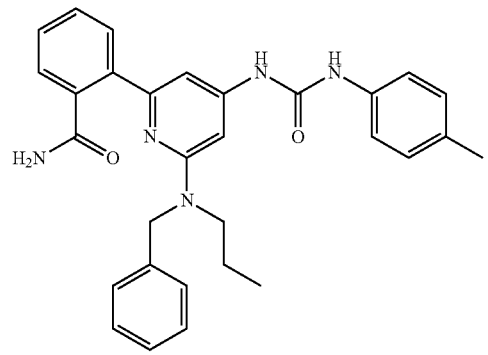 [SMILES: CCCN(Cc1ccccc1)c1cc(NC(=O)Nc2ccc(C)cc2)cc(-c2ccccc2C(N)=O)n1]

Example 38 was obtained as by product during synthesis of 31B. LC-MS Analysis Calc'd for $C_{30}H_{31}N_5O_2$, 493.59 found [M+H] 494.2. $T_r$=3.22 min (Method U). $^1$H NMR (400 MHz, DMSO-$d_6$) δ 8.80 (brs, 1H), 7.71-7.60 (m, 1H), 7.56-7.44 (m, 4H), 7.39-7.20 (m, 8H), 7.10-7.08 (d, J=8.4

Hz, 2H), 6.88-6.87 (m, 2H), 4.78 (s, 2H), 3.53-3.45 (m, 2H), 2.24 (s, 3H), 1.66-1.56 (m, 2H), 0.87 (t, J=7.6 Hz, 3H).

Example 39

6-(2-(1H-tetrazol-5-yl)phenyl)-N2-(4-fluorobenzyl)-N4-(4-fluorophenyl)-N2-isobutylpyridine-2,4-diamine

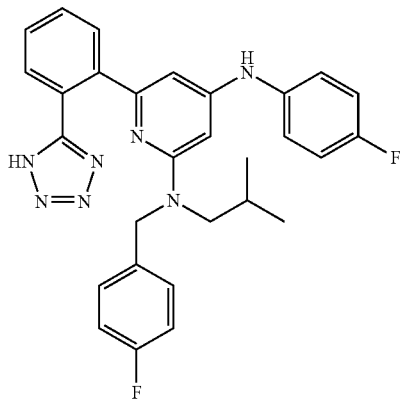 [SMILES: CC(C)CN(Cc1ccc(F)cc1)c1cc(Nc2ccc(F)cc2)cc(-c2ccccc2-c2nnn[nH]2)n1]

39A. N-(4-fluorobenzyl)-2-methylpropan-1-amine

To a stirred solution of 2-methylpropan-1-amine (5.89 g, 81 mmol) in THF (100 mL) and MeOH (100 mL) was added 4-fluorobenzaldehyde (10 g, 81 mmol) followed by 4 Å molecular sieves (3 g) at ambient temperature and stirred for 12 h. The reaction mixture was cooled to 0° C., added NaBH$_4$ (9.14 g, 242 mmol) portion wise and stirred at RT for 3 h. The solvent was removed completely under reduced pressure and the resultant semi solid was treated with 10% NaHCO$_3$ solution (100 mL), extracted with ethyl acetate (3×100 mL). The organic layer was washed with brine (100 mL), dried over Na$_2$SO$_4$ and concentrated under reduced pressure to afford the N-(4-fluorobenzyl)-2-methylpropan-1-amine (11 g, 60.7 mmol, 75% yield) as a light yellow oil which was carried for next step without further purification. LC-MS Anal. Calc'd for C$_{11}$H$_{16}$FN 181.127, found [M+H] 182.2, T$_r$=2.087 (Method U).

39B. 6-bromo-N-(4-fluorobenzyl)-N-isobutyl-4-nitropyridin-2-amine

To a sealable reaction flask containing 2,6-dibromo-4-nitropyridine (2 g, 7.09 mmol) was added 39A (1.929 g, 10.64 mmol) followed by dioxane (20 mL). The flask was sealed and the reaction was heated at 100° C. for 12 h. The mixture was cooled to RT. The reaction mixture was partitioned between ethyl acetate and water (20 mL). The layers were separated and the organic layer was washed with brine (20 mL), dried over anhydrous sodium sulfate, filtered and concentrated under reduced pressure to afford 39B (2.5 g, 4.64 mmol, 65.5% yield) as an orange colored semi solid. The solid compound was carried for next step without further purification. LC-MS Anal. Calc'd for C$_{16}$H$_{17}$BrFN$_3$O$_2$ 381.049, found [M+H] 382.0, T$_r$=4.011 min (Method U).

39C. 6-bromo-N2-(4-fluorobenzyl)-N2-isobutylpyridine-2,4-diamine

To a stirred solution of 39B (3 g, 7.85 mmol) in acetic acid (30 mL), was added iron powder (2.192 g, 39.2 mmol) and stirred at RT for 4 h. The reaction mixture was filtered through celite bed. The celite bed washed with excess of methanol (100 mL) and the solution was concentrated under reduced pressure. The residue was basified with aqueous saturated sodium bicarbonate solution (pH~8-9) and extracted with ethyl acetate (3×50 mL). Combined organic layers were dried over sodium sulfate, filtered and concentrated under reduced pressure to afford brown color solid. The solid was purified by silica gel column chromatography using pet ether/ethyl acetate (0-20%) as an eluant to afford 39C (2 g, 5.68 mmol, 72% yield) as a brown colored semi-solid. LC-MS Anal. Calc'd for C$_{16}$H$_{19}$BrFN$_3$ 351.075, found [M+H] 352.0, T$_r$=3.448 min (Method N).

39D. 6-(2-(1H-tetrazol-5-yl)phenyl)-N2-(4-fluorobenzyl)-N2-isobutylpyridine-2,4-diamine To a stirred solution of (2-(1H-tetrazol-5-yl)phenyl)boronic acid (0.475 g, 2.498 mmol), 39C (0.8 g, 2.271 mmol), K$_2$CO$_3$ (1.569 g, 11.36 mmol) in DMF (10 mL) and water (1 mL), nitrogen gas was bubbled for 10 mins. Pd(Ph3P)$_4$ (0.262 g, 0.227 mmol) was added to the reaction mixture and nitrogen gas was bubbled for 10 mins. The reaction mixture was heated at 98° C. for 6 h. The reaction mixture was cooled to RT and filtered through celite bed. The celite bed was washed with excess of methanol. The filtrate was concentrated under reduced pressure to afford brown color residue. The residue was purified by silica gel column chromatography using methanol in chloroform as an eluant to afford 39D (off-white solid, 0.45 g, 1.078 mmol, 47.5% yield). LC-MS Anal. Calc'd for C$_{23}$H$_{24}$FN$_7$ 417.208, found [M+H] 418.2, T$_r$=0.83 min (Method T).

Example 39

To a 100 mL sealed tube 39D (50 mg, 0.120 mmol), 1-bromo-4-fluorobenzene (20.96 mg, 0.120 mmol), Xantphos (17.32 mg, 0.030 mmol), sodium t-butoxide (34.5 mg, 0.359 mmol) in dioxane (5 mL) were added and the solution was purged with nitrogen gas for 10 mins. Bis(dibenzylideneacetone)palladium (6.89 mg, 0.012 mmol) was added and nitrogen gas was bubbled through the reaction mixture for 10 mins. The reaction mixture was heated at 100° C. for 6 h, then was cooled to RT and concentrated under reduced pressure. The residue so obtained was reconstituted in ethyl acetate (30 mL) and filtered through celite pad. The celite pad was washed with excess of ethyl acetate (50 mL) and concentrated under reduced pressure to afford brown color residue. The residue was purified by prep HPLC to afford Example 39 (off-white solid, 9 mg, 0.018 mmol, 14.69% yield). LC-MS Anal. Calc'd for C$_{29}$H$_{27}$F$_2$N$_7$ 511.230, found [M+H] 512.2, T$_r$=2.067 (Method O). $^1$H NMR (400 MHz, CD$_3$OD) δ 7.81-7.83 (m, 1H), 7.51-7.62 (m, 3H), 7.16-7.19 (m, 2H), 7.06-7.13 (m, 4H), 6.98-7.01 (m, 2H), δ 6.26 (d, J=2.00 Hz, 1H), 5.89 (d, J=2.00 Hz, 1H), 4.63 (s, 2H), 3.30 (d, J=7.60 Hz, 2H), 1.76 (s, 1H), 0.86-0.90 (m, 6H).

Examples 40-48 were prepared following the procedure for Example 39 using the corresponding halides.

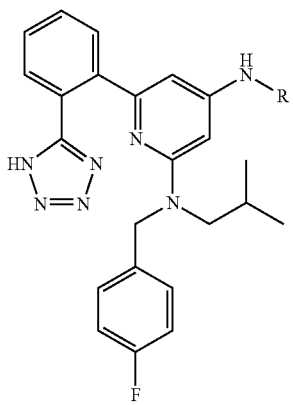

| Ex. No. | Name | R | $T_r$ (min) | [M + H]$^+$ |
|---|---|---|---|---|
| 40 | 6-(2-(1H-tetrazol-5-yl)phenyl)-N2-(4-fluorobenzyl)-N2-isobutyl-N4-(5-methylpyrimidin-2-yl)pyridine-2,4-diamine, TFA | | 2.422 (Method U) | 510.2 |
| 41 | 6-(2-(1H-tetrazol-5-yl)phenyl)-N2-(4-fluorobenzyl)-N2-isobutyl-N4-(6-methylpyridazin-3-yl)pyridine-2,4-diamine, TFA | | 1.988 (Method U) | 510.2 |
| 42 | 6-(2-(1H-tetrazol-5-yl)phenyl)-N2-(4-fluorobenzyl)-N2-isobutyl-N4-(pyrazolo[1,5-a]pyrimidin-5-yl)pyridine-2,4-diamine, TFA | | 2.217 (Method U) | 535.2 |
| 43 | 6-(2-(1H-tetrazol-5-yl)phenyl)-N4-(benzo[d]thiazol-2-yl)-N2-(4-fluorobenzyl)-N2-isobutylpyridine-2,4-diamine, TFA | | 3.449 (Method U) | 551.2 |
| 44 | 6-(2-(1H-tetrazol-5-yl)phenyl)-N2-(4-fluorobenzyl)-N4-(5-fluoropyrimidin-2-yl)-N2-isobutylpyridine-2,4-diamine, TFA | | 2.27 (Method O) | 514.2 |
| 45 | 6-(2-(1H-tetrazol-5-yl)phenyl)-N2-(4-fluorobenzyl)-N2-isobutyl-N4-(2-methylpyridin-3-yl)pyridine-2,4-diamine, TFA | | 1.879 (Method U) | 509.4 |
| 46 | 6-(2-(1H-tetrazol-5-yl)phenyl)-N4-(benzo[d][1,3]dioxol-5-yl)-N2-(4-fluorobenzyl)-N2-isobutylpyridine-2,4-diamine | | 2.326 (Method U) | 538.2 |

-continued

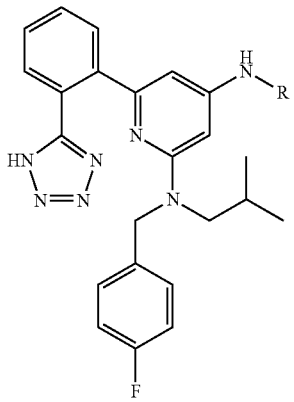

| Ex. No. | Name | R | $T_r$ (min) | $[M+H]^+$ |
|---|---|---|---|---|
| 47 | 6-(2-(1H-tetrazol-5-yl)phenyl)-N4-(6-(difluoromethyl)pyridin-2-yl)-N2-(4-fluorobenzyl)-N2-isobutylpyridine-2,4-diamine | 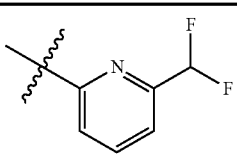 | 2.566 (Method U) | 545.2 |
| 48 | 6-(2-(1H-tetrazol-5-yl)phenyl)-N2-(4-fluorobenzyl)-N4-(5-fluoropyridin-2-yl)-N2-isobutylpyridine-2,4-diamine | 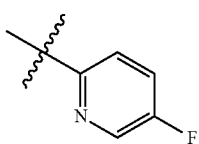 [SMILES: *c1ccc(F)cn1] | 1.994 (Method O) | 513.2 |

Example 49

6-(2-(1H-tetrazol-5-yl)phenyl)-N2-benzyl-N2-isobutyl-N4-(5-methylpyrazin-2-yl)pyridine-2,4-diamine, TFA

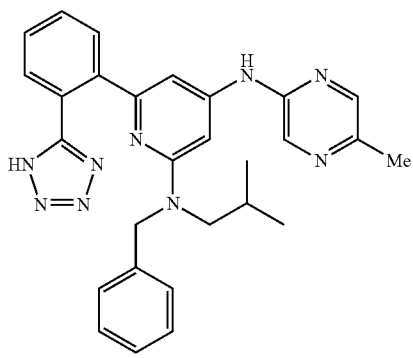 [SMILES: Cc1cnc(Nc2cc(-c3ccccc3-c3nnn[nH]3)nc(N(Cc3ccccc3)CC(C)C)c2)cn1]

49A. N-benzyl-2-methylpropan-1-amine

To a stirred solution of 2-methylpropan-1-amine (2.76 g, 37.7 mmol) in THF (15 mL) and MeOH (15 mL) was added benzaldehyde (4 g, 37.7 mmol) followed by 4 Å molecular sieves (3 g) at ambient temperature and stirred for overnight. The reaction mixture was cooled to 0° C. and NaBH$_4$ (4.28 g, 113 mmol) was added portion wise and the reaction was stirred at RT for 3 h. The solvent was removed under reduced pressure and the resultant semi solid was quenched with 10% NaHCO$_3$ solution (50 mL), extracted with ethyl acetate (3×50 mL). The organic layer was washed with brine (50 mL), dried over Na$_2$SO$_4$ and concentrated under reduced pressure to afford 49A (colorless oil, 4.2 g, 25.7 mmol, 68.3% yield) which was carried for next step without further purification. LC-MS Anal. Calc'd for $C_{11}H_{17}N$ 163.136, found [M+H] 164.4, $T_r$=1.701 min (Method U).

49B.
N-benzyl-6-bromo-N-isobutyl-4-nitropyridin-2-amine

To a sealable reaction flask containing 2,6-dibromo-4-nitropyridine (6 g, 21.28 mmol) was added 49A (10.42 g, 63.9 mmol) followed by dioxane (50 mL). The flask was sealed and the reaction was heated at 110° C. for 12 h. The mixture was cooled to RT, then was partitioned between ethyl acetate (50 mL) and water (50 mL). The layers were separated and the organic layer was washed with brine (50 mL), dried over anhydrous sodium sulfate, filtered and concentrated under reduced pressure to afford light yellow residue. The residue was purified by silica gel column chromatography using ethyl acetate in pet ether (0-10%) as an eluant to afford 49B (orange color semi solid, 4.8 g, 13.18 mmol, 61.9% yield). LC-MS Anal. Calc'd for $C_{16}H_{18}BrN_3O_2$ 363.058, found [M+H] 366.0, $T_r$=3.977 min (Method U).

49C.
N2-benzyl-6-bromo-N2-isobutylpyridine-2,4-diamine

To a stirred solution of 49B (4 g, 10.98 mmol) in acetic acid (30 mL) was added iron (3.07 g, 54.9 mmol) and stirred at RT for 4 h. The reaction mixture was filtered through celite bed, then was washed with methanol (100 mL). The filtrate was concentrated under reduced pressure. The residue so obtained was basified with aqueous saturated sodium bicarbonate solution (pH~8-9) and extracted with ethyl acetate (3×50 mL). Combined organic layers were dried over sodium sulfate, filtered and concentrated under reduced pressure to afford brown color solid. The solid was purified by silica gel column chromatography using ethyl acetate in pet ether (0-45%) to afford 49C (brown color semi-solid, 1.88 g, 5.17 mmol, 47% yield) as a. LC-MS Anal. Calc'd for $C_{16}H_{20}BrN_3$ 333.084, found [M+H] 334.2, $T_r$=3.577 (Method U).

49D. 6-(2-(1H-tetrazol-5-yl)phenyl)-N2-benzyl-N2-isobutylpyridine-2,4-diamine Through the solution of 5-(2-(4,4,5,5-tetramethyl-1,3,2-dioxaborolan-2-yl)phenyl)-1H-tetrazole (1.791 g, 6.58 mmol), 49C (2 g, 5.98 mmol), $K_2CO_3$ (4.13 g, 29.9 mmol) in DMF (20 mL) and water (2 mL), nitrogen gas was purged with for 10 mins. $Pd(Ph_3P)_4$ (0.691 g, 0.598 mmol) was added to the reaction mixture and the solution was purged with nitrogen gas for another 10 mins. The reaction mixture was heated at 98° C. for 6 h, then was cooled to RT and filtered through celite bed. The celite bed was rinsed with dichloromethane (100 mL). The filtrate was concentrated under reduced pressure to afford brown color residue which was purified by silica gel column chromatography using methanol in chloroform as an eluant (0-20%) to afford 49D (light yellow colored solid, 2.2 g, 5.51 mmol, 92% yield) as a. LC-MS Anal. Calc'd for $C_{23}H_{25}N_7$ 399.217, found [M+H] 400.2, $T_r$=2.61 min (Method U).

Example 49

To a 100 mL sealed tube 49D (54 mg, 0.135 mmol), 2-bromo-5-methylpyrazine (23.39 mg, 0.135 mmol), XantPhos (19.55 mg, 0.034 mmol), sodium t-butoxide (39.0 mg, 0.406 mmol) in dioxane (5 mL) were added and the resulting solution was purged with nitrogen gas for 10 mins. Bis (dibenzylideneacetone)palladium (7.77 mg, 0.014 mmol) was added to The reaction mixture and nitrogen gas was purged through the solution with for 10 mins. The reaction mixture was heated at 100° C. for 6 h. The reaction mixture was cooled to RT and reaction mixture was concentrated under reduced pressure. The residue was reconstituted in ethyl acetate (30 mL) and filtered through celite. The celite bed washed with ethyl acetate (50 mL) and filtrate was concentrated under reduced pressure to afford brown colored residue. The residue was purified by prep. Purification by preparative HPLC gave Example 49 (light yellow solid, 14 mg, 0.022 mmol, 16% yield). LC-MS Anal. Calc'd for $C_{28}H_{29}N_9$ 491.255, found [M+H] 492.4, $T_r$=2.095 (Method U). $^1$H NMR (400 MHz, $CD_3OD$) δ 8.16-8.20 (m, 2H), 7.96-8.04 (m, 2H), 7.72-7.80 (m, 2H), 7.59-7.61 (m, 1H), 7.31-7.39 (m, 2H), 7.26-7.29 (m, 3H), 6.74 (s, 1H), 4.83 (s, 2H), 3.48 (d, J=7.60 Hz, 2H), 2.49 (s, 3H), 1.99-2.06 (m, 1H), 0.96-0.98 (m, 6H).

Examples 50-57 were prepared following the procedure for Example 49 using the corresponding halides.

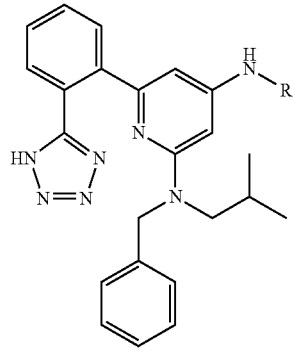

| Ex. No. | Name | R | $T_r$ (min) | [M + H]$^+$ |
|---|---|---|---|---|
| 50 | 6-(2-(1H-tetrazol-5-yl)phenyl)-N2-benzyl-N2-isobutyl-N4-(pyrazolo[1,5-a]pyrimidin-5-yl)pyridine-2,4-diamine | 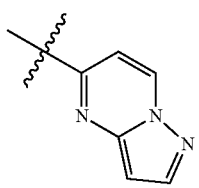 [SMILES: *c1ccn2nccc2n1] | 2.147 (Method U) | 517.2 |
| 51 | 6-(2-(1H-tetrazol-5-yl)phenyl)-N2-benzyl-N2-isobutyl-N4-(5-methylpyrimidin-2-yl)pyridine-2,4-diamine | 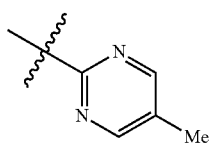 [SMILES: *c1ncc(C)cn1] | 2.318 (Method U) | 492.2 |

-continued

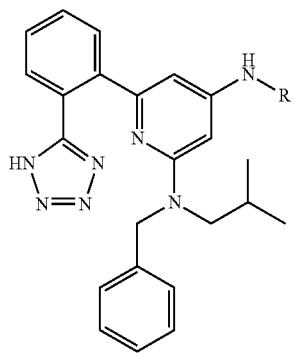

| Ex. No. | Name | R | $T_r$ (min) | $[M + H]^+$ |
|---|---|---|---|---|
| 52 | 6-(2-(1H-tetrazol-5-yl)phenyl)-N2-benzyl-N2-isobutyl-N4-(5-phenyl-1,3,4-thiadiazol-2-yl)pyridine-2,4-diamine | 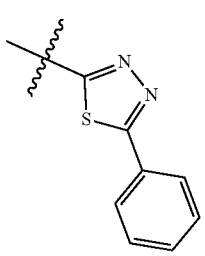 [SMILES: *c1nnc(-c2ccccc2)s1] | 3.13 (Method U) | 560.2 |
| 53 | 6-(2-(1H-tetrazol-5-yl)phenyl)-N2-benzyl-N2-isobutyl-N4-(4-morpholinopyrimidin-2-yl)pyridine-2,4-diamine, TFA | 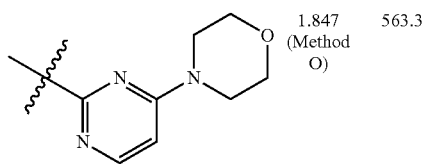 | 1.847 (Method O) | 563.3 |
| 54 | 6-(2-(1H-tetrazol-5-yl)phenyl)-N2-benzyl-N4-(2-fluoropyridin-3-yl)-N2-isobutylpyridine-2,4-diamine, TFA | 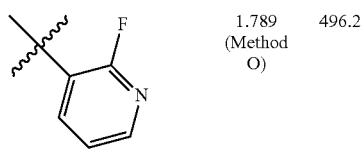 | 1.789 (Method O) | 496.2 |
| 55 | 6-(2-(1H-tetrazol-5-yl)phenyl)-N2-benzyl-N4-(5-fluoropyrimidin-2-yl)-N2-isobutylpyridine-2,4-diamine, 1.5 TFA | 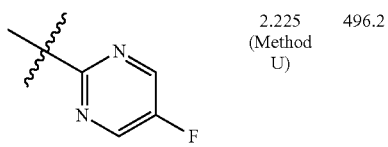 | 2.225 (Method U) | 496.2 |
| 56 | 6-(2-(1H-tetrazol-5-yl)phenyl)-N2-benzyl-N4-(2,4-difluorophenyl)-N2-isobutylpyridine-2,4-diamine | 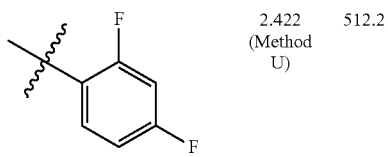 | 2.422 (Method U) | 512.2 |
| 57 | 6-(2-(1H-tetrazol-5-yl)phenyl)-N4-(benzo[d][1,3]dioxol-5-yl)-N2-benzyl-N2-isobutylpyridine-2,4-diamine | 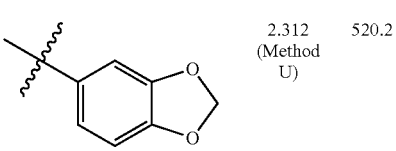 | 2.312 (Method U) | 520.2 |

Example 58

6-(2-(1H-tetrazol-5-yl)phenyl)-N2-benzyl-N4-(2-methylbenzo[d]thiazol-6-yl)-N2-propylpyridine-2,4-diamine

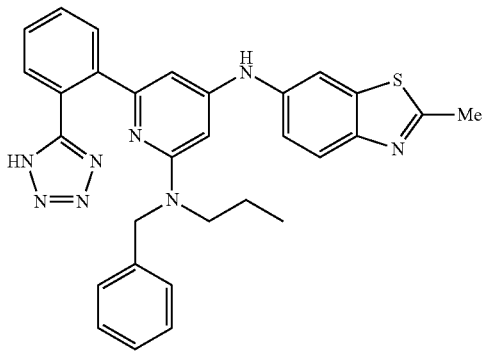 [SMILES: CCCN(Cc1ccccc1)c1cc(Nc2ccc3nc(C)sc3c2)cc(-c2ccccc2-c2nnn[nH]2)n1]

Example 58 was prepared using the steps described for synthesis of Example 39 by using 6-bromo-2-methylbenzo[d]thiazole. LC-MS Anal. Calc'd for $C_{30}H_{28}N_8S$ 532.216, found [M+H] 533.4, $T_r$=2.345 (Method U). $^1$H NMR (400 MHz, $CD_3OD$) δ 7.99-8.01 (m, 1H), 7.73-7.81 (m, 3H), 7.64-7.66 (m, 1H), 7.57 (d, J=2.00 Hz, 1H), 7.33-7.40 (m, 3H), 7.16-7.17 (m, 2H), 7.08-7.11 (m, 1H), 6.31 (d, J=2.00 Hz, 1H), 6.04 (d, J=2.40 Hz, 1H), 4.68 (s, 2H), 3.46-3.50 (m, 2H), 2.84 (s, 3H), 1.53-1.59 (m, 2H), 0.86 (t, J=14.64 Hz, 3H).

Examples 59-62 were prepared following the procedure for Example 39 using the corresponding halides.

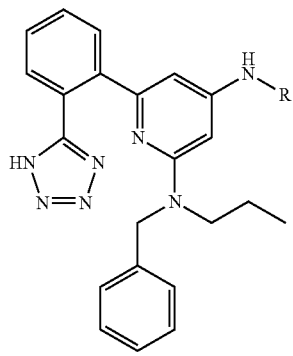

| Ex. No. | Name | R | $T_r$ (min) | [M + H]$^+$ |
|---|---|---|---|---|
| 59 | 6-(2-(1H-tetrazol-5-yl)phenyl)-N2-benzyl-N4-(4-phenylthiazol-2-yl)-N2-propylpyridine-2,4-diamine | 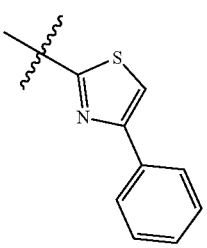 [SMILES: *c1nc(-c2ccccc2)cs1] | 3.111 (Method U) | 545.2 |

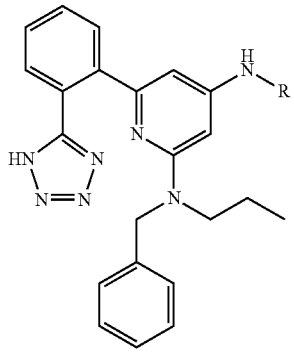

| Ex. No. | Name | R | $T_r$ (min) | $[M + H]^+$ |
|---|---|---|---|---|
| 60 | 6-(2-(1H-tetrazol-5-yl)phenyl)-N2-benzyl-N4-(5-methyl-1,3,4-thiadiazol-2-yl)-N2-propylpyridine-2,4-diamine | 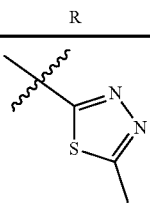 | 2.005 (Method U) | 484.2 |
| 61 | 6-(2-(1H-tetrazol-5-yl)phenyl)-N2-benzyl-N4-(1-methyl-1H-pyrazol-3-yl)-N2-propylpyridine-2,4-diamine | 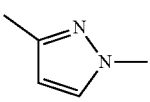 | 2.047 (Method U) | 466.4 |
| 62 | 6-(2-(1H-tetrazol-5-yl)phenyl)-N2-benzyl-N4-(6-fluorobenzo[d]thiazol-2-yl)-N2-propylpyridine-2,4-diamine | 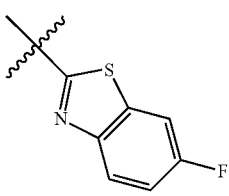 [SMILES: *c1nc2ccc(F)cc2s1] | 3.375 (Method U) | 537.2 |

Example 64

N-(6-(2-(1H-tetrazol-5-yl)phenyl)-2-((cyclopropylmethyl)(propyl)amino) pyrimidin-4-yl)-2-(p-tolyl)acetamide, TFA

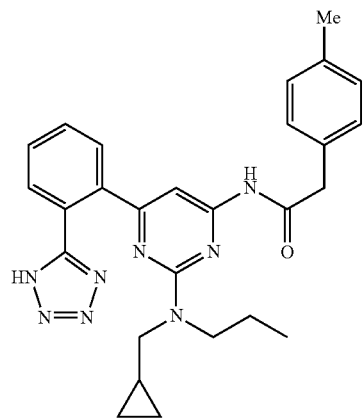 [SMILES: CCCN(CC1CC1)c1nc(NC(=O)Cc2ccc(C)cc2)cc(-c2ccccc2-c2nnn[nH]2)n1]

64A. 6-chloro-N2-(cyclopropylmethyl)-N2-propylpyrimidine-2,4-diamine

To sealable reaction flask containing 2,6-dichloropyrimidin-4-amine (1.5 g, 9.15 mmol) was added N-(cyclopropylmethyl)propan-1-amine (1.553 g, 13.72 mmol), DIPEA (7.99 mL, 45.7 mmol) followed by dioxane (10 mL). The flask was sealed and the reaction was heated at 80° C. for 12 h. The mixture was cooled to RT and partitioned between ethyl acetate (20 mL) and water (20 mL). The layers were separated and the organic layer was washed with brine, dried over anhydrous sodium sulfate, filtered and concentrated under reduced pressure to afford the crude product as light yellow oil. The light yellow oil was purified by silica gel column chromatography using ethyl acetate in pet ether (0-10%) to afford 64A (light yellow oil, 1.4 g, 5.82 mmol, 63% yield). LC-MS Anal. Calc'd for $C_{11}H_{17}ClN_4$ 240.114, found [M+H] 241.2. $T_r$=2.427 min (Method U).

64B. N2-(cyclopropylmethyl)-N2-propyl-6-(2-(1-trityl-1H-tetrazol-5-yl)phenyl)pyrimidine-2,4-diamine To a stirred solution of 5-(2-(4,4,5,5-tetramethyl-1,3,2-dioxaborolan-2-yl)phenyl)-1-trityl-1H-tetrazole (0.769 g, 1.495 mmol), 64A (0.3 g, 1.246 mmol), potassium phosphate, tribasic (0.794 g, 3.74 mmol) in dioxane (5 mL) was purged nitrogen gas for 10 mins. $PdCl_2(dppf)-CH_2Cl_2$ adduct (0.102 g, 0.125 mmol) was added to the reaction mixture and nitrogen gas was bubbled through the mixture for 10 mins. The reaction mixture was heated in microwave at 95° C. for 12 h. The reaction mixture was cooled to RT and concentrated under reduced pressure. The residue was reconstituted in ethyl acetate (30 mL) and water (30 mL), and the biphasic mixture was filtered through celite bed. The celite bed was washed with ethyl acetate (50 mL). The organic layer was dried over sodium sulfate, filtered and concentrated under reduced pressure. The crude material so obtained was purified by silica gel column chromatography using ethyl acetate in pet ether (0-50%) to afford 64B (500 mg, 0.845 mmol, 67.8% yield) as an off-white semi solid. LC-MS Anal. Calc'd for $C_{38}H_{37}N_7$ 591.311, found [M+H] 593.2.2. $T_r$=3.602 min (Method U).

64C. N-(2-((cyclopropylmethyl)(propyl)amino)-6-(2-(1-trityl-1H-tetrazol-5-yl)phenyl)pyrimidin-4-yl)-2-(p-tolyl)acetamide To stirred solution of 2-(p-tolyl)acetic acid (0.082 g, 0.548 mmol) in DMF (5 mL), was added DIPEA (0.368 mL, 2.109 mmol), 2,4,6-tripropyl-1,3,5,2,4,6-trioxatriphosphorinane-2,4,6-trioxide in ethyl acetate (0.805 g, 1.265 mmol) followed by addition of 64B (0.25 g, 0.422 mmol) and stirred at RT for 5 h. The reaction mixture was concentrated under reduced pressure to afford the brown colored semi solid. The solid compound was partitioned between ethyl acetate (30 mL) and water (30 mL). The organic layer was separated out, dried over sodium sulfate, filtered and concentrated under reduced pressure to afford 64C (0.15 g, 0.207 mmol, 49.1% yield) as a brown colored solid. LC-MS Anal. Calc'd for $C_{46}H_{44}N_8O$ 724.364, found [M+H] 725.2.2. $T_r$=4.577 min (Method U).

Example 64

To a stirred solution of 64C (150 mg, 0.058 mmol) in DCM (5 mL) at 0° C., TFA (0.089 mL, 1.159 mmol) was added dropwise to The reaction mixture and stirred for 10 mills. The reaction mixture was warmed to RT and stirred for 4 h. The reaction mixture was concentrated under reduced pressure to afford brown colored semi solid which was purified by Prep HPLC to afford Example 64 (off-white solid, 5.05 mg, 8.27 μmol, 14%). LC-MS Anal. Calc'd for $C_{27}H_{30}N_8O$ 482.254, found [M+H] 483.2.2. $T_r$=2.498 min (Method U). $^1$H NMR (400 MHz, DMSO-$d_6$) δ 10.50 (s, 1H), 7.64-7.70 (m, 4H), 7.40-7.41 (m, 1H), 7.09-7.21 (m, 4H), 6.96 (s, 1H), 3.68-3.71 (m, 4H), 2.92-3.06 (m, 2H), 2.27 (s, 3H), 1.39-1.43 (m, 2H), 0.67-0.86 (m, 4H), 0.18-0.45 (m, 4H).

Example 65

1-(6-(2-(1H-tetrazol-5-yl)phenyl)-2-((cyclopropylmethyl)(propyl)amino) pyrimidin-4-yl)-3-(4-fluorophenyl)urea, TFA

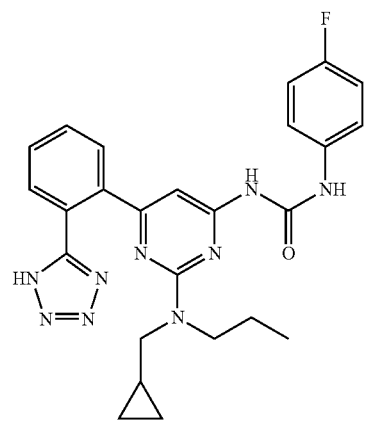 [SMILES: CCCN(CC1CC1)c1nc(NC(=O)Nc2ccc(F)cc2)cc(-c2ccccc2-c2nnn[nH]2)n1]

65A. 1-(2-((cyclopropylmethyl)(propyl)amino)-6-(2-(1-trityl-1H-tetrazol-5-yl)phenyl)pyrimidin-4-yl)-3-(4-fluorophenyl)urea To stirred solution of 64B (0.15 g, 0.253 mmol) in DCE (5 mL) was added 1-fluoro-4-isocyanatobenzene (0.042 g, 0.304 mmol) and stirred at 80° C. for 4 h. The reaction mixture was cooled to RT and concentrated under reduced pressure to afford 65A (0.16 g, 0.118 mmol, 46.8% yield) as a brown colored solid. The solid was carried for next step without further purification. LC-MS Anal. Calc'd for $C_{44}H_{40}FN_9O$ 729.334, found [M+H] 730.2. $T_r$=2.230 min (Method U).

Example 65

To a stirred solution of 65A (150 mg, 0.111 mmol) in DCM (5 mL) cooled at 0° C., TFA (0.171 mL, 2.220 mmol) was added dropwise and stirred for 10 mins. The reaction mixture was warmed to RT and stirred for 4 h. The reaction mixture was concentrated under reduced pressure to afford brown colored semi solid which was purified by Prep HPLC to afford Example 65 (18 mg, 0.030 mmol, 26.7%) as a white solid. LC-MS Anal. Calc'd for $C_{25}H_{26}FN_9O$ 487.224, found [M+H] 488.3. $T_r$=2.29 min (Method AT). $^1$H NMR (400 MHz, DMSO-$d_6$) δ 10.18 (s, 1H), 9.29 (s, 1H), 7.63-7.72 (m, 4H), 7.49-7.52 (m, 2H), 7.11-7.16 (m, 2H), 6.77 (s, 1H), 3.24-3.31 (m, 4H), 1.45-1.48 (m, 2H), 0.92-0.94 (m, 1H), 0.76-0.80 (m, 3H), 0.37-0.42 (m, 2H), 0.19-0.20 (m, 2H).

Example 66

1-(6-(2-(1H-tetrazol-5-yl)phenyl)-2-((cyclopropylmethyl)(propyl)amino)pyrimidin-4-yl)-3-(p-tolyl)urea, TFA

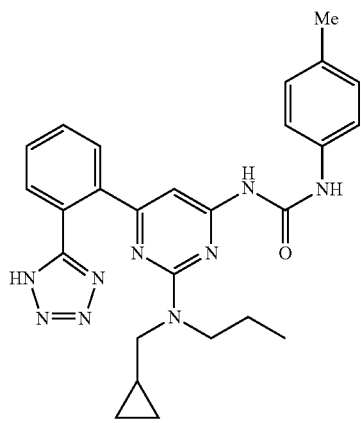 [SMILES: CCCN(CC1CC1)c1nc(NC(=O)Nc2ccc(C)cc2)cc(-c2ccccc2-c2nnn[nH]2)n1]

Example 66 was prepared as described in Example 65 utilizing 1-isocyanato-4-methylbenzene. LC-MS Anal. Calc'd for $C_{26}H_{29}N_9O$ 483.250, found [M+H] 484.2. $T_r$=2.399 min (Method U). $^1$H NMR (400 MHz, DMSO-d$_6$) δ 10.08 (s, 1H), 9.24 (s, 1H), 7.64-7.72 (m, 4H), 5.38 (m, 2H), 7.13 (d, J=7.60 Hz, 2H), 6.76 (s, 1H), 3.23-3.34 (m, 4H), 2.28 (s, 3H), 1.44-1.47 (m, 2H), 0.77-0.93 (m, 4H), 0.40-0.43 (m, 2H), 0.20-0.21 (m, 2H).

Example 67

1-(6-(2-(1H-tetrazol-5-yl)phenyl)-2-((cyclopropylmethyl)(propyl)amino)pyrimidin-4-yl)-3-(4-(trifluoromethoxy)phenyl)urea

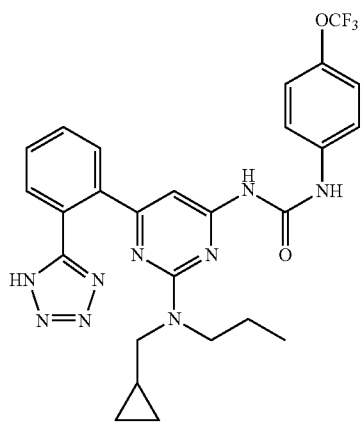 [SMILES: CCCN(CC1CC1)c1nc(NC(=O)Nc2ccc(OC(F)(F)F)cc2)cc(-c2ccccc2-c2nnn[nH]2)n1]

Example 67 was prepared as described in Example 65 by utilizing 1-isocyanato-4-(trifluoromethoxy) benzene. LC-MS Anal. Calc'd for $C_{26}H_{26}F_3N_9O_2$ 553.216, found [M+H] 554.2. $T_r$=2.644 min (Method U). $^1$H NMR (400 MHz, DMSO-d$_6$) δ 10.22 (s, 1H), 9.29 (s, 1H), 7.59-7.73 (m, 7H), 7.29 (d, J=8.40 Hz, 2H), 6.81 (s, 1H), 3.24-3.41 (m, 4H), 1.43-1.46 (m, 2H), 0.77-0.95 (m, 4H), 0.40-0.42 (m, 2H), 0.20-0.22 (m, 2H).

Example 68

N-(2-(2-(1H-tetrazol-5-yl)phenyl)-6-(3,4-dihydroquinolin-1(2H)-yl)pyridin-4-yl)-2-(p-tolyl)acetamide, TFA

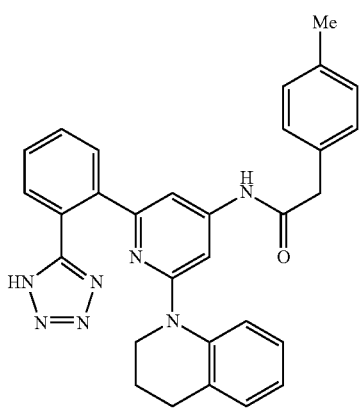 [SMILES: Cc1ccc(CC(=O)Nc2cc(-c3ccccc3-c3nnn[nH]3)nc(N3CCCc4ccccc43)c2)cc1]

68A. N-(2,6-dichloropyridin-4-yl)-2-(p-tolyl)acetamide

To stirred solution of 2-(p-tolyl)acetic acid (1.198 g, 7.98 mmol) in DMF (5 mL) was added DIPEA (5.36 mL, 30.7 mmol), 2,4,6-tripropyl-1,3,5,2,4,6-trioxatriphosphorinane-2,4,6-trioxide in ethyl acetate (11.71 g, 18.40 mmol) followed by addition of 2,6-dichloropyridin-4-amine (1 g, 6.13 mmol) and stirred at RT for 5 h. The reaction mixture was diluted with ice-water and stirred for 30 mins. The reaction mixture was extracted with ethyl acetate (2×50 mL), combined organics were separated, dried over sodium sulfate, concentrated under reduced pressure to afford 68A (off white solid, 1.4 g, 4.74 mmol, 77% yield) as an. The product was carried for next step without further purification. LC-MS Anal. Calc'd for $C_{14}H_{12}Cl_2N_2O$ 294.033, found [M+H] 295.0, $T_r$=1.10 min (Method O).

68B. N-(2-chloro-6-(2-(1-trityl-1H-tetrazol-5-yl)phenyl)pyridin-4-yl)-2-(p-tolyl)acetamide To a stirred solution of 5-(2-(4,4,5,5-tetramethyl-1,3,2-dioxaborolan-2-yl)phenyl)-1-trityl-1H-tetrazole (0.45 g, 0.875 mmol), 79A (0.25 g, 0.847 mmol), potassium phosphate, tribasic (0.539 g, 2.54 mmol) in dioxane (5 mL), nitrogen gas was bubbled for 10 mins. PdCl$_2$(dppf)-CH$_2$Cl$_2$ adduct (0.069 g, 0.085 mmol) was added and nitrogen gas was bubbled through the reaction mixture for 10 mins. The reaction mixture was heated in microwave at 95° C. for 12 h. The reaction mixture was cooled to RT and concentrated under reduced pressure. The residue was reconstituted in ethyl acetate (30 mL) and water (30 mL) and biphasic mixture was filtered through celite. The celite was washed with ethyl acetate (50 mL). The aqueous layer was separated out and the organic layer was dried over sodium sulfate, filtered and concentrated under reduced pressure and the crude material was purified by silica gel column chromatography using ethyl acetate in pet ether as an eluant (0-50%) to afford 68B (off-white semi solid, 0.35 g, 0.541 mmol, 63.9% yield). LC-MS Anal. Calc'd for $C_{40}H_{31}ClN_6O$ 646.225, found [M−H] 645.0, $T_r$=3.478 min (Method U).

68C. N-(2-(3,4-dihydroquinolin-1(2H)-yl)-6-(2-(1-trityl-1H-tetrazol-5-yl)phenyl)pyridin-4-yl)-2-(p-tolyl)acetamide To a stirred solution of 68B (0.06 g, 0.093 mmol), 1,2,3,4-tetrahydroquinoline (0.015 g, 0.111 mmol), $Cs_2CO_3$ (0.060 g, 0.185 mmol), XantPhos (0.021 g, 0.037 mmol) in dioxane (5 mL), nitrogen gas was purged for 10 mins. $Pd(OAc)_2$ (4.16 mg, 0.019 mmol) was added and nitrogen gas was bubbled through the reaction mixture for 10 mins. The reaction mixture was heated at 85° C. for 12 h. The reaction mixture was cooled to RT and concentrated under reduced pressure. The residue was reconstituted in ethyl acetate (30 mL) and filtered through celite. The celite was washed with ethyl acetate (50 mL). The aqueous layer was separated out and the organic layer was dried over sodium sulfate, filtered and concentrated under reduced pressure to afford brown color residue. The residue was purified by silica gel column chromatography using ethyl acetate in pet ether (0-50%) as an eluant to afford 68C (off-white solid, 0.045 g, 0.060 mmol, 65.2% yield). LC-MS Anal. Calc'd for $C_{49}H_{41}N_7O$ 743.337, found [M+H] 744.2, $T_r$=3.949 min (Method U).

Example 68

To a stirred solution of 68C (45 mg, 0.020 mmol) in DCM (5 mL) cooled at 0° C., TFA (0.031 mL, 0.399 mmol) was added dropwise to the reaction mixture and stirred for 10 mins. The reaction mixture was warmed to RT and stirred for 4 h. The reaction mixture was concentrated under reduced pressure to afford brown colored semi solid which was purified by Prep HPLC to afford Example 68 (light yellow solid, 5 mg, 8.04 μmol, 40%). LC-MS Anal. Calc'd for $C_{30}H_{27}N_7O$ 501.228, found [M+H] 502.3, $T_r$=2.203 min (Method U). $^1$H NMR (400 MHz, $CD_3OD$) δ 7.70-7.87 (m, 4H), 7.57 (d, J=1.60 Hz, 1H), 7.33 (d, J=2.00 Hz, 1H), 6.99-7.19 (m, 8H), 3.64 (s, 2H), 3.41-3.44 (m, 2H), 2.73-2.77 (m, 2H), 2.31 (s, 3H), 1.84-1.91 (m, 2H).

Example 69

1-(2-(2-(1H-tetrazol-5-yl)phenyl)-6-(benzyl(isobutyl)amino) pyridin-4-yl)-3-(4-fluorophenyl)urea, TFA

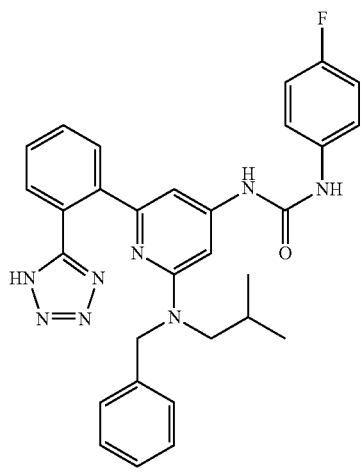 [SMILES: CC(C)CN(Cc1ccccc1)c1cc(NC(=O)Nc2ccc(F)cc2)cc(-c2ccccc2-c2nnn[nH]2)n1]

69A. 1-(2-(benzyl(isobutyl)amino)-6-bromopyridin-4-yl)-3-(4-fluorophenyl)urea To stirred solution of N2-benzyl-6-bromo-N2-isobutylpyridine-2,4-diamine (0.15 g, 0.449 mmol) in DCE (5 mL) was added 1-fluoro-4-isocyanatobenzene (0.074 g, 0.539 mmol) and stirred at 80° C. for 4 h. The reaction mixture was cooled to RT and concentrated under reduced pressure to afford brown color semi solid. The solid compound was purified by silica-gel column chromatography using ethyl acetate in pet ether as an eluant to afford 69A (off-white semi solid, 100 mg, 0.212 mmol, 47.3% yield). LC-MS Anal. Calc'd for $C_{23}H_{24}BrFN_4O$ 470.112, found [M+H] 471.0, $T_r$=3.954 min (Method U).

69B. 1-(2-(benzyl(isobutyl)amino)-6-(2-(1-trityl-1H-tetrazol-5-yl)phenyl)pyridin-4-yl)-3-(4-fluorophenyl)urea To a stirred solution of (2-(1-trityl-1H-tetrazol-5-yl)phenyl)boronic acid (119 mg, 0.276 mmol), 69A (100 mg, 0.212 mmol), potassium phosphate, tribasic (135 mg, 0.636 mmol) in dioxane (5 mL), was purged with nitrogen gas for 10 mins. $PdCl_2(dppf)$-$CH_2Cl_2$ adduct (17.32 mg, 0.021 mmol) was added and nitrogen gas was bubbled through the reaction mixture for 10 mins. The reaction mixture was heated in microwave at 95° C. for 5 h. The reaction mixture was cooled to RT and concentrated under reduced pressure. The residue was reconstituted in ethyl acetate (30 mL) and water (30 mL) and biphasic mixture was filtered through celite. The celite was washed with ethyl acetate (50 mL). The aqueous layer was separated out and the organic layer was dried over sodium sulfate, filtered and concentrated under reduced pressure to afford the 69B (off-white semi solid, 60 mg, 0.077 mmol, 36.3% yield) which was carried for next step without further purification. LC-MS Anal. Calc'd for $C_{49}H_{43}FN_8O$ 778.354, found [M+H] 779.5, $T_r$=1.54 min (Method O).

Example 69

To a stirred solution of 69B (60 mg, 0.044 mmol) in DCM (5 mL) cooled at 0° C., TFA (0.068 mL, 0.878 mmol) was added dropwise to the reaction mixture and stirred for 10 mins. The reaction mixture was warmed to RT and stirred for 4 h. The reaction mixture was concentrated under reduced pressure to afford brown colored semi solid which was purified by prep HPLC to afford Example 69 (off-white semi solid, 5 mg, 7.48 μmol, 17.03%). LC-MS Anal. Calc'd for $C_{30}H_{29}FN_8O$ 536.245, found [M+H] 537.4, $T_r$=2.6 min (Method AT). $^1$H NMR (400 MHz, $CD_3OD$) δ 7.96-7.96 (m, 1H), 7.60-7.76 (m, 3H), 7.20-7.45 (m, 8H), 7.04-7.08 (m, 2H), 6.76 (d, J=2.00 Hz, 1H), 4.78 (s, 2H), 3.37 (d, J=7.20 Hz, 2H), 1.94-1.98 (m, 1H), 0.88-0.95 (m, 6H).

Example 70

N-(2-(2-(1H-tetrazol-5-yl)phenyl)-6-((cyclopropylmethyl)(propyl)amino) pyridin-4-yl)-2-(2,4-difluorophenyl)acetamide, TFA

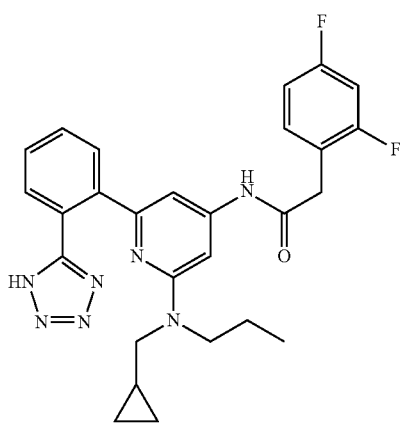 [SMILES: CCCN(CC1CC1)c1cc(NC(=O)Cc2ccc(F)cc2F)cc(-c2ccccc2-c2nnn[nH]2)n1]

70A. 6-bromo-N-(cyclopropylmethyl)-4-nitro-N-propylpyridin-2-amine

To sealable reaction flask containing 2,6-dibromo-4-nitropyridine (3 g, 10.64 mmol) was added N-(cyclopropylmethyl)propan-1-amine (1.807 g, 15.96 mmol), $K_2CO_3$ (2.94 g, 21.28 mmol) followed by dioxane (20 mL). The flask was sealed and the reaction was heated at 100° C. for 6 h. The mixture was cooled to RT and partitioned between EtOAc and water (20 mL). The layers were separated and the organic layer was washed with brine, dried over anhydrous sodium sulfate, filtered and concentrated in vacuo to afford the crude product as a light yellow residue. The residue was purified by silicagel column chromatography using ethyl acetate in pet ether as an eluant (0-10%) and concentrated to afford 70A (colorless oil, 2.2 g, 7.00 mmol, 65.8% yield). LC-MS Anal. Calc'd for $C_{12}H_{16}BrN_3O_2$ 313.043, found [M+H] 314.2, $T_r$=1.26 min (Method AA).

70B. 6-bromo-N2-(cyclopropylmethyl)-N2-propylpyridine-2,4-diamine

To a stirred solution of 70A (1.5 g, 4.77 mmol) in Acetic acid (10 mL) was added iron powder (1.333 g, 23.87 mmol) and stirred at RT for 4 h. The reaction mixture was cooled to RT and filtered through celite bed. The celite bed was washed with excess of methanol and the solution was concentrated under reduced pressure to give brown colored solid. The solid compound was basified with aqueous saturated sodium bicarbonate solution (PH~8-9) and extracted with ethyl acetate (3×50 mL). Combined organic layer was dried over sodium sulphate, filtered and evaporated under reduced pressure to get brown color semi solid. The solid compound was purified by silica gel column chromatography using ethyl acetate in pet ether as an eluant (0-40%) to afford 70B (brown color semi-solid, 0.6 g, 2.111 mmol, 44% yield) which was used to the next step without further purification. LC-MS Anal. Calc'd for $C_{12}H_{18}BrN_3$ 283.068, found [M+H] 284.2, $T_r$=3.046 min (Method U).

70C. 6-(2-(1H-tetrazol-5-yl)phenyl)-N2-(cyclopropylmethyl)-N2-propylpyridine-2,4-diamine To a stirred solution of (2-(1H-tetrazol-5-yl) phenyl) boronic acid (0.802 g, 4.22 mmol), 70B (1 g, 3.52 mmol), $K_2CO_3$ (2.432 g, 17.59 mmol) in DMF (10 mL) and Water (1 mL), nitrogen gas was bubbled for 10 mins. $Pd(Ph_3P)_4$ (0.407 g, 0.352 mmol) was added and nitrogen gas was bubbled through the reaction mixture for 10 mins. The reaction mixture was heated at 98° C. for 12 h. The reaction mixture was cooled to RT and filtered through celite bed. The celite bed was washed with excess of ethyl acetate. The reaction mixture was concentrated under reduced pressure to afford brown colored residue. To the residue, 1.5N HCl solution (20 mL) was added dropwise at RT and stirred for 30 mins. The orange color solid was settled out. The solid compound was filtered, dried to afford 70C (orange colored solid, 1 g, 2.86 mmol, 81% yield) which was carried for next step without further purification. LC-MS Anal. Calc'd for $C_{19}H_{23}N_7$ 349.201, found [M+H] 350.2, $T_r$=1.314 min (Method U).

Example 70

To stirred solution of 2-(2,4-difluorophenyl)acetic acid (51.9 mg, 0.301 mmol) in DMF (5 mL), was added DIPEA (0.202 mL, 1.159 mmol), 2,4,6-tripropyl-1,3,5,2,4,6-trioxatriphosphorinane-2,4,6-trioxide in ethyl acetate (443 mg, 0.695 mmol) followed by addition of 70C (100 mg, 0.232 mmol) and stirred at RT for 5 h. The reaction mixture was concentrated under reduced pressure to afford the brown color semi solid. The solid compound was partitioned between ethyl acetate (30 mL) and water (30 mL). The organic layer was separated out, dried over sodium sulfate, filtered and concentrated to afford the crude 81 (40 mg, 0.066 mmol, 28.6% yield) as a brown color solid which was purified by prep HPLC to afford Example 70 (off-white solid, 40 mg, 0.066 mmol, 28.6%). LC-MS Anal. Calc'd for $C_{27}H_{27}F_2N_7O$ 503.225, found [M+H] 504.2, $T_r$=2.259 min (Method U). $^1$H NMR (400 MHz, $CD_3OD$) δ 7.99-8.00 (m, 1H), 7.67-7.77 (m, 4H), 7.38-7.40 (m, 1H), 6.96-7.02 (m, 2H), 6.79 (d, J=1.20 Hz, 1H), 4.86 (s, 2H), 3.46-3.50 (m, 2H), 3.34-3.38 (m, 2H), 1.57-1.62 (m, 2H), 0.90-0.94 (m, 4H), 0.55-0.58 (m, 2H), 0.31-0.35 (m, 2H).

Example 71

1-(2-(2-(1H-tetrazol-5-yl)phenyl)-6-(benzyl(propyl)amino) pyridin-4-yl)-3-(2,4-difluorophenyl)urea, TFA

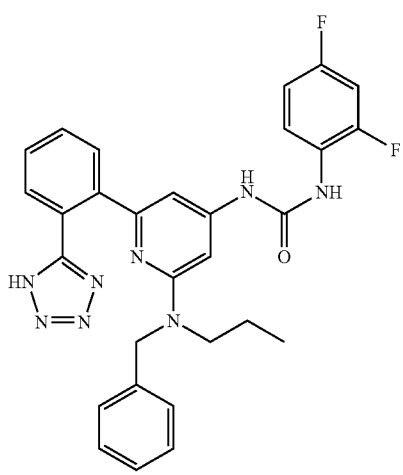 [SMILES: CCCN(Cc1ccccc1)c1cc(NC(=O)Nc2ccc(F)cc2F)cc(-c2ccccc2-c2nnn[nH]2)n1]

71A.
N-benzyl-6-bromo-4-nitro-N-propylpyridin-2-amine

To sealable reaction flask containing 2,6-dibromo-4-nitropyridine (3 g, 10.64 mmol) was added N-benzylpropan-1-amine hydrochloride (2.371 g, 12.77 mmol), DIPEA (4.65 mL, 26.6 mmol) followed by dioxane (10 mL). The flask was sealed and the reaction was heated at 100° C. for 4 h. The reaction mixture was cooled to RT and was partitioned between ethyl acetate and water (20 mL). The layers were separated and the organic layer was washed with brine, dried over anhydrous sodium sulfate, filtered and concentrated under reduced pressure to afford the crude product as a light yellow residue. The residue was purified by silica gel column chromatography using ethyl acetate in pet ether as an eluant (0-10%) to afford 82A (light orange colored semi solid, 3 g, 4.54 mmol, 42.7% yield). LC-MS Anal. Calc'd for $C_{15}H_{16}BrN_3O_2$ 349.043, found [M−H] 348.0, $T_r$=4.078 min (Method U).

71B.
N2-benzyl-6-bromo-N2-propylpyridine-2,4-diamine

To a stirred solution of 71A (1.5 g, 2.142 mmol) in acetic acid (10 mL) was added iron (0.598 g, 10.71 mmol) and stirred at RT for 4 h. The reaction mixture was filtered through celite bed. The celite bed washed with methanol (100 mL) and the filtrate was concentrated under reduced pressure. The residue was basified with aqueous saturated sodium bicarbonate solution (pH~8-9) and extracted with ethyl acetate (3×50 mL). Combined organic layers were dried over sodium sulfate, filtered and concentrated under reduced pressure to afford brown color semi-solid. The solid was purified by silica gel column chromatography using ethyl acetate in pet ether as an eluant to afford 71B (brown color semi-solid, 550 mg, 1.718, 80% yield). LC-MS Anal. Calc'd for $C_{15}H_{18}BrN_3$ 319.05, found [M+H] 320.0, $T_r$=3.382 min (Method U).

71C. 6-(2-(1H-tetrazol-5-yl)phenyl)-N2-benzyl-N2-propylpyridine-2,4-diamine

To a stirred solution of (2-(1H-tetrazol-5-yl)phenyl)boronic acid (0.890 g, 4.68 mmol), 71B (0.5 g, 1.561 mmol), $K_2CO_3$ (1.079 g, 7.81 mmol) in DMF (10 mL) and water (1 mL), nitrogen gas was bubbled for 10 mins. $Pd(Ph_3P)_4$ (0.180 g, 0.156 mmol) was added and nitrogen gas was bubbled through The reaction mixture for 10 mins. The reaction mixture was heated at 98° C. for 6 h. The reaction mixture was cooled to RT and filtered through celite bed. The celite bed was rinsed with excess of methanol. The reaction mixture was concentrated under pressure to afford brown colored residue. To the residue, 1.5N HCl solution (10 mL) was added dropwise at RT and stirred for 30 mins. The orange color solid was settled out. The solid compound was filtered, dried to afford 71C (orange color solid, 0.28 g, 0.726 mmol, 46.5% yield) which was carried for next step without further purification. LC-MS Anal. Calc'd for $C_{22}H_{23}N_7$ 385.201, found [M+H] 386.2, $T_r$=1.721 min (Method U).

Example 71

To stirred solution of 71C (0.12 g, 0.249 mmol) in THF (5 mL) was added TEA (0.069 mL, 0.498 mmol) followed by 2,4-difluoro-1-isocyanatobenzene (0.046 g, 0.299 mmol) and stirred at 60° C. for 12 h. The reaction mixture was cooled to RT and concentrated under reduced pressure to afford a brown colored solid which was purified by prep. HPLC to afford Example 71 (off white solid, 58 mg, 0.085 mmol, 34.0% yield). LC-MS Anal. Calc'd for $C_{29}H_{26}F_2N_8O$ 540.220, found [M+H] 541.2, $T_r$=2.421 min (Method U). $^1$H NMR (400 MHz, $CD_3OD$) δ 7.94-8.01 (m, 2H), 7.65-7.77 (m, 3H), 7.23-7.42 (m, 6H), 6.95-7.07 (m, 2H), 6.74 (d, J=1.60 Hz, 1H), 4.78 (s, 2H), 3.47-3.51 (m, 2H), 1.58-1.64 (m, 2H), 0.91 (t, J=14.80 Hz, 3H).

Example 72

1-(2-(2-(1H-tetrazol-5-yl)phenyl)-6-(benzyl(propyl)amino) pyridin-4-yl)-3-(4-chloro-2-fluorophenyl) urea, TFA

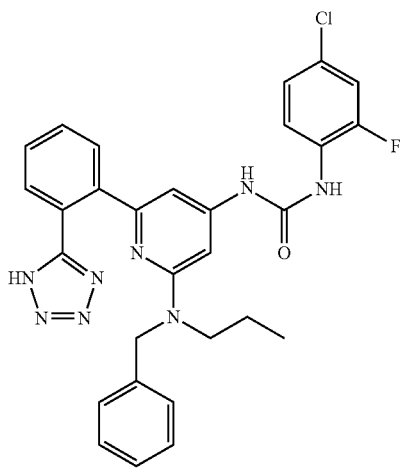 [SMILES: CCCN(Cc1ccccc1)c1cc(NC(=O)Nc2ccc(Cl)cc2F)cc(-c2ccccc2-c2nnn[nH]2)n1]

Example 72 was prepared as an off-white solid described in Example 71 by utilizing 4-chloro-2-fluoro-1-isocyanatobenzene. LC-MS Anal. Calc'd for $C_{29}H_{26}ClFN_8O$ 556.190, found [M+H] 557.2, $T_r$=2.688 min (Method U). $^1$H NMR (400 MHz, $CD_3OD$) δ 8.04-8.09 (m, 1H), 7.88-7.90 (m, 1H), 7.68-7.71 (m, 3H), 7.16-7.36 (m, 8H), 6.79 (d, J=1.60 Hz, 1H), 4.68 (s, 2H), 3.36-3.40 (m, 2H), 1.52-1.57 (m, 2H), 0.89 (t, J=14.80 Hz, 3H).

Example 73

N-(2-(2-(1H-tetrazol-5-yl)phenyl)-6-((cyclopropylmethyl)(propyl)amino) pyridin-4-yl)-2-(4-fluorophenyl)acetamide, TFA

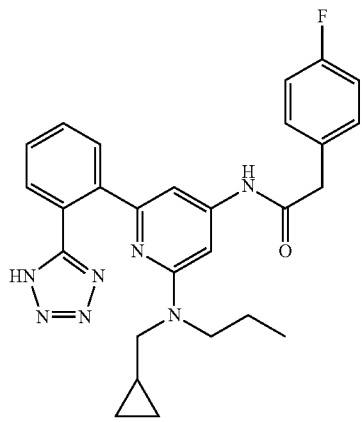 [SMILES: CCCN(CC1CC1)c1cc(NC(=O)Cc2ccc(F)cc2)cc(-c2ccccc2-c2nnn[nH]2)n1]

Example 73 was prepared as an off-white solid described in Example 70 by utilizing 4-fluoro phenyl acetic acid. LC-MS Anal. Calc'd for $C_{27}H_{28}FN_7O$ 485.234, found [M+H] 486.2, $T_r$=2.209 min (Method U). $^1$H NMR (400 MHz, $CD_3OD$) δ 7.99-8.01 (m, 1H), 7.68-7.78 (m, 4H), 7.34-7.38 (m, 2H), 7.07-7.11 (m, 2H), 6.80 (d, J=2.00 Hz, 1H), 3.76 (s, 2H), 3.46-3.51 (m, 2H), 3.35-3.37 (m, 2H), 1.57-1.63 (m, 2H), 0.90-0.91 (m, 4H), 0.57-0.59 (m, 2H), 0.33-0.34 (m, 2H).

Example 74

6-(2-(1H-tetrazol-5-yl)phenyl)-N2-benzyl-N2-isobutyl-N4-(5-(trifluoromethyl) pyrimidin-2-yl) pyridine-2,4-diamine, TFA

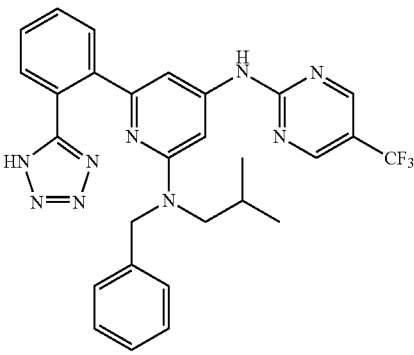 [SMILES: CC(C)CN(Cc1ccccc1)c1cc(Nc2ncc(C(F)(F)F)cn2)cc(-c2ccccc2-c2nnn[nH]2)n1]

74A. N2-benzyl-6-bromo-N2-isobutyl-N4-(5-(trifluoromethyl)pyrimidin-2-yl)pyridine-2,4-diamine To a stirred solution of 49C (300 mg, 0.898 mmol), 2-chloro-5-(trifluoromethyl)pyrimidine (197 mg, 1.077 mmol), BINAP (224 mg, 0.359 mmol), $Cs_2CO_3$ (585 mg, 1.795 mmol) in dioxane (10 mL), nitrogen gas was purged for 10 mins. $Pd(OAc)_2$ (30.2 mg, 0.135 mmol) was added and nitrogen gas was bubbled through the reaction mixture for 10 mins. The reaction mixture was heated at 80° C. for 6 h. The reaction mixture was cooled to RT and filtered through celite bed. The celite bed washed with excess of ethyl acetate and the solution was concentrated under reduced pressure to afford the brown colored residue. The brown residue was purified by silica gel column chromatography using ethyl acetate in pet ether as an eluant to afford 74A (brown colored semi-solid, 160 mg, 0.250 mmol, 27.8% yield). LC-MS Anal. Calc'd for $C_{21}H_{21}BrF_3N_5$ 479.093, found [M+H] 480.0, $T_r$=4.202 min (Method U).

Example 74

To a stirred solution of (2-(1H-tetrazol-5-yl)phenyl)boronic acid (28.9 mg, 0.152 mmol), 74A (75 mg, 0.117 mmol), $K_2CO_3$ (81 mg, 0.586 mmol) in DMF (5 mL) and water (1 mL), nitrogen gas was purged for 10 mins. $Pd(Ph_3P)_4$ (27.1 mg, 0.023 mmol) was added and nitrogen gas was bubbled through The reaction mixture for 10 mins. The reaction mixture was heated at 95° C. for 5 h. The reaction mixture was cooled to RT and concentrated under reduced pressure. The residue was reconstituted in ethyl acetate (30 mL) and water (30 mL) and biphasic mixture was filtered through celite. The celite was washed with ethyl acetate (50 mL). The aqueous layer was separated out and organic layer was dried over sodium sulfate, filtered and concentrated under reduced pressure to afford the brown colored semi solid which was purified by prep HPLC to afford Example 74 (pale yellow solid, 3 mg, 4.55 μmol, 3.88%). LC-MS Anal. Calc'd for $C_{28}H_{26}F_3N_9$ 545.226, found [M+H] 546.3, $T_r$=1.76 min (Method O). $^1$H NMR (400 MHz, DMSO-d6) δ 10.49 (s, 1H), 8.89 (s, 2H), 7.61-7.70 (m, 4H), 6.96-7.31 (m, 7H), 4.50 (s, 2H), 2.98-3.02 (m, 2H), 1.89-1.90 (m, 1H), 0.81-0.86 (m, 6H).

Example 75

N-(2-(2-(1H-tetrazol-5-yl)phenyl)-6-((4-fluorobenzyl)(propyl)amino) pyridin-4-yl)-2-(2-fluoro-4-methylphenyl)acetamide, TFA

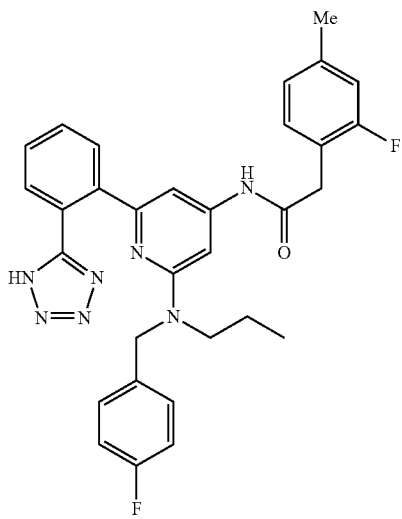 [SMILES: CCCN(Cc1ccc(F)cc1)c1cc(NC(=O)Cc2ccc(C)cc2F)cc(-c2ccccc2-c2nnn[nH]2)n1]

75A. N-(4-fluorobenzyl)propan-1-amine

To a stirred solution of propan-1-amine (2.381 g, 40.3 mmol) in THF (15 mL) and MeOH (15 mL) was added 4-fluorobenzaldehyde (5 g, 40.3 mmol) followed by 4 Å molecular sieves (3 g) at ambient temperature and stirred for overnight. The reaction mixture was cooled to 0° C., added NaBH$_4$ (4.57 g, 121 mmol) portion wise and stirred at RT for 3 h. The solvent was removed completely and resultant semi solid was quenched with 10% NaHCO$_3$ solution, extracted with ethyl acetate (3×25 mL), the organic layer was washed with brine (50 mL), dried over Na$_2$SO$_4$ and concentrated to afford 75A (colorless oil, 6 g, 35.9 mmol, 89% yield) which was carried for next step without further purification. LC-MS Anal. Calc'd for C$_{10}$H$_{14}$FN 167.111, found [M+H] 168.2, $T_r$=2.535 min (Method U).

75B. 6-bromo-N-(4-fluorobenzyl)-4-nitro-N-propylpyridin-2-amine

To sealable reaction flask containing 2,6-dibromo-4-nitropyridine (4 g, 14.19 mmol) was added 75A (3.56 g, 21.28 mmol) followed by dioxane (40 mL). The flask was sealed and the reaction was heated at 100° C. for 12 h. The mixture was cooled to RT. The reaction mixture was partitioned between ethyl acetate (20 mL) and water (20 mL). The layers were separated and the organic layer was washed with brine, dried over anhydrous sodium sulfate, filtered and concentrated under reduced pressure to afford light yellow residue. The residue was purified by silica gel column chromatography using ethyl acetate in pet ether as an eluant (0-10%) to afford 75B (orange colored solid, 5 g, 5.57 mmol, 39.2% yield). LC-MS Anal. Calc'd for C$_{15}$H$_{15}$BrFN$_3$O$_2$ 367.033, found [M+H] 369.0, $T_r$=3.992 min (Method U).

75C. 6-bromo-N2-(4-fluorobenzyl)-N2-propylpyridine-2,4-diamine

To a stirred solution of 75B (3 g, 8.15 mmol) in Acetic acid (40 mL), was added iron (2.275 g, 40.7 mmol) and stirred at RT for 4 h. The reaction mixture was filtered through celite bed. The celite bed washed with excess of ethyl acetatel (100 mL) and the solution was concentrated under reduced pressure to afford brown colored solid. The solid was basified with aqueous saturated sodium bicarbonate solution (pH~8-9) and extracted with ethyl acetate (3×50 mL). Combined the organic layer was dried over sodium sulphate, filtered and evaporated under reduced pressure to afford brown color semi-solid. The solid was purified by silicagel column chromatography using ethyl acetate in pet ether as an eluant (0-40%) and concentrated under reduced pressure to afford 75C (brown color oil, 1.4 g, 4.14 mmol, 50% yield). LC-MS Anal. Calc'd for C$_{15}$H$_{17}$BrFN$_3$ 337.059, found [M+H] 338.0, $T_r$=3.333 min (Method U).

75D. 6-(2-(1H-tetrazol-5-yl)phenyl)-N2-(4-fluorobenzyl)-N2-propylpyridine-2,4-diamine To a stirred solution of (2-(1H-tetrazol-5-yl)phenyl)boronic acid (1.685 g, 8.87 mmol), 75C (1 g, 2.96 mmol), K$_2$CO$_3$ (2.043 g, 14.78 mmol) in DMF (10 mL) and water (1 mL), nitrogen gas was bubbled for 10 mins. Pd(Ph$_3$P)$_4$ (0.342 g, 0.296 mmol) was added and nitrogen gas was bubbled through the reaction mixture for 10 mins. The reaction mixture was heated at 98° C. for 6 h. The reaction mixture was cooled to RT and filtered through celite bed. The celite bed was rinsed with excess of methanol. The filtrate was concentrated under reduced pressure to afford brown colored residue. To the residue, 1.5N HCl solution (10 mL) was added dropwise at RT and stirred for 30 mins. The off white color solid was settled out. The solid compound was filtered, dried to afford 75D (orange colored solid, 1.01 g, 2.178 mmol, 73.7% yield). LC-MS Anal. Calc'd for C$_{22}$H$_{22}$FN$_7$ 403.192, found [M+H] 404.2, $T_r$=1.616 min (Method U).

Example 75

To stirred solution of 2-(2-fluoro-4-methylphenyl)acetic acid (54.2 mg, 0.322 mmol) in DMF (5 mL) was added DIPEA (0.216 mL, 1.239 mmol), 2,4,6-tripropyl-1,3,5,2,4,6-trioxatriphosphorinane-2,4,6-trioxide in DMF (473 mg, 0.744 mmol) followed by addition of 75D (100 mg, 0.248 mmol) and stirred at RT for 5 h. The reaction mixture was concentrated under reduced pressure to afford the brown color semi solid. The solid compound was partitioned between ethyl acetate (30 mL) and water (30 mL). The organic layer was separated out, dried over sodium sulfate, filtered and concentrated to afford the brown colored solid. The crude product was purified by prep HPLC to afford Example 75 (off-white solid, 15 mg, 0.021 mmol, 8.59%). LC-MS Anal. Calc'd for C$_{31}$H$_{29}$F$_2$N$_7$O 553.240, found [M+H] 554.2, $T_r$=2.511 min (Method U). $^1$H NMR (400 MHz, CD$_3$OD) δ 7.89-7.91 (m, 1H), 7.68-7.90 (m, 3H), 7.40 (s, 1H), 7.16-7.22 (m, 3H), 6.91-6.07 (m, 5H), 4.63 (s, 2H), 3.72 (s, 2H), 3.33-3.39 (m, 2H), 2.34 (s, 3H), 1.51-1.57 (m, 2H), 0.87 (t, J=14.80 Hz, 3H).

Example 76

N-(2-(2-(1H-tetrazol-5-yl)phenyl)-6-(4-benzyl-3-oxopiperazin-1-yl) pyridin-4-yl)-2-(p-tolyl)acetamide, TFA

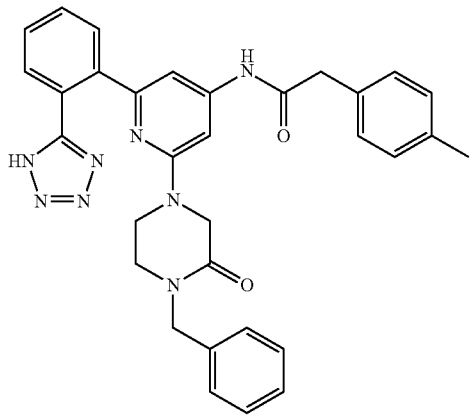 [SMILES: Cc1ccc(CC(=O)Nc2cc(-c3ccccc3-c3nnn[nH]3)nc(N3CCN(Cc4ccccc4)C(=O)C3)c2)cc1]

76A. tert-butyl 4-benzyl-3-oxopiperazine-1-carboxylate

To a stirred solution of tert-butyl 3-oxopiperazine-1-carboxylate (3 g, 14.98 mmol) in DMF (20 mL) cooled at 0° C., was added NaH (2.157 g, 90 mmol) followed by dropwise addition of Benzyl bromide (2.317 mL, 19.48 mmol) and stirred for 10 mins. The reaction mixture was warmed to RT and stirred for 12 h. The reaction mixture was diluted with water (100 mL) and MTBE (100 mL), then stirred for 10 mins. The MTBE layer was separated out and the aqueous layer was back extracted with MTBE (2×50 mL). Combined the organic extracts were dried over sodium sulphate, filtered and concentrated to 76A (3.2 g, 11.02 mmol, 73% yield) afford off-white semi solid which was carried for next step without further purification. LC-MS Anal. Calc'd for $C_{16}H_{22}N_2O_3$, 290.163, found [M+H] 291.1, $T_r$=0.92 min (Method T).

76B. 1-benzylpiperazin-2-one

To a stirred solution of 76A (2 g, 6.89 mmol) in DCM (10 mL) cooled at 0° C., TFA (2.65 mL, 34.4 mmol) was added drop wise to the reaction mixture and stirred for 10 mins. The reaction mixture was warmed to RT and stirred for 4 h. The reaction mixture was concentrated and the residue was poured into cold saturated sodium bicarbonate solution and basified (PH~8-9). The reaction mass were extracted with ethyl acetate (3×20 mL). Combined the organic extracts were dried over sodium sulphate, filtered and concentrated under reduced pressure to afford 76B (brown color semi solid, 1.1 g, 5.78 mmol, 84% yield). LC-MS Anal. Calc'd for $C_{11}H_{14}N_2O_3$, 190.11, found [M+H] 191.5, $T_r$=0.51 min (Method AA).

76C. 1-benzyl-4-(6-bromo-4-nitropyridin-2-yl)piperazin-2-one

To sealable reaction flask containing 2,6-dibromo-4-nitropyridine (1.4 g, 4.97 mmol) was added 76B (1.039 g, 5.46 mmol), $K_2CO_3$ (1.373 g, 9.93 mmol) followed by dioxane (10 mL). The flask was sealed and the reaction was heated at 100° C. for 12 h. The reaction mixture was cooled to RT and was partitioned between EtOAc and water (20 mL). The layers were separated and the organic layer was washed with brine, dried over anhydrous sodium sulfate, filtered and concentrated in vacuo to afford the crude product as a light yellow residue. The residue was purified by silica gel column chromatography using ethyl acetate in pet ether as an eluant (0-10%) and concentrated to afford 76C (orange color semi solid, 0.75 g, 1.917 mmol, 38.6% yield). LC-MS Anal. Calc'd for $C_{16}H_{15}BrN_4O_3$, 391.219, found [M+H] 392.2, $T_r$=2.812 min (Method U).

76D. 4-(4-amino-6-bromopyridin-2-yl)-1-benzylpiperazin-2-one

To a stirred solution of 76C (0.75 g, 1.917 mmol) in Acetic acid (10 mL), was added iron (0.535 g, 9.59 mmol) and stirred at RT for 6 h. The reaction mixture was cooled to RT and filtered through celite bed. The celite bed was washed with excess of methanol and the solution was concentrated under reduced pressure to give brown colored solid. The solid compound was basified with aqueous saturated sodium bicarbonate solution (pH~8-9) and extracted with ethyl acetate (3×50 mL). Combined the organic layer, dried over sodium sulphate, filtered and concentrated under reduced pressure to afford 76D (500 mg, 1.384 mmol, 72.2% yield) as a brown colored semi-solid which was used to the next step without further purification. LC-MS Anal. Calc'd for $C_{16}H_{17}BrN_4O$, 361.236, found [M+H] 362.2, $T_r$=3.044 min (Method T).

76E. N-(2-(4-benzyl-3-oxopiperazin-1-yl)-6-bromopyridin-4-yl)-2-(p-tolyl)acetamide To stirred solution of 2-(p-tolyl)acetic acid (0.162 g, 1.080 mmol) in DMF (5 mL), was added DIPEA (0.725 mL, 4.15 mmol), 2,4,6-tripropyl-1,3,5,2,4,6-trioxatriphosphorinane-2,4,6-trioxide in ethyl acetate (1.585 g, 2.491 mmol) followed by addition of 76D (0.3 g, 0.830 mmol) and stirred at RT for 5 h. The reaction mixture was concentrated under reduced pressure to afford brown colored semi solid which was purified by silica gel column chromatography using ethyl acetate in pet ether as an eluant (0-40%) to afford 76E (brown colored semi solid, 320 mg, 0.649 mmol, 78% yield). LC-MS Anal. Calc'd for $C_{25}H_{25}BrN_4O_2$, 492.116, found [M+H] 493.2, $T_r$=3.044 min (Method U).

76F. N-(2-(4-benzyl-3-oxopiperazin-1-yl)-6-(2-(1-trityl-1H-tetrazol-5-yl)phenyl)pyridin-4-yl)-2-(p-tolyl)acetamide To a stirred solution of (2-(1-trityl-1H-tetrazol-5-yl)phenyl)boronic acid (0.171 g, 0.395 mmol), 76E (0.15 g, 0.304 mmol), potassium phosphate, tribasic (0.129 g, 0.608 mmol) in dioxane (5 mL), nitrogen gas was purged for 10 mins. $PdCl_2(dppf)$-$CH_2Cl_2$ adduct (0.025 g, 0.030 mmol) was added and nitrogen gas was bubbled through the reaction mixture for 10 mins. The reaction mixture was heated at 100° C. for 12 h. The reaction mixture was cooled to RT and concentrated under reduced pressure. The residue was reconstituted in ethyl acetate (30 mL) and water (30 mL) and biphasic mixture was filtered through celite bed. The celite bed was washed with ethyl acetate (50 mL). The aqueous layer was separated out and the organic layer was dried over sodium sulfate, filtered and concentrated under reduced pressure to give brown colored solid. The solid material was purified by silica gel column chromatography using ethyl acetate in pet ether as an eluant (0-50%) to afford 76F (colorless oil, 140 mg, 0.175 mmol, 57.5% yield). LC-MS Anal. Calc'd for $C_{51}H_{44}N_8O_2$, 800.539, found [M+H] 801.2, $T_r$=3.268 min (Method U).

Example 76

To a stirred solution of 76F (150 mg, 0.187 mmol) in DCM (5 mL) cooled at 0° C., TFA (0.289 mL, 3.75 mmol) was added dropwise to the reaction mixture and stirred for 10 mins. The reaction mixture was warmed to RT and stirred for 4 h. The reaction mixture was concentrated under reduced pressure to afford brown colored semi solid which was purified by prep HPLC to afford Example 76 (off white solid, 15 mg, 0.021 mmol, 11% yield). LC-MS Anal. Calc'd for $C_{32}H_{30}N_8O_2$, 558.2, found [M+H] 559.4, $T_r$=1.449 min (Method O). $^1H$ NMR (400 MHz, $CD_3OD$) δ 7.66-7.78 (m, 4H), 7.22-7.36 (m, 5H), 7.13-7.20 (m, 6H), 4.65 (s, 2H), 4.03 (s, 2H), 3.66 (s, 2H), 3.49-3.51 (m, 2H), 3.31-3.33 (m, 2H), 2.31 (s, 3H).

Example 77

N-(2-(2-(1H-tetrazol-5-yl)phenyl)-6-(isobutyl(tetrahydro-2H-pyran-4-yl) amino)pyridin-4-yl)-2-(p-tolyl)acetamide, TFA

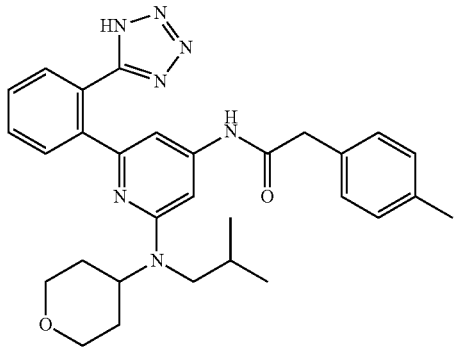 [SMILES: Cc1ccc(CC(=O)Nc2cc(-c3ccccc3-c3nnn[nH]3)nc(N(CC(C)C)C3CCOCC3)c2)cc1]

77A. N-(tetrahydro-2H-pyran-4-yl)isobutyramide

To a stirred solution of tetrahydro-2H-pyran-4-amine (5 g, 49.4 mmol) in dry DCM (30 mL), cooled to −10° C. was added TEA (10.33 mL, 74.1 mmol), followed by addition of isobutyryl chloride (5.70 mL, 54.4 mmol) in 30 min under nitrogen atmosphere. The reaction mixture was stirred at RT overnight. The reaction was quenched carefully by addition of satd. aq. ammonium chloride solution (50 mL) at −10-25° C. The reaction mixture was then extracted with ethyl acetate (2×50 mL). The combined organic extracts were washed with 1.5 N HCl solution (100 mL) and satd. aq. sodium bicarbonate solution (100 mL), followed by water (100 mL). The organic extracts were dried over sodium sulfate and concentrated under reduced pressure to afford 77A (waxy solid, 5.0 g, 29.2 mmol, 59.1% yield). LC-MS Anal. Calc'd for $C_9H_{17}NO_2$, 171.12, found [M+H] 171.2, $T_r$=0.43 min (Method U).

77B. N-isobutyltetrahydro-2H-pyran-4-amine

To a stirred solution of 77A (3.8 g, 22.19 mmol) in THF (25 mL) cooled at 0° C., was added borane dimethyl sulfide complex (10.52 mL, 111 mmol) slowly in 20 min. The reaction mixture was warmed to RT and stirred for 30 min. The reaction mixture was refluxed at 84° C. for 12 h. The reaction mixture was cooled to 0° C. quenched with 1.5 N HCl solution, (exothermic reaction) and stirred at RT for 2 h. The reaction mixture was basified (pH~8) with aqueous saturated sodium bicarbonate solution and extracted with ethyl acetate (3×50 mL). The organic layer was dried over sodium sulfate, filtered and concentrated to afford 77B (1.7 g, 10.81 mmol, 48% yield) as a colorless oil which was carried for next step without further purification. LC-MS Anal. Calc'd for $C_9H_{19}NO$, 157.147, found [M+H] 158.2, $T_r$=1.494 min (Method U).

77C. 6-bromo-N-isobutyl-4-nitro-N-(tetrahydro-2H-pyran-4-yl)pyridin-2-amine

To sealable reaction flask containing 2,6-dibromo-4-nitropyridine (1.2 g, 4.26 mmol) was added 77B (0.803 g, 5.11 mmol), $K_2CO_3$ (1.177 g, 8.51 mmol) followed by dioxane (5 mL). The flask was sealed and The reaction was heated at 100° C. for 12 h. The mixture was allowed to cool to RT. The reaction mixture was partitioned between ethyl acetate and water (20 mL). The layers were separated and the organic layer was washed with brine, dried over anhydrous sodium sulfate, filtered and concentrated under reduced pressure to afford the crude product as a light yellow residue. The residue was purified by silica gel column chromatography using ethyl acetate in pet ether as an eluant (0-10%) to afford 77C (light orange colored semi solid, 0.35 g, 0.977 mmol, 22.95% yield). LC-MS Anal. Calc'd for $C_{14}H_{20}BrN_3O_3$, 357.069, found [M+H] 358.0, $T_r$=3.825 min (Method U).

77D. 6-bromo-N2-isobutyl-N2-(tetrahydro-2H-pyran-4-yl)pyridine-2,4-diamine

To a stirred solution of 77C (0.3 g, 0.837 mmol) in acetic acid (10 mL) was added iron powder (0.234 g, 4.19 mmol) and stirred at RT for 6 h. The reaction mixture was filtered through celite bed. The celite bed washed with methanol (100 mL) and the solution was concentrated under reduced pressure. The residue was basified with aqueous saturated sodium bicarbonate solution (pH~8-9) and extracted with ethyl acetate (3×50 mL). The combined organic extracts were dried over sodium sulfate, filtered and concentrated under reduced pressure to afford 77D (orange colored semi-solid, 0.2 g, 0.609 mmol, 72.8% yield). LC-MS Anal. Calc'd for $C_{14}H_{22}BrN_3O$, 327.069, found [M+H] 328.2, $T_r$=2.905 min (Method U)

77E. N-(2-bromo-6-(isobutyl(tetrahydro-2H-pyran-4-yl)amino)pyridin-4-yl)-2-(p-tolyl)acetamide To stirred solution of 2-(p-tolyl)acetic acid (0.119 g, 0.792 mmol) in DMF (5 mL), was added DIPEA (0.532 mL, 3.05 mmol), 2,4,6-tripropyl-1,3,5,2,4,6-trioxatriphosphorinane-2,4,6-trioxide in ethyl acetate (1.163 g, 1.828 mmol) followed by addition of 77D (0.2 g, 0.609 mmol) and stirred at RT for 5 h. The reaction mixture was concentrated under reduced pressure to afford the brown color semi solid which was purified by silica gel column chromatography using ethyl acetate in pet ether as an eluant (0-40%) to afford 77E (off-white semi-solid, 0.24 g, 0.521 mmol, 86% yield). The product was carried for next step without further purification. LC-MS Anal. Calc'd for $C_{23}H_{30}BrN_3O_2$, 459.152, found [M+H] 460.2, $T_r$=2.661 min (Method U).

77F. N-(2-(isobutyl(tetrahydro-2H-pyran-4-yl) amino)-6-(2-(1-trityl-1H-tetrazol-5-yl)phenyl)pyridin-4-yl)-2-(p-tolyl)acetamide To a stirred solution of (2-(1-trityl-1H-tetrazol-5-yl)phenyl)boronic acid (0.183 g, 0.424 mmol), 77E (0.15 g, 0.326 mmol), potassium phosphate, tribasic (0.207 g, 0.977 mmol) in dioxane (5 mL) and the solution was purged with nitrogen gas for 10 mins. PdCl$_2$(dppf)-CH$_2$Cl$_2$ adduct (0.040 g, 0.049 mmol) was added and nitrogen gas was bubbled through the reaction mixture for 10 mins. The reaction mixture was heated at 100° C. for 12 h. The reaction mixture was cooled to RT and concentrated under reduced pressure. The residue was reconstituted in ethyl acetate (30 mL) and water (30 mL) and biphasic mixture was filtered through celite. The celite was washed with ethyl acetate (50 mL). The aqueous layer was separated out and the organic layer was dried over sodium sulfate, filtered and concentrated under reduced pressure to afford the 77F (off-white solid, 0.1 g, 0.130 mmol, 40.0% yield). LC-MS Anal. Calc'd for C$_{49}$H$_{49}$N$_7$O$_2$, 767.95, found [M+H] 768.5 T$_r$=1.12 min (Method AA).

Example 77

To a stirred solution of 77F (100 mg, 0.130 mmol) in DCM (5 mL) cooled at 0° C., TFA (0.201 mL, 2.60 mmol) was added dropwise to The reaction mixture and stirred for 10 mins. The reaction mixture was warmed to RT and stirred for 4 h. The reaction mixture was concentrated under reduced pressure to afford brown color semi solid which was purified by prep HPLC to afford Example 77 (off white solid, 12 mg, 0.019 mmol, 14% yield). LC-MS Anal. Calc'd for C$_{30}$H$_{35}$N$_7$O$_2$, 525.285, found [M+H] 526.4, T$_r$=1.501 min (Method O). $^1$H NMR (400 MHz, CD$_3$OD) δ 7.92-7.95 (m, 1H), 7.73-7.76 (m, 3H), 7.54 (s, 1H), 7.15-7.22 (m, 4H), 7.01 (d, J=1.60 Hz, 1H), 3.94-4.03 (m, 3H), 3.70 (s, 2H), 3.38-3.44 (m, 2H), 3.13 (d, J=7.60 Hz, 2H), 2.32 (s, 3H), 1.93-1.99 (m, 1H), 1.77-1.83 (m, 2H), 1.55-1.58 (m, 2H), 0.90-0.92 (m, 6H).

Example 78

1-(2-(2-(1H-tetrazol-5-yl)phenyl)-6-((4-fluorobenzyl)(isobutyl)amino) pyridin-4-yl)-3-(p-tolyl)urea, TFA

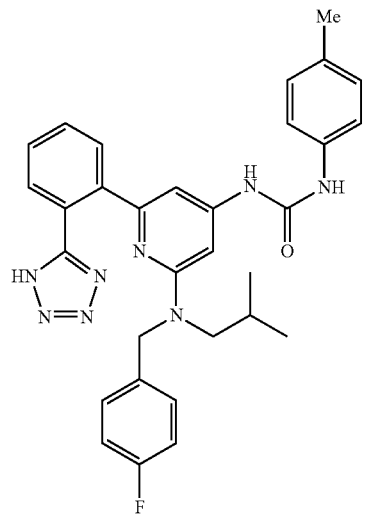 [SMILES: Cc1ccc(NC(=O)Nc2cc(-c3ccccc3-c3nnn[nH]3)nc(N(Cc3ccc(F)cc3)CC(C)C)c2)cc1]

To a stirred solution of 39D (80 mg, 0.192 mmol) in THF (5 mL) was added TEA (0.053 mL, 0.383 mmol) followed by 1-isocyanato-4-methylbenzene (30.6 mg, 0.230 mmol) and stirred at 60° C. for 6 h. The reaction mixture was cooled to RT and concentrated under reduced pressure to afford brown solid which was purified by prep HPLC to afford Example 78 (off-white solid, 38 mg, 0.056 mmol, 29.2% yield). LC-MS Anal. Calc'd for C$_{31}$H$_{31}$FN$_8$O, 550.26 found [M+H] 551.2, T$_r$=2.539 min (Method U). $^1$H NMR (400 MHz, CD$_3$OD) δ 8.00-8.02 (m, 1H), 7.73-7.80 (m, 2H), 7.65-7.67 (m, 1H), 7.50 (s, 1H), 7.32-7.34 (m, 2H), 7.25-7.29 (m, 2H), 7.08-7.16 (m, 4H), 6.77 (d, J=1.60 Hz, 1H), 4.78 (s, 2H), 3.38-3.50 (m, 2H), 2.32 (s, 3H), 1.97-2.05 (m, 1H), 0.95-0.97 (m, 6H).

Example 79

N-(2-(2-(1H-tetrazol-5-yl)phenyl)-6-(benzyl (isobutyl)amino)pyridin-4-yl)-2-(2-fluoro-4-methylphenyl)acetamide, TFA

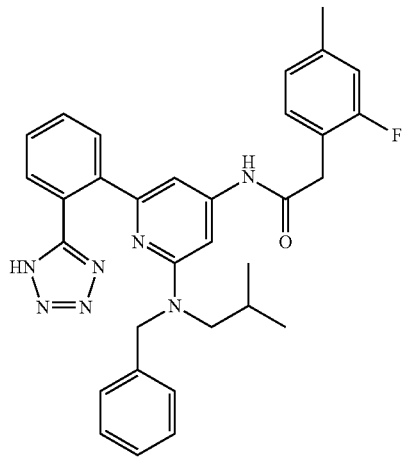 [SMILES: Cc1ccc(CC(=O)Nc2cc(-c3ccccc3-c3nnn[nH]3)nc(N(Cc3ccccc3)CC(C)C)c2)c(F)c1]

To stirred solution of 2-(2-fluoro-4-methylphenyl)acetic acid (65.7 mg, 0.390 mmol) in DMF (5 mL) was added DIPEA (0.262 mL, 1.502 mmol), 2,4,6-tripropyl-1,3,5,2,4,6-trioxatriphosphorinane-2,4,6-trioxide (50% in DMF) (573 mg, 0.901 mmol) followed by addition of 49D (200 mg, 0.300 mmol) and stirred at RT for 5 h. The reaction mixture was concentrated under reduced pressure to afford brown colored semi solid which was partitioned between ethyl acetate (30 mL) and water (30 mL). The organic layer was separated out, dried over sodium sulfate, filtered and concentrated to afford brown colored solid. The solid compound was purified by prep HPLC to afford Example 79 (off-white solid, 25 mg, 0.035 mmol, 11.81% yield). LC-MS Anal. Calc'd for C$_{32}$H$_{32}$FN$_7$O, 549.265, found [M–H] 550.2, T$_r$=2.607 min (Method U). $^1$H NMR (400 MHz, CD$_3$OD) δ 7.92-7.94 (m, 1H), 7.69-7.73 (m, 2H), 7.63-7.65 (m, 1H), 7.50-0.00 (m, 1H), 7.17-7.36 (m, 6H), 6.92-6.99 (m, 3H), 4.726 (s, 2H), 3.744 (s, 2H), 3.29-3.32 (m, 2H), 2.355 (s, 3H), 1.96-1.99 (m, 1H), 0.91-0.93 (m, 6H).

Example 80

N-(2-(2-(1H-tetrazol-5-yl)phenyl)-6-(benzyl (isobutyl)amino) pyridin-4-yl)-2-(4-fluorophenyl) acetamide, TFA

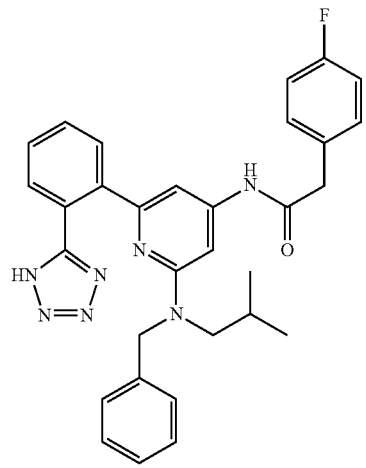 [SMILES: CC(C)CN(Cc1ccccc1)c1cc(NC(=O)Cc2ccc(F)cc2)cc(-c2ccccc2-c2nnn[nH]2)n1]

Example 80 was prepared using the procedure described for Example 79 utilizing p-fluoro phenyl acetic acid and 49D. LC-MS Anal. Calc'd for $C_{31}H_{30}FN_7O$, 535.250, found [M+H] 536.2. $T_r$=2.445 min (Method U): $^1$H NMR (400 MHz, CD$_3$OD) δ 7.83-7.85 (m, 1H), 7.64-7.69 (m, 3H), 7.23-7.33 (m, 6H), 7.03-7.14 (m, 4H), 6.94 (d, J=1.60 Hz, 1H), 4.64 (s, 2H), 3.68 (s, 2H), 3.13-3.20 (m, 2H), 1.87-1.94 (m, 1H), 0.87-0.90 (m, 6H).

Example 81

1-(2-(2-(1H-tetrazol-5-yl)phenyl)-6-(benzyl (isobutyl)amino) pyridin-4-yl)-3-(p-tolyl)urea, TFA

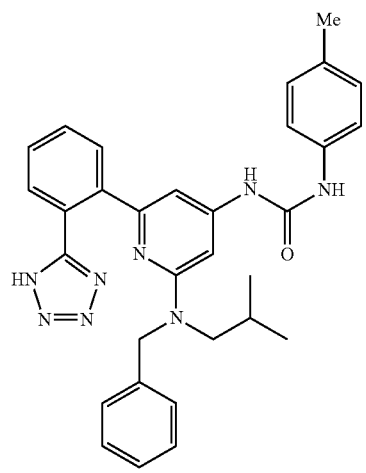 [SMILES: Cc1ccc(NC(=O)Nc2cc(-c3ccccc3-c3nnn[nH]3)nc(N(Cc3ccccc3)CC(C)C)c2)cc1]

Example 81 was prepared using the procedure described for Example 78 utilizing 1-isocyanato-4-methylbenzene and 49D. LC-MS Anal. Calc'd for $C_{31}H_{32}N_8O$, 532.27, found [M+H] 533.2, $T_r$=0.835 min (Method AD). $^1$H NMR (400 MHz, CD$_3$OD) δ 7.96-7.98 (m, 1H), 7.70-7.74 (m, 2H), 7.59-7.61 (m, 1H), 7.44-7.44 (m, 1H), 7.28-7.37 (m, 5H), 7.12-7.22 (m, 4H), 6.763 (d, J=1.60 Hz, 1H), 4.77 (s, 2H), 3.37-3.49 (m, 2H), 2.29 (s, 3H), 1.93-2.01 (m, 1H), 0.93-0.94 (m, 6H).

Example 82

N-(2-(2-(1H-tetrazol-5-yl)phenyl)-6-((cyclopropylmethyl)(propyl)amino) pyridin-4-)-2-(2-fluoro-4-methylphenyl)acetamide, TFA

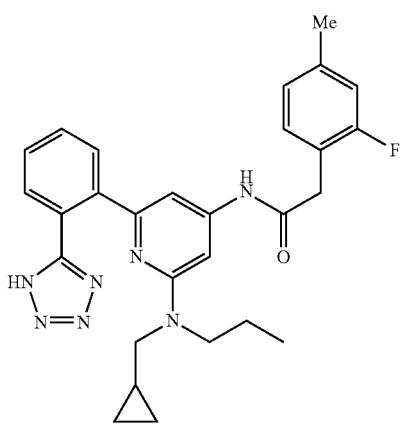 [SMILES: CCCN(CC1CC1)c1cc(NC(=O)Cc2ccc(C)cc2F)cc(-c2ccccc2-c2nnn[nH]2)n1]

Example 82 was prepared using the procedure described for Example 70 utilizing 2-(2-fluoro-4-methylphenyl)acetic acid and 70C. LC-MS Anal. Calc'd for $C_{28}H_{30}FN_7O$, 499.250, found [M+H] 500.2. $T_r$=2.523 min (Method U): $^1$H NMR (400 MHz, CD$_3$OD) δ 8.00 (d, J=8.80 Hz, 1H), 7.69-7.77 (m, 4H), 7.56-7.65 (m, 1H), 7.19-7.23 (m, 1H), 6.93-6.99 (m, 1H), 6.77 (d, J=2.00 Hz, 1H), 3.77 (s, 2H), 3.45-3.49 (m, 2H), 3.30-3.32 (m, 2H), 2.35 (s, 3H), 1.58-1.60 (m, 2H), 0.89-0.93 (m, 4H), 0.56-0.58 (m, 2H), 0.31-0.33 (m, 2H).

Example 83

1-(2-(2-(1H-tetrazol-5-yl)phenyl)-6-((cyclopropylmethyl)(propyl)amino) pyridin-4-yl)-3-(2,4-dichlorophenyl)urea, TFA

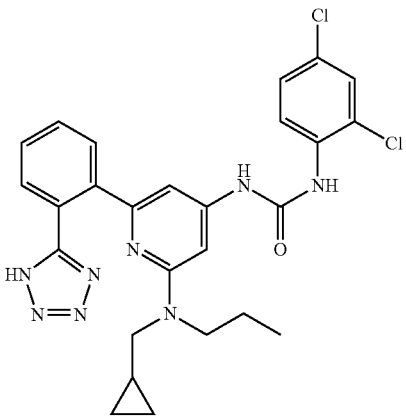 [SMILES: CCCN(CC1CC1)c1cc(NC(=O)Nc2ccc(Cl)cc2Cl)cc(-c2ccccc2-c2nnn[nH]2)n1]

Example 83 was prepared using the procedure described for Example 71 utilizing 70C and 2,4-dichloro phenyl isocyanate. LC-MS Anal. Calc'd for $C_{26}H_{26}Cl_2N_8O$, 536.161, found [M+H] 537.2. $T_r$=2.753 min (Method U): $^1$H NMR (400 MHz, CD$_3$OD) δ 8.17 8.19 (m, 1H), 8.02-8.04 (m, 1H), 7.73-7.82 (m, 3H), 7.61 (s, 1H), 7.53-7.54 (m, 1H), 7.35-7.38 (m, 1H), 6.93 (s, 1H), 3.50-3.55 (m, 2H), 3.41-3.42 (m, 2H), 1.59-1.66 (m, 2H), 0.89-1.02 (m, 4H), 0.59-0.64 (m, 2H), 0.36-0.39 (m, 2H).

Example 84

6-(2-(1H-tetrazol-5-yl)phenyl)-N2-(cyclopropylmethyl)-N2-propyl-N4-(5-yl)pyrimidin-2-yl)pyridine-2,4-diamine, TFA

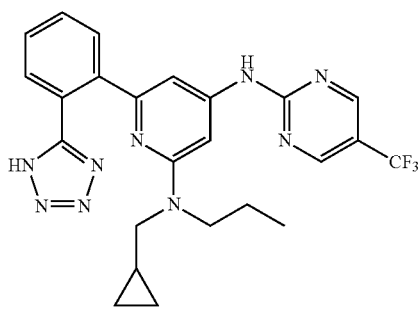 [SMILES: CCCN(CC1CC1)c1cc(Nc2ncc(C(F)(F)F)cn2)cc(-c2ccccc2-c2nnn[nH]2)n1]

To a stirred solution of 70C (0.1 g, 0.229 mmol), 2-chloro-5-(trifluoromethyl)pyrimidine (0.050 g, 0.275 mmol), BINAP (0.071 g, 0.114 mmol), Cs$_2$CO$_3$ (0.149 g, 0.458 mmol) in dioxane (5 mL) and the solution was purged with nitrogen gas for 10 mins. Pd(OAc)$_2$ (10.28 mg, 0.046 mmol) was added to the reaction mixture and again the solution was purged with nitrogen gas for another 10 mins. The reaction mixture was heated in microwave at 100° C. for 2 h. The reaction mixture was cooled to RT and concentrated under reduced pressure to afford brown colored solid. The solid was reconstituted in ethyl acetate (30 mL) and filtered through celite bed. The celite bed was washed with ethyl acetate (50 mL) and concentrated under reduced pressure to afford brown colored solid. The solid compound was purified by prep HPLC to afford Example 84 (off-white solid, 4 mg, 6.10 μmol, 2.67% yield). LC-MS Anal. Calc'd for $C_{24}H_{24}F_3N_9$, 495.211, found [M+H] 496.2, $T_r$=2.338 min (Method U): $^1$H NMR (400 MHz, CD$_3$OD) δ 8.91-8.93 (m, 2H), 7.97-8.04 (m, 2H), 7.74-7.79 (m, 3H), 7.029 (s, 1H), 3.54-3.58 (m, 2H), 3.44-3.48 (m, 2H), 1.63-1.69 (m, 2H), 0.90-1.02 (m, 4H), 0.60-0.64 (m, 2H), 0.34-0.37 (m, 2H).

Example 85

N-(2-(2-(1H-tetrazol-5-yl)phenyl)-6-((4-fluorobenzyl)(propyl)amino) pyridin-4-yl)-2-(p-tolyl)acetamide, TFA

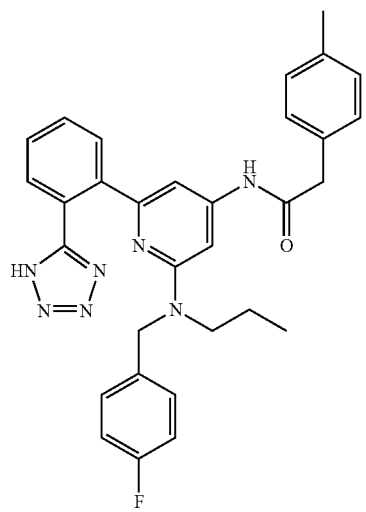 [SMILES: CCCN(Cc1ccc(F)cc1)c1cc(NC(=O)Cc2ccc(C)cc2)cc(-c2ccccc2-c2nnn[nH]2)n1]

Example 85 was prepared following the procedure described in Example 75 by utilizing p-tolyl acetic acid. LC-MS Anal. Calc'd for $C_{31}H_{30}FN_7O$, 535.250, found [M+H] 536.2. $T_r$=2.438 min (Method U). $^1$H NMR (400 MHz, CD$_3$OD) δ 7.92-7.94 (m, 1H), 7.71-7.73 (m, 2H), 7.66-7.70 (m, 1H), 7.48 (s, 1H), 7.13-7.23 (m, 6H), 7.04-7.09 (m, 2H), 6.88 (d, J=1.60 Hz, 1H), 4.67 (s, 2H), 3.65 (s, 2H), 3.38-3.42 (m, 2H), 2.31 (s, 3H), 1.53-1.59 (m, 2H), 0.88 (t, J=14.80 Hz, 3H).

Example 86

1-(2-(2-(1H-tetrazol-5-yl)phenyl)-6-((4-fluorobenzyl)(propyl)amino)pyridin-4-yl)-3-(2,4-dichlorophenyl)urea

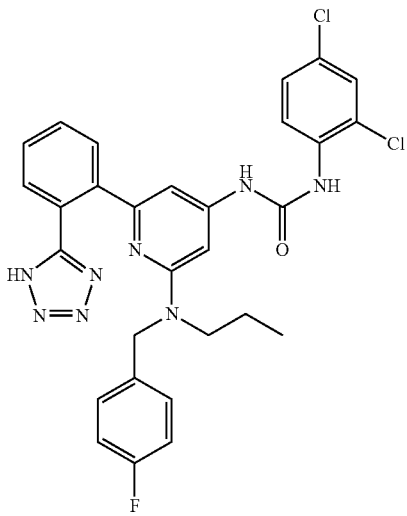 [SMILES: CCCN(Cc1ccc(F)cc1)c1cc(NC(=O)Nc2ccc(Cl)cc2Cl)cc(-c2ccccc2-c2nnn[nH]2)n1]

To stirred solution of 75D (50 mg, 0.124 mmol) in THF (5 mL) was added TEA (0.035 mL, 0.248 mmol) followed by 2,4-dichloro-1-isocyanatobenzene (28.0 mg, 0.149 mmol) and stirred at 60° C. for 12 h. The reaction mixture was cooled to RT and concentrated under reduced pressure to afford a brown solid which was purified by prep HPLC to afford Example 86 (Off white solid, 6 mg, 9.64 μmol, 7.78% yield). LC-MS Anal. Calc'd for $C_{29}H_{25}Cl_2FN_8O$, 590.151, found [M+H] 591.2, $T_r$=2.814 min (Method U). $^1$H NMR (400 MHz, DMSO-d6) δ 9.44 (s, 1H), 8.46 (s, 1H), 8.11-8.14 (m, 1H), 7.49-7.65 (m, 5H), 7.36-7.39 (m, 1H), 7.07-7.18 (m, 4H), 6.68-6.69 (m, 2H), 4.47 (s, 2H), 3.13-3.15 (m, 2H), 1.40-1.44 (m, 2H), 0.77-0.81 (m, 3H).

Example 87

N-(2-(2-(1H-tetrazol-5-yl)phenyl)-6-(benzyl (isobutyl)amino)pyridin-4-yl)-2-(p-tolyl)acetamide, TFA

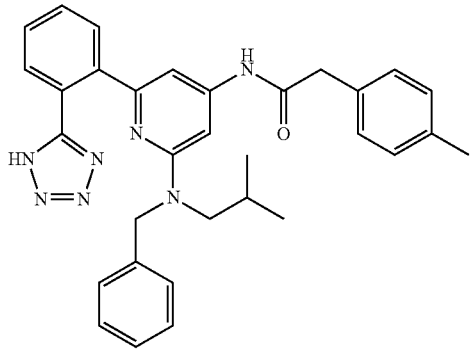 [SMILES: Cc1ccc(CC(=O)Nc2cc(-c3ccccc3-c3nnn[nH]3)nc(N(Cc3ccccc3)CC(C)C)c2)cc1]

87A. N-(2-(benzyl(isobutyl)amino)-6-bromopyridin-4-yl)-2-(p-tolyl)acetamide

To a stirred solution of 2-(p-tolyl)acetic acid (0.117 g, 0.778 mmol) in DMF (5 mL) was added DIPEA (0.523 mL, 2.99 mmol), 2,4,6-tripropyl-1,3,5,2,4,6-trioxatriphosphorinane-2,4,6-trioxide in ethyl acetate (1.142 g, 1.795 mmol) followed by addition of 49C (0.4 g, 0.598 mmol) and stirred at RT for 5 h. The reaction mixture was concentrated under reduced pressure to afford the brown semi solid which was purified by silica gel column chromatography using ethyl acetate in pet ether as an eluant (0-40%) to afford 87A (brown semi solid, 0.26 g, 0.557 mmol, 93% yield). LC-MS Anal. Calc'd for $C_{25}H_{28}BrN_3O$, 465.142, found [M+H] 466.0, $T_r$=4.15 min (Method U).

87B. N-(2-(benzyl(isobutyl)amino)-6-(2-(1-trityl-1H-tetrazol-5-yl)phenyl)pyridin-4-yl)-2-(p-tolyl) acetamide To a stirred solution of (2-(1-trityl-1H-tetrazol-5-yl)phenyl)boronic acid (0.181 g, 0.418 mmol), 87A (0.15 g, 0.322 mmol), potassium phosphate, tribasic (0.137 g, 0.643 mmol) in dioxane (5 mL) nitrogen gas was purged for 10 mins. $PdCl_2$(dppf)-$CH_2Cl_2$ adduct (0.026 g, 0.032 mmol) was added and nitrogen gas was bubbled through the reaction mixture for another 10 mins. The reaction mixture was heated at 95° C. for 12 h.

The reaction mixture was cooled to RT and concentrated under reduced pressure to afford brown colored solid. The solid was reconstituted in ethyl acetate (30 mL) and water (30 mL), and biphasic mixture was filtered through celite bed. The celite bed was washed with ethyl acetate (50 mL). The organic layer was dried over sodium sulfate, filtered and concentrated under reduced pressure to afford 87B (brown colored semi solid, 120 mg, 0.155 mmol, 48.2% yield). LC-MS Anal. Calc'd for $C_{51}H_{47}N_7O$, 773.384, found [M+H] 775.4, $T_r$=2.439 min (Method U).

Example 87

To a stirred solution of 98B (130 mg, 0.168 mmol) in DCM (5 mL) cooled at 0° C., TFA (0.259 mL, 3.36 mmol) was added dropwise to The reaction mixture and stirred for 10 min. The reaction mixture was allowed to warm to RT and stirred for 4 h. The reaction mixture was concentrated under reduced pressure to afford brown semi solid. The compound was purified by prep HPLC to afford example 87 (white colored solid, 32 mg, 0.049, 29.2%). LC-MS Anal. Calc'd for $C_{32}H_{33}N_7O$, 531.275, found [M+H] 532.4, $T_r$=1.843 min (Method O). $^1$H NMR (400 MHz, $CD_3OD$) δ 7.90-7.92 (m, 1H), 7.68-7.73 (m, 2H), 7.60-7.62 (m, 1H), 7.50 (s, 1H), 7.23-7.34 (m, 3H), 7.13-7.19 (m, 6H), 6.88-6.89 (d, J=1.60 Hz, 1H), 4.71 (s, 2H), 3.65 (s, 2H), 3.28-3.31 (m, 2H), 2.31 (s, 3H), 1.92-2.31 (m, 1H), 0.89-0.91 (m, 6H).

Example 88

1-(2-(benzyl(propyl)amino)-6-(5-methyl-2-(1H-tetrazol-5-yl)phenyl)pyridin-4-yl)-3-(2-fluorophenyl) urea, TFA

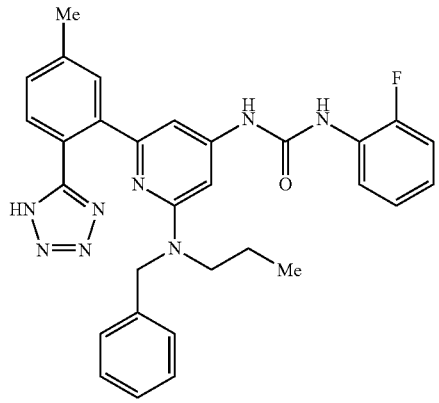 [SMILES: CCCN(Cc1ccccc1)c1cc(NC(=O)Nc2ccccc2F)cc(-c2cc(C)ccc2-c2nnn[nH]2)n1]

88A. 1-(2-(Benzyl(propyl)amino)-6-bromopyridin-4-yl)-3-(2-fluorophenyl)urea

To stirred solution of 71B (1 g, 3.12 mmol) in THF (10 mL) was added TEA (0.871 mL, 6.25 mmol) followed by 1-fluoro-2-isocyanatobenzene (0.514 g, 3.75 mmol) and stirred at 54° C. for 6 h. The reaction mixture was cooled to RT and evaporated under reduced pressure to afford a brown colored semi-solid was purified by silica gel column chromatography using ethyl acetate in pet ether as an eluant (0-30%) to afford 88A (light yellow semi solid, 0.35 g, 0.689 mmol, 22.06% yield). LC-MS Anal. Calc'd for $C_{22}H_{22}BrFN_4O$, 456.096, found [M+H] 457.0, $T_r$=3.815 min ((Method U)

Example 88

To a stirred solution of 5-(4-methyl-2-(4,4,5,5-tetramethyl-1,3,2-dioxaborolan-2-yl)phenyl)-1H-tetrazole (68.8 mg, 0.241 mmol), 88A (100 mg, 0.219 mmol), K$_2$CO$_3$ (151 mg, 1.093 mmol) in DMF (5 mL) and water (1 mL) nitrogen gas was purged for 10 mins. Pd(Ph$_3$P)$_4$ (25.3 mg, 0.022 mmol) was added and nitrogen gas was bubbled through the reaction mixture for 10 mins. The reaction mixture was heated at 98° C. for 6 h. The reaction mixture was cooled to RT and filtered through celite bed. The celite bed was washed with 10 mL of methanol and concentrated under reduced pressure to afford brown solid which was purified by prep HPLC to afford Example 88 (Off white solid, 22 mg, 0.032 mmol, 14.69% yield). LC-MS Anal. Calc'd for C$_{30}$H$_{29}$FN$_8$O, 536.245, found [M+H] 537.4, T$_r$=2.836 min (Method U). $^1$H NMR (400 MHz, CD$_3$OD) δ: δ 8.02-8.06 (m, 1H), 7.85 (d, J=8.00 Hz, 1H), 7.57 (d, J=8.00 Hz, 1H), 7.36-7.45 (m, 4H), 7.24-7.32 (m, 3H), 7.09-7.17 (m, 3H), 6.72 (d, J=1.60 Hz, 1H), 4.78 (s, 2H), 3.47-3.51 (m, 2H), 2.51 (s, 3H), 1.59-1.65 (m, 2H), 0.92 (t, J=14.80 Hz, 3H).

Example 89

N-(2-(benzyl(isobutyl)amino)-6-(5-fluoro-2-(1H-tetrazol-5-yl)phenyl) pyridin-4-yl)-2-(p-tolyl)acetamide, TFA

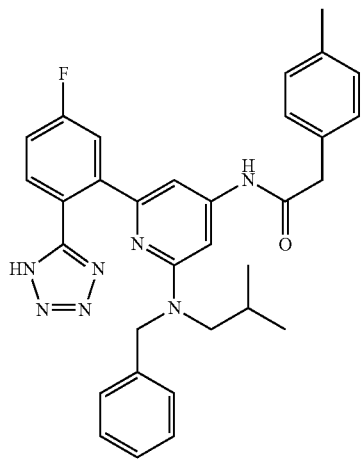 [SMILES: Cc1ccc(CC(=O)Nc2cc(-c3cc(F)ccc3-c3nnn[nH]3)nc(N(Cc3ccccc3)CC(C)C)c2)cc1]

89A. 4-fluoro-2-(4,4,5,5-tetramethyl-1,3,2-dioxaborolan-2-yl)benzonitrile

To a stirred solution of 2-bromo-4-fluorobenzonitrile (5 g, 25.00 mmol), bis(pinacolato)diboron (9.52 g, 37.5 mmol), potassium acetate (7.36 g, 75.0 mmol), in dioxane (50 mL) argon was purged for 5 mins. PdCl$_2$(dppf)-CH$_2$Cl$_2$ adduct (12.25 g, 15.00 mmol) was added and argon was bubbled through the reaction mixture and heated at 94° C. (silicon oil bath) for 14 h. The reaction mixture was cooled to RT, filtered through celite pad, washed with ethyl acetate (200 mL). The organic layer was washed with water (100 mL) and the aq. layer was separated and re-extracted with ethyl acetate (2×100 mL). Combined organic extracts were washed with brine, dried over sodium sulfate and solvent was removed under reduced pressure to give the brown colored crude product. The product was purified by silica gel column chromatography using ethyl acetate in pet ether as an eluant to afford 89A (4 g, 16.19 mmol, 64.8% yield) as a off-white semi solid. $^1$H NMR (400 MHz, CDCl$_3$) δ 7.89-7.93 (m, 1H), 7.54-7.59 (m, 1H), 7.39-7.50 (m, 1H).

89B. 5-(4-fluoro-2-(4,4,5,5-tetramethyl-1,3,2-dioxaborolan-2-yl)phenyl)-1H-tetrazole To a sealed vessel, 89A (1.4 g, 5.67 mmol) in DME (15 mL) was added TMS-N3 (3.76 mL, 28.3 mmol) and dibutyltin oxide (0.169 g, 0.680 mmol) were added to the reaction mixture. The mixture was sealed and heated at 110° C. for 4 h. The reaction mixture was cooled to RT and concentrated under reduced pressure. The residue was purified by silica gel column chromatography using ethyl acetate in pet ether as an eluant (0-70%) to afford 89B (light yellow gummy oil, 0.5 g, 1.724 mmol, 30.4% yield). $^1$H NMR (400 MHz, DMSO-d6) δ 7.76-7.84 (m, 1H), 7.53-7.61 (m, 1H), 7.38-7.42 (m, 1H), 1.18 (s, 12H).

89C. N2-benzyl-6-(5-fluoro-2-(1H-tetrazol-5-yl)phenyl)-N2-isobutylpyridine-2,4-diamine To a stirred solution of 89B (0.15 g, 0.449 mmol), K$_2$CO$_3$ (0.062 g, 0.449 mmol) in DMF (5 mL), nitrogen gas was purged for 10 mins. Pd(PPh$_3$)$_4$ (0.519 g, 0.449 mmol) was added and nitrogen gas was bubbled through the reaction mixture for 10 mins. The reaction mixture was heated at 98° C. for 6 h. The reaction mixture was cooled to RT and concentrated under reduced pressure. The residue was purified by silica-gel column chromatography using methanol in chloroform and 0.1% TEA (0-10%) to afford 89C (off-white semi-solid, 0.11 g, 0.263 mmol, 58.7% yield). LC-MS Anal. Calc'd for C$_{23}$H$_{24}$FN$_7$, 417.208, found [M+H] 418.2, T$_r$=0.84 min (Method O).

Example 89

To stirred solution of 2-(p-tolyl)acetic acid (46.8 mg, 0.311 mmol) in DMF (5 mL) was added DIPEA (0.209 mL, 1.198 mmol), 89C in DMF (457 mg, 0.719 mmol) followed by addition of 80C (100 mg, 0.240 mmol) and stirred at RT for 5 h. The reaction mixture was evaporated under reduced pressure to afford the brown color semi solid. The solid compound was partitioned between ethyl acetate (30 mL) and water (30 mL). The organic layer was separated out, dried over sodium sulfate, filtered and evaporated to afford brown colored solid. The solid compound was purified by Preparative HPLC to afford example 89 (Off white solid 5 mg, 7.65 μmol, 3.19% yield). LC-MS Anal. Calc'd for C$_{32}$H$_{32}$FN$_7$O, 549.265, found [M+H] 550.2, T$_r$=2.487 min. (Method U). $^1$H NMR (400 MHz, CD$_3$OD) δ 7.60-7.63 (m, 2H), 7.39-7.44 (m, 1H), 7.11-7.31 (m, 10H), 6.94 (s, 1H), 4.62 (s, 2H), 3.63 (s, 2H), 3.13-3.18 (m, 2H), 2.31 (s, 3H), 1.90-1.93 (m, 1H), 0.86-0.92 (m, 6H).

Example 90

N-(2-(2-(1H-tetrazol-5-yl)phenyl)-6-((4-fluorobenzyl)(isobutyl)amino)pyridin-4-yl)-2-(p-tolyl)acetamide, TFA

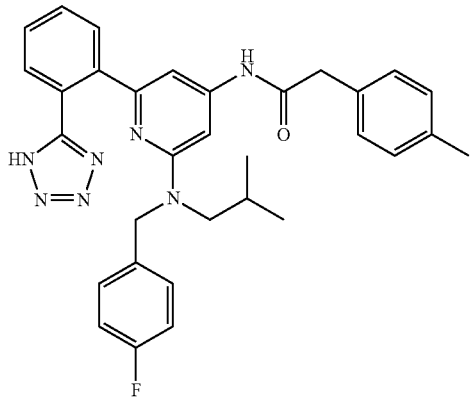 [SMILES: Cc1ccc(CC(=O)Nc2cc(-c3ccccc3-c3nnn[nH]3)nc(N(Cc3ccc(F)cc3)CC(C)C)c2)cc1]

Example 90 was prepared using the procedure described for Example 79 by utilizing 39D and 2-(p-tolyl)acetic acid. LC-MS Anal. Calc'd for $C_{32}H_{32}FN_7O$, 549.3, found [M+H] 550.2. $T_r$=2.522 min (Method U). $^1$H NMR (400 MHz, CD$_3$OD) δ 7.88-7.90 (m, 1H), 7.66-7.88 (m, 3H), 7.44 (s, 1H), 7.15-7.21 (m, 6H), 7.03-7.07 (m, 2H), 6.93 (d, J=1.60 Hz, 1H), 4.66 (s, 2H), 3.65 (s, 2H), 3.25-3.27 (m, 2H), 2.33 (s, 3H), 1.94-1.98 (m, 1H), 0.90-0.91 (m, 6H).

Example 91

N-(2-(2-(1H-tetrazol-5-yl) phenyl)-6-(3,4-dihydroisoquinolin-2(1H)-yl) pyridin-4-yl)-2-(2-fluoro-4-methylphenyl) acetamide

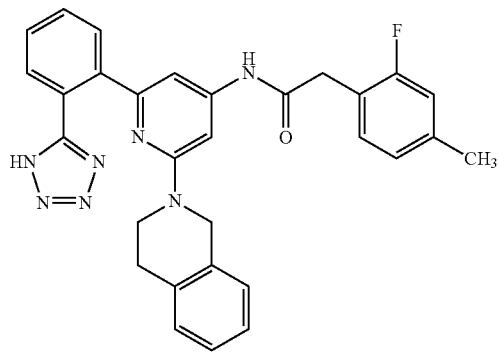 [SMILES: Cc1ccc(CC(=O)Nc2cc(-c3ccccc3-c3nnn[nH]3)nc(N3CCc4ccccc4C3)c2)c(F)c1]

91A. 2-(6-bromo-4-nitropyridin-2-yl)-1,2,3,4-tetrahydroisoquinoline

The solution of 2,6-dibromo-4-nitropyridine (0.4 g, 1.419 mmol) and 1,2,3,4-tetrahydroisoquinoline (0.378 g, 2.84 mmol) in dioxane (2 mL) was stirred at 100° C. for 14 h. The reaction mixture was concentrated under reduced pressure and the residue so obtained was purified through silica gel column chromatography by using 10-30% ethyl acetate and pet ether as an eluant to afford 91A (brown solid, 0.75 g, 1.369 mmol, 48.3% yield). LC-MS Anal. Calc'd for $C_{14}H_{12}BrN_3O_2$ 333.0, found [M+2] 335.0 $T_r$=3.76 min (Method N).

91B. 2-(6-(2-(1H-tetrazol-5-yl) phenyl)-4-nitropyridin-2-yl)-1,2,3,4-tetrahydroisoquinoline To a solution of 91A (0.25 g, 0.456 mmol) in DMF (4.00 mL) was added 5-(2-(4,4,5,5-tetramethyl-1,3,2-dioxaborolan-2-yl)phenyl)-1H-tetrazole (0.149 g, 0.548 mmol) followed by $K_2CO_3$ (0.189 g, 1.369 mmol) in water (1 mL) then degassed with nitrogen for 15 min. (PPh$_3$)$_4$Pd (0.026 g, 0.023 mmol) was added and heated to 90° C. for overnight. The reaction mass was diluted with ethyl acetate and filtered through celite bed, washed with excess of ethyl acetate. Filtrate was concentrated under reduced pressure and residue so obtained was purified through silica gel flash chromatography (50-100% ethyl acetate and pet ether) to afford 91B (0.16 g, 0.337 mmol, 73.7% yield). LC-MS Anal. Calc'd for $C_{21}H_{17}N_7O_2$ 399.1, found [M+H] 400.2 $T_r$=1.76 min (Method N).

91C. 2-(2-(1H-tetrazol-5-yl) phenyl)-6-(3,4-dihydroisoquinolin-2(1H)-yl) pyridin-4-amine To a homogeneous mixture of 91B (0.15 g, 0.315 mmol) in ethanol (5 mL) and water (0.5 mL), ammonium chloride (0.084 g, 1.577 mmol) was added. The mixture was stirred at RT for 10 min before zinc powder (0.144 g, 2.208 mmol) was added. The mixture was heated at 50° C. for 12 h. The reaction was cooled to RT then filtered through a pad of celite. The filtrate was concentrated under reduced pressure and co distilled twice with toluene (20 mL). The reaction mass washed with 50% of ethyl acetate and hexanes and dried over vacuum to afford 91C (off white solid, 0.11 g, 0.211 mmol, 67.0% yield). LC-MS Anal. Calc'd for $C_{21}H_{19}N_7$ 369.17, found [M+H] 370.4 $T_r$=0.69 min (Method T).

Example 91

To the solution of 2-(2-fluoro-4-methylphenyl)acetic acid (0.046 g, 0.271 mmol) in DCM (4 mL), SOCl$_2$ (0.5 ml, 6.85 mmol) was added and heated at 42° C. for 14 h. The reaction mass was concentrated under reduced pressure. The solution of acid chloride in DCM (1 ml) was added to the mixture of 91C (0.1 g, 0.271 mmol) and DMAP (3.31 mg, 0.027 mmol) in DCM (4 mL) at 0° C. The reaction mass was stirred at RT for 14 h. The reaction mixture was diluted with water and extracted with DCM (2×10 mL). Combined organic layers were dried over sodium sulphate and concentrated under reduced pressure. Compound was purified by reverse phase HPLC to afford Example 91 (off white solid, 0.016 g, 0.023 mmol, 8.41% yield). LC-MS Anal. Calc'd for $C_{30}H_{26}FN_7O$ 519.22, found [M+H] 520.2. $T_r$=2.18 min (Method N). $^1$H NMR (400 MHz, METHANOL-d4) δ 7.96-7.93 (m, J=3.0 Hz, 1H), 7.81-7.74 (m, 3H), 7.63 (s, 1H), 7.26-7.16 (m, 5H), 7.00-6.95 (m, 2H), 6.94-6.92 (m, 1H), 4.51 (s, 2H), 3.78 (s, 2H), 3.62 (t, J=5.8 Hz, 2H), 2.97 (t, J=5.8 Hz, 2H), 2.35 (s, 3H).

Example 92

N-(6-(2-(1H-tetrazol-5-yl)phenyl)-2-(isobutyl(pyrimidin-2-ylmethyl)amino) pyrimidin-4-yl)-2-(p-tolyl)acetamide

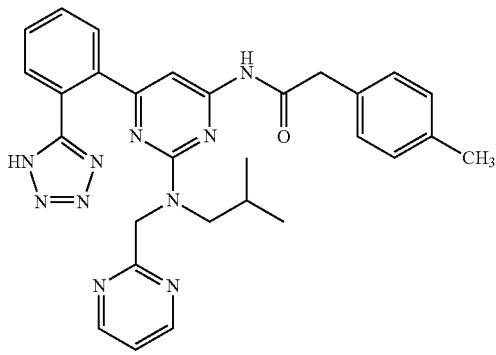 [SMILES: Cc1ccc(CC(=O)Nc2cc(-c3ccccc3-c3nnn[nH]3)nc(N(Cc3ncccn3)CC(C)C)n2)cc1]

92A. 6-chloro-N2-isobutyl-N2-(pyrimidin-2-ylmethyl)pyrimidine-2,4-diamine

To the stirred solution of 2-methyl-N-(pyrimidin-2-ylmethyl)propan-1-amine, TFA (0.221 g, 0.793 mmol) in dioxane (10 mL), 2,6-dichloropyrimidin-4-amine (0.13 g, 0.793 mmol) and DIPEA (0.415 mL, 2.378 mmol) were added. The reaction mixture was heated to 100° C. for 14 h in a pressure tube. The reaction mass was concentrated under reduced pressure and residue so obtained was purified through silica gel column chromatography by using the gradient of ethyl acetate in pet ether (10-20%). Desired fractions were concentrated under reduced pressure to afford 92A (yellow oil, 0.065 g, 0.193 mmol, 24.37% yield). LC-MS Anal. Calc'd for $C_{13}H_{17}ClN_6$ 292.7, found [M+H] 293.4. $T_r$=0.90 min (Method T).

92B. N-(6-chloro-2-(isobutyl(pyrimidin-2-ylmethyl)amino)pyrimidin-4-yl)-2-(p-tolyl)acetamide To the solution of 92A (0.065 g, 0.193 mmol) in DCM (2 mL), 2-(p-tolyl)acetic acid (0.044 g, 0.290 mmol) was added and cooled to 0° C. $POCl_3$ (0.126 mL, 1.352 mmol) was added followed by pyridine (0.156 mL, 1.932 mmol) and stirred at RT for 14 h. The reaction mass was concentrated under reduced pressure. To the reaction mass aq. saturated bicarbonate solution was added and extracted with ethyl acetate (3×20 mL). Combined organic layers were dried over sodium sulfate and concentrated under reduced pressure to afford 92B (yellow oil, 0.120 g, 0.186 mmol, 96% yield). LC-MS Anal. Calc'd for $C_{22}H_{25}ClN_6O$ 424.1, found [M+H] 425.4. $T_r$=1.18 min (Method T).

Example 92

To a solution of 92B (0.12 g, 0.186 mmol) in DMF (4 mL), was added 5-(2-(4,4,5,5-tetramethyl-1,3,2-dioxaborolan-2-yl)phenyl)-1H-tetrazole (0.061 g, 0.224 mmol) followed by $K_2CO_3$ (0.077 g, 0.559 mmol) in water (1 mL) then degassed with nitrogen for 15 min. To this mixture, $Pd(PPh_3)_4$ (10.77 mg, 9.32 µmol) was added and heated at 90° C. for 14 h. The reaction mass was filtered through celite bed and washed with ethyl acetate. Filtrate was concentrated under reduced pressure. Crude was purified by reverse phase HPLC to afford Example 92 (0.004 g, 5.92 µmol, 3.18% yield) as a pale yellow solid. LC-MS Anal. Calc'd for $C_{29}H_{30}N_{10}O$ 534.26, found [M+H] 535.2. $T_r$=1.84 min (Method N). $^1$H NMR (400 MHz, METHANOL-$d_4$) δ 8.69 (br. s., 2H), 7.89-7.53 (m, 5H), 7.34 (t, J=5.0 Hz, 1H), 7.25-7.09 (m, 4H), 5.02-4.92 (m, 2H), 3.65 (br. s., 2H), 3.05 (br. s., 2H), 2.32 (s, 3H), 1.68 (br. s., 1H), 0.81 (br. s., 6H).

Example 93

1-(6-(2-(1H-tetrazol-5-yl)phenyl)-2-(3,4-dihydroisoquinolin-2(1H)-yl) pyrimidin-4-yl)-3-(p-tolyl)urea

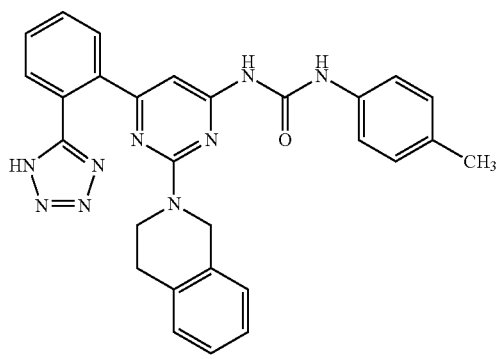 [SMILES: Cc1ccc(NC(=O)Nc2cc(-c3ccccc3-c3nnn[nH]3)nc(N3CCc4ccccc4C3)n2)cc1]

93A. 6-chloro-2-(3,4-dihydroisoquinolin-2(1H)-yl)pyrimidin-4-amine

To the stirred solution of 2,6-dichloropyrimidin-4-amine (0.4 g, 2.439 mmol) and 1,2,3,4-tetrahydroisoquinoline (0.390 g, 2.93 mmol) in dioxane (10 mL), DIPEA (1.278 mL, 7.32 mmol) was added drop wise and stirred at 100° C. for 14 h. The reaction mass was concentrated under reduced pressure. The residue so obtained was purified through silica gel column chromatography (0-20% ethyl acetate in pet ether) to afford 93A (yellow solid, 0.5 g, 1.649 mmol, 67.6% yield). LC-MS Anal. Calc'd for $C_{13}H_{13}ClN_4$ 260.7, found [M+H] 261.1. $T_r$=0.87 min (Method AA).

93B. 1-(6-chloro-2-(3,4-dihydroisoquinolin-2(1H)-yl)pyrimidin-4-yl)-3-(p-tolyl)urea To the solution of 93A (0.1 g, 0.384 mmol) in DMF (2 mL) cooled to 0° C., NaH (0.017 g, 0.422 mmol) was added and stirred for 30 min. 1-Isocyanato-4-methylbenzene (0.073 mL, 0.575 mmol) in DMF (2 mL) was added drop wise over a period of 5 min and stirred at for 12 h. The reaction mass was cooled to 0° C., quenched with ice water and extracted with ethyl acetate (2×20 ml). Combined organic layers were dried over sodium sulfate and concentrated under reduced pressure. The residue so obtained was washed with 30% ethyl acetate and hexanes (twice) to afford 93B (0.125 g, 0.203 mmol, 53.0% yield) as a white solid. LC-MS Anal. Calc'd for $C_{21}H_{20}ClN_5O$ 393.14, found [M+H] 394.2. $T_r$=1.23 min (Method: AA).

Example 93

To a solution of 92B (0.125 g, 0.209 mmol) in DMF (2 mL) was added 5-(2-(4,4,5,5-tetramethyl-1,3,2-dioxaborolan-2-yl)phenyl)-1H-tetrazole (0.085 g, 0.314 mmol) followed by K₂CO₃ (0.087 g, 0.628 mmol) in water (0.5 mL) and purged with nitrogen for 15 min. To this Pd(PPh₃)₄ (0.012 g, 10.47 μmol) was added and heated at 90° C. for overnight. The reaction mass was concentrated under reduced pressure. The residue so obtained was purified by prep HPLC to afford Example 93 (pale yellow solid, 0.011 g, 0.017 mmol, 8.08% yield). LC-MS Anal. Calc'd for C₂₈H₂₅N₉O 503.22, found [M+H] 504.2. T$_r$=2.25 min (Method N). ¹H NMR (400 MHz, METHANOL-d4) δ 7.87 (d, J=7.5 Hz, 1H), 7.77-7.65 (m, 3H), 7.43 (d, J=8.5 Hz, 2H), 7.22-7.10 (m, 6H), 6.73 (s, 1H), 3.65 (br. s., 2H), 3.41-3.33 (m, 2H), 2.81 (br. s., 2H), 2.32 (s, 3H).

Example 94

N-(6-(2-(1H-tetrazol-5-yl)phenyl)-2-(3,4-dihydroisoquinolin-2(1H)-yl)pyrimidin-4-yl)-2-(p-tolyl)acetamide

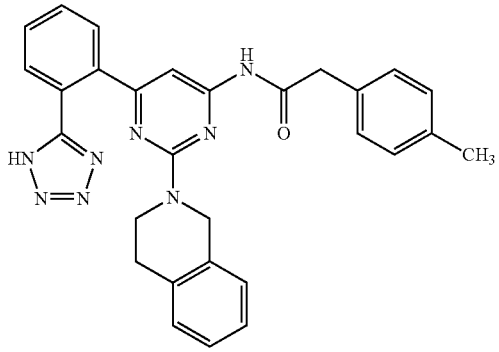 [SMILES: Cc1ccc(CC(=O)Nc2cc(-c3ccccc3-c3nnn[nH]3)nc(N3CCc4ccccc4C3)n2)cc1]

94A. N-(6-chloro-2-(3,4-dihydroisoquinolin-2(1H)-yl)pyrimidin-4-yl)-2-(p-tolyl)acetamide To the solution of 93A (0.1 g, 0.330 mmol) in DCM (2 mL), 2-(p-tolyl)acetic acid (0.074 g, 0.495 mmol) was added and cooled to 0° C. POCl₃ (0.215 mL, 2.309 mmol) was added followed by pyridine (0.267 mL, 3.30 mmol) and stirred at RT for 14 h. The reaction mass was concentrated under reduced pressure. To the reaction mass aq. saturated bicarbonate solution was added and extracted with ethyl acetate (3×20 mL). Combined organic layers were dried over sodium sulfate and concentrated under reduced pressure. The residue so obtained was purified through silica gel column chromatography by using (10-40% ethyl acetate in pet ether) to afford 94A (yellow oil, 0.065 g, 0.154 mmol, 46.6% yield). LC-MS Anal. Calc'd for C₂₂H₂₁ClN₄O 392.1, found [M+H] 393.0. T$_r$=3.84 min (Method N).

Example 94

To a solution of 94A (0.06 g, 0.142 mmol) in DMF (2 mL) was added 5-(2-(4,4,5,5-tetramethyl-1,3,2-dioxaborolan-2-yl)phenyl)-1H-tetrazole (0.046 g, 0.170 mmol) followed by K₂CO₃ (0.059 g, 0.426 mmol) in Water (1 mL) and purged with nitrogen for 15 min. Pd(PPh₃)₄ (8.21 mg, 7.10 μmol) was added and heated to 90° C. for overnight. The reaction mass was concentrated under reduced pressure. The residue so obtained was purified by prep HPLC to afford Example 94 (0.018 g, 0.028 mmol, 19.94% yield) as a pale yellow solid. LC-MS Anal. Calc'd for C₂₉H₂₆N₈O 502.2, found [M+H] 503.2. T$_r$=2.36 min (Method N). ¹H NMR (400 MHz, METHANOL-d₄) δ 7.84-7.88 (m, 1H), 7.66-7.76 (m, 4H), 7.21-7.25 (m, 2H), 7.11-7.20 (m, 6H), 4.52 (br. s., 2H), 3.64-3.74 (m, 4H), 2.78 (t, J=5.77 Hz, 2H), 2.32 (s, 3H).

Example 95

N-(6-(2-(1H-tetrazol-5-yl)phenyl)-2-(3,4-dihydroisoquinolin-2(1H)-yl) pyrimidin-4-yl)-2-(4-isopropylphenyl)acetamide

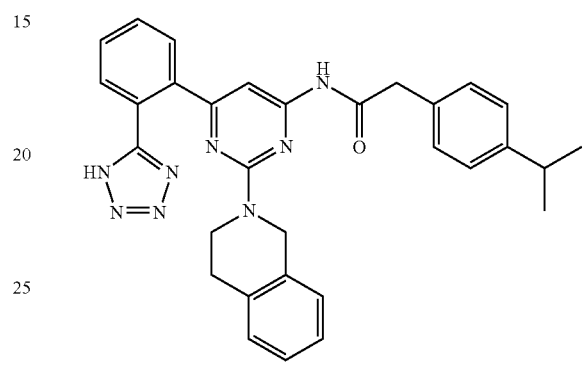

95A. N-(6-chloro-2-(3,4-dihydroisoquinolin-2(1H)-yl)pyrimidin-4-yl)-2-(4-isopropylphenyl)acetamide To the solution of 93A (0.1 g, 0.330 mmol) in DCM (2 mL), 2-(4-isopropylphenyl)acetic acid (0.088 g, 0.495 mmol) was added and cooled to 0° C. POCl₃ (0.215 mL, 2.309 mmol) was added followed by pyridine (0.267 mL, 3.30 mmol) and stirred at RT for 14 h. The reaction mass was concentrated under reduced pressure. To the reaction mass aq. saturated bicarbonate solution (5 mL) was added and extracted with ethyl acetate (3×20 mL). Combined organic layers were dried over sodium sulfate and concentrated under reduced pressure. The residue so obtained was purified through silica gel column chromatography by using (10-40% ethyl acetate in pet ether) to afford 95A (yellow oil, 0.068 g, 0.162 mmol, 49.0% yield). LC-MS Anal. Calc'd for C₂₄H₂₅ClN₄O 420.17, found [M+H] 421.2. T$_r$=4.17 min (Method N).

Example 95

To a solution of 95A (0.068 g, 0.162 mmol) in DMF (2 mL) was added 5-(2 (4,4,5,5-tetramethyl-1,3,2-dioxaborolan-2-yl)phenyl)-1H-tetrazole (0.053 g, 0.194 mmol) followed by K₂CO₃ (0.067 g, 0.485 mmol) in water (1 mL) and purged with nitrogen for 15 min. Pd(PPh₃)₄ (9.33 mg, 8.08 μcool) was added and heated at 90° C. for overnight. The reaction mass was concentrated under reduced pressure. The reaction mixture was purified by prep HPLC to afford Example 95 (pale yellow solid, 20.65 mg, 0.030 mmol, 18.84% yield). LC-MS Anal. Calc'd for C₃₁H₃₀N₈O 530.25, found [M+H] 531.2. T$_r$=2.39 min (Method: N). ¹H NMR (400 MHz, METHANOL-d₄) δ 7.88-7.84 (m, 1H), 7.76-7.66 (m, 4H), 7.29-7.25 (m, 2H), 7.23-7.18 (m, 2H), 7.18-7.11 (m, 4H), 4.53 (br. s., 2H), 3.73 (s, 2H), 3.69 (br. s., 2H), 2.94-2.85 (m, 1H), 2.78 (t, J=5.8 Hz, 2H), 1.24 (d, J=7.0 Hz, 6H).

Example 96

1-(6-(2-(1H-tetrazol-5-yl)phenyl)-2-(4-benzyl-3-oxopiperazin-1-yl) pyrimidin-4-yl)-3-(p-tolyl)urea

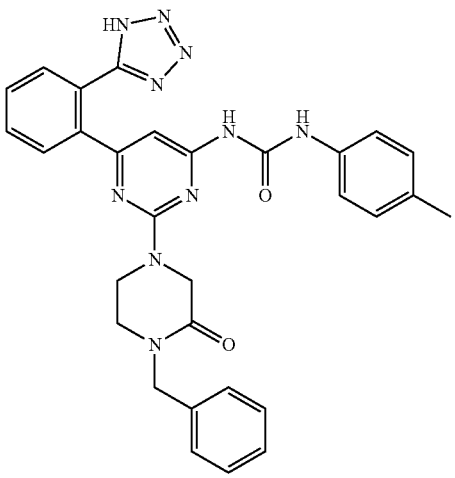 [SMILES: Cc1ccc(NC(=O)Nc2cc(-c3ccccc3-c3nnn[nH]3)nc(N3CCN(Cc4ccccc4)C(=O)C3)n2)cc1]

96A. tert-butyl 4-benzyl-3-oxopiperazine-1-carboxylate

To a solution of tert-butyl 3-oxopiperazine-1-carboxylate (3 g, 14.98 mmol) in DMF (45 mL) cooled to 0° C. was added NaH (1.198 g, 30.0 mmol) and stirred at 0° C. for 30 min. Then was added benzyl bromide (4.45 mL, 37.5 mmol) slowly warmed to RT for 4 h. The reaction mass was quenched with aqueous sodium bicarbonate (10%) solution (25 mL), extracted with DCM (2×25 mL), the combined organic layer was dried over sodium sulfate and concentrated under reduced pressure, the residue was purified by flash chromatography to give 96A (white solid, 3 g, 10.23 mmol, 68.3% yield). LC-MS Anal. Calc'd for $C_{16}H_{22}N_2O_3$ 290.16, found [M+H] 235.2 (t-Butyl cleavage mass). $T_r$ 2.35 min (Method U).

96B. 1-benzylpiperazin-2-one, HCl

To a solution of 96A (3 g, 10.33 mmol) in 1,4-Dioxane (25 mL) was added 4 M HCl in dioxane (25 mL, 100 mmol) and stirred at RT for 4 h. The reaction mass was concentrated under reduced pressure which was washed with ethyl acetate (2×50 mL) and dried to afford 96B (white solid, 2.4 g, 8.94 mmol, 87% yield). LC-MS Anal. Calc'd for $C_{11}H_{14}N_2O$ 190.11, found [M+H] 191.2 $T_r$=1.994 min (Method O).

96C. 4-(4-amino-6-chloropyrimidin-2-yl)-1-benzylpiperazin-2-one

To a solution of 96B (1.204 g, 4.57 mmol) in 1,4-Dioxane (25 mL) was added DIPEA (3.20 mL, 18.29 mmol) followed by 2,6-dichloropyrimidin-4-amine (0.75 g, 4.57 mmol). Then sealed the tube and heated to 110° C. for 14 h. The reaction mass was cooled to RT concentrated under reduced pressure. To that residue water (15 mL) was added and extracted with ethyl acetate (2×25 mL), the combined organic layer was dried over sodium sulfate and concentrated under reduced pressure. Purification by flash chromatography gave 96C (off white solid, 1.2 g, 3.78 mmol, 83% yield). LC-MS Anal. Calc'd for $C_{15}H_{16}ClN_5O$ 317.15, found [M+H] 318.2. $T_r$=0.84 min (Method T).

96D. 1-(2-(4-benzyl-3-oxopiperazin-1-yl)-6-chloropyrimidin-4-yl)-3-(p-tolyl)urea To a solution of 1C (0.25 g, 0.787 mmol) in DMF (10 mL) at 0° C. was added NaH (0.038 g, 0.944 mmol), stirred for 30 min. Then was added 1-isocyanato-4-methylbenzene (0.136 g, 1.023 mmol) in DMF (2 mL), slowly warmed to RT for overnight. The reaction mass was quenched with ice cold water and extracted with ethyl acetate (2×75 mL), the combined organic layer was dried over sodium sulfate and concentrated under reduced pressure to got crude was washed with pet ether (2×25 ml) and the solid was dried under reduced pressure to afford 96D (off white solid, 0.23 g, 0.479 mmol, 60.9% yield). LC-MS Anal. Calc'd for $C_{23}H_{23}ClN_6O_2$ 450.15, found [M+H] 451.2. $T_r$=1.07 min (Method T).

Example 96

To a solution of 96D (0.045 g, 0.100 mmol) and (2-(1H-tetrazol-5-yl)phenyl)boronic acid (0.038 g, 0.200 mmol) in DMF (3 mL) and $H_2O$ (0.5 mL) was added $K_2CO_3$ (0.041 g, 0.299 mmol). The reaction was then purged with nitrogen for 15 min, followed by addition of tetrakis(triphenylphosphine) palladium (5.77 mg, 4.99 µmol) and heated to 95° C. for overnight. LCMS indicates product formation. The reaction mass was concentrated under reduced pressure. To that residue water (10 mL) was added and extracted with ethyl acetate (2×15 mL). The combined organic layer was dried over sodium sulfate and concentrated under reduced pressure to get crude which was purified by prep HPLC to obtain Example 96 (yellow solid, 8 mg, 0.014 mmol, 13.58% yield). LC-MS Anal. Calc'd for $C_{30}H_{28}N_{10}O_2$ 560.24, found [M+H] 561.2. $T_r$=1.382 min (Method R). $^1$H NMR (400 MHz, DMSO-d6) δ 9.85 (s, 1H), 9.59 (s, 1H), 7.76-7.78 (m, 2H), 7.67-7.71 (m, 2H), 7.37-7.40 (m, 2H), 7.35 (d, J=7.20 Hz, 2H), 7.25-7.30 (m, 3H), 7.13 (d, J=8.40 Hz, 2H), 7.07 (brs, 1H), 4.56 (s, 2H), 4.11 (brs, 2H), 3.54 (brs, 2H), 3.21 (br, s, 2H), 2.26 (s, 3H).

Example 97

N-(6-(2-(1H-tetrazol-5-yl)phenyl)-2-(4-benzyl-3-oxopiperazin-1-yl)pyrimidin-4-yl)-2-(p-tolyl)acetamide

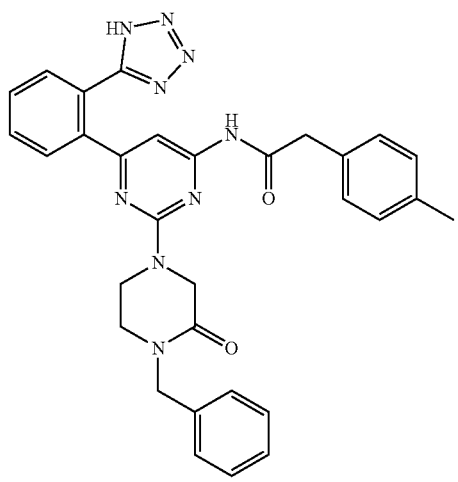 [SMILES: Cc1ccc(CC(=O)Nc2cc(-c3ccccc3-c3nnn[nH]3)nc(N3CCN(Cc4ccccc4)C(=O)C3)n2)cc1]

97A. N-(2-(4-benzyl-3-oxopiperazin-1-yl)-6-chloro-pyrimidin-4-yl)-2-(p-tolyl)acetamide To a solution of 96C (0.25 g, 0.787 mmol) in DCM (5 mL) cooled to 0° C. were added 2-(p-tolyl)acetic acid (0.177 g, 1.180 mmol), POCl$_3$ (0.110 mL, 1.180 mmol) followed by Py (0.191 mL, 2.360 mmol) and slowly warmed to RT for 2 h. The reaction mass was diluted with 25 mL of DCM and washed with sodium bicarbonate (10%) solution (25 mL) and brine solution (25 mL). The organic layer was dried over sodium sulfate and concentrated under reduced pressure. Purification by flash chromatography gave 97A (brown gummy, 0.21 g, 0.429 mmol, 54.6% yield). LC-MS Anal. Calc'd for $C_{24}H_{24}ClN_5O_2$ 449.16, found [M+H] 450.2. $T_r$=1.08 min (Method AA).

Example 97

Example 97 was prepared following the procedure for Example 96 by using 97A. LC-MS Anal. Calc'd for $C_{31}H_{29}N_9O_2$ 559.24, found [M+H] 560.2. $T_r$=1.852 min (Method O). $^1$H NMR (400 MHz, DMSO-d6) δ 10.74 (s, 1H), 7.67-7.78 (m, 4H), 7.56 (s, 1H), 7.36 (t, J=14.40 Hz, 2H), 7.25-7.31 (m, 3H), 7.21 (d, J=8.00 Hz, 2H), 7.14 (d, J=7.60 Hz, 2H), 4.55 (s, 2H), 4.11 (brs, 2H), 3.70 (s, 2H), 3.57 (brs, 2H), 3.18 (brs, 2H), 2.29 (s, 3H).

Example 98

1-(6-(2-(1H-tetrazol-5-yl)phenyl)-2-((1 S,4S)-5-benzyl-2,5-diazabicyclo [2.2.1]heptan-2-yl)pyrimidin-4-yl)-3-(p-tolyl)urea

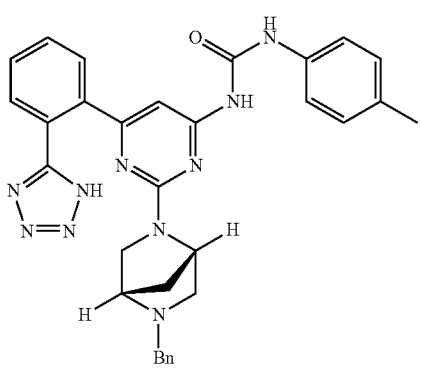 [SMILES: Cc1ccc(NC(=O)Nc2cc(-c3ccccc3-c3nnn[nH]3)nc(N3C[C@@H]4C[C@H]3CN4Cc3ccccc3)n2)cc1]

98A. (1 S,4S)-tert-butyl 5-benzyl-2,5-diazabicyclo[2.2.1]heptane-2-carboxylate To a solution of (1S,4S)-2-Boc-2,5-diazabicyclo[2.2.1]heptane (0.25 g, 1.261 mmol) in DMF (5 mL) was added K$_2$CO$_3$ (0.436 g, 3.15 mmol) followed by benzyl bromide (0.165 mL, 1.387 mmol). The reaction mixture was stirred at rt for 14 h. The reaction mass was concentrated under reduced pressure. To that crude 25 mL water was added and stirred for 30 min. The solid material was filtered and dried under reduced pressure to afford 98A (off white solid, 0.25 g, 0.763 mmol, 60.5% yield). LC-MS Anal. Calc'd for $C_{17}H_{24}N_2O_2$ 288.18, found [M+H] 289.2. $T_r$=1.824 min (Method U).

98B. (1 S,4S)-2-benzyl-2,5-diazabicyclo[2.2.1]heptane, HCl

To a solution of 98A (0.25 g, 0.867 mmol) in 1,4-Dioxane (5 mL) was added 4N Dioxane HCl (5 mL, 20.00 mmol) and stirred at RT for 3 h. The reaction mass was concentrated under reduced pressure, then washed with ethyl acetate and dried under reduced pressure to afford 98B (off white solid, 0.18 g, 0.793 mmol, 91% yield). LC-MS Anal. Calc'd for $C_{12}H_{16}N_2$ 188.13, found [M+H] 189.2. $T_r$=1.509 min (Method O).

Example 98

Example 98 was prepared following the procedure for Example 96 by using 98B & 1-isocyanato-4-methylbenzene. LC-MS Anal. Calc'd for $C_{31}H_{30}N_{10}O$ 558.26, found [M+H] 559.2 $T_r$=1.397 min (Method O). $^1$H NMR (400 MHz, DMSO-d6) δ 10.36 (s, 1H), 9.81 (s, 1H), 9.34 (s, 1H), 7.75 (s, 2H), 7.68 (d, J=7.20 Hz, 2H), 7.55 (s, 2H), 7.46 (s, 3H), 7.38 (d, J=6.40 Hz, 2H), 7.08-7.15 (m, 2H), 6.89 (s, 1H), 4.47-4.54 (m, 2H), 4.22-4.26 (m, 2H), 3.79 (s, 1H), 3.70 (s, 1H), 3.17 (s, 1H), 2.93 (s, 2H), 2.27 (s, 3H), 2.05-2.08 (m, 1H).

Example 99

1-(6-(2-(1H-tetrazol-5-yl)phenyl)-2-(ethyl(3,3,3-trifluoropropyl)amino)pyrimidin-4-yl)-3-(p-tolyl)urea

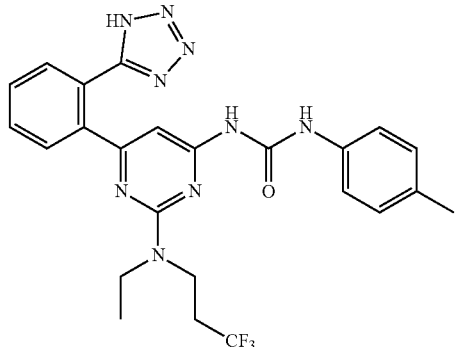

99A. N-ethyl-3,3,3-trifluoropropan-1-amine, HCl

To a solution of 3,3,3-trifluoropropanal (5 g, 44.6 mmol) and ethanamine, HCl (3.64 g, 44.6 mmol) in MeOH (100 mL) was added 4 Å molecular sieves (2.5 g) followed by borane-pyridine complex (5.58 mL, 44.6 mmol) drop wise and then was stirred at RT for 14 h. The reaction mass was filtered through celite, cooled to 0° C., was added 6 N HCl (75 mL) and stirred at RT for 1 h. Then the reaction mass was concentrated under reduced pressure to got crude which was diluted with ethyl acetate (100 mL), stirred for 30 min, filtered, dried under reduced pressure to give 99A (white solid, 4.5 g, 25.3 mmol, 56.8% yield). LC-MS Anal. Calc'd for $C_5H_{10}F_3N$ 141.07, found [M+H] 142.2. $T_r$=0.408 min (Method U)

Example 99

Example 99 was prepared following the procedure for Example 96 by using 99A & 1-isocyanato-4-methylbenzene.

LC-MS Anal. Calc'd for $C_{24}H_{24}F_3N_9O$ 511.2, found [M+H] 512.2, $T_r$=1.939 min (Method O). $^1$H NMR (400 MHz, DMSO-d6) δ 9.78 (s, 1H), 9.24 (s, 1H), 7.65-7.72 (m, 4H), 7.35 (d, J=8.00 Hz, 2H), 7.13 (d, J=8.40 Hz, 2H), 6.92 (s, 1H), 3.52 (t, J=14.80 Hz, 2H), 3.43 (q, J=12.80 Hz, 2H), 2.30-2.35 (m, 2H), 2.28 (s, 3H), 1.04 (t, J=13.60 Hz, 3H).

Example 100

N-(6-(2-(1H-tetrazol-5-yl)phenyl)-2-(ethyl(3,3,3-trifluoropropyl)amino)pyrimidin-4-yl)-2-(p-tolyl) acetamide

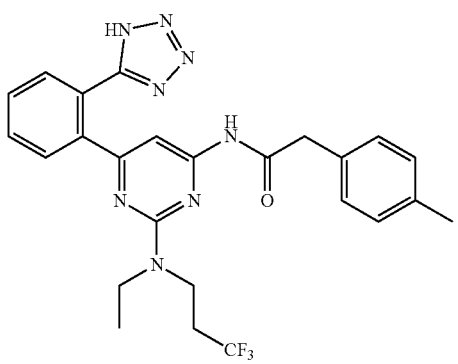 [SMILES: CCN(CCC(F)(F)F)c1nc(NC(=O)Cc2ccc(C)cc2)cc(-c2ccccc2-c2nnn[nH]2)n1]

Example 100 was prepared following the procedure for Example 97 by using 99A & 2-(p-tolyl)acetic acid. LC-MS Anal. Calc'd for $C_{25}H_{25}F_3N_8O$ 510.21, found [M+H] 511.2 $T_r$=1.601 min (Method O). $^1$H NMR (400 MHz, DMSO-d6) δ 10.17 (s, 1H), 7.62-7.72 (m, 4H), 7.37 (s, 1H), 7.21 (d, J=8.00 Hz, 2H), 7.13 (d, J=8.00 Hz, 2H), 3.73 (s, 2H), 3.50 (t, J=14.40 Hz, 2H), 3.40 (q, J=20.40 Hz, 2H), 2.33-2.40 (m, 2H), 2.29 (s, 3H), 0.99 (t, J=14.00 Hz, 3H).

Example 101

N-(2-(2-(1H-tetrazol-5-yl)phenyl)-6-(ethyl(3,3,3-trifluoropropyl)amino)pyridin-4-yl)-2-(p-tolyl)acetamide

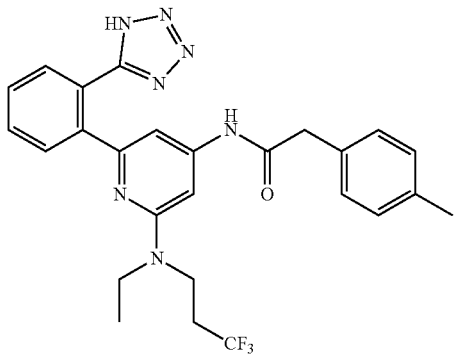 [SMILES: CCN(CCC(F)(F)F)c1cc(NC(=O)Cc2ccc(C)cc2)cc(-c2ccccc2-c2nnn[nH]2)n1]

101A. 6-bromo-N-ethyl-4-nitro-N-(3,3,3-trifluoropropyl)pyridin-2-amine

To a solution of 99A (0.473 g, 2.66 mmol) in 1,4-Dioxane (20 mL) was added DIPEA (1.239 mL, 7.09 mmol) followed by 2,6-dibromo-4-nitropyridine (0.5 g, 1.774 mmol) sealed the tube and heated to 100° C. for overnight. The reaction mass was cooled to RT and concentrated under reduced pressure. Purification by flash chromatography gave 101A (brown solid, 0.32 g, 0.842 mmol, 47.5% yield). LC-MS Anal. Calc'd for $C_{10}H_{11}BrF_3N_3O_2$ 340.99, found [M+H] 342.2 $T_r$=3.652 min (Method U).

101B. 6-bromo-N2-ethyl-N2-(3,3,3-trifluoropropyl) pyridine-2,4-diamine

To a solution of 101A (0.3 g, 0.877 mmol) in Ethanol (5 mL), THF (2 mL) and Water (1 mL) was added ammonium chloride (0.469 g, 8.77 mmol) stirred for 10 min then was added zinc (0.573 g, 8.77 mmol) and stirred at RT for 14 h. The reaction mass was filtered through celite and celite pad was washed with DCM (50 mL), the filtrate was concentrated under reduced pressure. To that residue water (15 mL) was added and extracted with ethyl acetate (2×25 mL). The combined organic layer was dried over sodium sulfate and concentrated under reduced pressure. Purification by flash chromatography gave 101B (brown gummy, 0.12 g, 0.361 mmol, 41.2% yield). LC-MS Anal. Calc'd for $C_{10}H_{13}BrF_3N_3$ 311.02, found [M+H] 312.2 $T_r$=0.81 min (Method AA).

101C. N-(2-bromo-6-(ethyl(3,3,3-trifluoropropyl) amino)pyridin-4-yl)-2-(p-tolyl)acetamide To a solution of 101B (0.11 g, 0.352 mmol) in DMF (3 mL) was added 2-(p-tolyl)acetic acid (0.064 g, 0.423 mmol) and DIPEA (0.185 mL, 1.057 mmol) followed by 2,4,6-tripropyl-1,3,5,2,4,6-trioxatriphosphorinane-2,4,6-trioxide in EtOAc (0.561 g, 0.881 mmol) and stirred at RT for overnight. The reaction mass was concentrated under reduced pressure. To that crude water (15 mL) was added and extracted with ethyl acetate (2×25 mL). The combined organic layer was dried over sodium sulfate and concentrated under reduced pressure. Purification by flash chromatography gave 101C (brown solid, 0.13 g; 0.293 mmol, 83% yield). LC-MS Anal. Calc'd for $C_{19}H_{21}BrF_3N_3O$ 443.08, found [M+H] 444.2 $T_r$=3.568 min (Method U).

Example 101

Example 101 was prepared following the procedure for final step of Example 96 by using 101C. LC-MS Anal. Calc'd for $C_{26}H_{26}F_3N_7O$ 509.21, found [M+H] 510.2 $T_r$=1.545 min (Method O). $^1$H NMR (400 MHz, DMSO-d6) δ 16.08 (s, 1H), 10.29 (s, 1H), 7.56-7.66 (m, 4H), 7.20 (d, J=8.00 Hz, 2H), 7.13 (d, J=8.00 Hz, 2H), 6.91 (s, 2H), 3.60 (s, 2H), 3.28 (t, J=8.00 Hz, 2H), 3.21 (q, J=14.40 Hz, 2H), 2.28 (s, 3H), 2.18-2.21 (m, 2H), 0.98 (t, J=14.00 Hz, 3H).

Example 102

6-(2-(1H-tetrazol-5-yl)phenyl)-N4-(benzo[d]oxazol-2-yl)-N2-benzyl-N2-isobutylpyrimidine-2,4-diamine

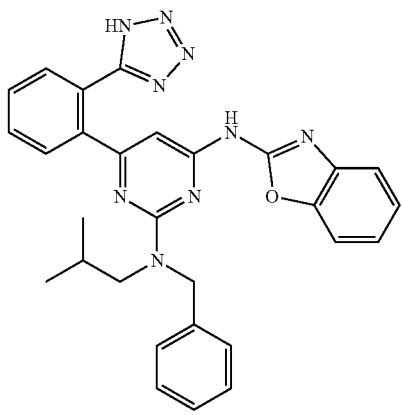 [SMILES: CC(C)CN(Cc1ccccc1)c1nc(Nc2nc3ccccc3o2)cc(-c2ccccc2-c2nnn[nH]2)n1]

102A. N4-(benzo[d]oxazol-2-yl)-N2-benzyl-6-chloro-N2-isobutylpyrimidine-2,4-diamine To a solution of 8A (0.2 g, 0.688 mmol) in Xylene (3 mL) was added 2-chlorobenzo[d]oxazole (0.158 g, 1.032 mmol) and DIPEA (0.360 mL, 2.063 mmol). The reaction was heated to 150° C. for overnight in a sealed tube. The reaction mass was concentrated under reduced pressure, then water (10 mL) was added and extracted with ethyl acetate (2×15 mL). The combined organic layer was dried over sodium sulfate and concentrated under reduced pressure. Purified by prep HPLC to give 102A (white solid, 0.03 g, 0.074 mmol, 10.69% yield). LC-MS Anal. Calc'd for $C_{22}H_{22}ClN_5O$ 407.15, found [M+H] 408.2. $T_r$=4.7 min (Method U).

Example 102

To a solution of 102A (20 mg, 0.049 mmol) in 1,4-Dioxane (2 mL) were added 5-(2-(4,4,5,5-tetramethyl-1,3,2-dioxaborolan-2-yl)phenyl)-1H-tetrazole (40.0 mg, 0.147 mmol) and $K_2CO_3$ (20.33 mg, 0.147 mmol) in water (0.5 mL). The reaction was purged with nitrogen for 15 min and was added tetrakis(triphenylphosphine)palladium (5.67 mg, 4.90 μmol). The reaction mixture was heated to 110° C. for overnight. LCMS indicates product formation. The reaction mass was concentrated under reduced pressure. To that residue water (10 mL) was added and extracted with ethyl acetate (2×15 mL). The combined organic layer was dried over sodium sulfate and concentrated under reduced pressure. The crude was purified by prep HPLC to obtain Example 102 (yellow solid, 13 mg, 0.020 mmol, 33.4% yield). LC-MS Anal. Calc'd for $C_{29}H_{27}N_9O$ 517.23, found [M+H] 518.2 $T_r$=1.356 min (Method AD). $^1$H NMR (400 MHz, DMSO-d6) δ 11.32 (s, 1H), 7.70-7.95 (m, 4H), 7.60-7.63 (m, 3H), 7.07-7.55 (m, 7H), 4.85 (s, 2H), 3.23-3.28 (m, 2H), 1.65-1.68 (m, 1H), 0.73 (s, 6H).

Example 103 tert-butyl 4-((6-(2-(1H-tetrazol-5-yl)phenyl)-4-(3-(2-fluorophenyl)ureido)pyridin-2-yl)(2-methoxyethyl)amino)piperidine-1-carboxylate

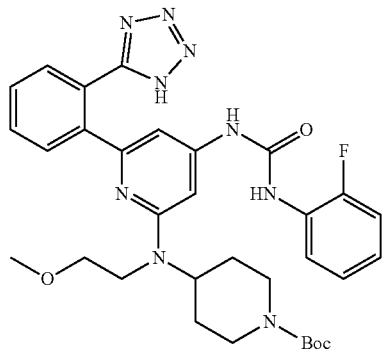 [SMILES: COCCN(c1cc(NC(=O)Nc2ccccc2F)cc(-c2ccccc2-c2nnn[nH]2)n1)C1CCN(C(=O)OC(C)(C)C)CC1]

103A. tert-butyl 4-((2-methoxyethyl)amino)piperidine-1-carboxylate

To a stirred solution of tert-butyl 4-oxopiperidine-1-carboxylate (2 g, 10.04 mmol), acetic acid (0.575 mL, 10.04 mmol) and 2-methoxyethanamine (0.754 g, 10.04 mmol) in MeOH (40 mL) under $N_2$ was cooled to 0° C. Then the mixture was added $NaCNBH_4$ (0.631 g, 10.04 mmol) and stirred at RT for 16 hrs. The reaction mixture was quenched with 50 mL of aqueous 10% $NaHCO_3$ solution and extracted with EtOAc (2×200 mL). The combined organic layer was dried over sodium sulfate and concentrated under reduced pressure. Purification by flash chromatography gave 103A (liquid, 1.5 g, 5.81 mmol, 58% yield). GC-MS Anal. Calc'd for $C_{13}H_{26}N_2O_3$ 258.2, found 157.2 (M-Boc). $T_r$=9.43 min (Method AE).

103B. tert-butyl 4-((6-bromo-4-nitropyridin-2-yl)(2-methoxyethyl)amino)piperidine-1-carboxylate A mixture of 2,6-dibromo-4-nitropyridine (4 g, 14.19 mmol) and 103A (9.17 g, 35.5 mmol) in 1,4 dioxane (40 mL) was refluxed in pressure tube at 130° C. for 16 h. 1,4 dioxane was removed completely. Purification by flash chromatography gave 103B (viscous liquid, 3 g, 6.53 mmol, 46.0% yield). LC-MS Anal. Calc'd for $C_{18}H_{27}BrN_4O_5$ 458.1, found [M+H] 459.2 $T_r$=1.40 min (Method T).

103C. tert-butyl 4-((4-amino-6-bromopyridin-2-yl)(2-methoxyethyl)amino)piperidine-1-carboxylate To a stirred solution of 103B (400 mg, 0.871 mmol) in acetic acid (5 mL) was added iron (243 mg, 4.35 mmol) at RT. The reaction mixture was stirred at RT for 1.5 h. LCMS indicated completion of reaction. The reaction mixture was diluted with EtOAc (25 mL) and basified with Sat.$Na_2CO_3$ (15 mL). This was extracted with EtOAc (2×20 ml). The combined organic layer was dried over sodium sulfate and concentrated under reduced pressure. Purification by flash chromatography gave 103C (300 mg, 0.699 mmol, 80% yield). LC-MS Anal. Calc'd for $C_{18}H_{29}BrN_4O_3$ 428.1, found [M+H] 429.2 $T_r$=3.7 min (Method U).

103D. tert-butyl 4-((6-(2-(1H-tetrazol-5-yl)phenyl)-4-aminopyridin-2-yl)(2-methoxyethyl)amino)piperidine-1-carboxylate A mixture of 103C (285 mg, 0.664 mmol), (2-(1H-tetrazol-5-yl)phenyl)boronic acid (151 mg, 0.797 mmol) and K$_2$CO$_3$ (459 mg, 3.32 mmol) in DMF (5 mL) in a pressure tube was added 0.5 ml of water. The reaction mixture was purged with Argon for 15 min, followed by addition of tetrakis(triphenylphosphine)palladium (115 mg, 0.100 mmol) and again bubbled with Argon for 5 min. The reaction mixture was heated to 97° C. for 16 h. LCMS indicated completion, then the reaction was quenched with 10 mL of water. Aqueous Layer was extracted with DCM (5×50 ml). The combined organic layer was dried over sodium sulfate and concentrated under reduced pressure. Purification by flash chromatography gave 103D (off white solid, 150 mg, 0.303 mmol, 45.7% yield). LC-MS Anal. Calc'd for C$_{25}$H$_{34}$N$_8$O$_3$ 494.3, found [M+H] 495.3 T$_r$=2.47 min (Method U).

Example 103

To a stirred solution 103D (40 mg, 0.081 mmol) in THF (3 mL) was added 1-fluoro-2-isocyanatobenzene (16.63 mg, 0.121 mmol) followed by Et3N (0.034 mL, 0.243 mmol). The reaction mixture was heated to 55° C. for 16 h. LCMS indicated complete conversion. The reaction mass was concentrated under reduced pressure. The crude was purified by prep HPLC to obtain Example 103 (Off white solid, 25 mg, 0.035 mmol, 43.6% yield). LC-MS Anal. Calc'd for C$_{32}$H$_{38}$FN$_9$O$_4$, 631.303, found [M+H] 632.0. T$_r$=2.47 min (Method U). $^1$H NMR (400 MHz, METHANOL-d$_4$) δ 8.10-8.01 (m, 2H), 7.87-7.78 (m, 3H), 7.69 (d, J=1.5 Hz, 1H), 7.24-7.09 (m, 3H), 6.80 (d, J=2.0 Hz, 1H), 4.26 (d, J=14.1 Hz, 2H), 4.06-3.96 (m, 1H), 3.59-3.47 (m, 4H), 3.18 (s, 3H), 3.02-2.88 (m, 2H), 1.90-1.82 (m, 2H), 1.77-1.70 (m, 2H), 1.49 (s, 9H).

Example 104 tert-butyl 4-((6-(2-(1H-tetrazol-5-yl)phenyl)-4-(3-(p-tolyl)ureido)pyridin-2-yl)(2-methoxyethyl)amino)piperidine-1-carboxylate

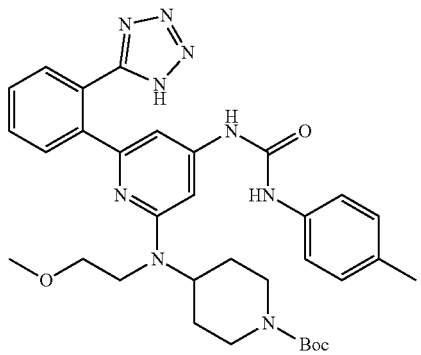 [SMILES: COCCN(c1cc(NC(=O)Nc2ccc(C)cc2)cc(-c2ccccc2-c2nnn[nH]2)n1)C1CCN(C(=O)OC(C)(C)C)CC1]

Example 104 was prepared following the procedure for Example 103 by utilizing 1-isocyanato-4-methylbenzene. LC-MS Anal. Calc'd for C$_{33}$H$_{41}$N$_9$O$_4$, 627.328, found [M+H] 628. T$_r$=2.48 min (Method U). $^1$H NMR (400 MHz, METHANOL-d$_4$) δ 7.99-7.93 (m, 1H), 7.78-7.70 (m, 3H), 7.52 (s, 1H), 7.35 (d, J=8.0 Hz, 2H), 7.15 (d, J=8.5 Hz, 2H), 6.80 (d, J=1.5 Hz, 1H), 4.20 (d, J=13.6 Hz, 2H), 3.98-3.88 (m, 1H), 3.50-3.44 (m, 2H), 3.39-3.33 (m, 2H), 3.17 (s, 3H), 2.99-2.82 (m, 2H), 2.31 (s, 3H), 1.77-1.69 (m, 2H), 1.67-1.57 (m, 2H), 1.47 (s, 9H).

Example 105 tert-butyl 4-((6-(2-(1H-tetrazol-5-yl)phenyl)-4-(3-(4-fluorophenyl)ureido)pyridin-2-yl)(2-methoxyethyl)amino)piperidine-1-carboxylate

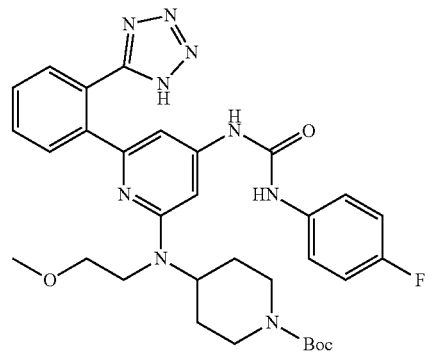 [SMILES: COCCN(c1cc(NC(=O)Nc2ccc(F)cc2)cc(-c2ccccc2-c2nnn[nH]2)n1)C1CCN(C(=O)OC(C)(C)C)CC1]

Example 105 was prepared following the procedure for Example 103 by utilizing 1-fluoro-4-isocyanatobenzene. LC-MS Anal. Calc'd for C$_{32}$H$_{38}$FN$_9$O$_4$, 631.303, found [M+H] 632. T$_r$=2.52 min (Method U). $^1$H NMR (400 MHz, METHANOL-d$_4$) δ 8.03 (dd, J=5.8, 3.3 Hz, 1H), 7.85-7.75 (m, 3H), 7.64 (d, J=1.5 Hz, 1H), 7.50-7.44 (m, 2H), 7.11-7.03 (m, 2H), 6.84 (d, J=1.5 Hz, 1H), 4.24 (d, J=13.6 Hz, 2H), 3.98 (t, J=11.8 Hz, 1H), 3.50 (dd, J=19.8, 4.8 Hz, 4H), 3.17-3.13 (m, 3H), 2.92 (br. s., 2H), 1.88-1.80 (m, 2H), 1.77-1.65 (m, 2H), 1.47 (s, 9H).

Example 106

1-(2-(2-(1H-tetrazol-5-yl)phenyl)-6-((2-methoxyethyl)(piperidin-4-yl)amino)pyridin-4-yl)-3-(2-fluorophenyl)urea

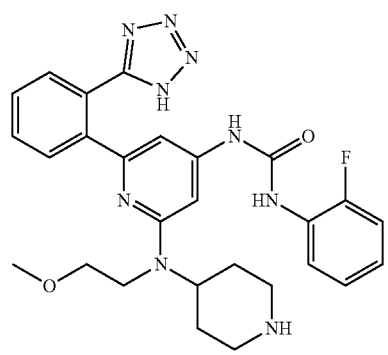 [SMILES: COCCN(c1cc(NC(=O)Nc2ccccc2F)cc(-c2ccccc2-c2nnn[nH]2)n1)C1CCNCC1]

To a stirred solution of Example 103 (25 mg, 0.040 mmol) in DCM (0.5 mL) was added 4M HCl in 1,4-Dioxane (0.1 mL, 0.400 mmol) and was stirred at RT for 16 h. LCMS indicated complete conversion. Solvent was removed under reduced pressure and the compound was lyophilized for 16 h to get Example 106 (off white solid, 18 mg, 0.033 mmol, 83% yield). LC-MS Anal. Calc'd for $C_{27}H_{30}FN_9O_2$, 531.251, found [M+H] 532. $T_r$=1.60 min (Method U). $^1$H NMR (400 MHz, METHANOL-$d_4$) δ 8.06-7.98 (m, 2H), 7.87-7.79 (m, 3H), 7.70-7.65 (m, 1H), 7.25-7.11 (m, 3H), 6.88 (d, J=1.5 Hz, 1H), 4.28-4.18 (m, 1H), 3.79-3.74 (m, 1H), 3.72-3.65 (m, 2H), 3.63-3.52 (m, 4H), 3.30-3.24 (m, 1H), 3.22 (s, 3H), 2.14-2.02 (m, 4H).

Example 107

1-(2-(2-(1H-tetrazol-5-yl)phenyl)-6-((2-methoxyethyl)(piperidin-4-yl)amino)pyridin-4-yl)-3-(p-tolyl)urea

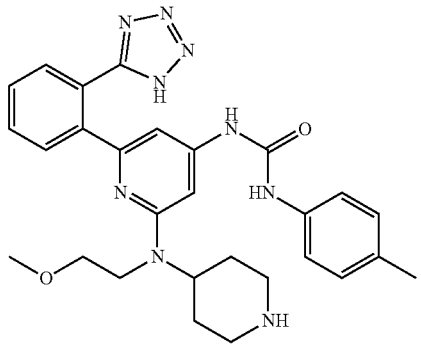 [SMILES: COCCN(c1cc(NC(=O)Nc2ccc(C)cc2)cc(-c2ccccc2-c2nnn[nH]2)n1)C1CCNCC1]

Example 107 was prepared following the procedure for Example 106 by utilizing Example 104. LC-MS Anal. Calc'd for $C_{25}H_{33}N_9O_2$, 527.276, found [M+H] 528. $T_r$=1.71 min (Method U). $^1$H NMR (400 MHz, METHANOL-$d_4$) d=8.03 (dd, J=5.8, 3.3 Hz, 1H), 7.88-7.80 (m, 3H), 7.70 (s, 1H), 7.38-7.32 (m, 2H), 7.17 (d, J=8.0 Hz, 2H), 6.89 (d, J=1.5 Hz, 1H), 4.22 (t, J=11.0 Hz, 1H), 3.79-3.74 (m, 1H), 3.71-3.66 (m, 2H), 3.61-3.52 (m, 4H), 3.27 (br. s., 1H), 3.21 (s, 3H), 2.33 (s, 3H), 2.17-2.02 (m, 4H)

Example 108

1-(2-(2-(1H-tetrazol-5-yl)phenyl)-6-((2-methoxyethyl)(piperidin-4-yl)amino)pyridin-4-yl)-3-(4-fluorophenyl)urea

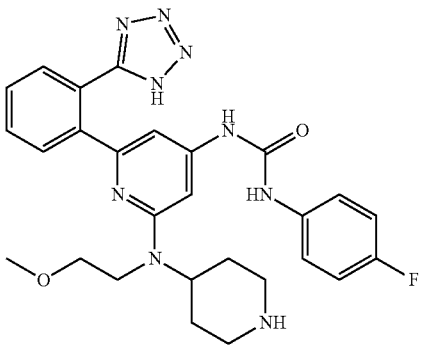 [SMILES: COCCN(c1cc(NC(=O)Nc2ccc(F)cc2)cc(-c2ccccc2-c2nnn[nH]2)n1)C1CCNCC1]

Example 108 was prepared following the procedure for Example 106 by utilizing Example 105. LC-MS Anal. Calc'd for $C_{27}H_{30}FN_9O_2$, 531.251, found [M+H] 532. $T_r$=1.60 min (Method U). $^1$H NMR (400 MHz, METHANOL-$d_4$) δ 8.04-7.98 (m, 1H), 7.87-7.79 (m, 3H), 7.65-7.60 (m, 1H), 7.52-7.45 (m, 2H), 7.14-7.05 (m, 2H), 6.96 (d, J=2.0 Hz, 1H), 4.27-4.14 (m, 1H), 3.79-3.74 (m, 1H), 3.72-3.66 (m, 1H), 3.61-3.52 (m, 4H), 3.30-3.24 (m, 2H), 3.22 (s, 3H), 2.13-1.98 (m, 4H).

Example 109

1-(2-(2-(1H-tetrazol-5-yl)phenyl)-6-(propyl(tetrahydro-2H-pyran-4-yl)amino)pyridin-4-yl)-3-(p-tolyl)urea

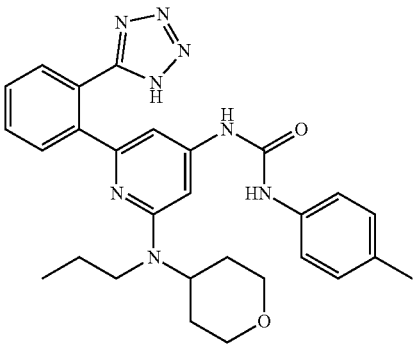 [SMILES: CCCN(c1cc(NC(=O)Nc2ccc(C)cc2)cc(-c2ccccc2-c2nnn[nH]2)n1)C1CCOCC1]

109A. N-propyltetrahydro-2H-pyran-4-amine

To a stirred solution of dihydro-2H-pyran-4(3H)-one (5 g, 49.9 mmol), propan-1-amine (4.11 mL, 49.9 mmol) in MeOH (50 mL) under N2 was stirred at RT for 16 h. To the reaction mixture was added NaBH$_4$ (3.78 g, 100 mmol) at 0° C. and was allowed to stirred RT for 5 h. The reaction mixture was quenched with 10 mL of (Aq) 10%-NH$_4$C$_1$ solution and extracted with EtOAc (2×20 mL). The combined organic layer was dried over sodium sulfate and concentrated to give 109A (colorless liquid, 7 g, 48.9 mmol, 98% yield). GC-MS Anal. Calc'd for $C_8H_{17}NO$ 143.1, found 143.1. $T_r$=6.417 min (Method AE).

Example 109

Example 109 was prepared following the procedure for Example 103 by utilizing 109A and 1-isocyanato-4-methylbenzene. LC-MS Anal. Calc'd for $C_{28}H_{32}N_8O_2$, 512.2, found [M+H] 513.2. $T_r$=2.86 min (Method U). $^1$H NMR (400 MHz, METHANOL-$d_4$) δ 8.01-7.94 (m, 1H), 7.81-7.73 (m, 3H), 7.52-7.42 (m, 3H), 7.13-7.04 (m, 2H), 6.81 (d, J=1.5 Hz, 1H), 4.14-4.06 (m, 1H), 4.01 (dd, J=11.5, 4.5 Hz, 2H), 3.51-3.43 (m, 4H), 2.30 (s, 3H), 1.90 (qd, J=12.2, 4.5 Hz, 2H), 1.67-1.58 (m, 4H), 1.03-0.95 (m, 3H).

Example 110

1-(2-(2-(1H-tetrazol-5-yl)phenyl)-6-(propyl(tetrahydro-2H-pyran-4-yl)amino)pyridin-4-yl)-3-(4-fluorophenyl)urea

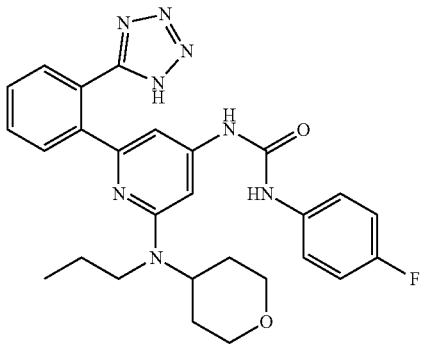 [SMILES: CCCN(c1cc(NC(=O)Nc2ccc(F)cc2)cc(-c2ccccc2-c2nnn[nH]2)n1)C1CCOCC1]

Example 110 was prepared following the procedure for Example 109 by utilizing 1-fluoro-4-isocyanatobenzene. LC-MS Anal. Calc'd for $C_{27}H_{29}FN_8O_2$, 516.240, found [M+H] 517.2. $T_r$=1.67 min (Method U). $^1$H NMR (400 MHz, METHANOL-$d_4$) δ 8.01-7.95 (m, 1H), 7.81-7.74 (m, 3H), 7.51-7.43 (m, 3H), 7.13-7.04 (m, 2H), 6.81 (d, J=1.5 Hz, 1H), 4.15-4.05 (m, 1H), 4.01 (dd, J=11.5, 4.5 Hz, 2H), 3.51-3.44 (m, 2H), 3.38-3.35 (m, 2H), 1.90 (qd, J=12.2, 4.5 Hz, 2H), 1.67-1.56 (m, 4H), 1.03-0.96 (m, 3H).

Example 111

1-(2-(2-(1H-tetrazol-5-yl)phenyl)-6-(propyl(tetrahydro-2H-pyran-4-yl)amino)pyridin-4-yl)-3-(2-fluorophenyl)urea

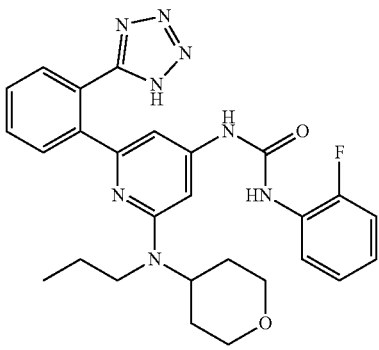 [SMILES: CCCN(c1cc(NC(=O)Nc2ccccc2F)cc(-c2ccccc2-c2nnn[nH]2)n1)C1CCOCC1]

Example 111 was prepared following the procedure for Example 109 by utilizing 1-fluoro-2-isocyanatobenzene. LC-MS Anal. Calc'd for $C_{27}H_{29}FN_8O_2$, 516.240, found [M+H] 517.2. $T_r$=2.75 min (Method U). $^1$H NMR (400 MHz, METHANOL-$d_4$) δ 8.14-8.05 (m, 1H), 8.01-7.94 (m, 1H), 7.81-7.75 (m, 3H), 7.44 (d, J=1.5 Hz, 1H), 7.23-7.08 (m, 3H), 6.79 (d, J=2.0 Hz, 1H), 4.10 (ddd, J=11.9, 7.7, 4.0 Hz, 1H), 4.01 (dd, J=11.5, 4.0 Hz, 2H), 3.53-3.44 (m, 2H), 3.37 (d, J=4.0 Hz, 1H), 1.89 (qd, J=12.1, 4.3 Hz, 2H), 1.66-1.58 (m, 5H), 1.04-0.96 (m, 3H).

Example 112

1-(2-(2-(1H-tetrazol-5-yl)phenyl)-6-((4,4-difluorocyclohexyl)(2-methoxyethyl)amino)pyridin-4-yl)-3-(2-fluorophenyl)urea

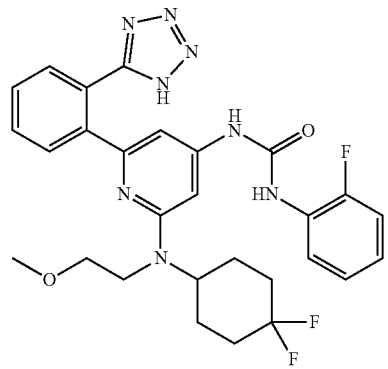 [SMILES: COCCN(c1cc(NC(=O)Nc2ccccc2F)cc(-c2ccccc2-c2nnn[nH]2)n1)C1CCC(F)(F)CC1]

112A. 4,4-difluoro-N-(2-methoxyethyl)cyclohexanamine

Compound 112A was prepared following the procedure for 109A by utilizing 4,4-difluorocyclohexanone and 2-methoxyethanamine. GC-MS Anal. Calc'd for $C_9H_{17}F_2NO$ 193.1, found 193.1. $T_r$=6.942 min (Method AE).

Example 112

Example 112 was prepared following the procedure for Example 103 by utilizing 112A. LC-MS Anal. Calc'd for $C_{28}H_{29}F_3N_8O_2$, 566.237, found [M+H] 567.2. $T_r$=2.33 min (Method U). $^1$H NMR (400 MHz, METHANOL-$d_4$) δ 8.11-7.99 (m, 2H), 7.87-7.77 (m, 3H), 7.62 (d, J=1.5 Hz, 1H), 7.24-7.08 (m, 3H), 6.82 (d, J=2.0 Hz, 1H), 4.05-3.95 (m, 1H), 3.59-3.45 (m, 4H), 3.22-3.17 (m, 3H), 2.20 (br. s., 3H), 1.96-1.85 (m, 5H).

Example 113

1-(2-(2-(1H-tetrazol-5-yl)phenyl)-6-((4,4-difluorocyclohexyl)(2-methoxyethyl)amino)pyridin-4-yl)-3-(p-tolyl)urea

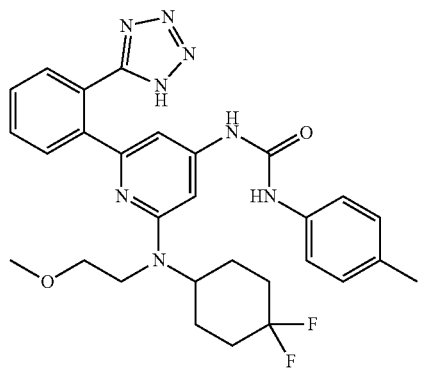 [SMILES: COCCN(c1cc(NC(=O)Nc2ccc(C)cc2)cc(-c2ccccc2-c2nnn[nH]2)n1)C1CCC(F)(F)CC1]

Example 113 was prepared following the procedure for Example 112 by utilizing 1-isocyanato-4-methylbenzene. LC-MS Anal. Calc'd for $C_{29}H_{32}F_2N_8O_2$, 562.262, found [M+H] 563.2 $T_r$=2.45 min (Method U). $^1$H NMR (400 MHz, METHANOL-$d_4$) δ 8.07-8.00 (m, 1H), 7.87-7.76 (m, 3H), 7.64-7.60 (m, 1H), 7.39-7.32 (m, 2H), 7.17 (d, J=8.0 Hz, 2H), 6.82 (d, J=1.5 Hz, 1H), 4.04-3.94 (m, 1H), 3.59-3.53 (m, 2H), 3.51-3.45 (m, 2H), 3.20-3.16 (m, 3H), 2.33 (s, 3H), 2.25-2.05 (m, 4H), 2.03-1.82 (m, 4H).

Example 114

1-(2-(2-(1H-tetrazol-5-yl)phenyl)-6-((4,4-difluorocyclohexyl)(2-methoxyethyl) amino)pyridin-4-yl)-3-(4-fluorophenyl)urea

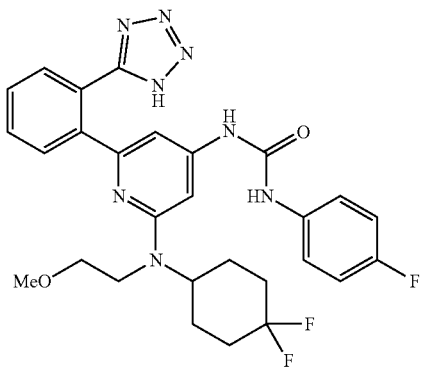 [SMILES: COCCN(c1cc(NC(=O)Nc2ccc(F)cc2)cc(-c2ccccc2-c2nnn[nH]2)n1)C1CCC(F)(F)CC1]

Example 114 was prepared following the procedure for Example 112 by utilizing 1-fluoro-4-isocyanatobenzene. LC-MS Anal. Calc'd for $C_{28}H_{29}F_3N_8O2$ 566.237, found [M+H] 567.2. $T_r$=2.31 min (Method U). $^1$H NMR (400 MHz, METHANOL-$d_4$) δ 8.07-8.01 (m, 1H), 7.87-7.78 (m, 3H), 7.64 (s, 1H), 7.52-7.46 (m, 2H), 7.14-7.06 (m, 2H), 6.84 (d, J=1.5 Hz, 1H), 3.99 (d, J=5.0 Hz, 1H), 3.60-3.47 (m, 4H), 3.18 (s, 3H), 2.21 (br. s., 2H), 1.99-1.86 (m, 2H), 1.90-2.0 (m, 4H).

Example 115

1-(2-(2-(1H-tetrazol-5-yl)phenyl)-6-((2-methoxyethyl)(tetrahydro-2H-pyran-4-yl)amino)pyridin-4-yl)-3-(2-fluorophenyl)urea

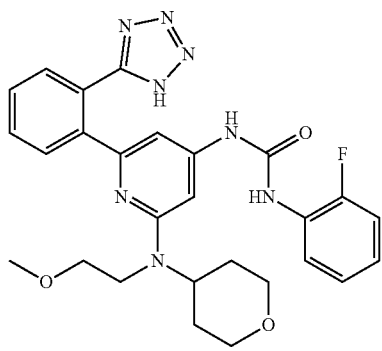 [SMILES: COCCN(c1cc(NC(=O)Nc2ccccc2F)cc(-c2ccccc2-c2nnn[nH]2)n1)C1CCOCC1]

115A.
4,4-difluoro-N-(2-methoxyethyl)cyclohexanamine

Compound 115A was prepared following the procedure for 109A by utilizing dihydro-2H-pyran-4(3H)-one and 2-methoxyethanamine. GC-MS Anal. Calc'd for $C_8H_{17}NO_2$ 159.1, found 159.1. $T_r$=7.01 min (Method AE).

Example 115

Example 115 was prepared following the procedure for Example 103 by utilizing 115A. LC-MS Anal. Calc'd for $C_{27}H_{29}FN_8O_3$, 532.235, found [M+H] 533.2. $T_r$=1.87 min (Method U). $^1$H NMR (400 MHz, METHANOL-$d_4$) δ 8.09-7.99 (m, 2H), 7.86-7.77 (m, 3H), 7.67 (s, 1H), 7.23-7.08 (m, 3H), 6.78 (d, J=2.0 Hz, 1H), 4.12-4.01 (m, 3H), 3.63-3.46 (m, 6H), 3.17 (s, 3H), 1.96-1.85 (m, 2H), 1.82-1.74 (m, 2H).

Example 116

1-(2-(2-(1H-tetrazol-5-yl)phenyl)-6-((2-methoxyethyl)(tetrahydro-2H-pyran-4-yl)amino)pyridin-4-yl)-3-(p-tolyl)urea

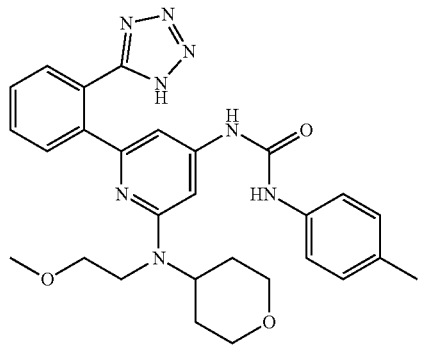 [SMILES: COCCN(c1cc(NC(=O)Nc2ccc(C)cc2)cc(-c2ccccc2-c2nnn[nH]2)n1)C1CCOCC1]

Example 116 was prepared following the procedure for Example 115 by utilizing 1-isocyanato-4-methylbenzene. LC-MS Anal. Calc'd for $C_{28}H_{32}N_8O_3$, 528.260, found [M+H] 529.2. $T_r$=2.15 min (Method U). $^1$H NMR (400 MHz, METHANOL-$d_4$) δ 8.03 (dd, J=6.0, 2.5 Hz, 1H), 7.85-7.73 (m, 3H), 7.65 (d, J=1.5 Hz, 1H), 7.37-7.31 (m, 2H), 7.15 (d, J=8.5 Hz, 2H), 6.80 (d, J=1.5 Hz, 1H), 4.05 (dd, J=11.5, 4.5 Hz, 3H), 3.63-3.45 (m, 6H), 3.16 (s, 3H), 2.31 (s, 3H), 1.89 (qd, J=12.0, 4.5 Hz, 2H), 1.82-1.74 (m, 2H).

Example 117

1-(2-(2-(1H-tetrazol-5-yl)phenyl)-6-((2-methoxyethyl)(tetrahydro-2H-pyran-4-yl)amino)pyridin-4-yl)-3-(4-fluorophenyl)urea

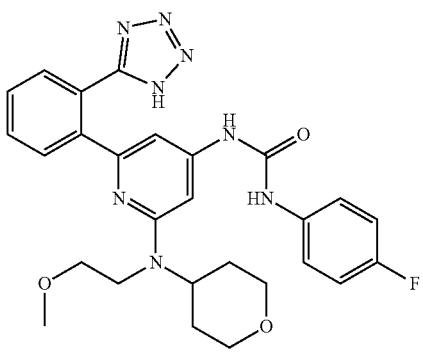 [SMILES: COCCN(c1cc(NC(=O)Nc2ccc(F)cc2)cc(-c2ccccc2-c2nnn[nH]2)n1)C1CCOCC1]

Example 117 was prepared following the procedure for Example 115 by utilizing 1-fluoro-4-isocyanatobenzene. LC-MS Anal. Calc'd for $C_{27}H_{29}FN_8O_3$, 532.235, found [M+H] 533.2. $T_r$=1.74 min (Method U). $^1$H NMR (400 MHz, METHANOL-$d_4$) δ 7.95-7.89 (m, 1H), 7.75-7.66 (m, 3H), 7.52-7.44 (m, 3H), 7.12-7.05 (m, 2H), 6.81 (d, J=2.0 Hz, 1H), 4.00 (dd, J=11.3, 4.3 Hz, 3H), 3.57-3.52 (m, 2H), 3.51-3.43 (m, 2H), 3.35 (d, J=5.0 Hz, 2H), 3.20 (s, 3H), 1.78 (qd, J=12.0, 5.0 Hz, 2H), 1.63 (d, J=10.5 Hz, 2H).

Example 118

1-(2-(2-(1H-tetrazol-5-yl)phenyl)-6-((4,4-dimethylcyclohexyl) (propyl)amino)pyridin-4-yl)-3-(2-fluorophenyl)urea

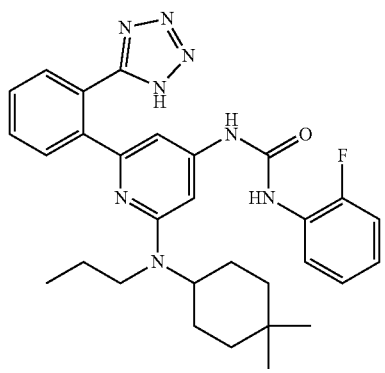 [SMILES: CCCN(c1cc(NC(=O)Nc2ccccc2F)cc(-c2ccccc2-c2nnn[nH]2)n1)C1CCC(C)(C)CC1]

118A. 4,4-dimethyl-N-propylcyclohexanamine

Compound 118A was prepared following the procedure for 109A by utilizing 4,4-dimethylcyclohexanone and propan-1-amine. GC-MS Anal. Calc'd for $C_{11}H_{23}N$ 169.2, found 169.2. $T_r$=6.783 min (Method AE).

Example 118

Example 118 was prepared following the procedure for Example 103 by utilizing 118A. LC-MS Anal. Calc'd for $C_{30}H_{35}FN_8O$, 542.292, found [M+H] 543.3. $T_r$=3.0 min (Method U). $^1$H NMR (400 MHz, METHANOL-$d_4$) δ 8.11-8.04 (m, 1H), 8.00-7.96 (m, 1H), 7.79-7.70 (m, 3H), 7.48 (d, J=1.8 Hz, 1H), 7.21-7.07 (m, 3H), 6.69 (d, J=1.8 Hz, 1H), 3.78-3.67 (m, 1H), 3.37 (d, J=8.0 Hz, 2H), 1.84-1.71 (m, 2H), 1.64-1.45 (m, 5H), 1.41-1.28 (m, 3H), 1.01-0.93 (m, 9H).

Example 119

1-(2-(2-(1H-tetrazol-5-yl)phenyl)-6-((4,4-dimethylcyclohexyl) (propyl)amino)pyridin-4-yl)-3-(p-tolyl)urea

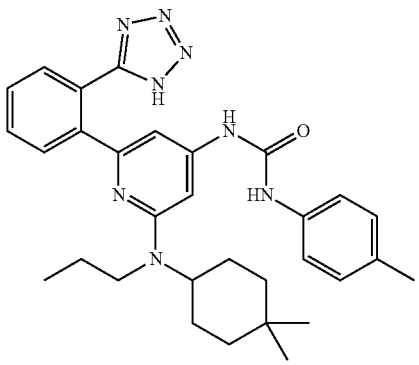 [SMILES: CCCN(c1cc(NC(=O)Nc2ccc(C)cc2)cc(-c2ccccc2-c2nnn[nH]2)n1)C1CCC(C)(C)CC1]

Example 119 was prepared following the procedure for Example 118 by utilizing 1-isocyanato-4-methylbenzene. LC-MS Anal. Calc'd for $C_{31}H_{38}N_8O$, 538.317, found [M+H] 539.3. $T_r$=3.12 min (Method U). $^1$H NMR (400 MHz, METHANOL-$d_4$) δ 8.01 (d, J=7.0 Hz, 1H), 7.82-7.71 (m, 3H), 7.50 (s, 1H), 7.35 (d, J=8.5 Hz, 2H), 7.16 (d, J=8.3 Hz, 2H), 6.72 (s, 1H), 3.78-3.66 (m, 1H), 3.38 (d, J=8.3 Hz, 2H), 2.33 (s, 3H), 1.86-1.73 (m, 2H), 1.66-1.47 (m, 5H), 1.43-1.29 (m, 3H), 1.04-0.94 (m, 9H).

Example 120

N-(2-(2-(1H-tetrazol-5-yl)phenyl)-6-(4-(tetrahydrofuran-2-carbonyl) piperazin-1-yl)pyridin-4-yl)-2-(p-tolyl)acetamide

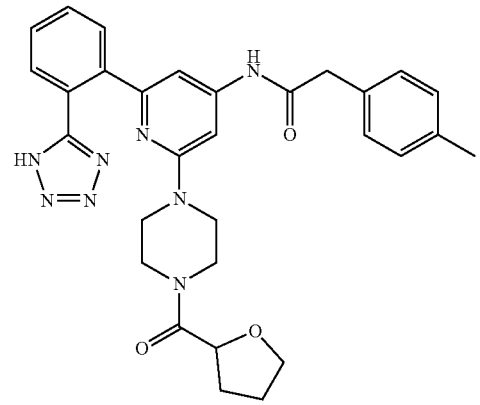 [SMILES: Cc1ccc(CC(=O)Nc2cc(-c3ccccc3-c3nnn[nH]3)nc(N3CCN(C(=O)C4CCCO4)CC3)c2)cc1]

120A. N-(2,6-dichloropyridin-4-yl)-2-(p-tolyl)acetamide

To a solution of 2,6-dichloropyridin-4-amine (2.5 g, 15.34 mmol) in DMF (50 mL) were added DIPEA (8.04 mL, 46.0 mmol), 2-(p-tolyl)acetic acid (2.418 g, 16.10 mmol) followed by 2,4,6-tripropyl-1,3,5,2,4,6-trioxatriphosphorinane-2,4,6-trioxide in DMF (24.40 g, 38.3 mmol) and stirred at rt for overnight. The reaction mass was concentrated under reduced pressure and to that residue ice water (150 mL) was added and stirred for 30 min. The solid was filtered and dried under vacuo to afford 120A (brown solid, 4.2 g, 13.38 mmol, 87% yield). LC-MS Anal. Calc'd $C_{14}H_{12}Cl_2N_2O$ for 294.03, found [M+H] 295.2 $T_r$=3.01 min (Method U).

120B. N-(2-(2-(1H-tetrazol-5-yl)phenyl)-6-chloropyridin-4-yl)-2-(p-tolyl)acetamide To a solution of 120A (100 mg, 0.339 mmol) in DMF (4 mL) were added 5-(2-(4,4,5,5-tetramethyl-1,3,2-dioxaborolan-2-yl)phenyl)-1H-tetrazole (138 mg, 0.508 mmol) and $K_2CO_3$ (117 mg, 0.847 mmol) in water (1 mL). Then the reaction mixture was purged with nitrogen for 15 min. Tetrakis(triphenylphosphine) palladium (19.57 mg, 0.017 mmol) was added to the solution and heated to 90° C. for over night. The reaction mass was diluted with methanol (30 mL) and filtered through celite. The filterate was concentrated under reduced pressure. The crude was purified by prep HPLC to get 120B (white solid, 60 mg, 0.145 mmol, 42.9% yield). LC-MS Anal. Calc'd $C_{21}H_{17}ClN_6O$ for 404.02, found [M+H] 405.2 $T_r$=1.65 min (Method U).

Example 120

In a microwave vial 120B (20 mg, 0.049 mmol) was mixed with piperazin-1-yl(tetrahydrofuran-2-yl)methanone (91 mg, 0.494 mmol). The vial was capped and the mixture was heated on a sand bath at 140° C. for 16 h. LC-MS analysis showed mass of desired product formation. The crude compound was purified by preparative LC/MS to get Example 120 (14 mg, 0.024 mmol, 50% yield). LC-MS Anal. Calc'd for $C_{30}H_{32}N_8O_3$, 552.26, found [M+H] 553.4. $T_r$=1.185 min (Method R). $^1$H N MIR (400 MHz, DMSO-d6) δ 10.38 (s, 1H), 7.71 (s, 1H), 7.60 (d, J=6.8 Hz, 1H), 7.21-7.20 (m, 3H), 7.14 (d, J=8.0 Hz, 2H), 7.08 (s, 1H), 7.00-6.95 (m, 2H), 4.68-4.65 (m, 1H), 3.78-3.73 (s, 2H), 3.61 (s, 2H), 3.44-3.39 (m, 4H), 3.08-3.05 (m, 4H), 2.28 (s, 3H), 2.04-1.99 (m, 2H), 1.85-1.81 (m, 2H).

Examples 121-135 were prepared following the procedure for Example 120 by using the corresponding amines.

| Ex. No. | Name | R | Tr (min) Method R | [M + H]⁺ |
|---|---|---|---|---|
| 121 | (R)-N-(2-(2-(1H-tetrazol-5-yl)phenyl)-6-(3-hydroxypyrrolidin-1-yl)pyridin-4-yl)-2-(p-tolyl)acetamide | | 1.114 | 456.3 |
| 122 | 1-(6-(2-(1H-tetrazol-5-yl)phenyl)-4-(2-(p-tolyl)acetamido)pyridin-2-yl)-N,N-diethylpiperidine-3-carboxamide | 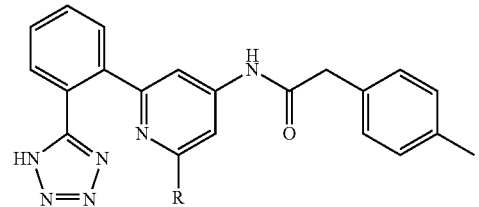 | 1.525 | 553.4 |

-continued

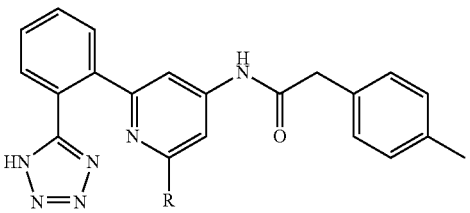

| Ex. No. | Name | R | Tr (min) Method R | [M + H]+ |
|---|---|---|---|---|
| 123 | N-(2-(2-(1H-tetrazol-5-yl)phenyl)-6-(4-(4-methylpiperazin-1-yl)piperidin-1-yl)pyridin-4-yl)-2-(p-tolyl)acetamide | | 1.152 | 552.5 |
| 124 | 2-(4-(6-(2-(1H-tetrazol-5-yl)phenyl)-4-(2-(p-tolyl)acetamido)pyridin-2-yl)piperazin-1-yl)-N-isopropylacetamide | | 1.358 | 554.4 |
| 125 | N-(2-(2-(1H-tetrazol-5-yl)phenyl)-6-(2,6-dimethylmorpholino)pyridin-4-yl)-2-(p-tolyl)acetamide | | 1.411 | 484.4 |
| 126 | N-(2-(2-(1H-tetrazol-5-yl)phenyl)-6-(3-methylpiperidin-1-yl)pyridin-4-yl)-2-(p-tolyl)acetamide | | 1.557 | 468.3 |
| 127 | N-(2-(2-(1H-tetrazol-5-yl)phenyl)-6-(azepan-1-yl)pyridin-4-yl)-2-(p-tolyl)acetamide | | 1.504 | 468.3 |
| 128 | N-(2-(2-(1H-tetrazol-5-yl)phenyl)-6-(2-methylpyrrolidin-1-yl)pyridin-4-yl)-2-(p-tolyl)acetamide | | 1.436 | 454.3 |

-continued

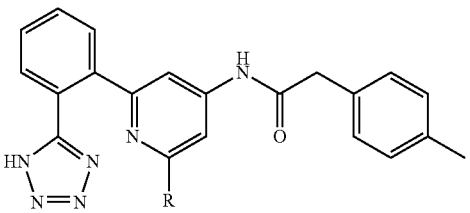

| Ex. No. | Name | R | Tr (min) Method R | [M + H]+ |
|---|---|---|---|---|
| 129 | N-(2-(2-(1H-tetrazol-5-yl)phenyl)-6-(4-(2-methoxyphenyl)piperazin-1-yl)pyridin-4-yl)-2-(p-tolyl)acetamide | 2-methoxyphenyl-piperazinyl | 1.531 | 561.4 |
| 130 | N-(2-(2-(1H-tetrazol-5-yl)phenyl)-6-(4-acetyl-1,4-diazepan-1-yl)pyridin-4-yl)-2-(p-tolyl)acetamide | 4-acetyl-1,4-diazepan-1-yl | 1.26 | 511.4 |
| 131 | N-(2-(2-(1H-tetrazol-5-yl)phenyl)-6-(pyrrolidin-1-yl)pyridin-4-yl)-2-(p-tolyl)acetamide | pyrrolidin-1-yl | 1.427 | 440.3 |
| 132 | N-(2-(2-(1H-tetrazol-5-yl)phenyl)-6-(3,4-dihydroisoquinolin-2(1H)-yl)pyridin-4-yl)-2-(p-tolyl)acetamide | 3,4-dihydroisoquinolin-2(1H)-yl | 1.643 | 502.3 |
| 133 | N-(2-(2-(1H-tetrazol-5-yl)phenyl)-6-(4-(hydroxymethyl)piperidin-1-yl)pyridin-4-yl)-2-(p-tolyl)acetamide | 4-(hydroxymethyl)piperidin-1-yl | 1.202 | 484.3 |
| 134 | N-(2-(2-(1H-tetrazol-5-yl)phenyl)-6-(4-hydroxy-4-phenylpiperidin-1-yl)pyridin-4-yl)-2-(p-tolyl)acetamide | 4-hydroxy-4-phenylpiperidin-1-yl | 1.535 | 546.4 |

-continued

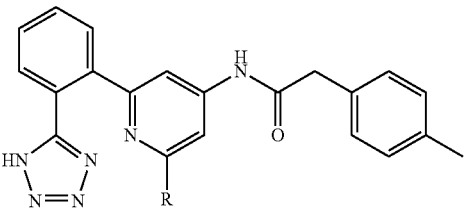

| Ex. No. | Name | R | Tr (min) Method R | [M + H]+ |
|---|---|---|---|---|
| 135 | N-(2-(2-(1H-tetrazol-5-yl)phenyl)-6-(3,3-dimethylpiperidin-1-yl)pyridin-4-yl)-2-(p-tolyl)acetamide | 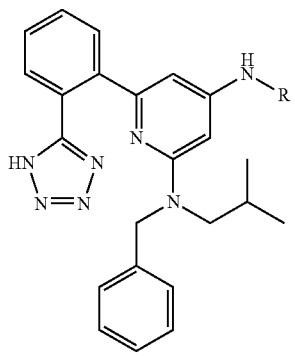 | 1.617 | 482.4 |

Examples 136-198 were prepared following the procedure for Example 49 by using the corresponding halides.

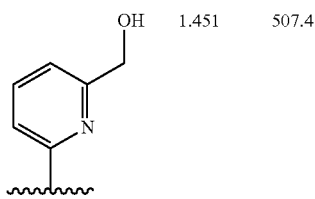

| Ex. No. | Name | R | Tr (min) Method R | [M + H]+ |
|---|---|---|---|---|
| 136 | 6-(2-(1H-tetrazol-5-yl)phenyl)-N2-benzyl-N2-isobutyl-N4-(6-methylpyrazin-2-yl)pyridine-2,4-diamine | 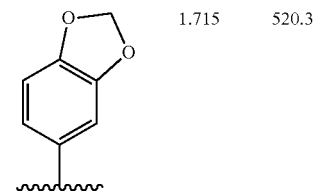 | 1.628 | 492.4 |
| 137 | (6-((2-(2-(1H-tetrazol-5-yl)phenyl)-6-(benzyl(isobutyl)amino)pyridin-4-yl)amino)pyridin-2-yl)methanol | | 1.451 | 507.4 |
| 138 | 6-(2-(1H-tetrazol-5-yl)phenyl)-N4-(benzo[d][1,3]dioxol-5-yl)-N2-benzyl-N2-isobutylpyridine-2,4-diamine | | 1.715 | 520.3 |

-continued

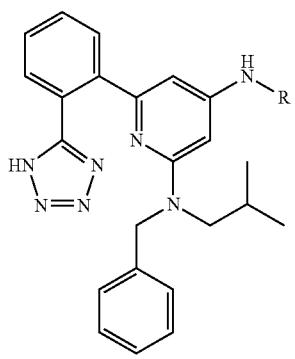

| Ex. No. | Name | R | Tr (min) Method R | [M + H]+ |
|---|---|---|---|---|
| 139 | 6-(2-(1H-tetrazol-5-yl)phenyl)-N2-benzyl-N4-(3-fluoropyridin-4-yl)-N2-isobutylpyridine-2,4-diamine | 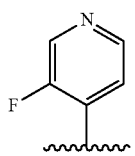 | 1.379 | 495.3 |
| 140 | 6-(2-(1H-tetrazol-5-yl)phenyl)-N2-benzyl-N2-isobutyl-N4-(2-methylpyrimidin-4-yl)pyridine-2,4-diamine | 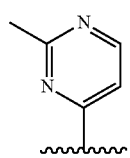 [SMILES: *c1ccnc(C)n1] | 1.550 | 492.4 |
| 141 | 6-(2-(1H-tetrazol-5-yl)phenyl)-N2-benzyl-N2-isobutyl-N4-(pyrimidin-2-yl)pyridine-2,4-diamine | 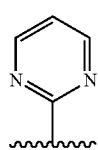 | 1.465 | 478.3 |
| 142 | 6-(2-(1H-tetrazol-5-yl)phenyl)-N2-benzyl-N2-isobutyl-N4-(5-methylpyridin-2-yl)pyridine-2,4-diamine | 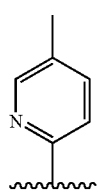 [SMILES: *c1ccc(C)cn1] | 1.755 | 491.4 |
| 143 | 6-(2-(1H-tetrazol-5-yl)phenyl)-N2-benzyl-N4-(5-fluoropyrimidin-2-yl)-N2-isobutylpyridine-2,4-diamine | 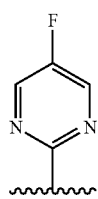 | 1.666 | 496.3 |
| 144 | 4-((2-(2-(1H-tetrazol-5-yl)phenyl)-6-(benzyl(isobutyl)amino)pyridin-4-yl)amino)benzamide | 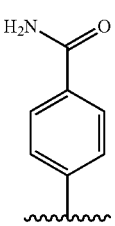 [SMILES: *c1ccc(C(N)=O)cc1] | 1.457 | 519.4 |

-continued

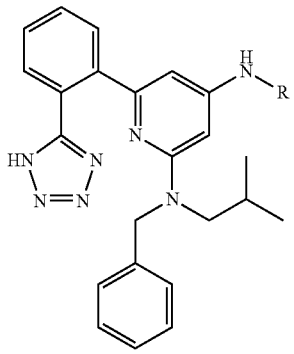

| Ex. No. | Name | R | Tr (min) Method R | [M + H]+ |
|---|---|---|---|---|
| 145 | 6-(2-(1H-tetrazol-5-yl)phenyl)-N2-benzyl-N2-isobutyl-N4-(4-methylpyrimidin-2-yl)pyridine-2,4-diamine | 4-methylpyrimidin-2-yl | 1.656 | 492.4 |
| 147 | 6-(2-(1H-tetrazol-5-yl)phenyl)-N2-benzyl-N4-(2-fluoro-4-methylphenyl)-N2-isobutylpyridine-2,4-diamine | 2-fluoro-4-methylphenyl | 1.762 | 508.4 |
| 148 | 6-(2-(1H-tetrazol-5-yl)phenyl)-N2-benzyl-N2-isobutyl-N4-(p-tolyl)pyridine-2,4-diamine | p-tolyl | 1.831 | 490.4 |
| 149 | 6-(2-(1H-tetrazol-5-yl)phenyl)-N2-benzyl-N2-isobutyl-N4-(5-propylpyrimidin-2-yl)pyridine-2,4-diamine | 5-propylpyrimidin-2-yl | 1.904 | 520.4 |
| 150 | 6-((2-(2-(1H-tetrazol-5-yl)phenyl)-6-(benzyl(isobutyl)amino)pyridin-4-yl)amino)nicotinonitrile | 5-cyanopyridin-2-yl | 1.576 | 502.4 |

-continued

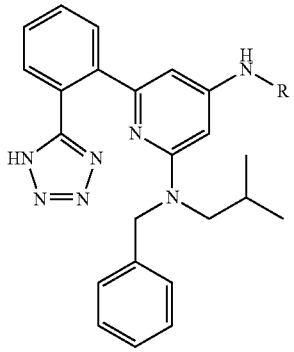

| Ex. No. | Name | R | Tr (min) Method R | [M + H]+ |
|---|---|---|---|---|
| 151 | 6-(2-(1H-tetrazol-5-yl)phenyl)-N2-benzyl-N4-(3-fluoro-6-(trifluoromethyl)pyridin-2-yl)-N2-isobutylpyridine-2,4-diamine | | 2.011 | 563.4 |
| 152 | 6-(2-(1H-tetrazol-5-yl)phenyl)-N2-benzyl-N4-(5-fluoro-3-methylpyridin-2-yl)-N2-isobutylpyridine-2,4-diamine | | 1.800 | 509.4 |
| 154 | 6-(2-(1H-tetrazol-5-yl)phenyl)-N2-benzyl-N2-isobutyl-N4-(quinolin-2-yl)pyridine-2,4-diamine | | 1.904 | 527.4 |
| 155 | 6-(2-(1H-tetrazol-5-yl)phenyl)-N2-benzyl-N2-isobutyl-N4-(pyrazolo[1,5-a]pyrimidin-7-yl)pyridine-2,4-diamine | | 1.522 | 517.4 |
| 156 | 6-(2-(1H-tetrazol-5-yl)phenyl)-N2-benzyl-N4-(6-fluorobenzo[d]thiazol-2-yl)-N2-isobutylpyridine-2,4-diamine | | 1.799 | 551.3 |
| 157 | 6-(2-(1H-tetrazol-5-yl)phenyl)-N2-benzyl-N2-isobutyl-N4-(6-methylpyridazin-3-yl)pyridine-2,4-diamine | | 1.455 | 492.4 |

-continued

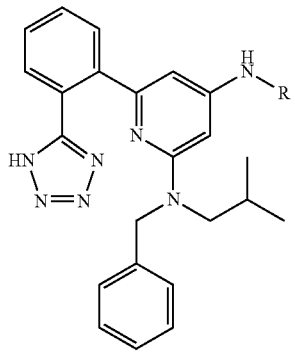

| Ex. No. | Name | R | Tr (min) Method R | [M + H]+ |
|---|---|---|---|---|
| 158 | 6-(2-(1H-tetrazol-5-yl)phenyl)-N2-benzyl-N2-isobutyl-N4-(5-isopropylpyrimidin-2-yl)pyridine-2,4-diamine | 5-isopropylpyrimidin-2-yl | 1.717 | 520.4 |
| 159 | 6-((2-(2-(1H-tetrazol-5-yl)phenyl)-6-(benzyl(isobutyl)amino)pyridin-4-yl)amino)-5-fluoronicotinamide | 5-fluoro-6-carbamoylpyridin-2-yl | 1.484 | 538.4 |
| 160 | 6-(2-(1H-tetrazol-5-yl)phenyl)-N2-benzyl-N4-(2-fluoropyridin-3-yl)-N2-isobutylpyridine-2,4-diamine | 2-fluoropyridin-3-yl | 1.871 | 495.2 |
| 161 | 6-(2-(1H-tetrazol-5-yl)phenyl)-N2-benzyl-N2-isobutyl-N4-(2-methylbenzo[d]thiazol-6-yl)pyridine-2,4-diamine | 2-methylbenzo[d]thiazol-6-yl | 1.813 | 547.2 |
| 162 | 6-(2-(1H-tetrazol-5-yl)phenyl)-N2-benzyl-N4-(5-ethylpyrimidin-2-yl)-N2-isobutylpyridine-2,4-diamine | 5-ethylpyrimidin-2-yl | 2.105 | 506.2 |
| 163 | 2-((2-(2-(1H-tetrazol-5-yl)phenyl)-6-(benzyl(isobutyl)amino)pyridin-4-yl)amino)nicotinonitrile | 3-cyanopyridin-2-yl | 2.007 | 502.2 |

-continued

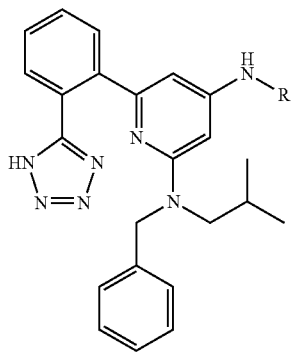

| Ex. No. | Name | R | Tr (min) Method R | [M + H]+ |
|---|---|---|---|---|
| 164 | 6-(2-(1H-tetrazol-5-yl)phenyl)-N2-benzyl-N4-(2-chloropyrimidin-5-yl)-N2-isobutylpyridine-2,4-diamine | 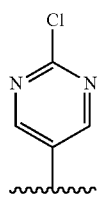 | 1.709 | 512.2 |
| 165 | 6-(2-(1H-tetrazol-5-yl)phenyl)-N4-([1,2,4]triazolo[4,3-b]pyridazin-6-yl)-N2-benzyl-N2-isobutylpyridine-2,4-diamine | 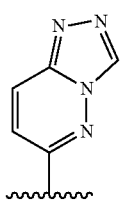 [SMILES: *c1ccc2nncn2n1] | 1.474 | 518.2 |
| 166 | 4-((2-(2-(1H-tetrazol-5-yl)phenyl)-6-(benzyl(isobutyl)amino)pyridin-4-yl)amino)-3-fluorobenzoic acid | 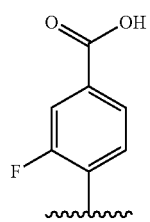 | 1.625 | 538.2 |
| 167 | 6-(2-(1H-tetrazol-5-yl)phenyl)-N2-benzyl-N2-isobutyl-N4-(3-methylpyrazin-2-yl)pyridine-2,4-diamine | 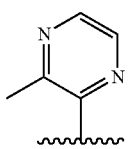 | 1.893 | 492.2 |
| 168 | 6-(2-(1H-tetrazol-5-yl)phenyl)-N2-benzyl-N2-isobutyl-N4-(3-methylpyridin-2-yl)pyridine-2,4-diamine | 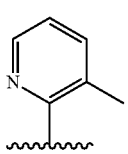 [SMILES: *c1ncccc1C] | 2.052 | 491.3 |
| 169 | 6-(2-(1H-tetrazol-5-yl)phenyl)-N2-benzyl-N4-(3-chloro-4-fluorophenyl)-N2-isobutylpyridine-2,4-diamine | 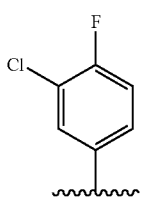 [SMILES: *c1ccc(F)c(Cl)c1] | 2.013 | 528.2 |

-continued

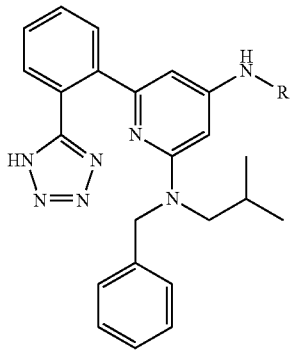

| Ex. No. | Name | R | Tr (min) Method R | [M + H]+ |
|---|---|---|---|---|
| 170 | 6-(2-(1H-tetrazol-5-yl)phenyl)-N2-benzyl-N4-(4-fluorophenyl)-N2-isobutylpyridine-2,4-diamine | 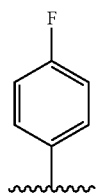 | 1.891 | 494.2 |
| 171 | 6-(2-(1H-tetrazol-5-yl)phenyl)-N2-benzyl-N4-(4-chlorophenyl)-N2-isobutylpyridine-2,4-diamine | 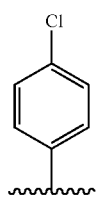 | 2.199 | 510.2 |
| 172 | 6-(2-(1H-tetrazol-5-yl)phenyl)-N2-benzyl-N2-isobutyl-N4-(5-methoxypyrimidin-2-yl)pyridine-2,4-diamine | 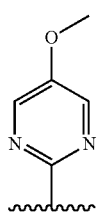 [SMILES: *c1ncc(OC)cn1] | 1.770 | 508.3 |
| 173 | 6-(2-(1H-tetrazol-5-yl)phenyl)-N2-benzyl-N2-isobutyl-N4-(7H-pyrrolo[2,3-d]pyrimidin-4-yl)pyridine-2,4-diamine | 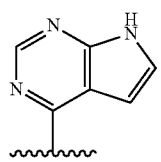 [SMILES: *c1ncnc2[nH]ccc12] | 1.621 | 517.2 |
| 174 | 6-(2-(1H-tetrazol-5-yl)phenyl)-N2-benzyl-N4-(2,4-dichlorophenyl)-N2-isobutylpyridine-2,4-diamine | 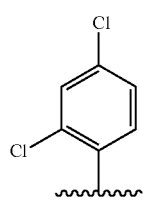 [SMILES: *c1ccc(Cl)cc1Cl] | 2.048 | 544.2 |
| 175 | 6-(2-(1H-tetrazol-5-yl)phenyl)-N2-benzyl-N4-(4-fluoro-2-methylphenyl)-N2-isobutylpyridine-2,4-diamine | 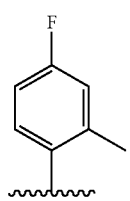 | 1.944 | 508.3 |

-continued

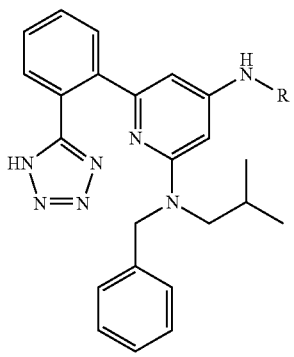

| Ex. No. | Name | R | Tr (min) Method R | [M + H]+ |
|---|---|---|---|---|
| 176 | 4-((2-(2-(1H-tetrazol-5-yl)phenyl)-6-(benzyl(isobutyl)amino)pyridin-4-yl)amino)-2-methylbenzonitrile | 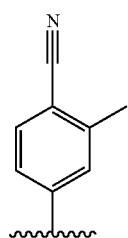 | 1.852 | 515.2 |
| 177 | 6-(2-(1H-tetrazol-5-yl)phenyl)-N2-benzyl-N4-(2-chlorophenyl)-N2-isobutylpyridine-2,4-diamine | 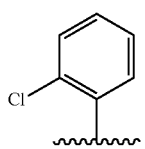 [SMILES: *c1ccccc1Cl] | 2.140 | 510.2 |
| 178 | 6-(2-(1H-tetrazol-5-yl)phenyl)-N2-benzyl-N4-(3-fluoropyridin-2-yl)-N2-isobutylpyridine-2,4-diamine | 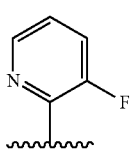 [SMILES: *c1ncccc1F] | 2.040 | 495.2 |
| 179 | 6-(2-(1H-tetrazol-5-yl)phenyl)-N2-benzyl-N4-(2-fluorophenyl)-N2-isobutylpyridine-2,4-diamine | 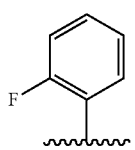 [SMILES: *c1ccccc1F] | 2.052 | 494.2 |
| 180 | 6-(2-(1H-tetrazol-5-yl)phenyl)-N2-benzyl-N4-(4-chloro-2-fluorophenyl)-N2-isobutylpyridine-2,4-diamine | 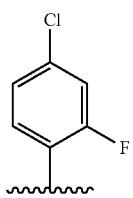 [SMILES: *c1ccc(Cl)cc1F] | 2.002 | 528.2 |
| 181 | 6-(2-(1H-tetrazol-5-yl)phenyl)-N2-benzyl-N4-(3,4-difluorophenyl)-N2-isobutylpyridine-2,4-diamine | 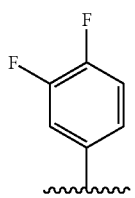 [SMILES: *c1ccc(F)c(F)c1] | 2.203 | 512.2 |

-continued

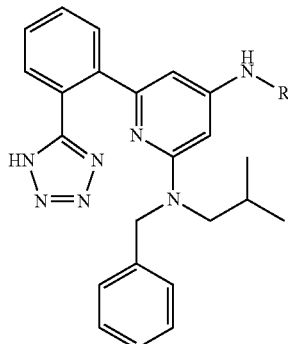

| Ex. No. | Name | R | Tr (min) Method R | [M + H]+ |
|---|---|---|---|---|
| 182 | 6-(2-(1H-tetrazol-5-yl)phenyl)-N2-benzyl-N4-(2,2-difluorobenzo[d][1,3]dioxol-5-yl)-N2-isobutylpyridine-2,4-diamine | 2,2-difluorobenzo[d][1,3]dioxol-5-yl | 2.250 | 556.2 |
| 183 | 6-(2-(1H-tetrazol-5-yl)phenyl)-N2-benzyl-N4-(5-fluoro-3-methylpyridin-2-yl)-N2-isobutylpyridine-2,4-diamine | 5-fluoro-3-methylpyridin-2-yl | 1.80 | 509.4 |
| 184 | 6-(2-(1H-tetrazol-5-yl)phenyl)-N2-benzyl-N4-(2-fluoro-4-methylphenyl)-N2-isobutylpyridine-2,4-diamine | 2-fluoro-4-methylphenyl | 1.762 | 508.4 |
| 185 | 2-((2-(2-(1H-tetrazol-5-yl)phenyl)-6-(benzyl(isobutyl)amino)pyridin-4-yl)amino)-4-fluorobenzoic acid | 4-fluoro-2-carboxyphenyl | 1.853 | 538.2 |
| 186 | 6-(2-(1H-tetrazol-5-yl)phenyl)-N2-benzyl-N4-(2-fluoro-4-methoxyphenyl)-N2-isobutylpyridine-2,4-diamine | 2-fluoro-4-methoxyphenyl | 1.731 | 524.4 |
| 187 | 2-((2-(2-(1H-tetrazol-5-yl)phenyl)-6-(benzyl(isobutyl)amino)pyridin-4-yl)amino)-5-methylbenzonitrile | 2-cyano-4-methylphenyl | 1.617 | 515.1 |

-continued

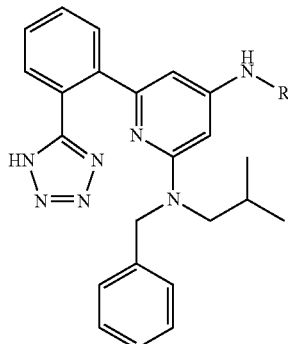

| Ex. No. | Name | R | Tr (min) Method R | [M + H]+ |
|---|---|---|---|---|
| 188 | 6-(2-(1H-tetrazol-5-yl)phenyl)-N2-benzyl-N4-(4-chloro-3-methoxyphenyl)-N2-isobutylpyridine-2,4-diamine | 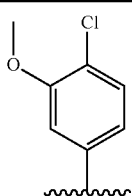 | 1.753 | 540.1 |
| 189 | 6-(2-(1H-tetrazol-5-yl)phenyl)-N2-benzyl-N2-isobutyl-N4-(3-(1,1,2,2-tetrafluoroethoxy)phenyl)pyridine-2,4-diamine | 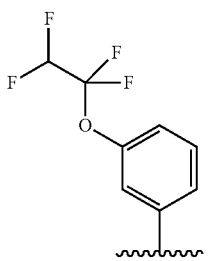 [SMILES: *c1cccc(OC(F)(F)C(F)F)c1] | 1.937 | 592.4 |
| 190 | 6-(2-(1H-tetrazol-5-yl)phenyl)-N2-benzyl-N4-(4-fluoro-3-methoxyphenyl)-N2-isobutylpyridine-2,4-diamine | 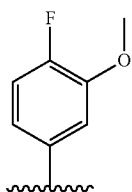 | 2.021 | 524.2 |
| 191 | 6-(2-(1H-tetrazol-5-yl)phenyl)-N2-benzyl-N4-(3-(difluoromethyl)phenyl)-N2-isobutylpyridine-2,4-diamine | 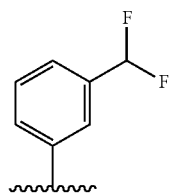 [SMILES: *c1cccc(C(F)F)c1] | 1.817 | 526.4 |
| 192 | 3-((2-(2-(1H-tetrazol-5-yl)phenyl)-6-(benzyl(isobutyl)amino)pyridin-4-yl)amino)benzonitrile | 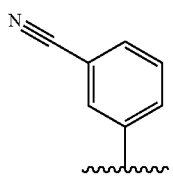 [SMILES: *c1cccc(C#N)c1] | 1.658 | 501.2 |
| 193 | 6-(2-(1H-tetrazol-5-yl)phenyl)-N2-benzyl-N2-isobutyl-N4-(3-(trifluoromethoxy)phenyl)pyridine-2,4-diamine | 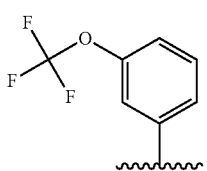 [SMILES: *c1cccc(OC(F)(F)F)c1] | 1.842 | 560.1 |

-continued

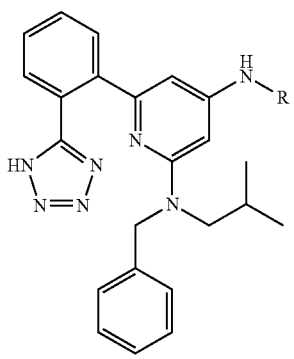

| Ex. No. | Name | R | Tr (min) Method R | [M + H]+ |
|---|---|---|---|---|
| 194 | 2-((2-(2-(1H-tetrazol-5-yl)phenyl)-6-(benzyl(isobutyl)amino)pyridin-4-yl)amino)benzonitrile | 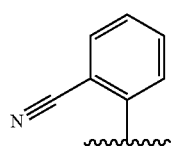 [SMILES: *c1ccccc1C#N] | 1.945 | 501.2 |
| 195 | 6-(2-(1H-tetrazol-5-yl)phenyl)-N2-benzyl-N4-(6-(difluoromethyl)pyridin-2-yl)-N2-isobutylpyridine-2,4-diamine | 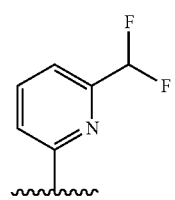 [SMILES: *c1cccc(C(F)F)n1] | 1.924 | 527.2 |
| 196 | 6-(2-(1H-tetrazol-5-yl)phenyl)-N2-benzyl-N2-isobutyl-N4-(3-methoxyphenyl)pyridine-2,4-diamine | 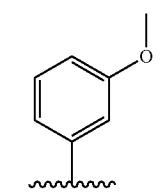 [SMILES: *c1cccc(OC)c1] | 1.743 | 506.4 |
| 197 | 6-(2-(1H-tetrazol-5-yl)phenyl)-N2-benzyl-N4-(3-fluoro-5-methoxyphenyl)-N2-isobutylpyridine-2,4-diamine | 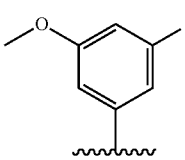 | 1.840 | 524.4 |
| 198 | 5-((2-(2-(1H-tetrazol-5-yl)phenyl)-6-(benzyl(isobutyl)amino)pyridin-4-yl)amino)-2-methoxybenzamide | 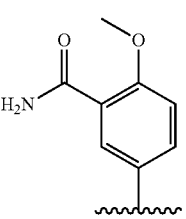 | 1.359 | 549.2 |

Example 199

N-(2-(2-(2H-tetrazol-5-yl)phenyl)-6-(benzyl(propyl)amino)-yl)-2-(5-bromopyridin-3-yl)acetamide

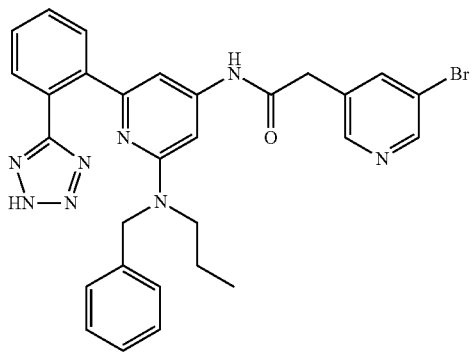 [SMILES: CCCN(Cc1ccccc1)c1cc(NC(=O)Cc2cncc(Br)c2)cc(-c2ccccc2-c2nn[nH]n2)n1]

199A. 6-(2-(2H-tetrazol-5-yl) phenyl)-N2-benzyl-N2-propylpyridine-2,4-diamine Compound 199A was prepared following the procedure for 49D by using N-benzylpropan-1-amine. LC-MS Anal. Calc'd for $C_{22}H_{23}N_7$ 385.2, found [M+H] 386.2. $T_r$=1.98 min (Method U).

Example 199

To a solution of 2-(5-bromopyridin-3-yl) acetic acid (10.09 mg, 0.047 mmol) in DMF (1.0 mL) was added HATU (17.76 mg, 0.047 mmol) and DIPEA (15.09 mg, 0.117 mmol). This mixture was stirred at RT for 30 min. Compound 199A (15 mg, 0.039 mmol) added to the reaction mixture. Resulting reaction mixture was stirred at RT for 16 h. LC-MS analysis showed desired product mass. The crude compound was purified by preparative HPLC to get Example 199 (3 mg, 0.006 mmol, 13% yield). LC-MS Anal. Calc'd for $C_{29}H_{27}BrN8O$, 582.15, found [M+H] 583.3. $T_r$=1.448 min (Method O). $^1$H NMR (400 MHz, DMSO-d6) δ 10.32 (s, 1H), 8.60 (d, J=2.0 Hz, 1H), 8.47 (d, J=2.0 Hz, 1H), 7.99 (d, J=2.0 Hz, 1H), 7.6-7.51 (m, 4H), 7.29-7.25 (m, 2H), 7.21-7.18 (m, 1H), 7.09 (d, J=7.2 Hz, 2H), 6.87-6.81 (m, 2H), 4.43 (s, 2H), 3.73 (s, 2H), 3.09-3.06 (m, 2H), 1.38-1.32 (m, 2H), 0.76 (t, J=7.20 Hz, 3H).

Examples 200-225 were prepared following the procedure for Example 199 using the corresponding acids.

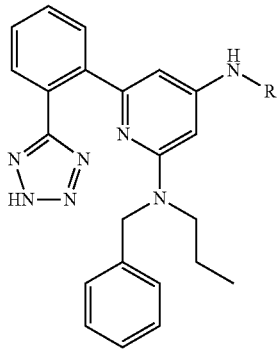

| Ex. No. | Name | R | Tr (min) Method O | [M +H]$^+$ |
|---|---|---|---|---|
| 200 | N-(2-(2-(2H-tetrazol-5-yl)phenyl)-6-(benzyl(propyl)amino)pyridin-4-yl)-2-(naphthalen-1-yl)acetamide | | 1.814 | 554.4 |
| 201 | N-(2-(2-(2H-tetrazol-5-yl)phenyl)-6-(benzyl(propyl)amino)pyridin-4-yl)-2-(naphthalen-2-yl)acetamide | | 1.845 | 554.4 |
| 202 | N-(2-(2-(2H-tetrazol-5-yl)phenyl)-6-(benzyl(propyl)amino)pyridin-4-yl)-2-(2-fluorophenyl)acetamide | | 1.581 | 522.3 |

-continued

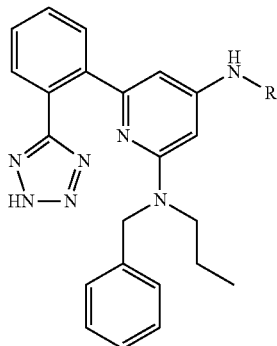

| Ex. No. | Name | R | Tr (min) Method O | [M +H]+ |
|---|---|---|---|---|
| 203 | N-(2-(2-(2H-tetrazol-5-yl)phenyl)-6-(benzyl(propyl)amino)pyridin-4-yl)-2-(2-methoxyphenyl)acetamide | | 1.588 | 534.4 |
| 204 | N-(2-(2-(2H-tetrazol-5-yl)phenyl)-6-(benzyl(propyl)amino)pyridin-4-yl)-2-(2,5-dimethoxyphenyl)acetamide | | 1.575 | 564.4 |
| 205 | N-(2-(2-(2H-tetrazol-5-yl)phenyl)-6-(benzyl(propyl)amino)pyridin-4-yl)-2-(2-(trifluoromethyl)phenyl)acetamide | | 1.724 | 572.4 |
| 206 | N-(2-(2-(2H-tetrazol-5-yl)phenyl)-6-(benzyl(propyl)amino)pyridin-4-yl)-2-(thiophen-2-yl)acetamide | | 1.54 | 510.3 |
| 207 | N-(2-(2-(2H-tetrazol-5-yl)phenyl)-6-(benzyl(propyl)amino)pyridin-4-yl)-2-(1H-imidazol-4-yl)acetamide | | 0.948 | 494.3 |
| 208 | N-(2-(2-(2H-tetrazol-5-yl)phenyl)-6-(benzyl(propyl)amino)pyridin-4-yl)-2-(3,5-dimethoxyphenyl)acetamide | | 1.653 | 564.4 |
| 209 | N-(2-(2-(2H-tetrazol-5-yl)phenyl)-6-(benzyl(propyl)amino)pyridin-4-yl)-2-(1H-tetrazol-5-yl)acetamide | | 0.985 | 496.3 |

-continued

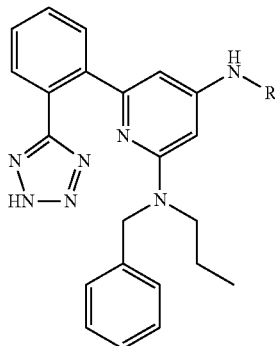

| Ex. No. | Name | R | Tr (min) Method O | [M +H]+ |
|---|---|---|---|---|
| 210 | N-(2-(2-(2H-tetrazol-5-yl)phenyl)-6-(benzyl(propyl)amino)pyridin-4-yl)-2-(pyrazin-2-yl)acetamide | 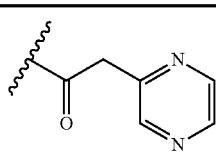 | 1.318 | 506.3 |
| 211 | N-(2-(2-(2H-tetrazol-5-yl)phenyl)-6-(benzyl(propyl)amino)pyridin-4-yl)-2-(2-methylthiazol-4-yl)acetamide | 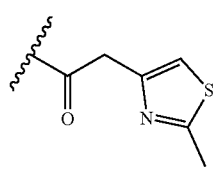 [SMILES: *C(=O)Cc1csc(C)n1] | 1.475 | 525.3 |
| 212 | N-(2-(2-(2H-tetrazol-5-yl)phenyl)-6-(benzyl(propyl)amino)pyridin-4-yl)-2-fluoro-2-phenylacetamide | 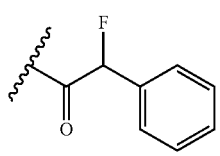 [SMILES: *C(=O)C(F)c1ccccc1] | 1.683 | 522.3 |
| 213 | N-(2-(2-(2H-tetrazol-5-yl)phenyl)-6-(benzyl(propyl)amino)pyridin-4-yl)-2-(3,5-dimethylisoxazol-4-yl)acetamide | 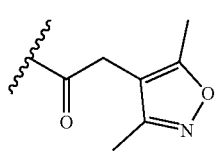 [SMILES: *C(=O)Cc1c(C)noc1C] | 1.365 | 523.4 |
| 214 | N-(2-(2-(2H-tetrazol-5-yl)phenyl)-6-(benzyl(propyl)amino)pyridin-4-yl)-2-morpholinoacetamide | 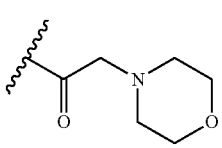 [SMILES: *C(=O)CN1CCOCC1] | 1.413 | 513.4 |
| 215 | N-(2-(2-(2H-tetrazol-5-yl)phenyl)-6-(benzyl(propyl)amino)pyridin-4-yl)-2-(4-(methylsulfonyl)phenyl)acetamide | 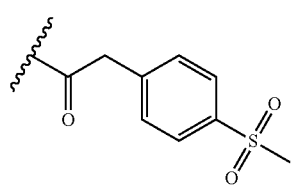 [SMILES: *C(=O)Cc1ccc(S(C)(=O)=O)cc1] | 1.344 | 582.3 |
| 216 | N-(2-(2-(2H-tetrazol-5-yl)phenyl)-6-(benzyl(propyl)amino)pyridin-4-yl)-2-(benzo[b]thiophen-3-yl)acetamide | 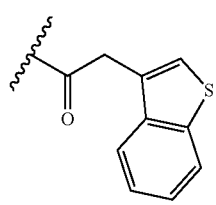 [SMILES: *C(=O)Cc1csc2ccccc12] | 1.755 | 560.3 |

-continued

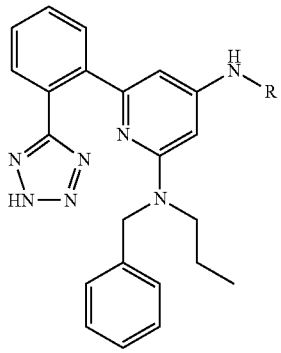

| Ex. No. | Name | R | Tr (min) Method O | [M +H]+ |
|---|---|---|---|---|
| 217 | N-(2-(2-(2H-tetrazol-5-yl)phenyl)-6-(benzyl(propyl)amino)pyridin-4-yl)-2-(3-bromophenyl)acetamide | 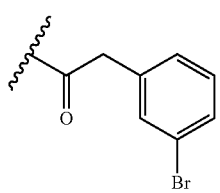 [SMILES: *C(=O)Cc1cccc(Br)c1] | 1.762 | 582.3 |
| 218 | N-(2-(2-(2H-tetrazol-5-yl)phenyl)-6-(benzyl(propyl)amino)pyridin-4-yl)-2-cyclopentylacetamide | 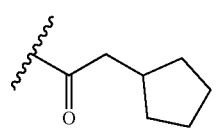 [SMILES: *C(=O)CC1CCCC1] | 1.777 | 496.4 |
| 219 | N-(2-(2-(2H-tetrazol-5-yl)phenyl)-6-(benzyl(propyl)amino)pyridin-4-yl)-2-cyclopentylacetamide | 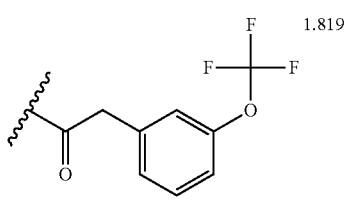 | 1.819 | 588.4 |
| 220 | N-(2-(2-(2H-tetrazol-5-yl)phenyl)-6-(benzyl(propyl)amino)pyridin-4-yl)-2-(4-isopropylphenyl)acetamide | 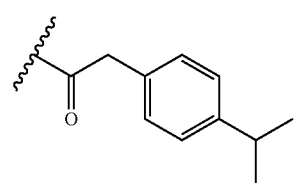 [SMILES: *C(=O)Cc1ccc(C(C)C)cc1] | 1.922 | 546.4 |
| 221 | N-(2-(2-(2H-tetrazol-5-yl)phenyl)-6-(benzyl(propyl)amino)pyridin-4-yl)-2-(1-methyl-1H-indol-3-yl)acetamide | 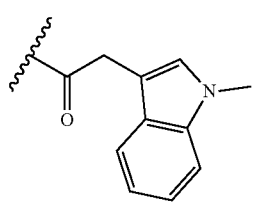 [SMILES: *C(=O)Cc1cn(C)c2ccccc12] | 1.726 | 557.4 |
| 222 | N-(2-(2-(2H-tetrazol-5-yl)phenyl)-6-(benzyl(propyl)amino)pyridin-4-yl)-2-(1H-imidazol-1-yl)acetamide | 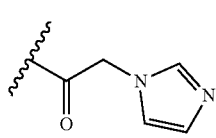 | 1.006 | 494.3 |

-continued

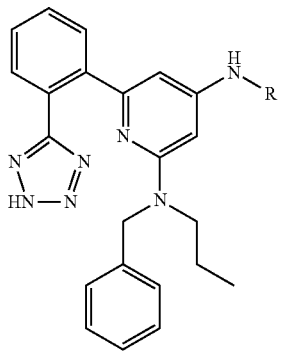

| Ex. No. | Name | R | Tr (min) Method O | [M +H]⁺ |
|---|---|---|---|---|
| 223 | N-(2-(2-(2H-tetrazol-5-yl)phenyl)-6-(benzyl(propyl)amino)pyridin-4-yl)-1-phenylcyclopropanecarboxamide | | 1.811 | 530.4 |
| 224 | N-(2-(2-(2H-tetrazol-5-yl)phenyl)-6-(benzyl(propyl)amino)pyridin-4-yl)-1-(3-fluorophenyl)cyclopropanecarboxamide | | 1.827 | 548.4 |
| 225 | N-(2-(2-(2H-tetrazol-5-yl)phenyl)-6-(benzyl(propyl)amino)pyridin-4-yl)-2-phenylacetamide | | 1.583 | 504.3 |
| 226 | N-(2-(2-(2H-tetrazol-5-yl)phenyl)-6-(benzyl(propyl)amino)pyridin-4-yl)-2-(pyridin-3-yl)acetamide | | 0.986 | 505.3 |
| 227 | N-(2-(2-(2H-tetrazol-5-yl)phenyl)-6-(benzyl(propyl)amino)pyridin-4-yl)-2-(4-cyanophenyl)acetamide | | 1.604 | 529.3 |

Examples 228-236 were prepared following the procedure for Example 199 by using Compound 49D and the corresponding acids.

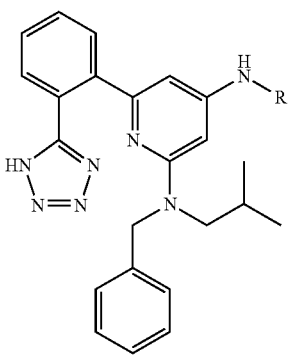

| Ex. No. | Name | R | Tr (min) Method O | [M + H]+ |
|---|---|---|---|---|
| 228 | N-(2-(2-(1H-tetrazol-5-yl)phenyl)-6-(benzyl(isobutyl)amino)pyridin-4-yl)-2-(3,4-difluorophenyl)acetamide | | 1.839 | 554.3 |
| 229 | N-(2-(2-(1H-tetrazol-5-yl)phenyl)-6-(benzyl(isobutyl)amino)pyridin-4-yl)-2-(2,4-difluorophenyl)acetamide | | 1.817 | 554.3 |
| 230 | N-(2-(2-(1H-tetrazol-5-yl)phenyl)-6-(benzyl(isobutyl)amino)pyridin-4-yl)-2-(4-isopropylphenyl)acetamide | | 2.032 | 560.4 |
| 231 | N-(2-(2-(1H-tetrazol-5-yl)phenyl)-6-(benzyl(isobutyl)amino)pyridin-4-yl)-2-(3-methylisoxazol-5-yl)acetamide | | 1.577 | 523.4 |
| 233 | N-(2-(2-(1H-tetrazol-5-yl)phenyl)-6-(benzyl(isobutyl)amino)pyridin-4-yl)-2-(3-chloro-4-fluorophenyl)acetamide | | 1.896 | 570.3 |
| 235 | N-(2-(2-(1H-tetrazol-5-yl)phenyl)-6-(benzyl(isobutyl)amino)pyridin-4-yl)-2-(4-(trifluoromethoxy)phenyl)acetamide | | 1.968 | 602.4 |
| 236 | N-(2-(2-(1H-tetrazol-5-yl)phenyl)-6-(benzyl(isobutyl)amino)pyridin-4-yl)-3,4-difluorobenzamide | | 1.857 | 540.3 |

Examples 237-240 were prepared following the procedure for Example 71 by using Compound 49D and the corresponding isocyanate.

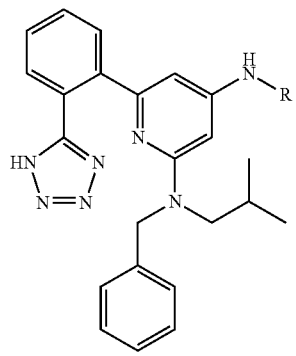

| Ex. No. | Name | R | Tr (min) Method O | [M + H]+ |
|---|---|---|---|---|
| 237 | 1-(2-(2-(1H-tetrazol-5-yl)phenyl)-6-(benzyl(isobutyl)amino)pyridin-4-yl)-3-(2,4-difluorophenyl)urea | 2,4-difluorophenyl-NHC(O)- | 1.824 | 555.4 |
| 238 | 1-(2-(2-(1H-tetrazol-5-yl)phenyl)-6-(benzyl(isobutyl)amino)pyridin-4-yl)-3-(2,4-dichlorophenyl)urea | 2,4-dichlorophenyl-NHC(O)- | 2.047 | 587.3 |
| 239 | 1-(2-(2-(1H-tetrazol-5-yl)phenyl)-6-(benzyl(isobutyl)amino)pyridin-4-yl)-3-(4-(trifluoromethoxy)phenyl)urea | 4-(OCF3)phenyl-NHC(O)- | 2.02 | 603.4 |
| 240 | 1-(2-(2-(1H-tetrazol-5-yl)phenyl)-6-(benzyl(isobutyl)amino)pyridin-4-yl)-3-(p-tolyl)urea | p-tolyl-NHC(O)- | 1.849 | 533.4 |

Example 241

3-(6-(benzyl(isopropyl)amino)-4-((4-chlorophenyl)amino)pyridin-2-yl)pentanoic acid

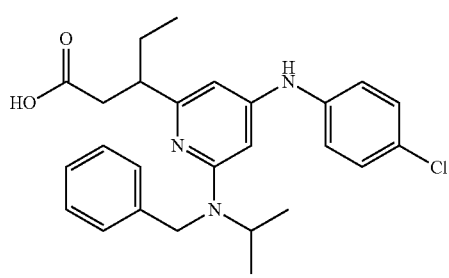

241A. N-benzylpropan-2-amine

To a solution of MeOH (50 mL) and THF (50.0 mL) containing 4 g of powdered and activated 4 Å molecular sieves was added sequentially the benzaldehyde (5 g, 47.1 mmol) and propan-2-amine (4.05 mL, 47.1 mmol). The reaction mixture was stirred for 6 h. The reaction mixture was cooled to 0° C., added NaBH$_4$ (5.35 g, 141 mmol) portion wise and stirred at RT for 2 h. LC-MS indicated completion. The reaction mass was concentrated and the residue was quenched with ice cold water, portioned between ethyl acetate and water. Combined organic layer was dried over Na$_2$SO$_4$, concentrated in vacuum to give 241A (pale yellow liquid, 6 g, 40.2 mmol, 85% yield). LC-MS Anal. Calc'd for C$_{10}$H$_{15}$N$_3$ 149.2, found [M+H] 150.2. T$_r$=0.74 min (Method N).

241B. N-benzyl-6-bromo-N-ethyl-4-nitropyridin-2-amine

A solution of 2,6-dibromo-4-nitropyridine (2.5 g, 8.87 mmol) in a sure seal bottle was added DIPEA (4.65 mL, 26.6 mmol) and 241A (2.65 g, 17.74 mmol), followed by 1,4-Dioxane (25 mL). The mixture was sealed and heated at 110° C. for 18 h. LC-MS indicated completion. The reaction mass was concentrated and the residue was portioned between ethyl acetate and water. Combined organic layer was dried over $Na_2SO_4$, concentrated in vacuum. Purification via flash chromatography gave 241B (yellow solid, 1.4 g, 4.00 mmol, 45.1% yield) LC-MS Anal. Calc'd for $C_{15}H_{16}BrN_3O_2$ 350.2, found [M+2] 352.2. $T_r$=3.8 min (Method N).

241C. N2-benzyl-6-bromo-N2-isopropylpyridine-2,4-diamine

To a stirred solution of 241B (1.4 g, 4.00 mmol) in acetic acid (20 mL) under nitrogen atmosphere at 0° C. was added iron (0.893 g, 15.99 mmol). The reaction mixture was stirred at RT for 2 h. LC-MS indicated completion. The reaction mixture was diluted with DCM and filtered through celite. The organic layer was washed with water and $NaHCO_3$ solution, dried over sodium sulfate and concentrated under vacuum. Purification via flash chromatography gave 241C (Yellow Liquid, 600 mg, 1.874 mmol, 46.9% yield) LCMS Anal. Calc'd for $C_{15}H_{18}BrN_3$ 320.2, found [M+H] 321.2. $T_r$=3.2 min (Method N).

241D. (E)-methyl 3-(4-amino-6-(benzyl(isopropyl)amino)pyridin-2-yl)pent-2-enoate To a solution of 241C (0.6 g, 1.874 mmol) in DMF (10 mL) were added (E)-methyl pent-2-enoate (0.509 mL, 4.68 mmol), tetrabutylammonium bromide (0.121 g, 0.375 mmol) and TEA (0.783 mL, 5.62 mmol), purged with nitrogen for 5 min. Then was added dichlorobis(tri-o-tolylphosphine)palladium(II) (0.074 g, 0.094 mmol) and the reaction was heated to 120° C. for 16 h in a sealed vessel. LC-MS indicated completion. The reaction mass was concentrated and diluted with ethyl acetate (25 mL), organic layer was washed with water (1×25 mL) and brine (2×15 mL), dried over $Na_2SO_4$, filtered, concentrated under vacuum. Purification via flash chromatography gave 241D (yellow liquid, 180 mg, 0.509 mmol, 27.2% yield) LCMS Anal. Calc'd for $C_{21}H_{27}N_3O_2$ 353.4, found [M+H] 354 $T_r$=3.4 min (Method U).

241E. methyl 3-(4-amino-6-(benzyl(isopropyl)amino)pyridin-2-yl)pentanoate

To a stirred solution of 241D (180 mg, 0.509 mmol) in ethyl acetate (8 mL) was added Pd/C (108 mg, 0.102 mmol), fitted with $H_2$ balloon and stirred under RT for 16 h. LC-MS indicated completion. The reaction mixture was filtered through celite, washed with methanol and concentrated to give 241E (Pale brown liquid, 140 mg, 0.394, mmol, 77% yield). LC-MS Anal. Calc'd for $C_{21}H_{29}N_3O_2$ 355.4, found [M+H] 356.2 $T_r$=3.2 min (Method U).

Example 241

To a solution of 241E (70 mg, 0.197 mmol) in 1,4-dioxane (4 mL) was added 1-bromo-4-chlorobenzene (56.6 mg, 0.295 mmol), 4,5-bis(diphenylphosphino)-9,9-dimethylxanthene (22.79 mg, 0.039 mmol), sodium tert-butoxide (56.8 mg, 0.591 mmol) followed by the addition of bis(dibenzylideneacetone)palladium (11.32 mg, 0.020 mmol). Then the reaction temperature was raised to 110° C. for 16 h in a sealed tube. The crude material was purified via preparative LC/MS to give Example 241 (Pale yellow solid, 4.9 mg, 10.52 μmol, 5.34% yield). LCMS Anal. Calc'd $C_{26}H_{30}ClN_3O_2$ 451.9 found [M+H] 452.2 $T_r$=2.1 min (Method AU). 1H NMR (400 MHz, DMSO-$d_6$) δ 12.03 (br s, 1H), 8.44 (s, 1H), 7.32 (t, J=7.60 Hz, 2H), 7.23 (t, J=10.00 Hz, 3H), 7.14 (d, J=8.80 Hz, 2H), 6.85 (d, J=8.80 Hz, 2H), 6.08 (s, 1H), 5.75 (s, 1H), 4.98-5.02 (m, 1H), 4.44-4.52 (m, 2H), 2.71-2.82 (m, 1H), 2.51-2.57 (m, 1H), 2.41-2.44 (m, 1H), 1.52-1.61 (m, 2H), 1.14 (d, J=6.80 Hz, 6H), 0.76 (t, J=7.60 Hz, 3H).

Example 242

3-(6-(benzyl(isopropyl)amino)-4-((2-methylbenzo[d]thiazol-6-yl)amino) pyridin-2-yl)pentanoic acid

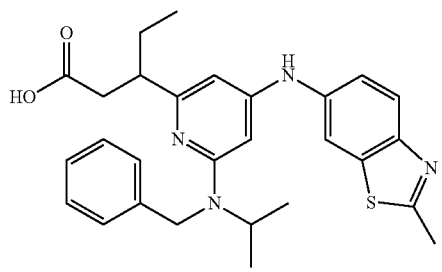 [SMILES: CCC(CC(=O)O)c1cc(Nc2ccc3nc(C)sc3c2)cc(N(Cc2ccccc2)C(C)C)n1]

Example 242 was prepared following the procedure for the synthesis of Example 241 by using 6-bromo-2-methylbenzo[d]thiazole. LC-MS Anal. Calc'd for $C_{28}H_{32}N_4O_2S$ 488.6, found [M+H] 489. $T_r$=1.67 min (Method AU). $^1$H NMR (400 MHz, DMSO-$d_6$) δ 8.53 (s, 1H), 7.64 (d, J=8.80 Hz, 1H), 7.44 (d, J=2.00 Hz, 1H), 7.23 (dd, J=10.80, 7.20 Hz, 3H), 7.31 (t, J=7.20 Hz, 2H), 6.99 (dd, J=8.80, 2.40 Hz, 1H), 6.14 (s, 1H), 5.80 (s, 1H), 4.98-5.02 (m, 1H), 4.40-4.45 (m, 2H), 3.17 (s, 3H), 2.61-2.77 (m, 1H), 2.44-2.50 (m, 2H), 1.50-1.60 (m, 2H), 1.13 (d, J=6.80 Hz, 6H), 0.77 (t, J=14.40 Hz, 3H).

Example 243

Enantiomer 1 & Enantiomer 2 3-(6-(benzyl(isobutyl)amino)-4-((2-methylbenzo [d]thiazol-6-yl)amino)pyridin-2-yl)pentanoic acid

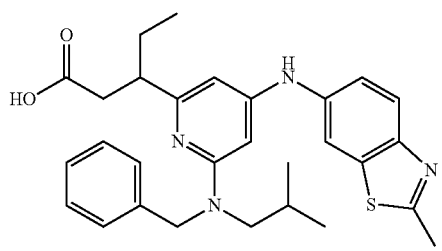 [SMILES: CCC(CC(=O)O)c1cc(Nc2ccc3nc(C)sc3c2)cc(N(Cc2ccccc2)CC(C)C)n1]

243A. N-benzyl-2-methylpropan-1-amine

Compound 243A was prepared following a procedure analogous to 241A, using 2-methylpropan-1-amine. LC-MS Anal. Calc'd for $C_{11}H_{17}N$ 163.2, found [M+H] 164. $T_r$=0.82 min (Method T).

243B. N-benzyl-6-bromo-N-isobutyl-4-nitropyridin-2-amine

Compound 243B was prepared following a procedure analogous to 241B by using 243A. LC-MS Anal. Calc'd for $C_{16}H_{18}BrN_3O_2$ 364.2, found [M+2] 366.2. $T_r$=1.66 min (Method T).

243C. (E)-methyl 3-(6-(benzyl(isobutyl)amino)-4-nitropyridin-2-yl)pent-2-enoate Compound 243C was prepared following a procedure analogous to 241D by using 243B. LC-MS Anal. Calc'd for $C_{22}H_{27}N_3O_4$ 397.4, found [M+H] 398.2. $T_r$=1.77 min (Method T).

243D. methyl 3-(4-amino-6-(benzyl(isobutyl)amino) pyridin-2-yl)pentanoate

To a stirred solution of 243C (300 mg, 0.755 mmol) in Methanol (15 mL) was added Pd/C (50 mg, 0.047 mmol), fitted with $H_2$ balloon and stirred under RT for 16 h. LC-MS indicated completion. The reaction mixture was filtered through celite, washed with methanol and concentrated to give 243D (Pale brown liquid, 160 mg, 0.433, mmol, 57.4%). LC-MS Anal. Calc'd for $C_{22}H_{31}N_3O_2$ 369.2, found [M+H] 370.2 $T_r$=1.55 min (Method T).

Example 243

Racemate Example 243 was prepared following a procedure analogous to that for the synthesis of Example 1 by using 6-bromo-2-methylbenzo[d]thiazole. Chiral separation of Racemate example 243 gave Diastereomer 1 and Diastereomer 2 (Method AV). Diastereomer 1 $T_r$=6.66 min, Diastereomer 2 $T_r$=7.86 min (Method AV).

Enantiomer 1 of Example 243: LC-MS Anal. Calc'd for $C_{29}H_{34}N_4O_2S_4$ 502.6, found [M+H] 503.3. $T_r$=1.6 min (Method O). $^1$H NMR (400 MHz, DMSO-$d_6$) δ 11.94-12.06 (s, 1H) 8.53 (s, 1H) 7.71 (d, J=9.04 Hz, 1H) 7.55 (d, J=2.01 Hz, 1H) 7.26-7.34 (m, 2H) 7.15-7.25 (m, 3H) 7.07 (dd, J=9.04, 2.01 Hz, 1H) 6.10 (s, 1H) 5.94 (s, 1H) 4.68 (d, J=13.05 Hz, 2H), 2.74 (s, 4H) 2.37-2.44 (m, 1H) 2.33 (s, 1H) 2.05 (s, 1H) 1.44-1.65 (m, 2H) 0.80-0.91 (m, 6H) 0.73 (t, J=7.28 Hz, 3H). (Note: one multiplet $CH_2$ buried under solvent peak).

Enantiomer 2 of Example 243: LC-MS Anal. Calc'd for $C_{29}H_{34}N_4O_2S_4$ 502.6, found [M+H] 503.3. $T_r$=1.6 min (Method O). $^1$H NMR (400 MHz, DMSO-$d_6$) δ 11.94-12.06 (s, 1H) 8.53 (s, 1H) 7.71 (d, J=9.04 Hz, 1H) 7.55 (d, J=2.01 Hz, 1H) 7.26-7.34 (m, 2H) 7.15-7.25 (m, 3H) 7.07 (dd, J=9.04, 2.01 Hz, 1H) 6.10 (s, 1H) 5.94 (s, 1H) 4.68 (d, J=13.05 Hz, 2H), 2.74 (s, 4H) 2.37-2.44 (m, 1H) 2.33 (s, 1H) 2.05 (s, 1H) 1.44-1.65 (m, 2H) 0.80-0.91 (m, 6H) 0.73 (t, J=7.28 Hz, 3H). (Note: one multiplet $CH_2$ buried under solvent peak).

Example 244

Enantiomer 1 & Enantiomer 2 3-(6-(benzyl (isobutyl)amino)-4-(3-(p-tolyl)ureido)pyridin-2-yl) pentanoic acid

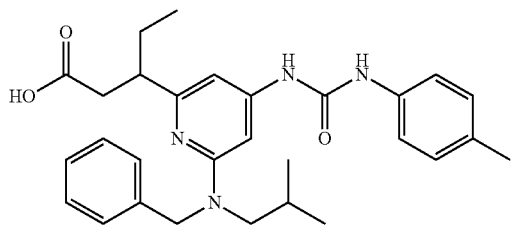 [SMILES: CCC(CC(=O)O)c1cc(NC(=O)Nc2ccc(C)cc2)cc(N(Cc2ccccc2)CC(C)C)n1]

244A. methyl 3-(6-(benzyl(isobutyl)amino)-4-(3-(p-tolyl)ureido)pyridin-2-yl)pentanoate To a solution of 243D (100 mg, 0.271 mmol) in THF (8 mL) was added 1-isocyanato-4-methylbenzene (0.051 mL, 0.406 mmol) and stirred at 60° C. for 2h. LC-MS indicated completion. The reaction mass was concentrated and the residue was portioned between ethyl acetate and water. Combined organic layer was dried over sodium sulfate, filtered and concentrated. Purification via flash chromatography gave 244A (Pale yellow Solid 80 mg, 0.159 mmol, 58.8% yield).) LC-MS Anal. Calc'd for $C_{30}H_{38}N_4O_3$ 502.6, found [M+H] 503.3. $T_r$=1.83 min (Method T).

Example 244

To a solution of methyl 244A (80 mg, 0.159 mmol) in mixture of THF (1 mL), MeOH (1 mL) and $H_2O$ (1 mL) was added NaOH (25.5 mg, 0.637 mmol) at RT and stirred for 2 h. LC-MS indicated completion. Solvent was concentrated under reduced pressure, the crude pH was adjusted to ~2 with 1.5 (N) HCl solution. The aqueous was extracted with EtOAc (2×25 mL). The combined organic layer was dried over anhydrous sodium sulfate and concentrated under reduced pressure. The crude material was purified via preparative LC/MS to give Racemate Example 4 (Pale yellow solid, 25 mg, 0.050 mmol, 31.2% yield). LCMS Anal. Calc' $C_{29}H_{36}N_4O_3$ 488.6 found [M+H] 489.0. $T_r$=2.05 min (Method R). Chiral separation of Racemate Example 244 gave Enantiomer 1 and Enantiomer 2 (Method AQ). Enantiomer 1 $T_r$=6.97 min, Enantiomer 2 $T_T$=8.01 min (Method AQ).

Enantiomer 1 of Example 244: LC-MS Anal. Calc'd for $C_{29}H_{36}N_4O_3$ 488.6, found [M+H] 489.4., $T_r$=2.2 min (Method O). $^1$H NMR (400 MHz, DMSO-$d_6$) δ 12.01 (bs, 1H), 8.9 (bs, 1H), 7.23-7.35 (m, 4H), 7.20 (d, J=7.53 Hz, 3H), 7.06 (d, J=8.03 Hz, 2H), 6.52 (m, 2H), 4.62-4.87 (m, 2H) 3.18-3.26 (m, 2H) 2.76-2.87 (m, 1H) 2.57-2.62 (m, 1H), 2.35-2.40 (m, 1H) 2.23 (s, 3H) 2.01-2.12 (m, 1H) 1.40-1.64 (m, 2H), 0.89 (d, J 5.52 Hz, 6H) 0.70 (t, J=7.28 Hz, 3H).

Enantiomer 2 of Example 244: LC-MS Anal. Calc'd for $C_{29}H_{36}N_4O_3$ 488.6, found [M+H] 489.4., $T_r$=2.2 min (Method O). $^1$H NMR (400 MHz, DMSO-$d_6$) δ 12.01 (bs, 1H), 8.9 (bs, 1H), 7.23-7.35 (m, 4H), 7.20 (d, J=7.53 Hz, 3H), 7.06 (d, J=8.03 Hz, 2H), 6.52 (m, 2H), 4.62-4.87 (m, 2H) 3.18-3.26 (m, 2H) 2.76-2.87 (m, 1H) 2.57-2.62 (m, 1H), 2.35-2.40 (m, 1H) 2.23 (s, 3H) 2.01-2.12 (m, 1H) 1.40-1.64 (m, 2H), 0.89 (d, J=5.52 Hz, 6H) 0.70 (t, J=7.28 Hz, 3H).

Example 245

3-(6-(benzyl(isobutyl)amino)-4-((4-chlorophenyl)amino)pyridin-2-yl)pentanoic acid

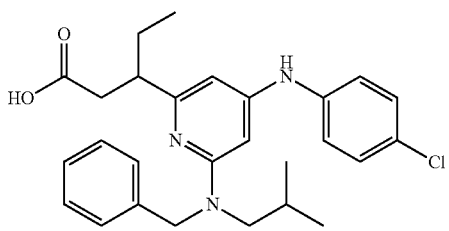 [SMILES: CCC(CC(=O)O)c1cc(Nc2ccc(Cl)cc2)cc(N(Cc2ccccc2)CC(C)C)n1]

Racemate Example 245 was prepared following the procedure for Example 241 by using 1-bromo-4-chlorobenzene. LC-MS Anal. Calc'd for $C_{27}H_{32}ClN_3O_2$ 466.1, found [M+2] 468. $T_r$=2.2 min (Method O). $^1$H NMR (400 MHz, DMSO-$d_6$): δ 7.28-7.35 (m, 4H), 7.20 (t, J=7.20 Hz, 2H), 6.96-7.00 (m, 2H), 6.25 (s, 1H), 5.92 (s, 1H), 4.74 (s, 2H), 3.41-3.44 (m, 2H), 2.67 (s, 2H), 2.62-2.66 (m, 2H), 2.02-2.06 (m, 2H), 1.55 (s, 2H), 0.89 (d, J=8.00 Hz, 6H), 0.73 (t, J=7.60 Hz, 3H).

Example 246

3-(4-((4-chlorophenyl)amino)-6-((4-fluorobenzyl)(isopropyl)amino)pyridin-2-yl)pentanoic acid

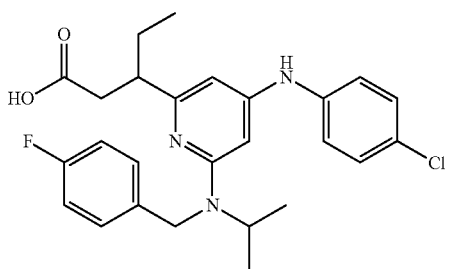 [SMILES: CCC(CC(=O)O)c1cc(Nc2ccc(Cl)cc2)cc(N(Cc2ccc(F)cc2)C(C)C)n1]

246A. N-(4-fluorobenzyl)propan-2-amine

Compound 246A was prepared following the procedure for 241A by using 4-fluorobenzaldehyde and propan-2-amine. LC-MS Anal. Calc'd for $C_{10}H_{14}FN$ 167.2, found [M+H] 168.2. $T_r$=1.12 min (Method U).

246B. 6-bromo-N-(4-fluorobenzyl)-N-isopropyl-4-nitropyridin-2-amine

Compound 246B was prepared following the procedure analogous to 241B by using 246A. $^1$H NMR (400 MHz, DMSO-d6) δ 8.47 (s, 1H), 7.28-7.35 (m, 2H), 7.09-7.18 (m, 3H), 4.78-4.82 (m, 1H), 4.69 (s, 2H), 1.18 (t, J=3.20 Hz, 6H).

246C. 6-bromo-N2-(4-fluorobenzyl)-N2-isopropylpyridine-2,4-diamine

Compound 246C was prepared following the procedure for 241C by using 246B. LC-MS Anal. Calc'd for $C_{15}H_{17}BrFN_3$, 338.2, found [M+2] 340.2. $T_r$=3.32 min (Method U).

246D. (E)-methyl 3-(4-amino-6-((4-fluorobenzyl)(isopropyl)amino)pyridin-2-yl)pent-2-enoate Compound 246D was prepared following the procedure for 241D by using 246C. LC-MS Anal. Calc'd for $C_{21}H_{26}FN_3O_2$, 371.4., found [M+H] 372.2. $T_r$=3.4 min (Method U).

246E. methyl 3-(4-amino-6-((4-fluorobenzyl)(isopropyl)amino)pyridin-2-yl)pentanoate Compound 246E was prepared following the procedure as for the synthesis of 241E by using 246D. LC-MS Anal. Calc'd for $C_{21}H_{28}FN_3O_2$, 373.4., Found [M+H] 374.2. $T_r$=3.8 min (Method U).

Example 246

Racemate Example 246 was prepared following the procedure for Example 241 by using 1-bromo-4-chlorobenzene. LC-MS Anal. Calc'd for $C_{26}H_{29}ClFN_3O_2$ 469.9, found [M+H] 470.2. $T_r$=2.1 min (Method O). $^1$H NMR (400 MHz, DMSO-$d_6$) δ 8.46 (s, 1H), 7.26-7.29 (m, 2H), 7.13-7.19 (m, 4H), 6.90-6.93 (m, 2H), 6.10 (d, J=1.60 Hz, 1H), 5.79 (s, 1H), 4.83-4.87 (m, 1H), 4.44-4.52 (m, 2H), 2.74-2.90 (m, 1H), 2.56-2.58 (m, 1H), 2.42-2.43 (m, 1H), 1.53-1.59 (m, 2H), 1.13 (d, J=6.80 Hz, 6H), 0.75 (t, J=7.60 Hz, 3H).

Example 247

Enantiomer 1 & Enantiomer 2 3-(6-((4-fluorobenzyl)(isopropyl)amino)-4-((2-methylbenzo[d]thiazol-6-yl)amino)pyridin-2-yl)pentanoic acid

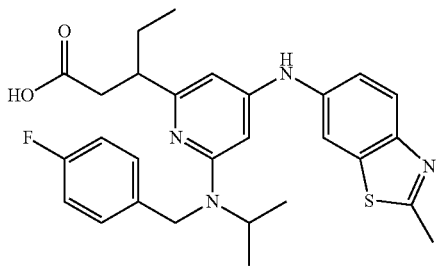 [SMILES: CCC(CC(=O)O)c1cc(Nc2ccc3nc(C)sc3c2)cc(N(Cc2ccc(F)cc2)C(C)C)n1]

Racemate Example 247 was prepared following the procedure as for the synthesis of Example 241 by using 6-bromo-2-methylbenzo[d]thiazole. Chiral separation of racemate Example 247 gave Enantiomer 1 and Enantiomer 2 (Method AQ). Diastereomer 1 $T_r$=9.03 min, Diastereomer 2 $T_r$=10.78 min (Method AQ) Enantiomer 1 Example 247: LC-MS Anal. Calc'd for $C_{28}H_{31}FN_4O_2S$ 506.6, found [M+H] 507 $T_r$=1.8 min (Method O). $^1$H NMR (400 MHz, DMSO-$d_6$) δ 8.52 (s, 1H), 7.67 (d, J=8.80 Hz, 1H), 7.46 (d, J=2.00 Hz, 1H), 7.26 (dd, J=8.40, 6.00 Hz, 2H), 7.11 (t, J=8.80 Hz, 2H), 7.03 (dd, J=8.40, 2.20 Hz, 1H), 6.12 (d, J=1.20 Hz, 1H), 5.82 (s, 1H), 4.81-4.88 (m, 1H), 4.43 (s, 2H), 2.76-0.00 (m, 4H), 2.59-2.62 (m, 1H), 2.38-2.40 (m, 1H), 1.52-1.53 (m, 2H), 1.12 (d, J=6.80 Hz, 6H), 0.75 (t, J=7.20 Hz, 3H).

Enantiomer 2 Example 247: LC-MS Anal. Calc'd for $C_{28}H_{31}FN_4O_2S$ 506.6, found [M+H] 507 $T_r$=1.8 min (Method O). $^1$H NMR (400 MHz, DMSO-d6) δ 8.52 (s, 1H), 7.67 (d, J=8.80 Hz, 1H), 7.46 (d, J=2.00 Hz, 1H), 7.26 (dd, J=8.40, 6.00 Hz, 2H), 7.11 (t, J=8.80 Hz, 2H), 7.03 (dd, J=8.40, 2.20 Hz, 1H), 6.12 (d, J=1.20 Hz, 1H), 5.82 (s, 1H), 4.81-4.88 (m, 1H), 4.43 (s, 2H), 2.76-0.00 (m, 4H), 2.59-2.62 (m, 1H), 2.38-2.40 (m, 1H), 1.52-1.53 (m, 2H), 1.12 (d, J=6.80 Hz, 6H), 0.75 (t, J=7.20 Hz, 3H).

Example 248

Enantiomer 1 & Enantiomer 2 3-(4-((4-chlorophenyl)amino)-6-((4-fluorobenzyl)(isobutyl)amino)pyridin-2-yl)pentanoic acid

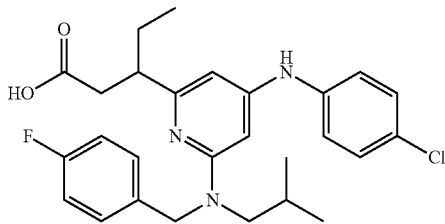 [SMILES: CCC(CC(=O)O)c1cc(Nc2ccc(Cl)cc2)cc(N(Cc2ccc(F)cc2)CC(C)C)n1]

248A. N-(4-fluorobenzyl)-2-methylpropan-1-amine

Compound 248A was prepared following a procedure analogous to that for the synthesis of 241A by using 4-fluorobenzaldehyde. LC-MS Anal. Calc'd for $C_{11}H_{16}FN$ 181.2, found [M+H] 182. $T_r$=1.8 min (Method U).

248B. 6-bromo-N-(4-fluorobenzyl)-N-isobutyl-4-nitropyridin-2-amine

Compound 248B was prepared following the procedure for 241B by using 248A. LC-MS Anal. Calc'd for $C_{16}H_{17}BrFN_3O_2$, 382.2, found [M+2] 384. $T_r$=4.04 min (Method U).

248C. 6-bromo-N2-(4-fluorobenzyl)-N2-isobutylpyridine-2,4-diamine

Compound 248C was prepared following the procedure for 241C by using 248B. LC-MS Anal. Calc'd for $C_{16}H_{19}BrFN_3$, 352.2., found [M+2] 354. $T_r$=4.3 min (Method U).

248D. (E)-methyl 3-(4-amino-6-((4-fluorobenzyl)(isobutyl)amino)pyridin-2-yl)pent-2-enoate Compound 248D was prepared following the procedure for 241D by using 248C. LC-MS Anal. Calc'd for $C_{22}H_{28}FN_3O_2$, 385.4., Found [M+H] 386.2. $T_r$=3.7 min (Method U).

248E. Methyl 3-(4-amino-6-((4-fluorobenzyl)(isobutyl)amino)pyridin-2-yl)pentanoate Compound 248E was prepared following the procedure for 241E by using 248D. LC-MS Anal. Calc'd for $C_{22}H_{30}FN_3O_2$, 387.4., Found [M+H] 388. $T_r$=1.64 min (Method T).

Example 248

Racemate Example 248 was prepared following the same procedure as for the synthesis of Example 241 by using 1-bromo-4-chlorobenzene. Chiral separation of racemate Example 248 gave Enantiomer 1 and Enantiomer 2 (Method AV). Enantiomer 1 $T_r$=7.7 min, Enantiomer 2 $T_r$=9.30 min (Method AV)

Enantiomer 1 of Example 248. LC-MS Anal. Calc'd $C_{27}H_{31}ClFN_3O_2$ for 483.0, found [M+H] 484.0. $T_r$=2.21 min (Method O). $^1$H NMR (400 MHz, DMSO-d$_6$) δ 8.49 (s, 1H), 7.21-7.26 (m, 4H), 7.12 (t, J=8.80 Hz, 2H), 6.99-7.02 (m, 2H), 6.09 (d, J=1.20 Hz, 1H), 5.86 (d, J=1.20 Hz, 1H), 4.66-4.68 (m, 2H), 3.17 (s, 2H), 2.67-2.68 (m, 1H), 2.53-2.55 (m, 1H), 2.39-2.41 (m, 1H), 2.02-2.07 (m, 1H), 1.49-1.55 (m, 2H), 0.88 (d, J=4.00 Hz, 6H), 0.71 (t, J=8.00 Hz, 3H).

Enantiomer 2 of Example 248. LC-MS Anal. Calc'd $C_{27}H_{31}ClFN_3O_2$ for 483.0, found [M+H] 484.0. $T_r$=2.21 min (Method O). $^1$H NMR (400 MHz, DMSO-d$_6$): δ 8.49 (s, 1H), 7.21-7.26 (m, 4H), 7.12 (t, J=8.80 Hz, 2H), 6.99-7.02 (m, 2H), 6.09 (d, J=1.20 Hz, 1H), 5.86 (d, J=1.20 Hz, 1H), 4.66-4.68 (m, 2H), 3.17 (s, 2H), 2.67-2.68 (m, 1H), 2.53-2.55 (m, 1H), 2.39-2.41 (m, 1H), 2.02-2.07 (m, 1H), 1.49-1.55 (m, 2H), 0.88 (d, J=4.00 Hz, 6H), 0.71 (t, J=8.00 Hz, 3H).

Example 249

Enantiomer 1 & Enantiomer 2 3-(6-((4-fluorobenzyl)(isobutyl)amino)-4-((2-methylbenzo [d]thiazol-6-yl)amino)pyridin-2-yl)pentanoic acid

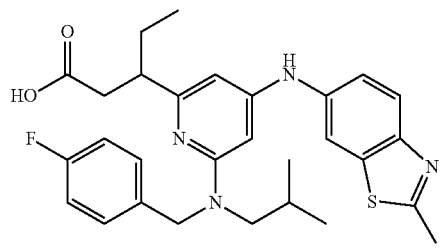 [SMILES: CCC(CC(=O)O)c1cc(Nc2ccc3nc(C)sc3c2)cc(N(Cc2ccc(F)cc2)CC(C)C)n1]

Racemate Example 249 was prepared following the procedure for Example 241 by using 6-bromo-2-methylbenzo [d]thiazole. Chiral separation of racemate Example 249 gave Enantiomer 1 and Enantiomer 2 (Method AQ). Enantiomer 1, $T_r$=8.62 min, Enantiomer 2, $T_r$=10.34 min (Method AQ)

Enantiomer 1 of Example 249. LC-MS Anal. Calc'd $C_{29}H_{33}FN_4O_2S$ for 520.6, found [M+H] 521.2 $T_r$=1.98 min (Method O). $^1$H NMR (400 MHz, DMSO-d$_6$) δ 8.55 (s, 1H), 7.73 (d, J=8.40 Hz, 1H), 7.58 (d, J=2.00 Hz, 1H), 7.22 (dd, J=8.40, 6.00 Hz, 2H), 7.09-7.13 (m, 3H), 6.12 (s, 1H), 5.93 (s, 1H), 4.66-4.68 (m, 2H), 3.12-3.18 (m, 2H), 2.74 (s, 4H), 2.51-2.51 (m, 1H), 2.41-2.46 (m, 1H), 2.01-2.07 (m, 1H), 1.50-1.58 (m, 2H), 0.87 (d, J=6.40 Hz, 6H), 0.72 (t, J=7.60 Hz, 3H)

Enantiomer 2 of Example 249. LC-MS Anal. Calc'd $C_{29}H_{33}FN_4O_2S$ for 520.6, found [M+H] 521.2 $T_r$=1.98 min (Method O). $^1$H NMR (400 MHz, DMSO-d6) δ 8.55 (s, 1H), 7.73 (d, J=8.40 Hz, 1H), 7.58 (d, J=2.00 Hz, 1H), 7.22 (dd, J=8.40, 6.00 Hz, 2H), 7.09-7.13 (m, 3H), 6.12 (s, 1H), 5.93 (s, 1H), 4.66-4.68 (m, 2H), 3.12-3.18 (m, 2H), 2.74 (s, 4H), 2.51-2.51 (m, 1H), 2.41-2.46 (m, 1H), 2.01-2.07 (m, 1H), 1.50-1.58 (m, 2H), 0.87 (d, J=6.40 Hz, 6H), 0.72 (t, J=7.60 Hz, 3H)

Example 250

Enantiomer 1 & Enantiomer 2 3-(6-((4-fluorobenzyl)(isobutyl)amino)-4-(3-(p-tolyl)ureido)pyridin-2-yl)pentanoic acid

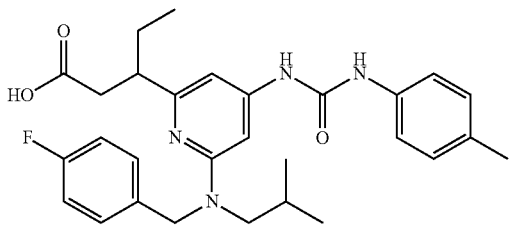 [SMILES: CCC(CC(=O)O)c1cc(NC(=O)Nc2ccc(C)cc2)cc(N(Cc2ccc(F)cc2)CC(C)C)n1]

Racemate Example 250 was prepared following the procedure for Example 244. Chiral separation of racemate Example 250 gave Enantiomer 1 and Enantiomer 2 (Method AW). Enantiomer 1, T$_r$=3.50 min, Enantiomer 2, T$_r$=4.70 min (Method AW) Enantiomer 1 of Example 250. LC-MS Anal. Calc'd C$_{29}$H$_{35}$FN$_4$O$_3$ for 506.6, found [M+H] 507. T$_r$=2.07 min (Method O). $^1$H NMR (400 MHz, DMSO-d$_6$) δ 8.71 (s, 1H), 8.59 (s, 1H), 7.30 (d, J=8.40 Hz, 2H), 7.23 (dd, J=8.40, 5.60 Hz, 2H), 7.06-7.10 (m, 4H), 6.56 (s, 1H), 6.51 (s, 1H), 4.70-4.72 (m, 2H), 3.27-3.29 (m, 2H), 2.71-2.76 (m, 1H), 2.56-2.59 (m, 1H), 2.33-2.35 (m, 1H), 2.23 (s, 3H), 2.02-2.06 (m, 1H), 1.49-1.55 (m, 2H), 0.88 (dd, J=8.00, Hz, 6H), 0.69 (t, J=8.00 Hz, 3H).

Enantiomer 2 of Example 250. LC-MS Anal. Calc'd C$_{29}$H$_{35}$FN$_4$O$_3$ for 506.6, found [M+H] 507. T$_r$=2.08 min (Method O). $^1$H NMR (400 MHz, DMSO-d$_6$): δ 8.71 (s, 1H), 8.59 (s, 1H), 7.30 (d, J=8.40 Hz, 2H), 7.23 (dd, J=8.40, 5.60 Hz, 2H), 7.06-7.10 (m, 4H), 6.56 (s, 1H), 6.51 (s, 1H), 4.70-4.72 (m, 2H), 3.27-3.29 (m, 2H), 2.71-2.76 (m, 1H), 2.56-2.59 (m, 1H), 2.33-2.35 (m, 1H), 2.23 (s, 3H), 2.02-2.06 (m, 1H), 1.49-1.55 (m, 2H), 0.88 (dd, J=8.00, Hz, 6H), 0.69 (t, J=8.00 Hz, 3H).

Example 251

2-(6-(diisobutylamino)-4-(3-(2-fluorophenyl)ureido)pyridin-2-yl)-4-fluorobenzoic acid

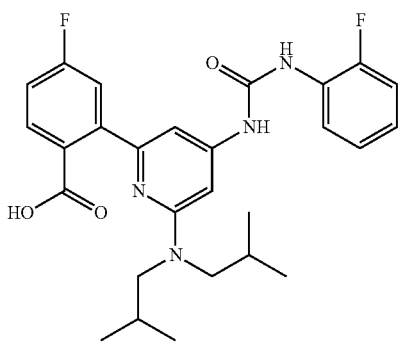 [SMILES: CC(C)CN(CC(C)C)c1cc(NC(=O)Nc2ccccc2F)cc(-c2cc(F)ccc2C(=O)O)n1]

251A.
6-bromo-N,N-diisobutyl-4-nitropyridin-2-amine

A solution of 2,6-dibromo-4-nitropyridine (0.564 g, 2 mmol) in NMP (0.4 mL) was treated with diisobutylamine (0.384 mL, 2.200 mmol) followed by Hunig's Base (0.419 mL, 2.400 mmol). The solution was stirred for 3 h at 80° C. then cooled and filtered through a plug of silica gel (etherhexanes). The product-containing fractions were pooled and stripped, and the resulting oily solid was triturated (to remove a less-soluble impurity) with 1:1 ether-hexanes. The filtrate was concentrated to afford 6-bromo-N,N-diisobutyl-4-nitropyridin-2-amine (0.4 g, 54.5% yield) as an orange oil which solidified upon standing. MS (ES): m/z=332 [M+H]$^+$. T$_r$=3.33 min (Method AX).

251B.
6-bromo-N2,N2-diisobutylpyridine-2,4-diamine

To a solution of 6-bromo-N,N-diisobutyl-4-nitropyridin-2-amine (0.35 g, 1.060 mmol) in Ethanol (8 mL) was added 1 mL of water followed by ammonium chloride (0.850 g, 15.90 mmol). This mixture was stirred for 5 min. at RT then treated with zinc (1.039 g, 15.90 mmol) in two portions, 1 min. apart. The resulting mixture was stirred 30 min. at RT then diluted with dichloromethane and filtered. The filtrate was washed with water, dried, and stripped to afford 6-bromo-N2,N2-diisobutylpyridine-2,4-diamine (0.3 g, 94% yield) as an orangish oil. MS (ES): m/z=300 [M+H]$^+$. T$_r$=2.84 min (Method AY).

251C. 1-(2-bromo-6-(diisobutylamino)pyridin-4-yl)-3-(2-fluorophenyl)urea

To a solution of 6-bromo-N2,N2-diisobutylpyridine-2,4-diamine (0.14 g, 0.466 mmol) in THF (0.5 mL) was added 1-fluoro-2-isocyanatobenzene (0.090 g, 0.653 mmol) The solution was stirred for 16 h at 55° C. then cooled, treated with 0.03 mL of N, N-dimethylethylenediamine, and purified by Isco chromatography. Concentration of the appropriate fractions afforded 1-(2-bromo-6-(diisobutylamino)pyridin-4-yl)-3-(2-fluorophenyl)urea (0.083 g, 39% yield). MS (ES): m/z=437 [M+H]$^+$. T$_r$=5.15 min (Method AY).

Example 251

To a suspension of 2-borono-4-fluorobenzoic acid (0.017 g, 0.091 mmol) and 1-(2-bromo-6-(diisobutylamino)pyridin-4-yl)-3-(2-fluorophenyl)urea (0.02 g, 0.046 mmol) and tetrakis(triphenylphosphine)palladium(0) (5.28 mg, 4.57 μmol) in degassed DMF (1 mL) was added aq. potassium carbonate (0.152 mL, 0.229 mmol). The mixture was placed under nitrogen and heated at 95° C. for 3 h. The reaction was cooled to 60° C., brought to pH 4 with glacial HOAc, filtered, and purified via preparative HPLC. Concentration of the appropriate fractions afforded 2-(6-(diisobutylamino)-4-(3-(2-fluorophenyl)ureido)pyridin-2-yl)-4-fluorobenzoic acid (0.009 g, 38% yield). MS (ES): m/z=497 [M+H]+. T$_r$=2.16 min (Method AZ). $^1$H NMR (400 MHz, DMSO-d$_6$) δ 9.29 (br. s, <1H), 8.69 (br. s, <1H), 8.12 (dd, 1H, J=12.4, 7.9 Hz), 7.65 (dd, 1H, J=8.4, 6.0 Hz), 7.35 (dd, 1H, J=9.9, 2.5 Hz), 7.22-7.30 (m, 2H), 7.16 (t, 1H, J=7.7 Hz), 7.01-7.08

(m, 1H), 6.80 (br. s, 1H), 6.77 (br. s, 1H), 3.29 (d, 4H, J=6.9 Hz), 2.04-2.14 (m, 2H), 0.88 (d, 12H, J=6.4 Hz).

Example 252

2-(6-(diisobutylamino)-4-(3-(2-fluorophenyl)ureido)pyridin-2-yl)benzoic acid

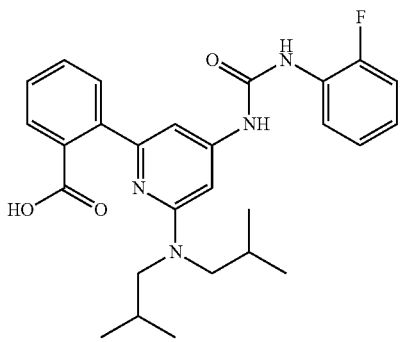 [SMILES: CC(C)CN(CC(C)C)c1cc(NC(=O)Nc2ccccc2F)cc(-c2ccccc2C(=O)O)n1]

Reaction of 1-(2-bromo-6-(diisobutylamino)pyridin-4-yl)-3-(2-fluorophenyl)urea and 2-boronobenzoic acid under the conditions described for Example 251 afforded Example 252 (0.018 g, 78% yield). MS (ES): m/z=479 [M+H]$^+$. T$_r$=2.04 min (Method AZ). $^1$H NMR (400 MHz, DMSO-d$_6$) δ 9.26 (br. s, <1H), 8.64 (br. s, <1H), 8.11-8.17 (m, 1H), 7.52-7.60 (m, 3H), 7.44 (td, 1H, J=7.2, 1.9 Hz), 7.25 (ddd, 1H, J=11.9, 8.4, 1.5 Hz), 7.16 (br. t, 1H, J=7.6 Hz), 7.01-7.07 (m, 1H), 6.81 (br. s, 1H), 6.71 (br. s, 1H), 3.29 (d, 4H, J=7.4 Hz), 2.04-2.14 (m, 2H), 0.87 (d, 12H, J=6.4 Hz).

Example 253

1-(2-(2-(1H-tetrazol-5-yl)phenyl)-6-(diisobutylamino) pyridin-4-yl)-3-(2-fluorophenyl)urea

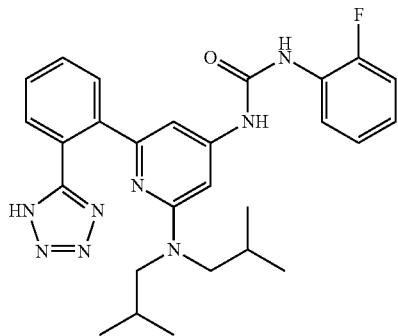 [SMILES: CC(C)CN(CC(C)C)c1cc(NC(=O)Nc2ccccc2F)cc(-c2ccccc2-c2nnn[nH]2)n1]

Reaction of 1-(2-bromo-6-(diisobutylamino)pyridin-4-yl)-3-(2-fluorophenyl)urea and (2-(1H-tetrazol-5-yl)phenyl) boronic acid under the conditions described for Example 251 afforded Example 253 (0.018 g, 74% yield). MS (ES): m/z=503 [M+H]$^+$. T$_r$=1.96 min (Method AZ). $^1$H NMR (400 MHz, DMSO-d$_6$) δ 9.20 (br. s, 1H), 8.64 (br. s, 1H), 8.10-8.16 (m, 1H), 7.73 (d, 1H), 7.65-7.70 (m, 1H), 7.55-7.62 (m, 2H), 7.25 (ddd, 1H, J=11.9, 8.2, 1.4 Hz), 7.16 (br. t, 1H, J=7.7 Hz), 7.01-7.07 (m, 1H), 6.67-6.70 (m, 2H), 2.95 (d, 4H, J=7.4 Hz), 1.78-1.86 (m, 2H), 0.77 (d, 12H, J=6.4 Hz).

Example 254

2-(6-(diisobutylamino)-4-(3-(p-tolyl)ureido)pyridin-2-yl)benzoic acid

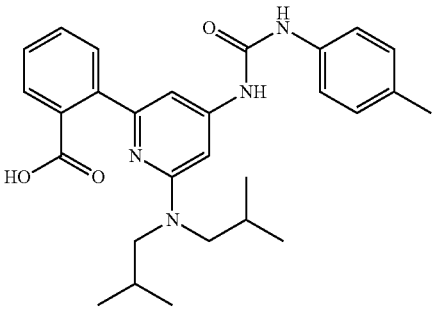 [SMILES: Cc1ccc(NC(=O)Nc2cc(-c3ccccc3C(=O)O)nc(N(CC(C)C)CC(C)C)c2)cc1]

254A. 1-(2-bromo-6-(diisobutylamino)pyridin-4-yl)-3-(p-tolyl)urea

To a solution of 6-bromo-N2,N2-diisobutylpyridine-2,4-diamine (0.15 g, 0.500 mmol) in THF (0.5 mL) was added 1-isocyanato-4-methylbenzene (0.080 g, 0.600 mmol). The solution was stirred for 1 h at 50° C. then cooled, treated with 0.03 mL of N, N-dimethylethylenediamine, and concentrated under reduced pressure. The resulting mixture was triturated with 1:1 ether-hexanes. Filtration afforded 254A (0.08 g, 31% yield) as an off-white solid. MS (ES): m/z=433 [M+H]+. T$_r$=5.14 min (Method AY).

Example 254

Reaction of 1-(2-bromo-6-(diisobutylamino)pyridin-4-yl)-3-(p-tolyl)urea and 2-boronobenzoic acid under the conditions described for the synthesis of Example 251 afforded Example 254 (0.005 g, 22% yield). MS (ES): m/z=475 [M+H]+. T$_r$=2.02 min (Method AZ). $^1$H NMR (400 MHz, DMSO-d$_6$) δ 8.87 (br. s, 1H), 8.71 (br. s, 1H), 7.50-7.60 (m, 3H), 7.42-7.46 (m, 1H), 7.34 (d, 2H, J=8.4 Hz), 7.10 (d, 2H, J=8.4 Hz), 6.84 (br. s, 1H), 6.71 (br. s, 1H), 3.28 (d, 4H, J=7.4 Hz), 2.26 (s, 3H), 2.04-2.13 (m, 2H), 0.87 (d, 12H, J=6.4 Hz).

Example 255

1-(2-(2-(1H-tetrazol-5-yl)phenyl)-6-(diisobutylamino)pyridin-4-yl)-3-(p-tolyl)urea

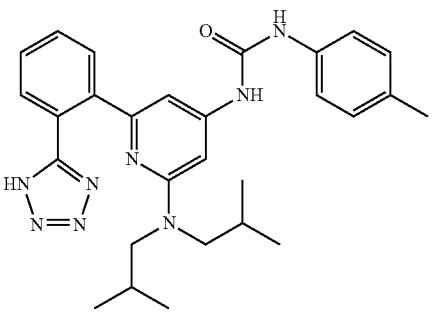 [SMILES: Cc1ccc(NC(=O)Nc2cc(-c3ccccc3-c3nnn[nH]3)nc(N(CC(C)C)CC(C)C)c2)cc1]

Reaction of 1-(2-bromo-6-(diisobutylamino)pyridin-4-yl)-3-(p-tolyl)urea and (2-(1H-tetrazol-5-yl)phenyl)boronic acid under the conditions described for the synthesis of Example 251 afforded Example 255 (0.004 g, 16% yield). MS (ES): m/z=499 [M+H]+. $T_r$=1.96 min (Method AZ). $^1$H NMR (400 MHz, DMSO-$d_6$) δ 8.72 (s, 1H), 8.67 (s, 1H), 7.69 (d, 1H, J=7.4 Hz), 7.61 (t, 1H, J=7.7 Hz), 7.57 (dd, 1H, J=7.4, 1.5 Hz), 7.52 (t, 1H, J=7.4 Hz), 7.32 (d, 2H, J=8.4 Hz), 7.10 (d, 2H, J=8.4 Hz), 6.74 (s, 1H), 6.55 (br. s, 1H), 3.00 (d, 4H, J=7.4 Hz), 2.25 (s, 3H), 1.82-1.90 (m, 2H), 0.79 (d, 12H, J=6.4 Hz).

Example 256

2-(6-(1)amino)-4-(3-(p-tolyl)ureido)pyridin-2-yl)-4-fluorobenzoic acid

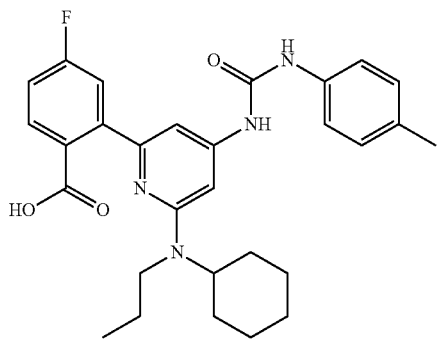 [SMILES: CCCN(c1cc(NC(=O)Nc2ccc(C)cc2)cc(-c2cc(F)ccc2C(=O)O)n1)C1CCCCC1]

256A. 6-bromo-N-cyclohexyl-4-nitro-N-propylpyridin-2-amine

Reaction of 2,6-dibromo-4-nitropyridine (0.564 g, 2 mmol) and N-propylcyclohexanamine under the conditions described for 251A afforded 256A (0.16 g, 18% yield) as an orange oil which solidified upon standing. MS (ES): m/z=344 [M+H]+. $T_r$=5.42 min (Method AY).

256B. 1-(2-bromo-6-(cyclohexyl(propyl)amino)pyridin-4-yl)-3-(p-tolyl)urea

To a solution of 6-bromo-N-cyclohexyl-4-nitro-N-propylpyridin-2-amine (0.145 g, 0.424 mmol) in ethanol (4 mL) was added 0.5 mL of water followed by ammonium chloride (0.227 g, 4.24 mmol). This mixture was stirred for 5 min. at RT then treated with zinc (0.277 g, 4.24 mmol) in two portions, 1 min. apart. The resulting mixture was stirred for 30 min. at RT then diluted with dichloromethane and filtered. The filtrate was washed with water, dried, and stripped to afford a dark oil. This material was dissolved in 0.5 mL of THF and treated with 1-isocyanato-4-methylbenzene (0.102 g, 0.763 mmol). The reaction was heated to 50° C. overnight then cooled and diluted with 0.5 mL of 30% ether-hexanes. The resulting white powder was filtered, rinsed with 30% ether-hexanes, and air-dried briefly to afford 256B (0.079 g, 38% yield). MS (ES): m/z=447 [M+H]+. $T_r$=5.22 min (Method AY).

Example 256

Reaction of 1-(2-bromo-6-(cyclohexyl(propyl)amino)pyridin-4-yl)-3-(p-tolyl)urea under the conditions described for the synthesis of Example 251 afforded Example 256 (0.005 g, 20% yield). MS (ES): m/z=505 [M+H]+. $T_r$=2.28 min (Method AZ). $^1$H NMR (400 MHz, DMSO-$d_6$) δ 8.91 (s, 1H), 8.76 (s, 1H), 7.61-7.68 (m, 1H), 7.24-7.37 (m, 4H), 7.10 (d, 2H, J=6.9 Hz), 6.87 (s, 1H), 6.70 (br. s, 1H), 4.29-4.37 (m, 1H), 3.14-3.21 (m, 2H), 2.25 (s, 3H), 1.31-1.81 (m, 11H), 1.09-1.18 (m, 1H), 0.91 (t, 3H, J=7.4 Hz).

Example 257

2-(6-(cyclohexyl(propyl)amino)-4-(3-(p-tolyl)ureido)pyridin-2-yl)benzoic acid

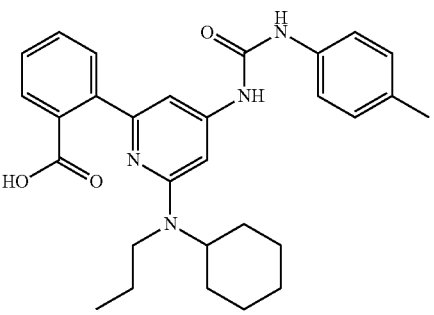 [SMILES: CCCN(c1cc(NC(=O)Nc2ccc(C)cc2)cc(-c2ccccc2C(=O)O)n1)C1CCCCC1]

Reaction of 1-(2-bromo-6-(cyclohexyl(propyl)amino)pyridin-4-yl)-3-(p-tolyl)urea and 2-boronobenzoic acid under the conditions described for the synthesis of Example 251 afforded Example 257 (0.0026 g, 11% yield). MS (ES): m/z=487 [M+H]+. $t_R$=2.25 min (Method AZ). $^1$H NMR (400 MHz, DMSO-$d_6$) δ 7.53-7.57 (m, 6H), 7.06-7.09 (m, 2H), 6.88 (s, 1H), 6.68 (br. s, 1H), 4.32-4.41 (m, 1H), 3.16-3.21 (m, 2H), 2.24 (s, 3H), 1.51-1.79 (m, 7H), 1.32-1.48 (m, 4H), 1.09-1.18 (m, 1H), 0.91 (t, 3H, J=7.4 Hz).

Example 258

1-(2-(2-(1H-tetrazol-5-yl)phenyl)-6-(cyclohexyl(propyl)amino) pyridin-4-yl)-3-(p-tolyl)urea

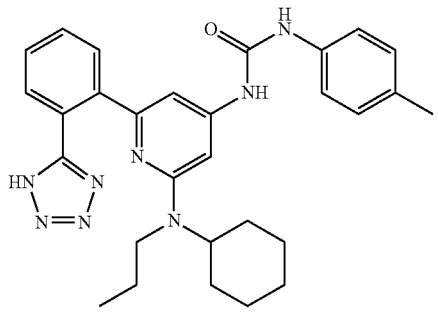 [SMILES: CCCN(c1cc(NC(=O)Nc2ccc(C)cc2)cc(-c2ccccc2-c2nnn[nH]2)n1)C1CCCCC1]

Reaction of 1-(2-bromo-6-(cyclohexyl(propyl)amino)pyridin-4-yl)-3-(p-tolyl)urea and (2-(1H-tetrazol-5-yl)phenyl)boronic acid under the conditions described for the synthesis of Example 251 afforded Example 258 (0.015 g, 62% yield). MS (ES): m/z=511 [M+H]+. $T_r$=2.17 min (Method AZ). $^1$H NMR (400 MHz, DMSO-$d_6$) δ 7.70 (d, 1H, J=7.4 Hz), 7.66 (t, 1H, J=7.9 Hz), 7.60 (d, 1H, J=7.4 Hz), 7.56 (t, 1H, J=7.4 Hz), 7.34 (d, 2H, J=8.4 Hz), 7.10 (d, 2H, J=8.4 Hz), 6.77 (br. s, 1H), 6.61 (s, 1H), 3.76-3.83 (m, 1H), 2.94-2.99 (m, 2H), 2.25 (s, 3H), 1.65-1.72 (m, 2H), 1.56-1.60 (m, 1H), 1.23-1.44 (m, 8H), 1.01-1.11 (m, 1H), 0.86 (t, 3H, J=7.2 Hz).

Example 259

2-(6-(benzyl(propyl)amino)-4-(3-(p-tolyl)ureido)pyridin-2-yl)-4-fluorobenzoic acid

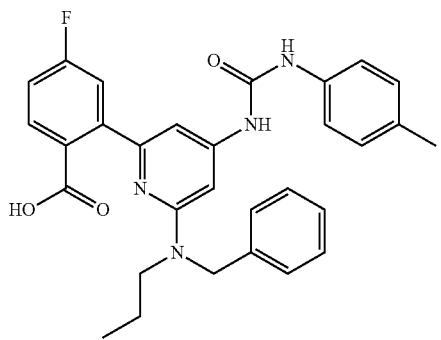 [SMILES: CCCN(Cc1ccccc1)c1cc(NC(=O)Nc2ccc(C)cc2)cc(-c2cc(F)ccc2C(=O)O)n1]

259A. N-benzyl-6-bromo-4-nitro-N-propylpyridin-2-amine

Reaction of 2,6-dibromo-4-nitropyridine (0.564 g, 2 mmol) and N-propylbenzylamine under the conditions described for the synthesis of 251A afforded 259A (0.4 g, 51% yield) as yellow oil. MS (ES): m/z=352 [M+H]$^+$. T$_r$=5.08 min (Method AY).

259B. 1-(2-(benzyl(propyl)amino)-6-bromopyridin-4-yl)-3-(p-tolyl)urea

Reaction of N-benzyl-6-bromo-4-nitro-N-propylpyridin-2-amine under the conditions used to prepare 256B followed by flash chromatography (EtOAc-hexanes) afforded 259B (0.106 g, 80% yield) as a tan solid. MS (ES): m/z=453 [M+H]+. T$_r$=5.00 min (Method AY).

Example 259

Reaction of 1-(2-(benzyl(propyl)amino)-6-bromopyridin-4-yl)-3-(p-tolyl)urea under the conditions described for the synthesis of Example 251 afforded Example 259 (0.003 g, 12% yield). MS (ES): m/z=513 [M+H]$^+$. T$_r$=2.04 min (Method AZ).

Example 260

1-(2-(2-(1H-tetrazol-5-yl)phenyl)-6-(benzyl(propyl)amino)pyridin-4-yl)-3-(p-tolyl)urea

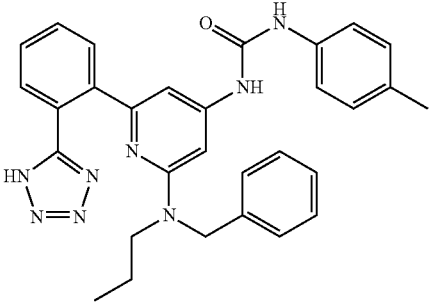 [SMILES: CCCN(Cc1ccccc1)c1cc(NC(=O)Nc2ccc(C)cc2)cc(-c2ccccc2-c2nnn[nH]2)n1]

Reaction of 1-(2-(benzyl(propyl)amino)-6-bromopyridin-4-yl)-3-(p-tolyl)urea and (2-(1H-tetrazol-5-yl)phenyl)boronic acid under the conditions described for the synthesis of Example 251 afforded Example 260 (0.0046 g, 20% yield). MS (ES): m/z=519 [M+H]$^+$. T$_r$=2.06 min (Method AZ). $^1$H NMR (400 MHz, MeOH-d4) δ 7.79 (d, 1H, J=7.4 Hz), 7.55-7.59 (m, 1H), 7.49-7.51 (m, 2H), 7.31 (d, 2H, J=8.4 Hz), 7.28 (d, 2H, J=7.4 Hz), 7.19-7.24 (m, 1H), 7.17 (br. s, 1H), 7.09-7.13 (m, 4H), 6.62 (br. s, 1H), 4.51 (s, integration obscured by water peak), 3.22-3.27 (m, 2H), 2.30 (s, 3H), 1.36-1.44 (m, 2H), 0.83 (t, 3H, J=7.4 Hz).

Example 261

2-(6-(benzyl(propyl)amino)-4-(3-(2-fluorophenyl)ureido) pyridin-2-yl)-4-fluorobenzoic acid

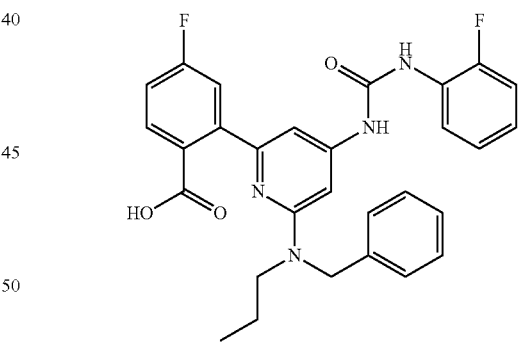

261A. 1-(2-(benzyl(propyl)amino)-6-bromopyridin-4-yl)-3-(2-fluorophenyl)urea Reaction of N-benzyl-6-bromo-4-nitro-N-propylpyridin-2-amine and 1-fluoro-2-isocyanatobenzene under the conditions used to prepare 256B afforded 261A (0.073 g, 54% yield) as a white solid. MS (ES): m/z=459 [M+H]$^+$. T$_r$=5.00 min (Method AY).

Example 261

Reaction of 1-(2-(benzyl(propyl)amino)-6-bromopyridin-4-yl)-3-(2-fluorophenyl)urea under the conditions described for the synthesis of Example 251 afforded Example 261 (0.014 g, 58% yield). MS (ES): m/z=517 [M+H]$^+$. T$_r$=2.06 min (Method AZ). $^1$H NMR (400 MHz, DMSO-d$_6$) δ 9.31 (br. s, 1H), 8.68 (br. s, 1H), 8.07 (t, 1H, J=7.9 Hz), 7.63 (t, 1H, J=6.7 Hz), 7.20-7.34 (m, 8H), 7.14 (t, 1H, J=7.7 Hz), 7.01-7.07 (m, 1H), 6.92 (s, 1H), 6.69 (br. s, 1H), 4.74 (s, 2H), 1.54-1.62 (m, 2H), 0.86 (t, 3H, J=7.4 Hz). Note: NCH$_2$ resonance likely obscured by solvent peak.

Example 262

1-(2-(2-(1H-tetrazol-5-yl)phenyl)-6-(benzyl(propyl) amino) pyridin-4-yl)-3-(2-fluorophenyl)urea

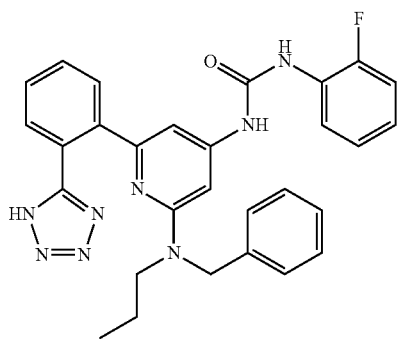 [SMILES: CCCN(Cc1ccccc1)c1cc(NC(=O)Nc2ccccc2F)cc(-c2ccccc2-c2nnn[nH]2)n1]

Reaction of 1-(2-(benzyl(propyl)amino)-6-bromopyridin-4-yl)-3-(p-tolyl)urea and (2-(1H-tetrazol-5-yl)phenyl)boronic acid under the conditions described for the synthesis of Example 251 afforded Example 262 (0.01 g, 41% yield). MS (ES): m/z=523 [M+H]$^+$. T$_r$=2.00 min (Method AZ). $^1$H NMR (400 MHz, MeOH-d4) δ 8.06 (td, 1H, J=7.9, 1.4 Hz), 7.73-7.77 (m, 1H), 7.56-7.61 (m, 3H), 7.31 (t, 2H, J=7.4 Hz), 7.23 (t, 1H, J=7.2 Hz), 7.01-7.17 (m, 6H), 6.71 (s, 1H), 4.59 (s, integration obscured by water peak), 3.31 (t, integration obscured by solvent peak, J=7.9 Hz), 1.45-1.53 (m, 2H), 0.87 (t, 3H, J=7.4 Hz).

Example 263

1-(2-(2-(1H-tetrazol-5-yl)phenyl)-6-(benzyl(propyl) amino)pyridin-4-yl)-3-(3,5-dimethylphenyl)urea

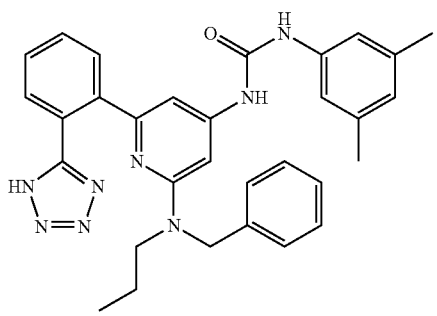 [SMILES: CCCN(Cc1ccccc1)c1cc(NC(=O)Nc2cc(C)cc(C)c2)cc(-c2ccccc2-c2nnn[nH]2)n1]

263A. 1-(2-(benzyl(propyl)amino)-6-bromopyridin-4-yl)-3-(3,5-dimethylphenyl)urea Reaction of N-benzyl-6-bromo-4-nitro-N-propylpyridin-2-amine and 1-isocyanato-3,5-dimethylbenzene under the conditions used to prepare 256B afforded 263A (0.07 g, 40% yield) as a white solid. MS (ES): m/z=469 [M+H]$^+$. T$_r$=5.14 min (Method AY).

Example 263

Reaction of 1-(2-(benzyl(propyl)amino)-6-bromopyridin-4-yl)-3-(3,5-dimethylphenyl)urea and (2-(1H-tetrazol-5-yl) phenyl)boronic acid under the conditions described for the synthesis of Example 251 afforded Example 263 (0.006 g, 25% yield). MS (ES): m/z=533 [M+H]$^+$. T$_r$=2.15 min (Method AZ). $^1$H NMR (400 MHz, DMSO-d$_6$) δ 8.78 (s, 1H), 8.59 (s, 1H), 7.69 (d, 1H, J=7.9 Hz), 7.64 (t, 1H, J=7.4 Hz), 7.54-7.61 (m, 2H), 7.30 (t, 2H, J=7.4 Hz), 7.21 (t, 1H, J=7.4 Hz), 7.11 (d, 2H, J=7.4 Hz), 7.04 (s, 2H), 6.76 (br. s, 1H), 6.63 (s, 1H), 6.59 (s, 1H), 4.44 (s, 2H), 3.59 (t, 2H, J=7.7 Hz), 2.23 (s, 6H), 1.33-1.40 (m, 2H), 0.77 (t, 3H, J=7.4 Hz).

Example 264

1-(2-(2-(1H-tetrazol-5-yl)phenyl)-6-(benzyl(propyl) amino)pyridin-4-yl)-3-butylurea

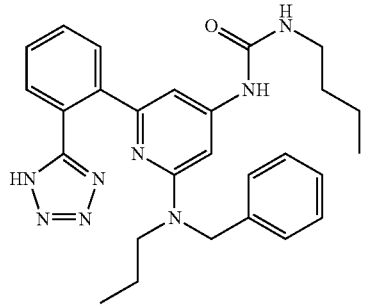 [SMILES: CCCCNC(=O)Nc1cc(-c2ccccc2-c2nnn[nH]2)nc(N(CCC)Cc2ccccc2)c1]

264A. 1-(2-(benzyl(propyl)amino)-6-bromopyridin-4-yl)-3-butylurea

Reaction of N-benzyl-6-bromo-4-nitro-N-propylpyridin-2-amine and butyl isocyanate under the conditions used to prepare 256B afforded 264A (0.08 g, 76% yield) as a white solid. MS (ES): m/z=469 [M+H]$^+$. T$_r$=5.14 min (Method AY).

Example 264

Reaction of 1-(2-(benzyl(propyl)amino)-6-bromopyridin-4-yl)-3-(3,5-dimethylphenyl)urea and (2-(1H-tetrazol-5-yl) phenyl)boronic acid under the conditions described for the synthesis of Example 251 afforded Example 264 (0.015 g, 61% yield). MS (ES): m/z=485 [M+H]$^+$. T$_r$=3.60 min (Method AY). $^1$H NMR (400 MHz, DMSO-d$_6$) δ 8.59 (s, 1H), 7.63-7.69 (m, 2H), 7.54-7.60 (m, 2H), 7.28 (t, 2H, J=7.4 Hz), 7.20 (t, 1H, J=7.4 Hz), 7.08 (d, 2H, J=7.4 Hz), 6.77 (s, 1H), 6.57 (s, 1H), 6.22 (t, 1H, J=5.7 Hz), 4.38 (s, 2H), 3.01-3.07 (m, 4H), 1.25-1.42 (m, 6H), 0.88 (t, 3H, J=7.2 Hz), 0.75 (t, 3H, J=7.2 Hz).

Example 265

1-(2-(2-(1H-tetrazol-5-yl)phenyl)-6-(benzyl(propyl)amino)pyridin-4-yl)-3-(2-fluoro-4-(trifluoromethyl)phenyl)urea

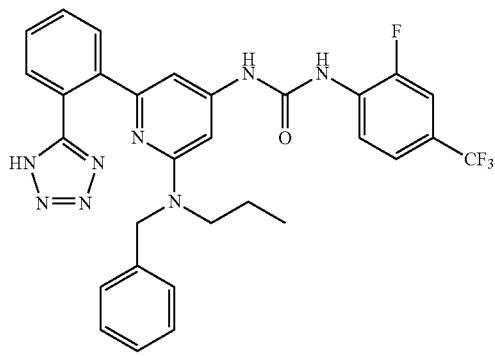 [SMILES: CCCN(Cc1ccccc1)c1cc(NC(=O)Nc2ccc(C(F)(F)F)cc2F)cc(-c2ccccc2-c2nnn[nH]2)n1]

To a solution of 6-(2-(1H-tetrazol-5-yl)phenyl)-N2-benzyl-N2-propylpyridine-2,4-diamine (50 mg, 0.130 mmol) in THF (1.2 mL) at RT was added 4-nitrophenyl carbonochloridate (52.3 mg, 0.259 mmol), followed by Hunig's Base (0.068 mL, 0.389 mmol). The mixture was stirred at RT for 1 h. 2-fluoro-4-(trifluoromethyl)aniline (7.81 mg, 0.044 mmol) was added, followed by Hunig's Base (0.011 mL, 0.065 mmol). The mixture was stirred at 50° C. for 15 min. Then it was cooled to RT. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-100% B over 25 min, then a 5-min hold at 100% B; Flow: 20 mL/min. Fractions containing the desired product were combined and dried via centrifugal evaporation to afford Example 265 (6.8 mg, 0.011 mmol, 50.7%) $^1$H NMR (500 MHz, DMSO-$d_6$) δ 9.24 (s, 1H), 9.00 (d, J=2.5 Hz, 1H), 8.39 (t, J=8.4 Hz, 1H), 7.96 (s, 1H), 7.74-7.62 (m, 2H), 7.59-7.42 (m, 4H), 7.31 (t, J=7.4 Hz, 2H), 7.22 (t, J=7.4 Hz, 1H), 7.16 (d, J=7.4 Hz, 2H), 6.71 (br. s., 1H), 6.58-6.38 (m, 1H), 4.54 (s, 2H), 3.18 (t, J=7.2 Hz, 2H), 1.51-1.34 (m, 2H), 0.86-0.75 (m, 3H) MS: Anal. Calc'd for $C_{30}H_{26}F_4N_8O$ 590.217, found [M+H] 591.2; $T_r$=1.94 min.

Examples 266 to 272 were obtained following the procedures in Example 265 using the corresponding aniline.

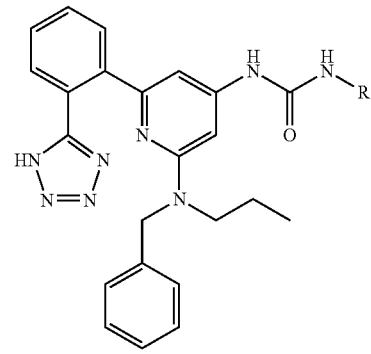

| Ex. No. | Name | R | Tr (min) Method O | [M + H]⁺ |
|---|---|---|---|---|
| 266 | 1-(2-(2-(1H-tetrazol-5-yl)phenyl)-6-(benzyl(propyl)amino)pyridin-4-yl)-3-(3-methylisoxazol-5-yl)urea | 3-methylisoxazol-5-yl | 1.47 | 510.2 |
| 267 | 1-(2-(2-(1H-tetrazol-5-yl)phenyl)-6-(benzyl(propyl)amino)pyridin-4-yl)-3-(6-methylpyridin-3-yl)urea | 6-methylpyridin-3-yl | 1.11 | 520.3 |
| 268 | 1-(2-(2-(1H-tetrazol-5-yl)phenyl)-6-(benzyl(propyl)amino)pyridin-4-yl)-3-(4-(trifluoromethoxy)phenyl)urea | 4-(trifluoromethoxy)phenyl | 1.93 | 589.2 |

-continued

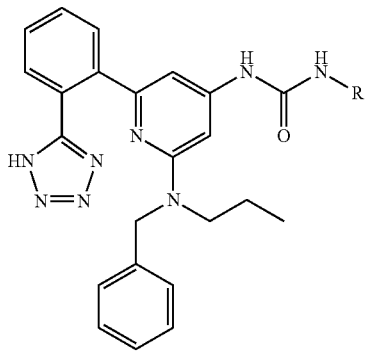

| Ex. No. | Name | R | Tr (min) Method O | [M + H]+ |
|---|---|---|---|---|
| 269 | 1-(2-(2-(1H-tetrazol-5-yl)phenyl)-6-(benzyl(propyl)amino)pyridin-4-yl)-3-(p-tolyl)urea | 4-methylphenyl | 1.47 | 510.2 |
| 271 | 1-(2-(2-(1H-tetrazol-5-yl)phenyl)-6-(benzyl(propyl)amino)pyridin-4-yl)-3-(4-(difluoromethoxy)phenyl)urea | 4-(difluoromethoxy)phenyl | 1.75 | 571.3 |
| 272 | 1-(2-(2-(1H-tetrazol-5-yl)phenyl)-6-(benzyl(propyl)amino)pyridin-4-yl)-3-(4-ethoxyphenyl)urea | 4-ethoxyphenyl | 1.71 | 548.3 |

Analytical Method: Waters Acquity UPLC BEH C18, 2.1 × 50 mm, 1.7-μm particles;
Mobile Phase A: 5:95 acetonitrile:water with 0.1% trifluoroacetic acid;
Mobile Phase B: 95:5 acetonitrile:water with 0.1% trifluoroacetic acid;
Temperature: 50° C.; Gradient: 0-100% B over 3 minutes, then a 0.75-5 minute hold at 100% B;
Flow: 1.0 mL/min; Detection: UV at 220 nm.

Example 273

1-(2-(2-(1H-Tetrazol-5-yl)phenyl)-6-(dibenzylamino) pyridin-4-yl)-3-(4-(trifluoromethoxy)-phenyl)urea

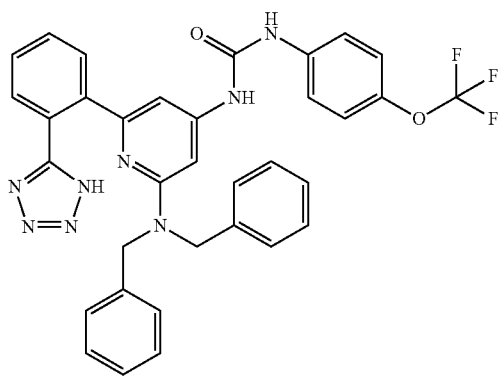 [SMILES: O=C(Nc1ccc(OC(F)(F)F)cc1)Nc1cc(-c2ccccc2-c2nnn[nH]2)nc(N(Cc2ccccc2)Cc2ccccc2)c1]

273A.
N,N-Dibenzyl-6-bromo-4-nitropyridin-2-amine

To a homogeneous mixture of 2,6-dibromo-4-nitropyridine (0.65 g, 2.3 mmol) in anhydrous dioxane (2 mL), in a sealable vial, was added dibenzylamine (1.36 g, 6.9 mmol). The vial was capped and the mixture was heated at 100° C. for 14 hrs. After cooling to RT, The reaction mixture was partitioned between EtOAc and 1N HCl (aq). The resultant heterogeneous mixture was filtered to remove solids. The filtrate was transferred to a separatory funnel where the organic layer was washed with water then brine, before being dried (MgSO$_4$), filtered and concentrated in vacuo to afford the crude product. Purification by Isco chromatography afforded 273A as an orange solid (0.81 g; 88% yield). MS (ES): m/z=398/400 [M+H]+. T$_r$=1.22 min (Method AAB). $^1$H NMR (400 MHz, DMSO-d$_6$) δ 7.39 (d, J=1.5 Hz, 1H), 7.37-7.32 (m, 4H), 7.31-7.25 (m, 6H), 7.22 (d, J=1.5 Hz, 1H), 4.88 (s, 4H).

273B. 6-(2-(1H-Tetrazol-5-yl)phenyl)-N,N-dibenzyl-4-nitropyridin-2-amine

To a homogeneous mixture of N,N-dibenzyl-6-bromo-4-nitropyridin-2-amine (0.33 g, 0.84 mmol) in anhydrous dioxane (5 mL), in a sealable reaction flask, was added (2-(1H-tetrazol-5-yl)phenyl)boronic acid (0.32 g, 1.67 mmol) and potassium phosphate, dibasic (0.44 g, 2.51 mmol). The resulting mixture was purged with argon for 20 min before PdCl$_2$(dppf)-CH$_2$Cl$_2$Adduct (0.034 g, 0.042 mmol) was added. The mixture was then purged with argon for 15 min before the flask was sealed and the reaction was heated at 95° C. After 14 hrs, the reaction was cooled to RT before EtOH (0.85 mL), dimethoxyethane (8.5 mL), water (2.5 mL) and NaOH (0.20 g) were added and the reaction mixture was purged with Argon for 20 min. Pd(PPh$_3$)$_4$ (0.097 g) was then added and the mixture was purged with Argon for 10 min before the flask was sealed and The reaction was heated at 95° C. After 22 hrs, the reaction mixture was cooled, then partitioned between EtOAc and water. The layers were separated and the aqueous layer was extracted twice more with EtOAc. The combined organic layers were washed with brine then dried (MgSO$_4$), filtered and concentrated in vacuo to afford the crude product. Purification by Isco chromatography afforded 273B as a solid (0.056 g; 14% yield). MS (ES): m/z=464 [M+H]$^+$. T$_r$=1.04 min (Method AAB). $^1$H NMR (400 MHz, DMSO-d$_6$) δ 7.82 (d, J=7.7 Hz, 1H), 7.74-7.62 (m, 3H), 7.38-7.20 (m, 7H), 7.16-7.06 (m, 5H), 4.53 (s, 4H).

273C. 6-(2-(1H-Tetrazol-5-yl)phenyl)-N2,N2-dibenzylpyridine-2,4-diamine

To a heterogeneous mixture of 6-(2-(1H-tetrazol-5-yl)phenyl)-N,N-dibenzyl-4-nitropyridin-2-amine (55.7 mg, 0.12 mmol) in ethanol (2 mL) and water (0.20 mL), under nitrogen atmosphere, was added ammonium chloride (25.7 mg, 0.48 mmol). The resulting mixture was stirred at RT for 20 min before zinc (79.0 mg, 1.20 mmol) was added. After 24 hrs, the reaction mixture was filtered through a plug of Celite, which was then thoroughly rinsed with EtOAc. The filtrate was partitioned between EtOAc and water. The layers were separated and the aqueous layer was extracted twice more with EtOAc. The organic extracts were combined, washed with brine, dried (MgSO$_4$), filtered and concentrated in vacuo to afford an off-white solid which was resubjected to the conditions of the reaction. To a mixture of the solid in ethanol (2 mL) and water (0.20 mL), under nitrogen atmosphere, was added ammonium chloride (25.7 mg, 0.48 mmol). The resulting mixture was stirred at RT for 15 min before zinc (79.0 mg, 1.20 mmol) was added. After 26 hrs, the reaction mixture was filtered through a plug of Celite, which was then thoroughly rinsed with EtOAc. The filtrate was partitioned between EtOAc and water. The layers were separated and the aqueous layer was extracted twice more with EtOAc. The organic extracts were combined, washed with brine, dried (MgSO$_4$), filtered and concentrated in vacuo to 273C as a solid (0.030 g; 58% yield). MS (ES): m/z=434 [M+H]$^+$. T$_r$=0.76 min (Method AAB).

Example 273

To a homogeneous mixture of 273C (15.2 mg, 0.035 mmol) in anhydrous THF (1 mL), at RT under nitrogen atmosphere, was added 1-isocyanato-4-(trifluoromethoxy)benzene (12.1 mg, 0.060 mmol). The resulting mixture was heated at 55° C. for 13.5 hrs. After cooling to RT, the reaction mixture was diluted with DMF, filtered through a syringe filter, then purified via preparative HPLC/MS to afford Example 273 (7.2 mg; 17% yield). MS (ES): m/z=637 [M+H]$^+$. T$_r$=2.85 min (Method AZ). $^1$H NMR (500 MHz, DMSO-d$_6$) δ 9.09 (br. s., 1H), 7.94 (s, 1H), 7.73-7.64 (m, 3H), 7.64-7.58 (m, 1H), 7.50 (d, J=8.8 Hz, 2H), 7.31-7.26 (m, 6H), 7.23 (d, J=7.1 Hz, 2H), 7.12-7.08 (m, 4H), 6.98 (s, 1H), 6.65 (br. s., 1H), 4.43 (s, 4H).

Example 274

1-(2-(2-(1H-Tetrazol-5-yl)phenyl)-6-(benzyl(ethyl)amino)pyridin-4-yl)-3-(p-tolyl)urea

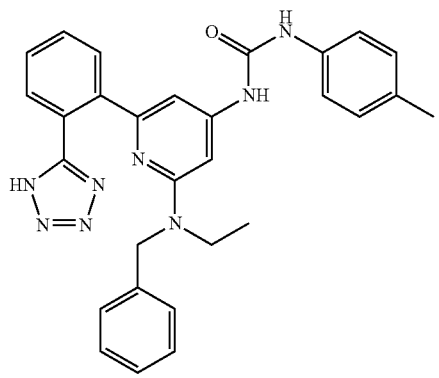 [SMILES: CCN(Cc1ccccc1)c1cc(NC(=O)Nc2ccc(C)cc2)cc(-c2ccccc2-c2nnn[nH]2)n1]

274A.
N-Benzyl-6-bromo-N-ethyl-4-nitropyridin-2-amine

N-Benzyl-6-bromo-N-ethyl-4-nitropyridin-2-amine (706 mg; 91% yield) was prepared following a procedure analogous to the procedure for 273A, except that N-benzylethanamine (935 mg, 6.9 mmol) was used instead of dibenzylamine. MS (ES): m/z=336/338 [M+H]$^+$. T$_r$=1.18 min (Method AAB). $^1$H NMR (400 MHz, DMSO-d$_6$) δ 7.40-7.31 (m, 3H), 7.29-7.24 (m, 3H), 7.22 (d, J=1.5 Hz, 1H), 4.80 (s, 2H), 3.61 (q, J=7.0 Hz, 2H), 1.12 (t, J=7.0 Hz, 3H).

274B. 2-(6-(Benzyl(ethyl)amino)-4-nitropyridin-2-yl)benzonitrile

To a homogeneous mixture of 274A (0.71 g, 2.10 mmol) in anhydrous dioxane (12 mL), in a sealable reaction flask, was added (2-cyanophenyl)boronic acid, neopentyl glycol ester (0.95 g, 4.20 mmol) and potassium phosphate, dibasic (1.10 g, 6.30 mmol). The resulting mixture was purged with argon for 20 min before PdCl$_2$(dppf)-CH$_2$Cl$_2$Adduct (0.09 g, 0.11 mmol) was added. The mixture was then purged with argon for 15 min before the flask was sealed and the reaction heated at 95° C. After 23 hrs, the reaction mixture was cooled, then partitioned between EtOAc and water. The layers were separated and the aqueous layer was extracted twice more with EtOAc. The combined organic layers were washed with brine then dried (MgSO$_4$), filtered and concentrated in vacuo to afford the crude product. Purification by Isco chromatography afforded 274B as an orange glass (0.64 g; 84% yield). MS (ES): m/z=359 [M+H]$^+$. T$_r$=1.14 min (Method AAB). $^1$H NMR (400 MHz, DMSO-d$_6$) δ 8.03-7.95 (m, 2H), 7.82 (m, 1H), 7.71-7.62 (m, 2H), 7.38-7.20 (m, 6H), 4.96 (s, 2H), 3.84-3.67 (m, 2H), 1.17 (t, J=7.0 Hz, 3H).

274C. 6-(2-(1H-Tetrazol-5-yl)phenyl)-N-benzyl-N-ethyl-4-nitropyridin-2-amine

To a homogeneous mixture of 274B (0.64 g, 1.77 mmol) in toluene (5 mL), under nitrogen atmosphere, was added azidotributyltin (1.3 mL, 4.74 mmol). The resulting mixture was stirred at 105° C. for 43 hrs before azidotributyltin (1.3 mL, 4.74 mmol) was added and stirring continued at 105° C. After 17 hrs the reaction was cooled then purified by Isco chromatography to afford 274C as an orange solid (0.64 g; 90% yield). MS (ES): m/z=402 [M+H]$^+$. T$_r$=0.99 min (Method AAB). $^1$H NMR (400 MHz, DMSO-d$_6$) δ 7.82 (d, J=7.5 Hz, 1H), 7.74-7.68 (m, 2H), 7.68-7.62 (m, 1H), 7.34-7.27 (m, 3H), 7.27-7.20 (m, 1H), 7.16-7.07 (m, 3H), 4.51 (s, 2H), 3.32-3.28 (m, 2H), 0.91 (t, J=6.9 Hz, 3H).

274D. 6-(2-(1H-Tetrazol-5-yl)phenyl)-N2-benzyl-N2-ethylpyridine-2,4-diamine

To a homogeneous mixture of 6-(2-(1H-tetrazol-5-yl) phenyl)-N-benzyl-N-ethyl-4-nitropyridin-2-amine (0.64 g, 1.60 mmol) in ethanol (12 mL) and water (2 mL), under nitrogen atmosphere, was added ammonium chloride (0.34 g, 6.38 mmol). The resulting mixture was stirred at RT for 20 min before zinc (1.04 g, 15.95 mmol) was added. After 65 hrs, the reaction mixture was filtered through a plug of Celite, which was then thoroughly rinsed with EtOAc. The filtrate was partitioned between EtOAc and water. The layers were separated and the aqueous layer was extracted twice more with EtOAc. The organic extracts were combined, washed with brine, dried (MgSO$_4$), filtered and concentrated in vacuo to afford a solid which was resubjected to the conditions of the reaction. To a mixture of the solid in ethanol (12 mL) and water (2 mL), under nitrogen atmosphere, was added ammonium chloride (0.34 g, 6.38 mmol). The resulting mixture was stirred at RT for 10 min before zinc (1.04 g, 15.95 mmol) was added and the mixture was stirred at 50° C. After 1 h, the reaction mixture was cooled then filtered through a plug of Celite, which was then thoroughly rinsed with EtOAc. The filtrate was partitioned between EtOAc and water. The layers were separated and the aqueous layer was extracted twice more with EtOAc. The organic extracts were combined, washed with brine, dried (MgSO$_4$), filtered and concentrated in vacuo to afford 274C as an off-white solid (0.35 g; 60% yield). MS (ES): m/z=372 [M+H]$^+$. T$_r$=0.70 min (Method AAB).

Example 274. 1-(2-(2-(1H-Tetrazol-5-yl)phenyl)-6-(benzyl(ethyl)amino)pyridin-4-yl)-3-(p-tolyl)urea To a mixture of 274C (28.2 mg, 0.076 mmol) in anhydrous THF (2 mL), in a sealable vial, was added 1-isocyanato-4-methylbenzene (20.22 mg, 0.152 mmol) followed by triethylamine (0.04 mL; 0.29 mmol). The vial was sealed and the resulting mixture was heated at 60° C. for 18 hrs. After cooling to RT, the reaction mixture was diluted with DMF, filtered through a syringe filter, then purified via preparative HPLC/MS to afford the title compound (22.5 mg; 56% yield). MS (ES): m/z=505 [M+H]$^+$. T$_r$=1.77 min (Method AZ). $^1$H NMR (500 MHz, DMSO-d$_6$) δ 8.97 (br. s, 1H), 7.94 (s, 1H), 7.74-7.68 (m, 4H), 7.32-7.30 (m, 4H), 7.26-7.24 (m, 1H), 7.15 (d, J=7.1 Hz, 2H), 7.09 (d, J=7.7 Hz, 2H), 6.88-6.82 (m, 2H), 4.51 (s, 2H), 3.53-3.16 (m, 2H), 2.23 (s, 3H), 0.94 (t, J=6.6 Hz, 3H).

Examples 275 to 281

Reaction of 6-(2-(1H-tetrazol-5-yl)phenyl)-N2-benzyl-N2-ethylpyridine-2,4-diamine with an appropriate isocyanate, under the conditions described for Example 274 affords Examples 275 to 281 of the invention shown in the table below.

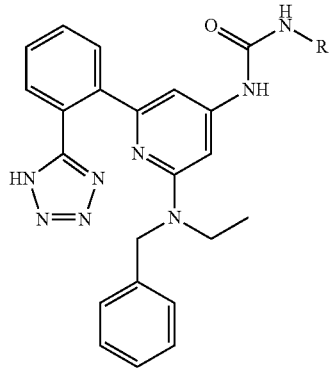

| Ex. No. | R | (M + H)$^+$ | T$_r$ (min.) |
|---|---|---|---|
| 275 | 2-F, 4-Cl-phenyl | 543 | 1.88$^{Method\ AZ}$ |
| 276 | 4-CF$_3$-phenyl | 559 | 1.93$^{Method\ AZ}$ |
| 277 | 4-OCF$_3$-phenyl | 575 | 1.87$^{Method\ AZ}$ |
| 278 | benzo[1,3]dioxol-5-yl | 535 | 1.65$^{Method\ AZ}$ |
| 279 | 4-ethoxyphenyl | 535 | 1.74$^{Method\ AZ}$ |
| 280 | 4-(OCHF$_2$)phenyl | 557 | 1.78$^{Method\ AZ}$ |
| 281 | 2,4-dichlorophenyl | 559 | 1.97$^{Method\ AZ}$ |

Example 282

N-(2-(2-(1H-Tetrazol-5-yl)phenyl)-6-(benzyl(ethyl)amino)pyridin-4-yl)-2-(4-cyanophenyl)acetamide

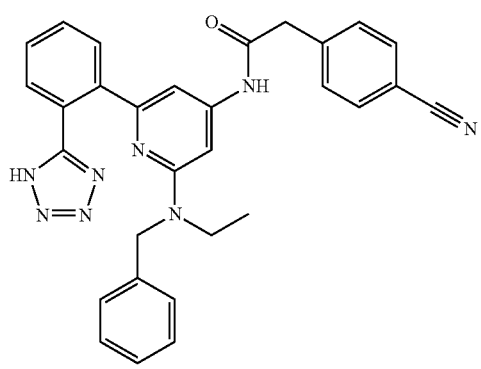 [SMILES: CCN(Cc1ccccc1)c1cc(NC(=O)Cc2ccc(C#N)cc2)cc(-c2ccccc2-c2nnn[nH]2)n1]

To a homogeneous mixture of 6-(2-(1H-tetrazol-5-yl)phenyl)-N2-benzyl-N2-ethylpyridine-2,4-diamine (28.2 mg, 0.076 mmol) and 2-(4-cyanophenyl)acetic acid (24.5 mg, 0.15 mmol) in anhydrous DMF (1 mL), was added DIPEA (0.04 mL, 0.23 mmol) followed by 2,4,6-tripropyl-1,3,5,2,4,6-trioxatriphosphinane 2,4,6-trioxide (0.05 mL, 0.15 mmol). The reaction was stirred at RT for 46 hrs before 2-(4-cyanophenyl)acetic acid (24.5 mg, 0.15 mmol), DIPEA (0.04 mL, 0.23 mmol) and 2,4,6-tripropyl-1,3,5,2,4,6-trioxatriphosphinane 2,4,6-trioxide (0.05 mL, 0.15 mmol) were added. After stirring at RT for 24 hrs, the reaction mixture was concentrated in vacuo to remove volatiles, diluted with DMF, filtered through a syringe filter then purified via preparative HPLC/MS to afford the title compound (14.1 mg; 35% yield). MS (ES): m/z=515 [M+H]$^+$. $T_r$=1.63 min (Method AZ). $^1$H NMR (500 MHz, DMSO-d$_6$) δ 10.36 (br. s., 1H), 7.79-7.76 (m, 2H), 7.64-7.60 (m, 2H), 7.58-7.52 (m, 2H), 7.48 (d, J=7.7 Hz, 2H), 7.28-7.23 (m, 2H), 7.21-7.16 (m, 1H), 7.06 (d, J=7.4 Hz, 2H), 6.89 (br. s., 1H), 6.79 (s, 1H), 4.35 (s, 2H), 3.74 (s, 2H), 3.15 (d, J=7.1 Hz, 2H), 0.86 (t, J=6.9 Hz, 3H).

Examples 283 to 285

Reaction of 6-(2-(1H-tetrazol-5-yl)phenyl)-N2-benzyl-N2-ethylpyridine-2,4-diamine, with an appropriate carboxylic acid, under the conditions described for Example 282, affords Examples 283 to 285 of the invention shown in the table below.

| Ex. No. | R | (M + H)$^+$ | $T_r$ (min.) |
|---|---|---|---|
| 283 | isoxazol-5-ylmethyl (3-methylisoxazol-5-yl)methyl | 495 | 1.50$^{Method\ AZ}$ |
| 284 | pyridin-3-ylmethyl | 491 | 1.43$^{Method\ AZ}$ |
| 285 | (6-methylpyridin-3-yl)methyl | 505 | 1.49$^{Method\ AZ}$ |

Example 286

1-(2-(2-(1H-Tetrazol-5-yl)phenyl)-6-(cyclohexyl(isobutyl)amino)pyridin-4-yl)-3-(p-tolyl)urea

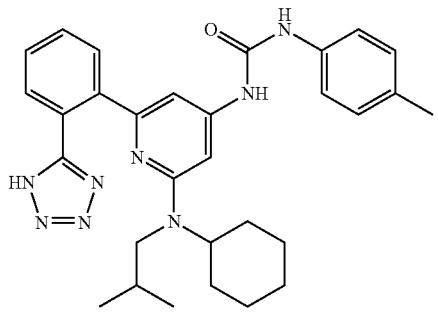 [SMILES: Cc1ccc(NC(=O)Nc2cc(-c3ccccc3-c3nnn[nH]3)nc(N(CC(C)C)C3CCCCC3)c2)cc1]

Example 286 (1.0 mg; 6% yield) was prepared following a procedure analogous to that for the synthesis of Example 274, except that N-isobutylcyclohexanamine (1.08 g, 6.96 mmol) was used instead of N-benzylethanamine in Step 274A. MS (ES): m/z=525 [M+H]$^+$. $T_r$=1.96 min (Method AAA). $^1$H NMR (500 MHz, DMSO-d$_6$) δ 9.25 (br. s, 1H), 8.97 (br. s, 1H), 7.76-7.61 (m, 4H), 7.33 (d, J=7.7 Hz, 2H), 7.16-7.03 (m, 3H), 6.91-6.83 (m, 1H), 3.61-3.42 (m, 1H), 2.24 (s, 3H), 1.85-1.76 (m, 1H), 1.71-1.60 (m, 2H), 1.52-1.52 (m, 1H), 1.57-1.48 (m, 1H), 1.41-0.96 (m, 8H), 0.79 (d, J=6.2 Hz, 6H).

Example 287

1-(2-(2-(1H-Tetrazol-5-yl)phenyl)-6-(cyclohexyl(isobutyl)amino)pyridin-4-yl)-3-(2,4-difluorophenyl)urea

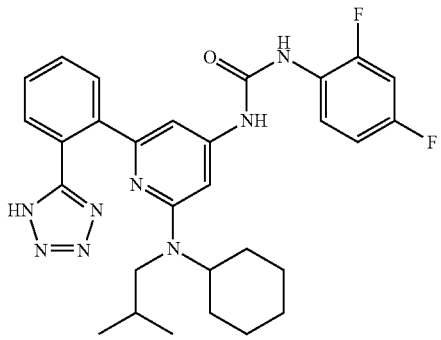 [SMILES: CC(C)CN(c1cc(NC(=O)Nc2ccc(F)cc2F)cc(-c2ccccc2-c2nnn[nH]2)n1)C1CCCCC1]

Example 287 (1.0 mg; 5% yield) was prepared following a procedure analogous to that for the synthesis of Example 286, except that 2,4-difluoro-1-isocyanatobenzene (9.8 mg, 0.06 mmol) was used instead of 1-isocyanato-4-methylbenzene. MS (ES): m/z=547 [M+H]$^+$. T$_r$=1.89 min (Method AAA). $^1$H NMR (500 MHz, DMSO-d$_6$) δ 9.05 (br. s., 1H), 8.59 (s, 1H), 8.25-7.97 (m, 1H), 7.66 (d, J=7.6 Hz, 1H), 7.61-7.45 (m, 3H), 7.37-7.25 (m, 1H), 7.11-6.99 (m, 1H), 6.81 (s, 1H), 6.43 (s, 1H), 4.01-3.82 (m, 1H), 2.96-2.86 (m, 2H), 1.95-1.87 (m, 1H), 1.74-1.65 (m, 2H), 1.61-1.52 (m, 1H), 1.51-1.43 (m, 2H), 1.34-1.23 (m, 4H), 1.11-1.00 (m, 1H), 0.83 (d, J=6.6 Hz, 6H).

Example 288

1-(2-(2-(1H-Tetrazol-5-yl)phenyl)-6-(benzyl(propyl)amino)pyridin-4-yl)-3-(benzo[d][1,3]dioxol-5-yl)urea

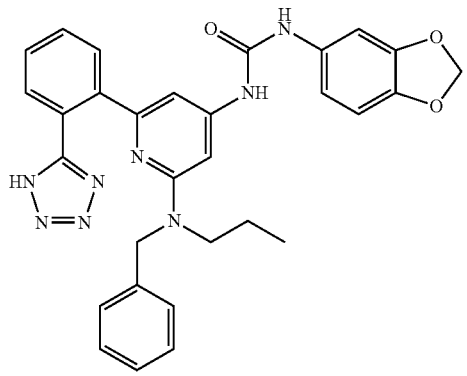 [SMILES: CCCN(Cc1ccccc1)c1cc(NC(=O)Nc2ccc3c(c2)OCO3)cc(-c2ccccc2-c2nnn[nH]2)n1]

288A. 6-(2-(1H-Tetrazol-5-yl)phenyl)-N2-benzyl-N2-propylpyridine-2,4-diamine 6-(2-(1H-Tetrazol-5-yl)phenyl)-N2-benzyl-N2-propylpyridine-2,4-diamine was prepared following a procedure analogous to that for the synthesis of 274C, except that N-benzylpropan-1-amine was used instead of N-benzylethanamine in Step 274A. MS (ES): m/z=386 [M+H]$^+$. T$_r$=0.70 min (LCMS5).

Example 288

Reaction of 288A and 5-isocyanatobenzo[d][1,3]dioxole under the conditions described for the synthesis of Example 274 afforded Example 288 (2.3 mg, 11% yield). MS (ES): m/z=549 [M+H]$^+$. T$_r$=1.74 min (Method AZ). $^1$H NMR (500 MHz, DMSO-d$_6$) δ 9.03 (br. s., 1H), 7.94 (s, 1H), 7.76-7.61 (m, 4H), 7.34-7.27 (m, 2H), 7.26-7.22 (m, 1H), 7.17-7.00 (m, 4H), 6.88 (s, 1H), 6.85-6.80 (m, 1H), 6.79-6.75 (m, 1H), 5.96 (s, 2H), 4.49 (s, 2H), 3.23-3.02 (m, 2H), 1.41-1.29 (m, 2H), 0.75 (t, J=7.2 Hz, 3H).

Example 289

1-(2-(2-(1H-Tetrazol-5-yl)phenyl)-6-(benzyl(propyl)amino)pyridin-4-yl)-3-(4-(trifluoromethyl)phenyl)urea

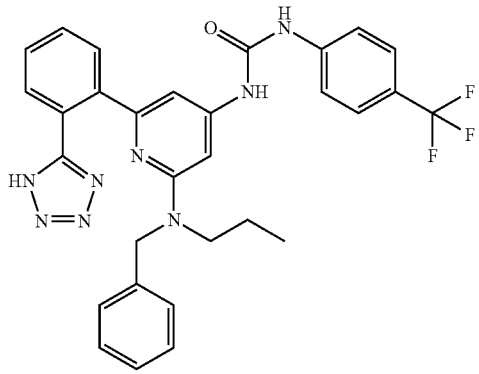 [SMILES: CCCN(Cc1ccccc1)c1cc(NC(=O)Nc2ccc(C(F)(F)F)cc2)cc(-c2ccccc2-c2nnn[nH]2)n1]

Example 289 (2.1 mg; 10% yield) was prepared following a procedure analogous to that for the synthesis of Example 288, except that 1-isocyanato-4-(trifluoromethyl)benzene (15.0 mg, 0.08 mmol) was used instead of 5-isocyanatobenzo[d][1,3]dioxole. MS (ES): m/z=573 [M+H]$^+$. T$_r$=1.94 min (Method AZ). $^1$H NMR (500 MHz, DMSO-d$_6$) δ 9.45 (br. s., 1H), 7.75-7.57 (m, 9H), 7.30-7.19 (m, 3H), 7.10 (d, J=7.4 Hz, 2H), 6.89 (s, 1H), 6.72 (s, 1H), 4.44 (s, 2H), 3.18-3.04 (m, 2H), 1.38-1.26 (m, 2H), 0.75 (t, J=7.2 Hz, 3H).

Example 290

N-(2-(2-(1H-Tetrazol-5-yl)phenyl)-6-(benzyl(propyl)amino)pyridin-4-yl)-2-(4-cyanophenyl)acetamide

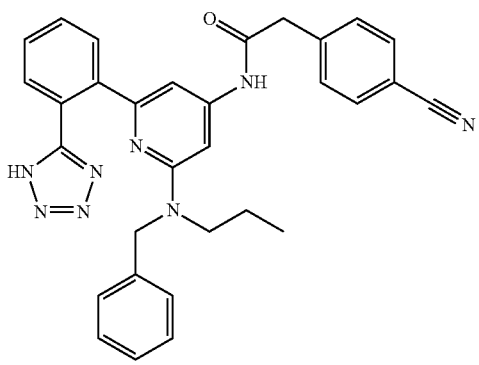 [SMILES: CCCN(Cc1ccccc1)c1cc(NC(=O)Cc2ccc(C#N)cc2)cc(-c2ccccc2-c2nnn[nH]2)n1]

Reaction of 6-(2-(1H-tetrazol-5-yl)phenyl)-N2-benzyl-N2-propylpyridine-2,4-diamine and 2-(4-cyanophenyl)acetic acid under the conditions described for the synthesis of Example 282 afforded Example 290 (11.2 mg, 39% yield). MS (ES): m/z=529 [M+H]$^+$. T$_r$=1.72 min (Method AAA). $^1$H NMR (500 MHz, DMSO-d$_6$) δ 7.82-7.75 (m, 3H), 7.68-7.63 (m, 2H), 7.62-7.53 (m, 2H), 7.49 (d, J=7.7 Hz, 2H), 7.31-7.23 (m, 2H), 7.23-7.15 (m, 1H), 7.05 (d, J=7.4 Hz, 2H), 6.99 (s, 1H), 6.76 (s, 1H), 4.36 (s, 2H), 3.76 (s, 2H), 3.07-2.97 (m, 2H), 1.34-1.26 (m, 2H), 0.73 (t, J=7.2 Hz, 3H).

Examples 291 to 296

Reaction of 6-(2-(1H-tetrazol-5-yl)phenyl)-N2-benzyl-N2-propylpyridine-2,4-diamine, with an appropriate carboxylic acid, under the conditions described for Example 290, affords Examples 291 to 296 of the invention shown in the tables below.

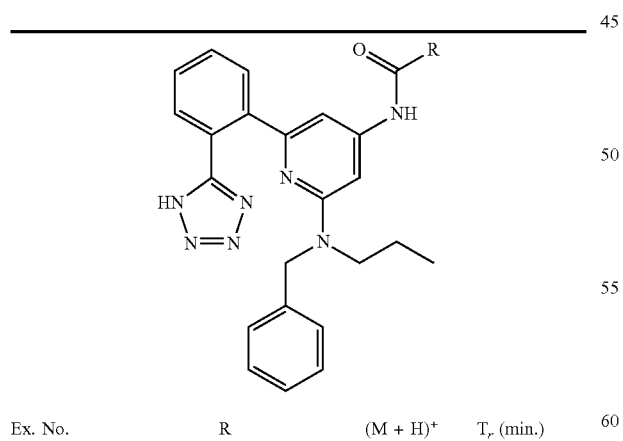

| Ex. No. | R | (M + H)$^+$ | T$_r$ (min.) |
|---|---|---|---|
| 291 | 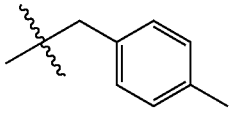 | 518 | 1.87$^{Method\ AZ}$ |

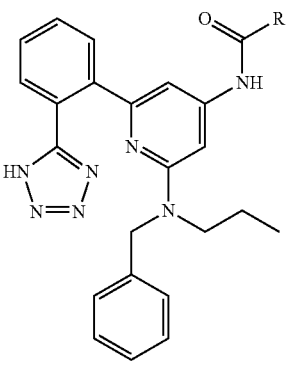

| Ex. No. | R | (M + H)$^+$ | T$_r$ (min.) |
|---|---|---|---|
| 292 | 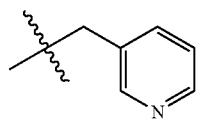 [SMILES: *Cc1cccnc1] | 505 | 1.53$^{Method\ AZ}$ |
| 293 | 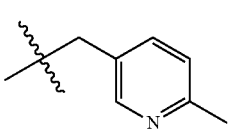 [SMILES: *Cc1ccc(C)nc1] | 519 | 1.58$^{Method\ AZ}$ |
| 294 | 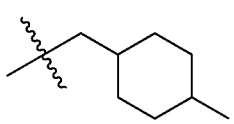 [SMILES: *CC1CCC(C)CC1] | 524 | 2.08$^{Method\ AZ}$ |
| 295 | 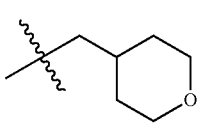 | 512 | 1.58$^{Method\ AZ}$ |
| 296 | 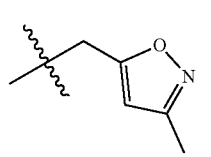 [SMILES: *Cc1cc(C)no1] | 509 | 1.60$^{Method\ AZ}$ |

Example 297

1-(2-(2-(1H-Tetrazol-5-yl)phenyl)-6-(benzyl(propyl)amino)pyridin-4-yl)-3-cyclohexylurea

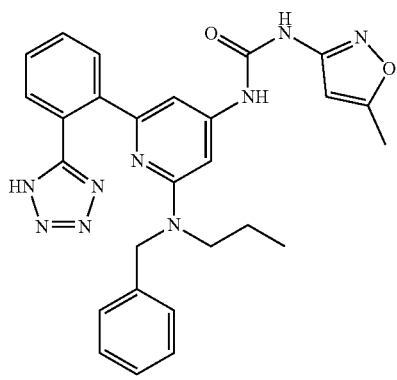 [SMILES: CCCN(Cc1ccccc1)c1cc(NC(=O)Nc2cc(C)on2)cc(-c2ccccc2-c2nnn[nH]2)n1]

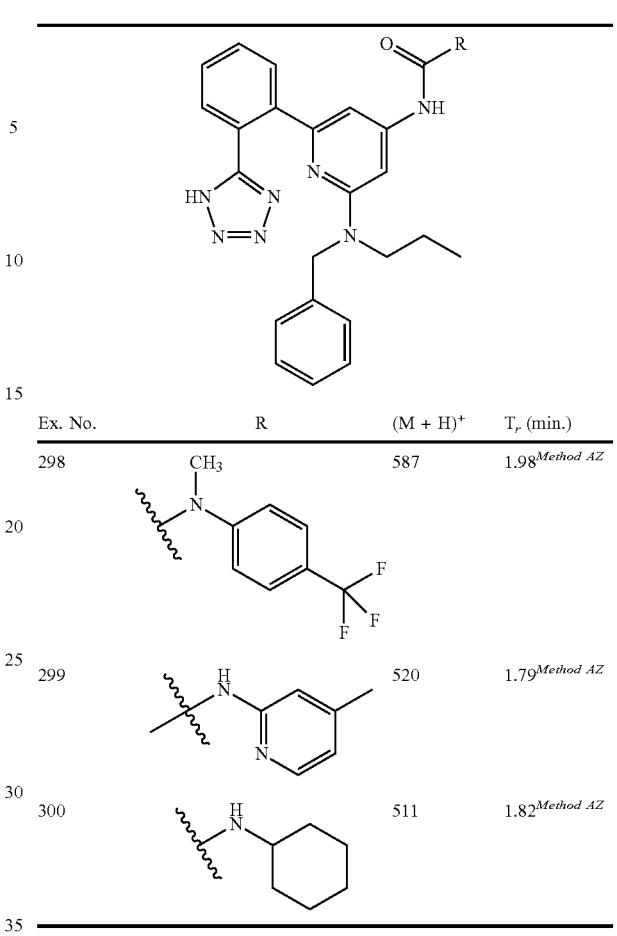

| Ex. No. | R | (M + H)⁺ | T_r (min.) |
|---|---|---|---|
| 298 | CH₃, N-(4-trifluoromethylphenyl) | 587 | 1.98 Method AZ |
| 299 | NH-(4-methylpyridin-2-yl) | 520 | 1.79 Method AZ |
| 300 | NH-cyclohexyl | 511 | 1.82 Method AZ |

To a mixture of 6-(2-(1H-tetrazol-5-yl)phenyl)-N2-benzyl-N2-propylpyridine-2,4-diamine (20 mg, 0.052 mmol) in anhydrous THF (0.5 mL) was added 4-nitrophenyl carbonochloridate (20.9 mg, 0.10 mmol) followed by DIPEA (0.03 mL, 0.16 mmol). The mixture was stirred at RT for 1 h before 5-methylisoxazol-3-amine (10.2 mg, 0.10 mmol) then DIPEA (0.03 mL, 0.16 mmol) were added. The mixture was stirred at 50° C. for 30 min. After cooling to RT, the mixture was concentrated in vacuo to remove volatiles, diluted with DMF, filtered through a syringe filter then purified via preparative HPLC/MS to afford Example 297 (4.5 mg; 16% yield). MS (ES): m/z=510 [M+H]+. T_r=1.67 min (Method AZ). ¹H NMR (500 MHz, DMSO-d₆) δ 8.98 (s, 1H), 7.95 (s, 1H), 7.73-7.63 (m, 2H), 7.62-7.53 (m, 2H), 7.32-7.25 (m, 2H), 7.24-7.17 (m, 1H), 7.08 (d, J=7.4 Hz, 2H), 6.80 (s, 1H), 6.58 (s, 1H), 6.53 (s, 1H), 4.40 (s, 2H), 3.10-3.00 (m, 2H), 2.35 (s, 3H), 1.38-1.27 (m, 2H), 0.75 (t, J=7.4 Hz, 3H).

Examples 298 to 300

Reaction of 6-(2-(1H-tetrazol-5-yl)phenyl)-N2-benzyl-N2-propylpyridine-2,4-diamine, with an appropriate amine, under the conditions described for Example 297, affords Examples 298 to 300 of the invention shown in the table below.

Example 301

1-(2-(Benzyl(propyl)amino)-6-(5-methyl-2-(1H-tetrazol-5-yl)phenyl) pyridin-4-yl)-3-(p-tolyl)urea

301A. 2-(5,5-Dimethyl-1,3,2-dioxaborinan-2-yl)-4-methylbenzonitrile

A mixture of 2-bromo-4-methylbenzonitrile (2.00 g, 10.2 mmol), 5,5,5',5'-tetramethyl-2,2'-bi(1,3,2-dioxaborinane) (3.06 g, 13.6 mmol) and potassium acetate (3.00 g, 30.6 mmol) in anhydrous DMSO (10 mL), in a sealable flask, was purged with Argon for 20 min before PdCl$_2$(dppf)-CH$_2$Cl$_2$ adduct (0.25 g, 0.34 mmol) was added, the flask was sealed and the reaction heated at 80° C. After 17 hrs, the reaction was cooled to RT before being partitioned between EtOAc and brine. The layers were separated and the aqueous layer was extracted once more with EtOAc. The organic layers were combined, washed with brine, dried (MgSO$_4$), filtered and concentrated in vacuo to afford a brown oil which solidified upon standing. Purification by Isco chromatography afforded 301A as an off-white solid (1.96 g; 84% yield). $^1$H NMR (400 MHz, DMSO-d$_6$) δ 7.72-7.63 (m, 2H), 7.43 (dd, J=7.9, 1.1 Hz, 1H), 3.79 (s, 4H), 2.38 (s, 3H), 0.98 (s, 6H).

301B. N2-Benzyl-6-(5-methyl-2-(1H-tetrazol-5-yl)phenyl)-N2-propylpyridine-2,4-diamine Compound 301B was prepared following a procedure analogous to that for the synthesis of 288A, except that 2-(5,5-dimethyl-1,3,2-dioxaborinan-2-yl)-4-methylbenzonitrile was used instead of (2-cyanophenyl)boronic acid, neopentyl glycol ester. MS (ES): m/z=400 [M+H]$^+$. T$_r$=0.74 min (LCMS5).

Example 301

Reaction of 301B and 1-isocyanato-4-methylbenzene, under the conditions described for the synthesis of Example 288 afforded Example 301 (1.8 mg; 8% yield). MS (ES): m/z=533 [M+H]$^+$. T$_r$=2.03 min (Method AZ). $^1$H NMR (500 MHz, DMSO-d6) δ 8.80 (s, 1H), 8.64 (s, 1H), 7.49-7.44 (m, 2H), 7.36 (d, J=8.2 Hz, 1H), 7.31-7.25 (m, 4H), 7.23-7.17 (m, 1H), 7.11-7.06 (m, 4H), 6.80 (s, 1H), 6.56 (s, 1H), 4.40 (s, 2H), 3.09-3.02 (m, 2H), 2.42 (s, 3H), 2.23 (s, 3H), 1.40-1.29 (m, 2H), 0.76 (t, J=7.3 Hz, 3H).

Example 302

1-(2-(Benzyl(propyl)amino)-6-(5-methyl-2-(1H-tetrazol-5-yl)phenyl)pyridin-4-yl)-3-(2,4-dichlorophenyl)urea

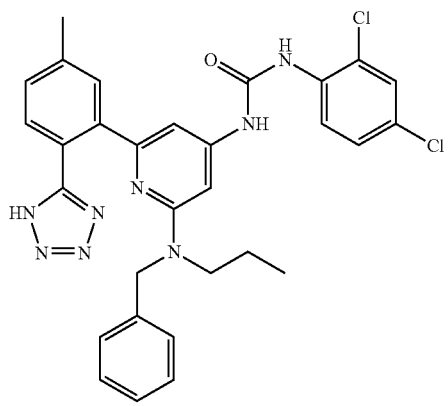 [SMILES: CCCN(Cc1ccccc1)c1cc(NC(=O)Nc2ccc(Cl)cc2Cl)cc(-c2cc(C)ccc2-c2nnn[nH]2)n1]

Reaction of N2-benzyl-6-(5-methyl-2-(1H-tetrazol-5-yl)phenyl)-N2-propylpyridine-2,4-diamine and 2,4-dichloro-1-isocyanatobenzene, under the conditions described for the synthesis of Example 301 afforded Example 302 (7.7 mg; 32% yield). MS (ES): m/z=587 [M+H]$^+$. T$_r$=2.04 min (Method AAA). $^1$H NMR (500 MHz, DMSO-d$_6$) δ 9.73 (br. s., 1H), 8.53 (br. s., 1H), 8.07 (d, J=9.1 Hz, 1H), 7.63 (d, J=2.4 Hz, 1H), 7.57 (d, J=6.7 Hz, 1H), 7.48 (s, 1H), 7.43 (d, J=7.4 Hz, 1H), 7.39 (dd, J=9.1, 2.0 Hz, 1H), 7.31-7.28 (m, 2H), 7.24-7.21 (m, 1H), 7.10 (d, J=7.4 Hz, 2H), 6.86 (s, 1H), 6.65 (br. s., 1H), 4.47 (s, 2H), 3.23-3.04 (m, 2H), 2.44 (s, 3H), 1.36-1.31 (m, 2H), 0.75 (t, J=7.2 Hz, 3H).

Example 303

N-(2-(Benzyl(propyl)amino)-6-(5-methyl-2-(1H-tetrazol-5-yl)phenyl)pyridin-4-yl)-2-(p-tolyl)acetamide

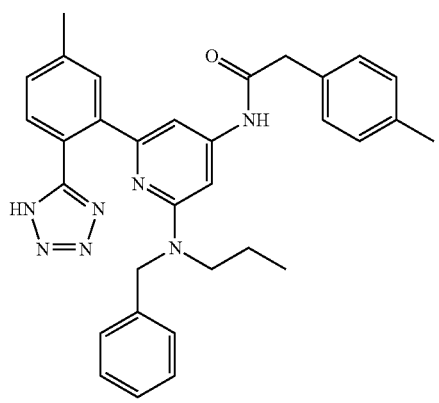 [SMILES: CCCN(Cc1ccccc1)c1cc(NC(=O)Cc2ccc(C)cc2)cc(-c2cc(C)ccc2-c2nnn[nH]2)n1]

Reaction of N2-benzyl-6-(5-methyl-2-(1H-tetrazol-5-yl)phenyl)-N2-propylpyridine-2,4-diamine and 2-(p-tolyl)acetic acid, under the conditions described for the synthesis of Example 290 afforded Example 303 (11.8 mg; 52% yield). MS (ES): m/z=532 [M+H]$^+$. T$_r$=1.88 min (Method AAA). $^1$H NMR (500 MHz, DMSO-d$_6$) δ 10.25 (s, 1H), 7.46 (d, J=7.7 Hz, 1H), 7.41 (s, 1H), 7.35 (d, J=7.7 Hz, 1H), 7.27-7.23 (m, 2H), 7.19-7.15 (m, 3H), 7.13-7.09 (m, 2H), 7.04 (d, J=7.4 Hz, 2H), 6.97 (s, 1H), 6.78 (s, 1H), 4.34 (s, 2H), 3.05-2.97 (m, 2H), 2.54 (s, 2H), 2.40 (s, 3H), 2.26 (s, 3H), 1.33-1.25 (m, 2H), 0.72 (t, J=7.4 Hz, 3H).

Example 304

N-(2-(Benzyl(propyl)amino)-6-(5-methyl-2-(1H-tetrazol-5-yl)phenyl)pyridin-4-yl)cyclohexanecarboxamide

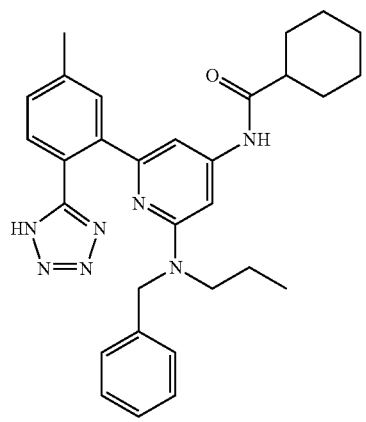 [SMILES: CCCN(Cc1ccccc1)c1cc(NC(=O)C2CCCCC2)cc(-c2cc(C)ccc2-c2nnn[nH]2)n1]

To a mixture of N2-benzyl-6-(5-methyl-2-(1H-tetrazol-5-yl)phenyl)-N2-propylpyridine-2,4-diamine (16.5 mg, 0.04 mmol) in anhydrous THF (1 mL), in a sealable vial, was added cyclohexanecarbonyl chloride (9.1 mg, 0.06 mmol) followed by DIPEA (0.01 mL, 0.06 mmol). The vial was sealed and the resulting mixture was stirred at 50° C. for 4.5 hrs. After cooling to RT, the mixture was concentrated in vacuo to remove volatiles, diluted with DMF, filtered through a syringe filter then purified via preparative HPLC/MS to afford Example 304 (10.5 mg; 50% yield). MS (ES): m/z=510 [M+H]$^+$. T$_r$=1.90 min (Method AAA). $^1$H NMR (500 MHz, DMSO-d$_6$) δ 7.92 (s, 1H), 7.56 (d, J=8.1 Hz, 1H), 7.46-7.41 (m, 2H), 7.29-7.26 (m, 2H), 7.24-7.18 (m, 1H), 7.06 (d, J=7.4 Hz, 2H), 7.03 (s, 1H), 6.94 (br. s., 1H), 4.42 (s, 2H), 3.14-3.01 (m, 2H), 2.54 (s, 3H), 2.33-2.24 (m, 1H), 1.77-1.70 (m, 4H), 1.65-1.58 (m, 1H), 1.36-1.28 (m, 4H), 1.25-1.13 (m, 3H), 0.73 (t, J=7.2 Hz, 3H).

EVALUATION OF BIOLOGICAL ACTIVITY

Materials and Methods

The following general materials and methods were used, where indicated, or may be used in the Examples below:

Standard methods in molecular biology are described in the scientific literature (see, e.g., Sambrook et al., *Molecular Cloning*, Third Edition, Cold Spring Harbor Laboratory Press, Cold Spring Harbor, N Y (2001); and Ausubel et al., *Current Protocols in Molecular Biology*, Vols. 1-4, John Wiley and Sons, Inc. New York, NY (2001), which describes cloning in bacterial cells and DNA mutagenesis (Vol. 1), cloning in mammalian cells and yeast (Vol. 2), glycoconjugates and protein expression (Vol. 3), and bioinformatics (Vol. 4)).

The literature is replete with assays and other experimental techniques that can serve as a basis for evaluation of the compounds described herein.

An IDO enzyme assay and cellular production of kynurenine (KYN) is described in Sarkar, S. A. et al., *Diabetes*, 56:72-79 (2007). Briefly, all chemicals can be purchased from Sigma-Aldrich (St. Louis, MO) unless specified otherwise. Groups of 1,000 human islets can be cultured for 24 h in 1 mL medium with cytokines, recovered by centrifugation for 5 min at 800×g and sonicated in 150 µL PBS containing a protease inhibitor cocktail (Set 2; Calbiochem, EMD Biosciences, San Diego, CA). The sonicate can be centrifuged for 10 min at 10,000×g, and the supernatant can be assayed in triplicate by incubating a 40 µl sample with an equal volume of 100 mmol/L potassium phosphate buffer, pH 6.5, containing 40 mmol/L ascorbic acid (neutralized to pH 7.0), 100 µmol/L methylene blue, 200 µg/mL catalase, and 400 µmol/l L-Trp for 30 min at 37° C. The assay can be terminated by the addition of 16 µL 30% (w/v) trichloroacetic acid (TCA) and further incubated at 60° C. for 15 min to hydrolyze N-formylkynurenine to KYN. The mixture can then be centrifuged at 12,000 rpm for 15 min, and KYN can be quantified by mixing equal volume of supernatant with 2% (w/v) Ehrlich's reagent in glacial acetic acid in 96-well microtiter plate and reading the absorbance at 480 nm using L-KYN as standard. Protein in the islet samples can be quantified by Bio-Rad Protein assay at 595 nm. For the detection of L-KYN in the islet culture supernatants, proteins can be precipitated with 5% (w/v) TCA and centrifuged at 12,000 rpm for 15 min, and determination of KYN in the supernatant with Ehrlich's reagent can be determined as described above. IL-4 (10 µg/mL; 500-2,000 units/mL) and 1-α-methyl Trp (1-MT; 40 µmol/L) can be added to the incubation media as indicated. This assay can also form the basis of a cell-based assay, and may be quantified via LCMS/MS as an alternative to UV/Vis detection.

Alternative means for evaluating the IDO inhibitors of the present invention are described in WO 2010/0233166 and are summarized hereafter.

Biochemical Assay. cDNA clones for both human and mouse IDO have been isolated and verified by sequencing and are commercially available. In order to prepare IDO for biochemical studies, C-terminal His-tagged IDO protein can be produced in *E. coli* using the IPTG-inducible pET5a vector system and isolated over a nickel column. The yield of the partially purified protein can be verified by gel electrophoresis and the concentration estimated by comparison to protein standards. To assay IDO enzymatic activity, a 96-well plate spectrophotometric assay for kynurenine production can be run following published procedures (see, e.g., Littlejohn, T. K. et al., *Prot. Exp. Purif.*, 19:22-29 (2000)). To screen for IDO inhibitory activity, compounds can be evaluated at a single concentration of, for example, 200 µM against 50 ng of IDO enzyme in 100 µL reaction volumes with tryptophan added at increasing concentrations at, for example, 0, 2, 20, and 200 µM. Kynurenine production can be measured at 1 hour.

Cell-based Assay. COS-1 cells can be transiently transfected with a CMV promoter-driven plasmid expressing IDO cDNA using Lipofectamine 2000 (Invitrogen) as recommended by the manufacturer. A companion set of cells can be transiently transfected with TDO-expressing plasmid. Forty-eight hours post-transfection, the cells can be apportioned into a 96-well format at 6×10$^4$ cells per well. The following day, the wells can be washed and new media (phenol red free) containing 20 µg/mL tryptophan can be added together with inhibitor. The reaction can be stopped at 5 hours and the supernatant removed and spectrophotometrically-assayed for kynurenine as previously described for the enzyme assay. To obtain initial confirmation of IDO activity, compounds can be evaluated at a single concentration of, for example, 100 µM. More extensive dose-escalation profiles can be collected for select compounds.

Pharmacodynamic and Pharmacokinetic Evaluation. A pharmacodynamic assay can be based on measuring serum levels of both kynurenine and tryptophan, and calculating the kynurenine/tryptophan ratio provides an estimate of IDO activity that is independent of baseline tryptophan levels. Serum tryptophan and kynurenine levels can be determined by HPLC analysis, and serum compound levels can optionally also be determined in the same HPLC run.

Compounds can be initially evaluated by challenging mice with LPS and then subsequently administering a bolus dose of compound at the time that the serum kynurenine level plateaus. As the kynurenine pool is rapidly turned over with a half-life in serum of less than 10 minutes, pre-existing kynurenine is not expected to unduly mask the impact that an IDO inhibitor has on kynurenine production. Each experiment can include non-LPS-exposed mice (to determine baseline kynurenine levels against which to compare the other mice) and a set of LPS-exposed mice dosed with vehicle alone (to provide a positive control for IDO activation). Each compound can initially be evaluated in mice at a single high i.p. bolus dose in the range of at least 100 mg/kg. Blood can be collected at defined time intervals (for example, 50 µL sample at 5, 15, 30 min., 1, 2, 4, 6, 8, and 24 hr. following compound administration) for HPLC analysis of kynurenine and tryptophan levels (pharmacodynamic analysis) as well as for the level of compound (pharmacokinetic analysis). From the pharmacokinetic data the peak serum concentration of compound achieved can be determined as well as the estimated rate of clearance. By comparing the level of compound in serum relative to the kynurenine/tryptophan ratio at various time points, the effective $IC_{50}$ for IDO inhibition in vivo can be roughly estimated. Compounds exhibiting efficacy can be evaluated to determine a maximum dose that achieves 100% IDO inhibition at the peak concentration.

Exemplary compounds were tested for inhibition of IDO activity. Experimental procedures and results are provided below.

HEK293 cells were transfected with a pCDNA-based mammalian expression vector harboring human IDO1 cDNA (NM 002164.2) by electroporation. They were cultured in medium (DMEM with 10% FBS) containing 1 mg/ml G418 for two weeks. Clones of HEK293 cells that stably expressed human IDO1 protein were selected and expanded for IDO inhibition assay.

The human IDO1/HEK293 cells were seeded at 10,000 cells per 50 μL per well with RPMI/phenol red free media contains 10% FBS in a 384-well black wall clear bottom tissue culture plate (Matrix Technologies LLC) 100 nL of certain concentration of compound was then added to each well using ECHO liquid handling systems. The cells were incubated for 20 hours in 37° C. incubator with 5% $CO_2$.

The compound treatments were stopped by adding trichloroacetic acid (Sigma-Aldrich) to a final concentration at 0.2%. The cell plate was further incubated at 50° C. for 30 minute. The equal volume supernatant (20 μL) and 0.2% (w/v) Ehrlich reagent (4-dimethylaminobenzaldehyde, Sigma-Aldrich) in glacial acetic acid were mixed in a new clear bottom 384-well plate. This plate was then incubated at RT for 30 minute. The absorbance at 490 nm was measured on Envision plate reader.

Compound $IC_{50}$ values were calculated using the counts of 500 nM of a reference standard treatment as one hundred percent inhibition, and counts of no compound but DMSO treatment as zero percent inhibition.

Assessment of Inhibitor Activity in HeLa Cell-Based Indoleamine 2,3-Dioxygenase (IDO) Assay:

HeLa (ATCC® CCL-2) cells were obtained from the ATCC® and cultured in Dulbecco's Modified Eagle Medium supplemented with 4.5 g/L glucose, 4.5 g/L L-glutamine and 4.5 g/L sodium pyruvate (#10-013-CV, Corning), 2 mM L-alanyl-L-glutamine dipeptide (#35050-061, Gibco), 100U/mL penicillin, 100 μg/mL streptomycin (#SV30010, HyClone) and 10% fetal bovine serum (#SH30071.03 HyClone). Cells were maintained in a humidified incubator at 37° C. in 5% $CO_2$.

IDO activity was assessed as a function of kynurenine production as follows: HeLa cells were seeded in a 96-well culture plate at a density of 5,000 cells/well and allowed to equilibrate overnight. After 24 hours, the media was aspirated and replaced with media containing IFNγ (#285-IF/CF, R&D Systems) at a final concentration of 25 ng/mL. A serial dilution of each test compound was added to the cells in a total volume of 200 μL of culture medium. After a further 48 hour incubation, 170 μL of supernatant was transferred from each well to a fresh 96-well plate. 12.1 μL of 6.1N trichloroacetic acid (#T0699, Sigma-Aldrich) was added to each well and mixed, followed by incubation at 65° C. for 20 minutes to hydrolyze N-formylkynurenine, the product of indoleamine 2,3-dioxygenase, to kynurenine. The reaction mixture was then centrifuged for 10 mins at 500×g to sediment the precipitate. 100 μL of the supernatant was transferred from each well to a fresh 96-well plate. 100 μl of 2% (w/v) p-dimethylaminobenzaldehyde (#15647-7, Sigma-Aldrich) in acetic acid (#A6283, Sigma-Aldrich) was added to each well mixed and incubated at RT for 20 mins. Kynurenine concentrations were determined by measuring absorbance at 480 nm and calibrating against an L-kynurenine (#K8625, Sigma-Aldrich) standard curve using a SPECTRAMAX® M2e microplate reader (Molecular Devices). The percentage activity at each inhibitor concentration was determined and $IC_{50}$ values assessed using nonlinear regression.

Results of the IDO assays are shown in the table below.

| Example # | IDO1 HEK Human $IC_{50}$ (μM) |
|---|---|
| 1 | 0.0454 |
| 2 | 1.0354 |
| 3 | 0.0263 |
| 4 | 0.9519 |
| 5 | 6.0000 |
| 6 | 6.0000 |
| 7 | 0.0890 |
| 8 | 0.0085 |
| 9 | 0.0740 |
| 10 | 0.4039 |
| 11 | 0.0181 |
| 12 | 0.0070 |
| 13 | 0.0132 |
| 14 | 0.1810 |
| 15 | |
| 16 | |
| 17 | 0.1608 |
| 18 | 2.4307 |
| 19 | 0.4845 |
| 20 | 0.5936 |
| 21 | 0.3284 |
| 22 | 0.0324 |
| 23 | 0.0162 |
| 24 | 0.2560 |
| 25 | 2.9089 |
| 26 | 0.0118 |
| 27 | 0.6068 |
| 28 | 0.0801 |
| 29 | 0.6162 |
| 30 | 0.0229 |
| 31 | 0.0139 |
| 32 | 4.1000 |
| 33 | 0.5079 |
| 34 | 0.2366 |
| 35 | 0.256 |
| 36 | 0.2054 |
| 37 | 3.1407 |
| 38 | 0.3019 |
| 39 | 0.0024 |
| 40 | 0.0331 |
| 41 | 0.5625 |
| 42 | 0.1204 |
| 43 | 0.0312 |
| 44 | 0.0357 |
| 45 | 0.2386 |
| 46 | 0.0011 |
| 47 | 0.0172 |
| 48 | 0.0107 |
| 49 | 0.0316 |
| 50 | 0.1307 |
| 51 | 0.0603 |
| 52 | 0.1912 |
| 53 | 0.0049 |
| 54 | 0.0248 |
| 55 | 0.0115 |
| 56 | 0.0086 |
| 57 | 0.0040 |
| 58 | 0.0042 |
| 59 | 0.1392 |
| 60 | 0.8305 |
| 61 | 0.4462 |
| 62 | 0.0568 |
| 63 | 6.0000 |
| 64 | 0.1614 |
| 65 | 4.5262 |
| 66 | 0.4401 |

| Example # | IDO1 HEK Human IC$_{50}$ (μM) |
|---|---|
| 67 | 2.4675 |
| 68 | 0.3236 |
| 69 | 0.1345 |
| 70 | 0.4215 |
| 71 | 0.0322 |
| 72 | 0.0085 |
| 73 | 0.3338 |
| 74 | 0.0756 |
| 75 | 0.0279 |
| 76 | 0.9983 |
| 77 | 2.0867 |
| 78 | 0.0082 |
| 79 | 0.0183 |
| 80 | 0.3505 |
| 81 | 0.0119 |
| 82 | 0.7310 |
| 83 | 0.1579 |
| 84 | 0.3730 |
| 85 | 0.0898 |
| 86 | 0.0086 |
| 87 | 0.0407 |
| 88 | 0.1093 |
| 89 | 0.1502 |
| 90 | 0.0409 |
| 91 | 6.0000 |
| 92 | 0.1464 |
| 93 | 3.1677 |
| 94 | 0.2600 |
| 95 | 1.3945 |
| 96 | 6.0000 |
| 97 | 1.1488 |
| 98 | 0.8457 |
| 99 | 3.6601 |
| 100 | 0.1267 |
| 101 | 0.5144 |
| 102 | 0.0086 |
| 103 | 6.0000 |
| 104 | 6.0000 |
| 105 | 6.0000 |
| 106 | 6.0000 |
| 107 | 6.0000 |
| 108 | 6.0000 |
| 109 | 4.1189 |
| 110 | 6.0000 |
| 111 | 6.0000 |
| 112 | 6.0000 |
| 113 | 6.0000 |
| 114 | 6.00 |
| 115 | 6.0000 |
| 116 | 6.0000 |
| 117 | 6.0000 |
| 118 | 6.0000 |
| 119 | 2.0086 |
| 120 | 6.0000 |
| 121 | 6.0000 |
| 122 | 6.0000 |
| 123 | 6.0000 |
| 124 | 6.0000 |
| 125 | 1.1119 |
| 126 | 1.9958 |
| 127 | 1.0501 |
| 128 | 1.8030 |
| 129 | 1.2506 |
| 130 | 6.0000 |
| 131 | 1.6017 |
| 132 | 0.5195 |
| 133 | 6.0000 |
| 134 | 6.0000 |
| 135 | 1.2400 |
| 136 | 0.0780 |
| 137 | 0.0487 |
| 138 | 0.012 |
| 139 | 0.0234 |
| 140 | 0.1417 |
| 141 | 0.0396 |
| 142 | 0.0368 |
| 143 | |
| 144 | 0.6652 |
| 145 | 0.0736 |
| 147 | 0.0073 |
| 148 | 0.0048 |
| 149 | 0.0176 |
| 150 | 0.0239 |
| 151 | 0.279 |
| 152 | 0.1292 |
| 154 | 0.0540 |
| 155 | 0.1307 |
| 156 | 0.1151 |
| 157 | 0.5403 |
| 158 | 0.4445 |
| 159 | 0.2753 |
| 160 | 0.0234 |
| 161 | 0.0021 |
| 162 | 0.0262 |
| 163 | 0.7365 |
| 164 | 0.0079 |
| 165 | 1.1151 |
| 166 | 4.0504 |
| 167 | 0.2060 |
| 168 | 0.3934 |
| 169 | 0.0111 |
| 170 | 0.0049 |
| 171 | 0.0011 |
| 172 | 0.0144 |
| 173 | 0.2586 |
| 174 | 0.0165 |
| 175 | 0.0549 |
| 176 | 0.0105 |
| 177 | 0.0175 |
| 178 | 0.0584 |
| 179 | 0.0109 |
| 180 | 0.0022 |
| 181 | 0.0043 |
| 182 | 0.0095 |
| 183 | 0.129 |
| 184 | 0.0073 |
| 185 | 2.7418 |
| 186 | 0.0035 |
| 187 | 0.1011 |
| 188 | 0.0020 |
| 189 | 0.0093 |
| 190 | 0.0085 |
| 191 | 0.0264 |
| 192 | 0.0198 |
| 193 | 0.0141 |
| 194 | 0.2303 |
| 195 | 0.0198 |
| 196 | 0.0070 |
| 197 | 0.0058 |
| 198 | 2.9587 |
| 199 | 0.2390 |
| 200 | 0.0824 |
| 201 | 0.0342 |
| 202 | 0.2024 |
| 203 | 0.3051 |
| 204 | 0.1590 |
| 205 | 0.0802 |
| 206 | 0.3230 |
| 207 | 3.4258 |
| 208 | 0.5439 |
| 209 | 6.0000 |
| 210 | 1.7132 |
| 211 | 0.9062 |
| 212 | 0.2239 |
| 213 | 0.6511 |
| 214 | 6.0000 |
| 215 | 6.0000 |
| 216 | 0.0768 |
| 217 | 0.239 |
| 218 | 1.9700 |
| 219 | 0.0598 |
| 220 | 0.0526 |

| Example # | IDO1 HEK Human IC$_{50}$ (μM) |
|---|---|
| 221 | 0.2493 |
| 222 | 3.43 |
| 223 | 0.9645 |
| 224 | 2.9955 |
| 225 | 0.3640 |
| 226 | 3.3624 |
| 227 | 3.35 |
| 228 | 0.6694 |
| 229 | 0.1880 |
| 230 | 0.1390 |
| 231 | 0.6754 |
| 233 | 0.9613 |
| 235 | 0.4004 |
| 236 | 0.6868 |
| 237 | 0.1306 |
| 238 | 0.0263 |
| 239 | 0.5664 |
| 240 | 0.0119 |
| 241 | 0.0213 |
| 242 | 0.9709 |
| 243 | 1.6134 |
| 244 | 0.1087 |
| 245 | 0.0475 |
| 246 | 0.0047 |
| 247 | 0.0111 |
| 248 | 0.2170 |
| 249 | 0.9344 |
| 250 | 0.1558 |
| 251 | 2.0000 |
| 252 | 0.9722 |
| 253 | 0.972 |
| 254 | 1.0787 |
| 255 | |
| 256 | 0.9798 |
| 257 | 1.8949 |
| 258 | 0.4106 |
| 259 | |
| 260 | 0.0099 |
| 261 | 1.6351 |
| 262 | 0.1049 |
| 263 | 0.1448 |
| 264 | 1.7975 |
| 265 | 0.0433 |
| 266 | 2.7011 |
| 267 | 1.3627 |
| 268 | 0.0302 |
| 269 | |
| 270 | 0.0322 |
| 271 | 0.0463 |
| 272 | 0.1292 |
| 273 | 0.6085 |
| 274 | 0.0268 |
| 275 | 0.0266 |
| 276 | 0.1478 |
| 277 | 0.7821 |
| 278 | 0.4776 |
| 279 | 0.5367 |
| 280 | 0.5541 |
| 281 | 0.0137 |
| 282 | 1.5842 |
| 283 | 1.1461 |
| 284 | 1.6235 |
| 285 | 2.3255 |
| 286 | 0.3649 |
| 287 | 5.9878 |
| 288 | 0.1554 |
| 289 | 0.0412 |
| 290 | 0.4830 |
| 291 | 0.1273 |
| 292 | 3.36 |
| 293 | 1.3661 |
| 294 | 0.7743 |
| 295 | 3.7255 |
| 296 | 0.7972 |
| 297 | 0.2701 |
| 298 | 0.0389 |
| 299 | 0.8451 |
| 300 | 5.2133 |
| 301 | 0.0461 |
| 302 | 0.0055 |
| 303 | 0.1015 |
| 304 | 1.3144 |

What is claimed:

1. A compound of formula (I):

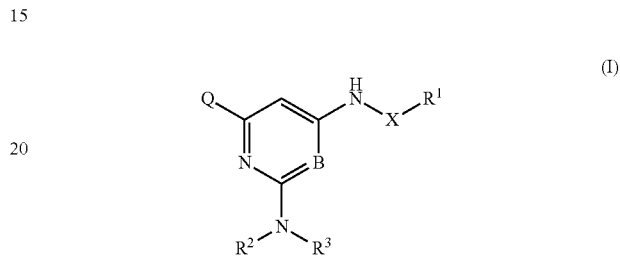

wherein:
B is CH;
Q is phenyl substituted with W and R$^4$;
X is selected from: a bond, C(O), —C(O)CR$^5$R$^6$— and —C(O)NR$^7$—;
W is

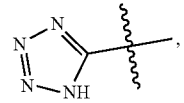

R$^1$ is selected from: C$_1$-C$_6$ alkyl, C$_3$-C$_6$ cycloalkyl, tetrahydro-2H-pyranyl, morpholinyl, phenyl, naphthalenyl, thiophenyl, thiazolyl, isoxazolyl, 1H-imidazolyl, pyrazolyl, 1,3,4-thiadiazolyl, 1H-tetrazolyl, pridinyl, pyrimidinyl, pyridazinyl, pyrazinyl, benzo[d][1,3]dioxolyl, benzo[b]thiophenyl, benzo[d]thiazolyl, benzo[d]oxazolyl, 1-(C$_1$-C$_4$alkyl)-1H-indolyl, pyrazolo[1,5-a]pyrimidinyl, [1,2,4]triazolo[4,3-b]pyridazinyl, 7H-pyrrolo[2,3-d]pyrimidinyl, and quinolin-2-yl; wherein each moiety is substituted with 0 to 2 R$^c$;

R$^2$ is selected from: C$_1$-C$_4$ alkyl, tetrahydro-2H-pyran-4-yl, pyrimidinylmethyl, 1-R$^d$-piperidin-4-yl, —(CH$_2$)$_{0-1}$—(C$_3$-C$_6$cycloalkyl substituted with 0 to 2 R$^e$), and —(CH$_2$)$_{0-1}$-(phenyl substituted with 0 to 2 R$^e$);

R$^3$ is C$_1$-C$_4$ alkyl substituted with 0 to 1 R$^f$, —CH$_2$—(C$_3$-C$_6$ cycloalkyl), or benzyl;

alternatively, —NR$^2$R$^3$ is selected from:

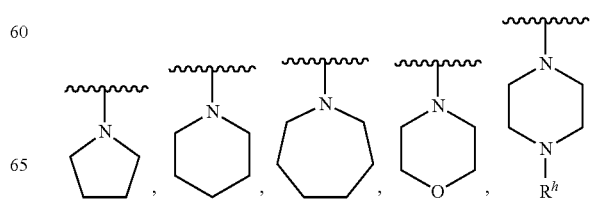

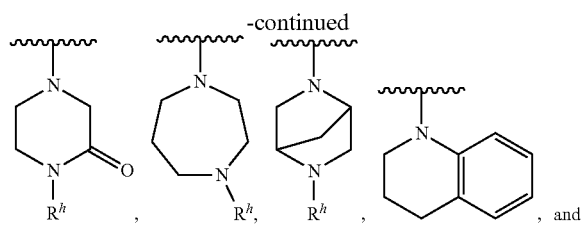

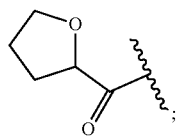 [SMILES: *C(=O)C1CCCO1]

wherein each moiety is substituted with 0 to 2 $R^g$;

$R^4$ is H, halo, $C_1$-$C_4$ alkyl, $C_1$-$C_4$haloalkyl, $C_1$-$C_4$ alkoxy or $C_1$-$C_4$ haloalkoxy;

$R^5$ and $R^6$ are independently H, F, Cl, or $C_1$-$C_4$ alkyl; alternatively, $R^5$ and $R^6$, together with the carbon atom to which they are attached, combine to form a $C_3$-$C_6$cycloalkylene;

$R^7$ is H or $C_1$-$C_4$ alkyl;

$R^c$ is independently selected from: halo, CN, $C_1$-$C_6$alkyl, $C_1$-$C_6$ haloalkyl, $C_1$-$C_6$ alkoxy, $C_1$-$C_6$ haloalkoxy, $CH_2OH$, $C(O)OH$, $C(O)NH_2$, —$S(O)_2$($C_1$-$C_4$ alkyl), phenyl, and morpholinyl;

$R^d$ is independently H or $C(O)O(C_1$-$C_4$ alkyl);

$R^e$ is independently selected from: halo, $C_1$-$C_4$alkyl, $C_1$-$C_4$ haloalkyl, $C_1$-$C_4$ alkoxy, and $C_1$-$C_4$haloalkoxy;

$R^f$ is independently selected from: halo, OH, $C_1$-$C_4$ haloalkyl, $C_1$-$C_4$ alkoxy, $C_1$-$C_4$ haloalkoxy, $C(O)N(C_1$-$C_4$ alkyl)$_2$, phenyl, 4-($C_1$-$C_4$ alkyl)-piperazin-1-yl, and $C_1$-$C_4$ alkyl substituted with 0 to 1 OH;

$R^g$ is independently selected from: halo, $C_1$-$C_4$haloalkyl, $C_1$-$C_4$ alkoxy, and $C_1$-$C_4$ haloalkoxy; and $R^h$ is independently selected from: H, $C_1$-$C_4$ alkyl, $C(O)$($C_1$-$C_4$ alkyl), $C(O)Ph$, —$CH_2C(O)NH(C_1$-$C_4$alkyl,), —$(CH_2)_{0-1}$-(phenyl substituted with 0 to 2 $R^e$), and

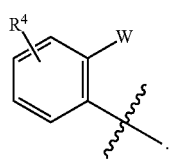

or a pharmaceutically acceptable salt thereof.

2. The compound according to claim 1, wherein:
Q is

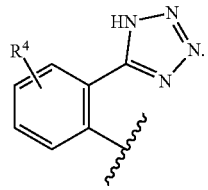

3. The compound according to claim 1, wherein:
Q is

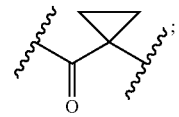 [SMILES: *C(=O)C1(*)CC1]

4. The compound according to claim 1, wherein:
X is selected from: a bond, C(O), —C(O)CHR$^5$—, —C(O)NR$^7$—, and

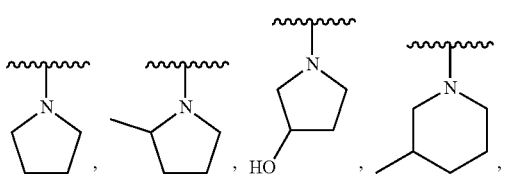

$R^2$ is selected from: $C_1$-$C_4$ alkyl, tetrahydro-2H-pyran-4-yl, pyrimidinylmethyl, 1-$R^d$-piperidin-4-yl, —$(CH_2)_{0-1}$—($C_3$-$C_6$ cycloalkyl substituted with 0 to 2 $R^e$), and —$(CH_2)_{0-1}$-(phenyl substituted with 0 to 2 $R^e$);

$R^3$ is $C_1$-$C_4$ alkyl substituted with 0 to 1 $R^f$, —$CH_2$—($C_3$-$C_6$ cycloalkyl), or benzyl;

alternatively, —$NR^2R^3$ is selected from:

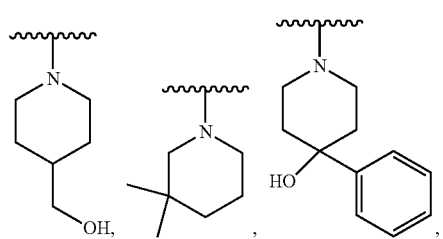

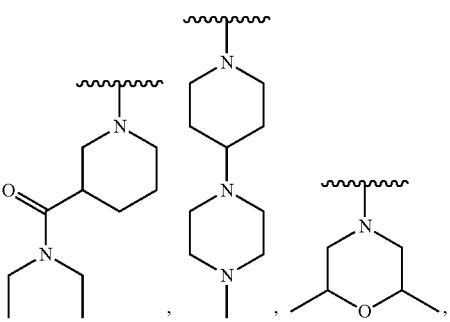

-continued

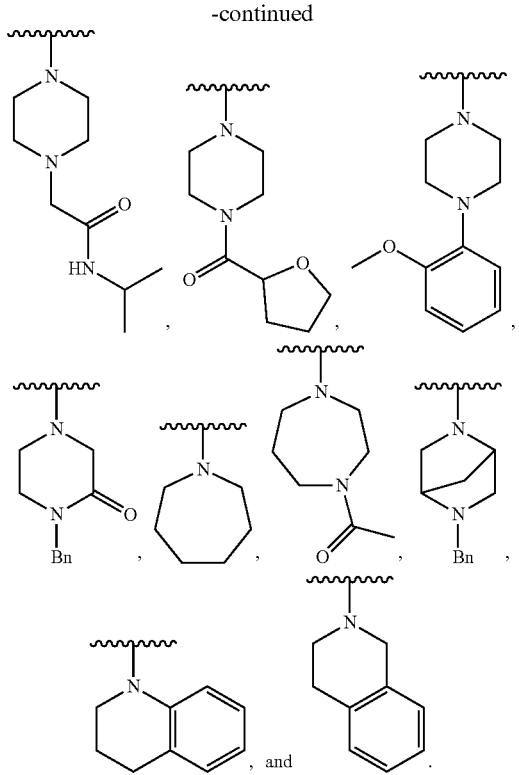

, and

5. The compound according to claim 1, wherein the compound is of formula (II):

(II)

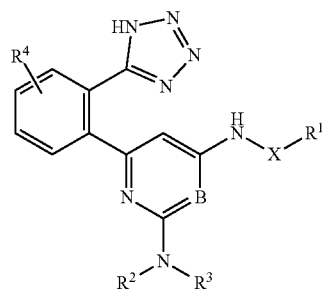

X is a bond, C(O), —C(O)CH₂—, —C(O)CHF—, —C(O)NH—, —C(O)N(CH₃)—, or

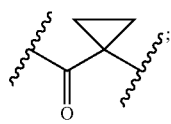 [SMILES: *C(=O)C1(*)CC1]

$R^1$ is selected from: $C_1$-$C_6$ alkyl, $C_5$-$C_6$ cycloalkyl, phenyl, naphthalenyl, thiophenyl, thiazolyl, isoxazolyl, pyrazolyl, 1,3,4-thiadiazolyl, pridinyl, pyrimidinyl, pyridazinyl, pyrazinyl, benzo[d][1,3]dioxolyl, benzo[b]thiophenyl, benzo[d]thiazolyl, benzo[d]oxazolyl, 1-methyl-1H-indolyl, pyrazolo[1,5-a]pyrimidinyl, [1,2,4]triazolo[4,3-b]pyridazinyl, 7H-pyrrolo[2,3-d]pyrimidinyl, and quinolinyl; wherein each moiety is substituted with 0 to 2 $R^c$;

$R^c$ is independently selected from: halo, CN, $C_1$-$C_4$ alkyl, $C_1$-$C_4$ alkoxy, CHF₂, CF₃, OCF₃, —OCF₂CHF₂, CH₂OH, C(O)NH₂, phenyl, and morpholinyl;

$R^2$ is selected from: $C_1$-$C_4$ alkyl, cyclopropylmethyl, cyclohexyl, benzyl, 4-F-benzyl, and pyrimidin-2-ylmethyl;

$R^3$ is $C_1$-$C_4$ alkyl substituted with 0 to 1 $R^f$, cyclopropylmethyl, or benzyl;

alternatively, —NR²R³ is

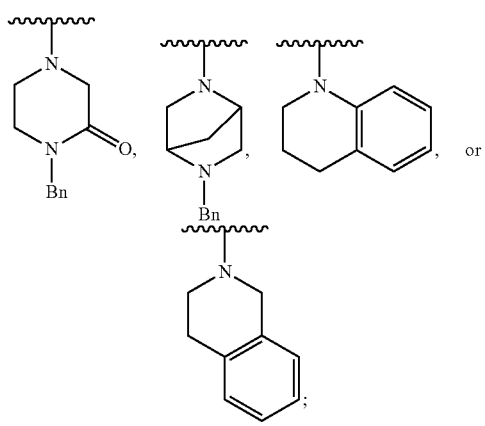

$R^4$ is H, F, or CH₃; and
$R^f$ is CF₃ or OCH₃;
or a pharmaceutically acceptable salt thereof.

6. A pharmaceutical composition comprising a compound according to claim 1 and a pharmaceutically acceptable excipient.

* * * * *

UNITED STATES PATENT AND TRADEMARK OFFICE
CERTIFICATE OF CORRECTION

PATENT NO. : 12,059,420 B2
APPLICATION NO. : 17/261954
DATED : August 13, 2024
INVENTOR(S) : James Aaron Balog et al.

It is certified that error appears in the above-identified patent and that said Letters Patent is hereby corrected as shown below:

In the Claims

Under Column no. 220, in Claim 1, Line no. 46, Replace:
"1-($C_1$-$C_4$alkyl)"
With:
--1-($C_1$-$C_4$ alkyl)--

Under Column no. 220, in Claim 1, Line no. 52, Replace:
"($C_3$-$C_6$cycloalkyl"
With:
--($C_3$-$C_6$ cycloalkyl--

Under Column no. 221, in Claim 1, Line no. 23, Replace:
"$C_1$-$C_4$haloalkyl,"
With:
--$C_1$-$C_4$ haloalkyl,--

Under Column no. 221, in Claim 1, Line no. 28, Replace:
"$C_3$-$C_6$cycloalkylene;"
With:
--$C_3$-$C_6$ cycloalkylene;--

Under Column no. 221, in Claim 1, Line no. 30, Replace:
"$C_1$-$C_6$alkyl,"
With:
--$C_1$-$C_6$ alkyl,--

Under Column no. 221, in Claim 1, Line no. 35, Replace:
"$C_1$-$C_4$alkyl,"

Signed and Sealed this
Twenty-ninth Day of April, 2025

Coke Morgan Stewart
*Acting Director of the United States Patent and Trademark Office*

With:
--$C_1$-$C_4$ alkyl,--

Under Column no. 221, in Claim 1, Line no. 42, Replace:
"$C_1$-$C_4$haloalkyl,"
With:
--$C_1$-$C_4$ haloalkyl,--

Under Column no. 221, in Claim 1, Line no. 45, Replace:
"($C_1$-$C_4$alkyl,),"
With:
--($C_1$-$C_4$ alkyl),--